United States Patent
Ho et al.

(10) Patent No.: US 10,766,865 B2
(45) Date of Patent: *Sep. 8, 2020

(54) PKM2 MODULATORS AND METHODS FOR THEIR USE

(71) Applicant: TOLERO PHARMACEUTICALS, INC., Lehi, UT (US)

(72) Inventors: Koc-Kan Ho, Holladay, UT (US); Yong Xu, Midvale, UT (US); Michael David Saunders, Sandy, UT (US); Xiaohui Liu, Holladay, UT (US); Scott Albert Pearce, Clearfield, UT (US); Kevin Bret Wright, Cottonwood Heights, UT (US); Jason Marc Foulks, Sandy, UT (US); Kenneth Mark Parnell, Kaysville, UT (US); Steven Brian Kanner, Salt Lake City, UT (US); David Lee Vollmer, South Jordan, UT (US); Jihua Liu, San Marcos, CA (US)

(73) Assignee: SUMITOMO DAINIPPON PHARMA ONCOLOGY, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/584,912

(22) Filed: Sep. 26, 2019

(65) Prior Publication Data

US 2020/0109120 A1 Apr. 9, 2020

Related U.S. Application Data

(63) Continuation of application No. 16/226,599, filed on Dec. 19, 2018, now Pat. No. 10,472,328, which is a
(Continued)

(51) Int. Cl.
| | | |
|---|---|---|
| *A61P 11/00* | (2006.01) | |
| *A61P 43/00* | (2006.01) | |
| *A61P 35/00* | (2006.01) | |
| *A61K 31/4155* | (2006.01) | |
| *C07D 231/14* | (2006.01) | |
| *C07D 231/38* | (2006.01) | |
| *C07F 9/6503* | (2006.01) | |
| *C07D 403/12* | (2006.01) | |
| *C07D 401/14* | (2006.01) | |
| *C07D 405/14* | (2006.01) | |
| *C07D 231/16* | (2006.01) | |
(Continued)

(52) U.S. Cl.
CPC ........ *C07D 231/14* (2013.01); *A61K 31/4155* (2013.01); *A61P 11/00* (2018.01); *A61P 35/00* (2018.01); *A61P 43/00* (2018.01); *C07D 231/16* (2013.01); *C07D 231/38* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/12* (2013.01); *C07D 417/14* (2013.01); *C07F 9/65031* (2013.01)

(58) Field of Classification Search
CPC combination set(s) only.
See application file for complete search history.

(56) References Cited

U.S. PATENT DOCUMENTS

| | | | |
|---|---|---|---|
| 2,779,780 A | | 1/1957 | Middleton |
| 5,366,991 A | * | 11/1994 | Bettarini ............... A01N 43/56 514/406 |

(Continued)

FOREIGN PATENT DOCUMENTS

| | | |
|---|---|---|
| EP | 0 606 046 A1 | 7/1994 |
| EP | 0 780 386 A1 | 6/1997 |

(Continued)

OTHER PUBLICATIONS

Anastasiou et al., "Inhibition of pyruvate kinase M2 by reactive oxygen species contributes to cellular antioxidant responses," *Science* 334(6060):1278-1283, 2011. (Author Manuscript, 12 pages).
Anastasiou et al., "Pyruvate kinase M2 activators promote tetramer formation and suppress tumorigenesis," *Nat. Chem. Biol.* 8(10):839-847, 2012.
Ashizawa et al., "In Vivo Regulation of Monomer-Tetramer Conversion of Pyruvate Kinase Subtype M2 by Glucose Is Mediated via Fructose 1,6-Bisphosphate," *The Journal of Biological Chemistry* 266(25):16842-16846, 1991.
Behar et al., "Abstract 4065: Modulation of cancer metabolism with novel PKM2 activators exerts anti-tumor activity," *Proceedings of the 102nd Annual Meeting of the American Association for Cancer Research*, Apr. 2-6, 2011, Orlando, Florida (4 pages).
(Continued)

*Primary Examiner* — Amanda L. Aguirre
(74) *Attorney, Agent, or Firm* — Seed Intellectual Property Law Group LLP

(57) ABSTRACT

Compounds having activity as PKM2 activators are disclosed. The compounds have the following structure (I):

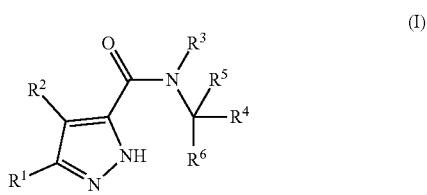

including stereoisomers, tautomers, pharmaceutically acceptable salts and prodrugs thereof, wherein $R^1$, $R^2$, $R^3$, $R^4$, $R^5$ and $R^6$ are as defined herein. Methods associated with preparation and use of such compounds, as well as pharmaceutical compositions comprising such compounds, are also disclosed.

17 Claims, 9 Drawing Sheets

Related U.S. Application Data continuation of application No. 15/183,581, filed on Jun. 15, 2016, now Pat. No. 10,207,996, which is a continuation of application No. 14/435,976, filed as application No. PCT/US2013/065296 on Oct. 16, 2013, now Pat. No. 9,394,257.

(60) Provisional application No. 61/875,855, filed on Sep. 10, 2013, provisional application No. 61/714,659, filed on Oct. 16, 2012.

(51) Int. Cl.
| | |
|---|---|
| *C07D 401/12* | (2006.01) |
| *C07D 403/14* | (2006.01) |
| *C07D 405/12* | (2006.01) |
| *C07D 409/12* | (2006.01) |
| *C07D 409/14* | (2006.01) |
| *C07D 413/12* | (2006.01) |
| *C07D 417/12* | (2006.01) |
| *C07D 417/14* | (2006.01) |

(56) References Cited

U.S. PATENT DOCUMENTS

| | | | |
|---|---|---|---|
| 5,587,458 | A | 12/1996 | King et al. |
| 5,621,002 | A | 4/1997 | Bosslet et al. |
| 5,747,498 | A | 5/1998 | Schnur et al. |
| 5,792,783 | A | 8/1998 | Tang et al. |
| 5,834,504 | A | 11/1998 | Tang et al. |
| 5,861,510 | A | 1/1999 | Piscopio et al. |
| 5,863,949 | A | 1/1999 | Robinson et al. |
| 5,877,305 | A | 3/1999 | Huston et al. |
| 5,883,113 | A | 3/1999 | Tang et al. |
| 5,886,020 | A | 3/1999 | Tang et al. |
| 6,284,764 | B1 | 9/2001 | Kath et al. |
| 8,349,832 | B2 | 1/2013 | Foley et al. |
| 8,354,443 | B2 | 1/2013 | Chen et al. |
| 8,501,953 | B2 | 8/2013 | Salituro et al. |
| 8,524,720 | B2 | 9/2013 | Bebbington et al. |
| 8,552,050 | B2 | 10/2013 | Cantley et al. |
| 8,637,550 | B2 | 1/2014 | Farrow et al. |
| 8,686,030 | B2 | 4/2014 | Huang |
| 8,841,305 | B2 | 9/2014 | Thomas et al. |
| 9,328,077 | B2 | 5/2016 | Salituro et al. |
| 9,394,257 | B2 * | 7/2016 | Ho ................ C07D 405/14 |
| 9,447,054 | B2 | 9/2016 | Song et al. |
| 9,458,132 | B2 | 10/2016 | Cianchetta et al. |
| 10,207,996 | B2 | 2/2019 | Ho et al. |
| 10,472,328 | B2 * | 11/2019 | Ho ................ C07D 409/12 |
| 2005/0085524 | A1 | 4/2005 | Okada et al. |
| 2007/0032529 | A1 | 2/2007 | Takagi et al. |
| 2007/0060589 | A1 | 3/2007 | Purandare et al. |
| 2016/0280697 | A1 | 9/2016 | Salituro et al. |

FOREIGN PATENT DOCUMENTS

| | | |
|---|---|---|
| EP | 0 818 442 A2 | 1/1998 |
| EP | 0 931 788 A2 | 7/1999 |
| EP | 1 004 578 A2 | 5/2000 |
| JP | 6-263738 A | 9/1994 |
| JP | 2861087 B2 | 2/1999 |
| JP | 2001-172261 A | 6/2001 |
| JP | 2002-363164 A | 12/2002 |
| JP | 2004-512277 A | 4/2004 |
| JP | 2008-534671 A | 8/2008 |
| JP | 2012-505247 A | 3/2012 |
| JP | 2012-522847 A | 9/2012 |
| WO | 90/05719 A1 | 5/1990 |
| WO | 95/19970 A1 | 7/1995 |
| WO | 95/21613 A1 | 8/1995 |
| WO | 96/27583 A1 | 9/1996 |
| WO | 96/33172 A1 | 10/1996 |
| WO | 97/13760 A1 | 4/1997 |
| WO | 97/25596 A1 | 6/1997 |
| WO | 97/32856 A1 | 9/1997 |
| WO | 98/02434 A1 | 1/1998 |
| WO | 98/02437 A1 | 1/1998 |
| WO | 98/02438 A1 | 1/1998 |
| WO | 98/03516 A1 | 1/1998 |
| WO | 98/07697 A1 | 2/1998 |
| WO | 98/14451 A1 | 4/1998 |
| WO | 98/30566 A1 | 7/1998 |
| WO | 98/33768 A1 | 8/1998 |
| WO | 98/34915 A1 | 8/1998 |
| WO | 98/34918 A1 | 8/1998 |
| WO | 98/50356 A1 | 11/1998 |
| WO | 98/54093 A1 | 12/1998 |
| WO | 99/07675 A1 | 2/1999 |
| WO | 99/10349 A1 | 3/1999 |
| WO | 99/16755 A1 | 4/1999 |
| WO | 99/24440 A1 | 5/1999 |
| WO | 99/29667 A1 | 6/1999 |
| WO | 99/35132 A1 | 7/1999 |
| WO | 99/35146 A1 | 7/1999 |
| WO | 99/52889 A1 | 10/1999 |
| WO | 99/52910 A1 | 10/1999 |
| WO | 99/61422 A1 | 12/1999 |
| WO | 99/62890 A1 | 12/1999 |
| WO | 00/35436 A2 | 6/2000 |
| WO | 00/74681 A1 | 12/2000 |
| WO | 01/60814 A2 | 8/2001 |
| WO | 02/06213 A2 | 1/2002 |
| WO | 02/066470 A1 | 8/2002 |
| WO | 03/076424 A1 | 9/2003 |
| WO | 03/077914 A1 | 9/2003 |
| WO | 2004/078163 A2 | 9/2004 |
| WO | 2006/106425 A1 | 10/2006 |
| WO | 2007/014011 A2 | 2/2007 |
| WO | 2007/084786 A1 | 7/2007 |
| WO | 2009/028280 A1 | 3/2009 |
| WO | 2009/036082 A2 | 3/2009 |
| WO | 2009/055730 A1 | 4/2009 |
| WO | 2012/056319 A1 | 5/2012 |
| WO | 2012/083246 A1 | 6/2012 |
| WO | 2012/092442 A1 | 7/2012 |
| WO | 2012/123076 A1 | 9/2012 |
| WO | 2012/160447 A1 | 11/2012 |
| WO | 2013/005157 A1 | 10/2013 |
| WO | 2014/074848 A1 | 5/2014 |

OTHER PUBLICATIONS

Boxer et al., "Evaluation of Substituted N,N'-Diarylsulfonamides as Activators of the Tumor Cell Specific M2 Isoform of Pyruvate Kinase," *J. Med. Chem.* 53(3):1048-1055, 2010 (NIH Public Access Author Manuscript, available in PMC Feb. 11, 2011)(25 pages).

Chen et al., "The oxygen sensor PHD3 limits glycolysis under hypoxia via direct binding to pyruvate kinase," *Cell Research* 21(6):983-986, 2011.

Gao et al., "Pyruvate Kinase M2 Regulates Gene Transcription by Acting as a Protein Kinase," *Mol. Cell.* 45(5):598-609, 2012.

Goldberg et al., "Pyruvate kinase M2-specific siRNA induces apoptosis and tumor regression," *J. Exp. Med.* 209(2):217-224, 2012.

Hitosugi et al., "Tyrosine Phosphorylation Inhibits PKM2 to Promote the Warburg Effect and Tumor Growth," *Sci. Signal.* 2(97):1-16, 2009 (NIH Public Access Author Manuscript, available in PMC Jan. 28, 2010)(16 pages).

Zhang et al., "New pyridin-3-ylmethyl carbamodithioic esters activate pyruvate kinase M2 and potential anticancer lead compounds," *Bioorganic & Medicinal Chemistry* 23:4815-4823, 2015.

Zwerschke et al., "Modulation of type M2 pyruvate kinase activity by the human papillomavirus type 16 E7 oncoprotein," *Proc. Natl. Acad. Sci. USA* 96:1291-1296, 1999.

Jiang et al., "Evaluation of Thieno[3,2-b]pyrrole[3,2-d]pyridazinones as Activators of the Tumor Cell Specific M2 Isoform of Pyruvate Kinase," *Bioorg. Med. Chem. Lett.* 20(11):3387-3393, 2010 (NIH Public Access Author Manuscript, available in PMC Jun. 1, 2011)(20 pages).

Kosugi et al., "MUC1-C Oncoprotein Regulates Glycolysis and Pyruvate Kinase m2 Activity in Cancer Cells," *PLoS ONE* 6(11):e28234:1-14, 2011.

(56) References Cited

OTHER PUBLICATIONS

Locasale et al., "Genetic selection for enhanced serine metabolism in cancer development," *Cell Cycle* 10(22):3812-3813, 2011.
Lv et al., "Acetylation Targets the M2 Isoform of Pyruvate Kinase for Degradation through Chaperone-Mediated Autophagy and Promotes Tumor Growth," *Molecular Cell* 42:719-730, 2011.
Mazurek et al., "Effect of Extracellular AMP on Cell Proliferation and Metabolism of Breast Cancer Cell Lines with High and Low Glycolytic Rates," *The Journal of Biological Chemistry* 272(8):4941-4952, 1997.
Parnell et al., "Pharmacologic Activation of PKM2 Slows Lung Tumor Xenograft Growth," *Molecular Cancer Therapeutics* 12(8):1453-1460, 2013.
Peterson et al., "Abstract B024: PKM2 activation suppresses cellular ROS scavenging capacity and potentiates doxorubicin antitumor activity," *Proceedings of the AACR-NCI-EORTC International Conference*, Oct. 26-30, 2017, Philadelphia, Pennsylvania. (5 pages).
Presek et al., "Pyruvate kinase type M2 is phosphorylated at tyrosine residues in cells transformed by Rous sarcoma virus," *FEBS Letters* 242(1):194-198, 1988.
Presek et al., "Similarities between a Phosphoprotein (pp60src)-associated Protein Kinase of Rous Sarcoma Virus and a Cyclic Adenosine 3':5'-Monophosphate-independent Protein Kinase That Phosphorylates Pyruvate Kinase Type M2," *Cancer Research* 40:1733-1741, 1980.
Shiga et al., "Insecticidal Activity of N-Acyl-N-(4-aryloxybenzyl)pyrazole-5-carboxamides," *J. Pestic. Sci.* 28:313-314, 2003.
STN Registry No. 1305273-34-0, "1H-Pyrazole-3-carboxamide, 5-amino-N-(1,3-benzodioxol-5-ylmethyl)-N-[(4-methylphenyl)methyl]-," Jun. 3, 2011, 1 page.
STN Registry No. 1287423-79-3, "1H-Pyrazole-3-carboxamide, N-[(2,3-dihydro-2-methyl-5-benzofuranyl)methyl]-N-(3-methoxypropyl)-5-(trifluoromethyl)-," Apr. 29, 2011, 1 page.
STN Registry No. 1268814-75-0, "1H-Pyrazole-5-carboxamide, N-(1,3-benzodioxol-5-ylmethyl)-3-cyclopropyl-N-ethyl-," Mar. 18, 2011, 1 page.
Tamada et al., "Modulation of Glucose Metabolism by CD44 Contributes to Antioxidant Status and Drug Resistance in Cancer Cells," *Cancer Res.* 72(6):1438-1448, 2012.
Tamada et al., "Pyruvate Kinase M2: Multiple Faces for Conferring Benefits on Cancer Cells," *Clin. Cancer Res.* 18(20):5554-5561, 2012.
Vander Heiden et al., "Understanding the Warburg Effect: The Metabolic Requirements of Cell Proliferation," *Science* 324(5930):1029-1033, 2009 (NIH Public Access Author Manuscript, available in PMC Apr. 5, 2010)(12 pages).
Walsh et al., "2-oxo-N-aryl-1,2,3,4-tetrahydroquinoline-6-sulfonamides as activators of the tumor cell specific M2 isoform of pyruvate kinase," *Bioorg. Med. Chem. Lett.* 21(21):6322-6327, 2011 (NIH Public Access Author Manuscript, available in PMC Dec. 1, 2011)(21 pages).
Xu et al., "Discovery of 3-(trifluoromethyl)-1H-pyrazole-5-carboxamide activators of the M2 isoform of pyruvate kinase (PKM2)," *Bioorganic & Medicinal Chemistry Letters* 24:515-519, 2014.
Ye et al., "Pyruvate kinase M2 promotes de novo serine synthesis to sustain mTORC1 activity and cell proliferation," *PNAS* 109(18):6904-6909, 2012.

* cited by examiner

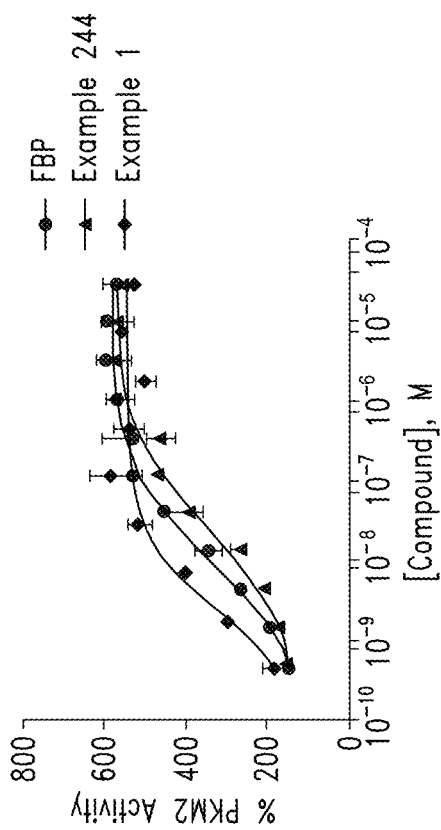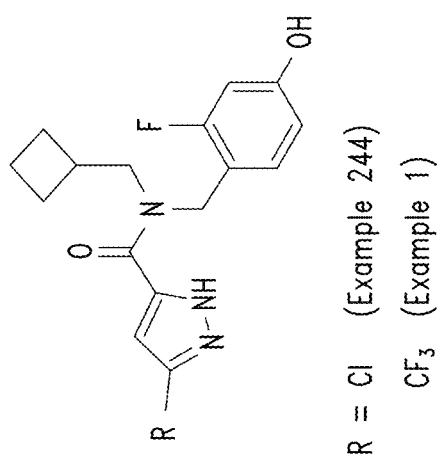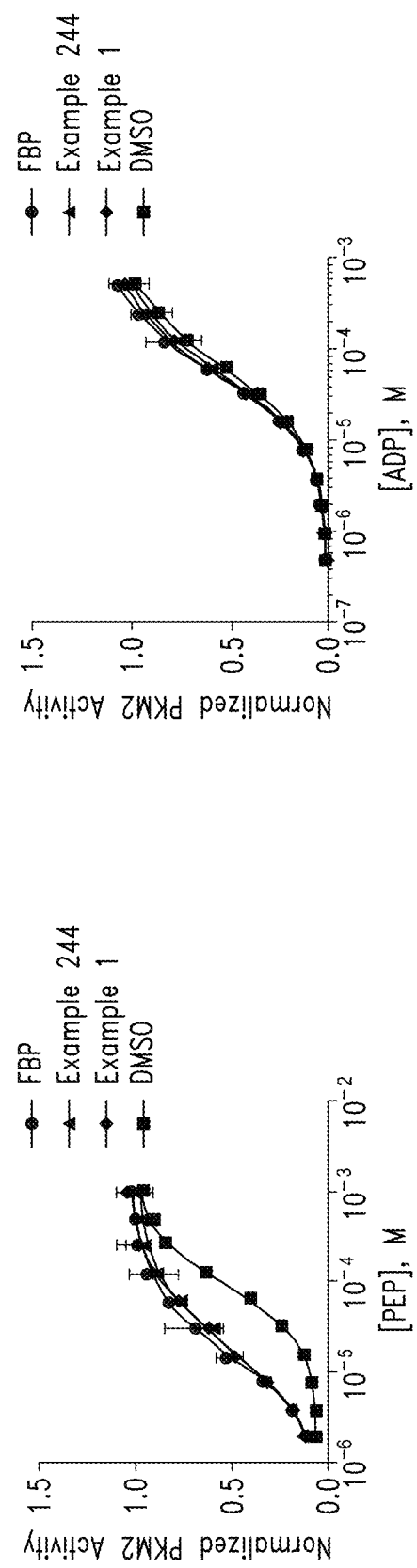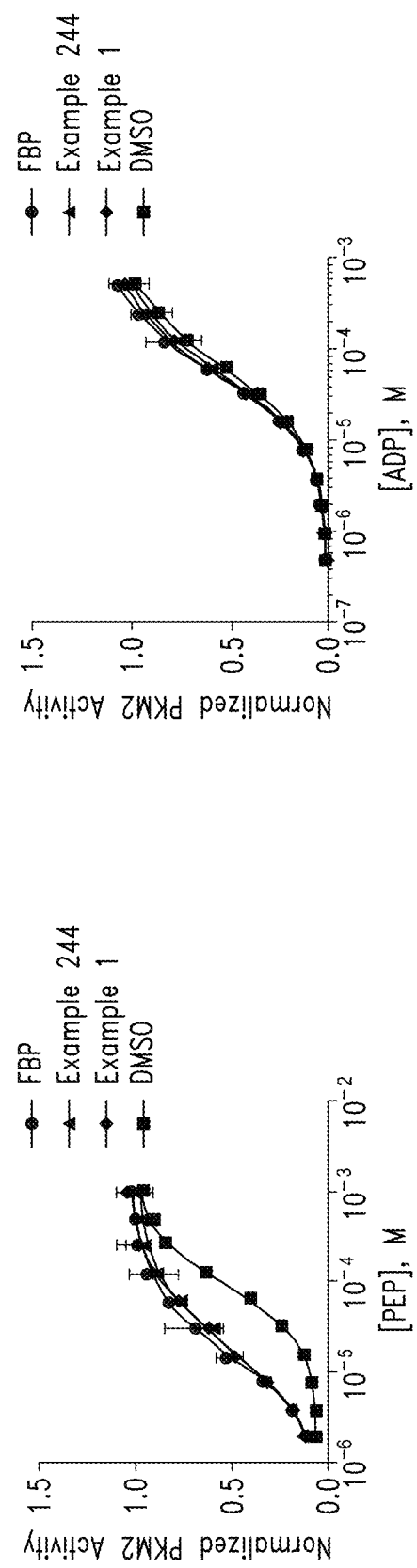

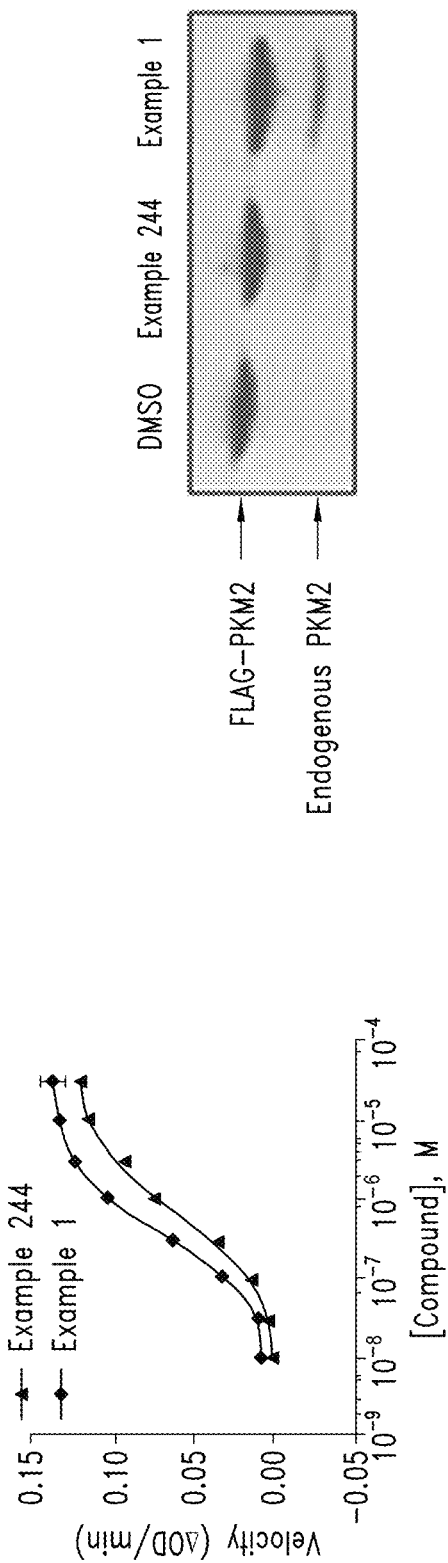
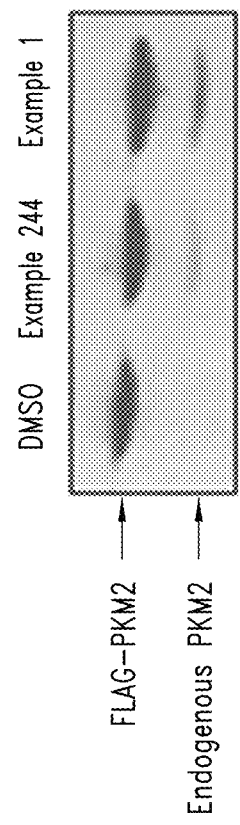
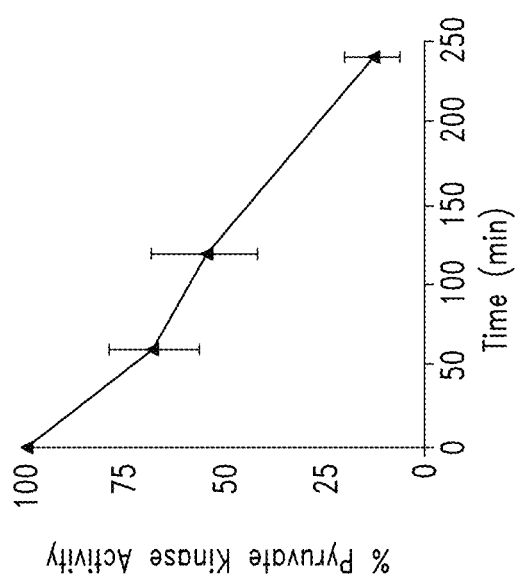
FIG. 3A
FIG. 3B
FIG. 3C

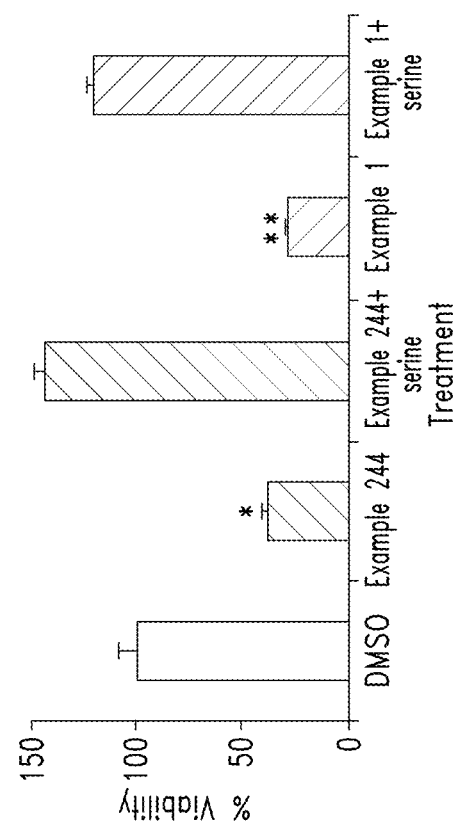
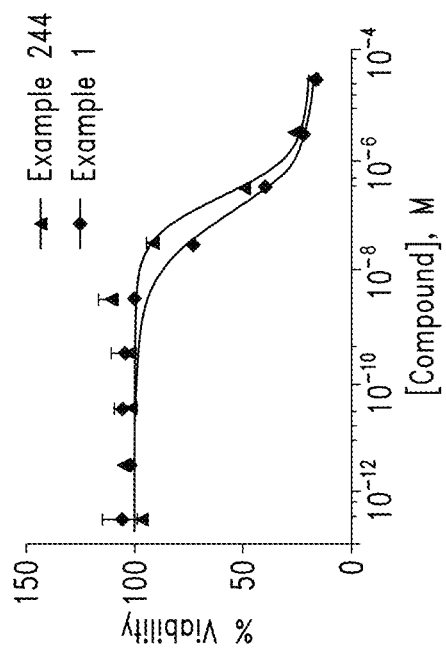
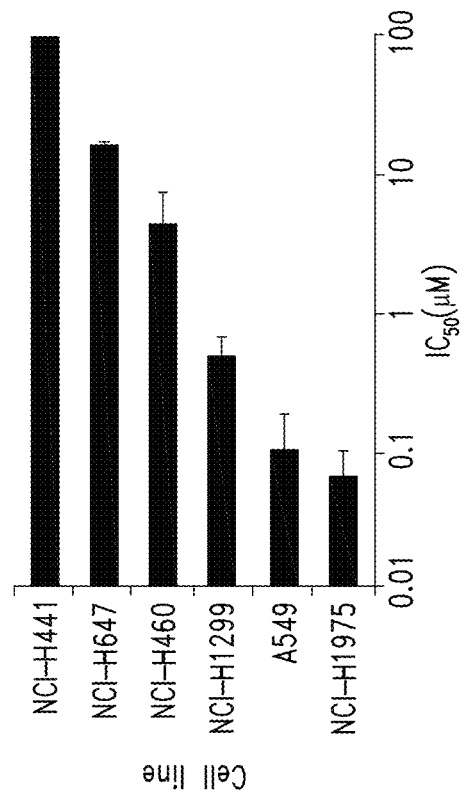
FIG. 4A
FIG. 4B
FIG. 4C

PKM2 MODULATORS AND METHODS FOR THEIR USE

BACKGROUND OF THE INVENTION

Field of the Invention

The present invention is generally directed to novel PKM2 modulators and use of the same for treatment of various cancers.

Description of the Related Art

Proliferation of cancer cells requires the accumulation of sufficient biosynthetic building blocks (i.e., biomass) to replicate each nucleic acid, protein and lipid in the cell. As a tumor grows, the need for nutrients and oxygen can exceed the capacity of poorly vascularized blood vessels. Faced with such challenges, cancer cells must be able to adjust metabolic pathways.

Glucose provides cancer cells with building blocks in the form of glycolytic pathway intermediates (Mazurek S., *Int. J. Biochem. Cell. Biol.* 43(7):969-80 (2010); Vander Heiden M. G., Cantley L. C., Thompson C. B., *Science* 324(5930): 1029-33 (2009)). The main enzyme regulating flux through the glycolitic pathway in cancer cells, and thus the level of available intermediates, is the M2 splice form of pyruvate kinase (PKM2), which controls the rate-limiting final step in glycolysis. PKM2 is allosterically regulated by fructose-1, 6-bisphosphate (FBP), an upstream glycolytic intermediate that binds to and converts PKM2 from a less active dimeric form with low affinity for its substrate, phosphoenolpyruvate (PEP), to an active tetrameric form with high PEP affinity (Ashizawa K., Willingham M. C., Liang C. M., Cheng S. Y., *J. Biol. Chem.* 266(25):16842-46 (1991); Mazurek S., Boschek C. B., Hugo F., Eigenbrodt E., *Semin. Cancer Biol.* 15(4):300-08 (2005)). When glucose is abundant, FBP levels increase and PKM2 is activated, leading to high glycolytic flux. When glucose is limiting, FBP levels decrease and PKM2 is inactivated, allowing upstream glycolytic intermediates to accumulate and be diverted into biosynthetic pathways (Mazurek S., Michel A., Eigenbrodt E., *J. Biol. Chem.* 272(8):4941-52 (1997)).

PKM2 is upregulated in cancer cells (Altenberg B., Greulich K. O., *Genomics* 84(6): 1014-20 (2004)), and has been shown to increase tumorigenicity compared to the alternatively spliced and constitutively active PKM1 isoform (Christofk H. R., Vander Heiden M. G., Harris M. H., et al., *Nature* 452(7184):230-33 (2008); Goldberg M. S., Sharp P. A., *J. Exp. Med.* 209(2):217-24 (2012)). Specific RNAi knockdown of PKM2 has also been shown to regress established xenograft tumors (Goldberg M. S., Sharp P. A., *J. Exp. Med.* 209(2):217-24 (2012)). These findings indicate that control of glycolytic flux through PKM2 activation/inactivation is important for tumor growth.

PKM2 has recently been shown to have a critical function in regulating serine biosynthesis. Serine is synthesized de novo from glycolytic intermediate 3-phosphoglycerate, and serine itself is used in the synthesis of nucleotides, proteins, lipids, and glutathione (Locasale J. W., Cantley L. C., *Cell Cycle* 10(22):3812-13 (2011)). When serine is absent from the growth media, PKM2 expressing cells reduce glycolytic flux (presumably through PKM2 inactivation) and accumulate glycolytic intermediates such as 3-phosphoglycerate. This allows PKM2 expressing cells to proliferate in serine-depleted media to a significantly greater degree than cells expressing PKM1 (Ye J., Mancuso A., Tong X., et al. *Proc. Nat'l Acad. Sci. U.S.A.* 109(18):6904-09 (2012)). Serine, like FBP, is an allosteric activator of PKM2 (Eigenbrodt E., Leib S., Kramer W., Friis R. R., Schoner W., *Biomed. Biochem. Acta.* 42(11-12):S278-82 (1983)). It is thus likely that when cellular serine levels are sufficiently high, PKM2 is converted to the active tetrameric form, restoring glycolytic flux to lactate.

Cancer cells inactivate PKM2 through multiple mechanisms, including oncoprotein binding (Kosugi M., Ahmad R., Alam M., Uchida Y., Kufe D., *PLoS One* 6(11):e28234 (2011); Zwerschke W., Mazurek S., Massimi P., Banks L., Eigenbrodt E., Jansen-Durr P., *Proc. Nat'l Acad. Sci. U.S.A.* 96(4):1291-96 (1999)), tyrosine phosphorylation (Hitosugi T., Kang S., Vander Heiden M. G., et al., *Sci. Signal* 2(97):ra73 (2009); Presek P., Glossmann H., Eigenbrodt E., et al., *Cancer Res.* 40(5): 1733-41 (1980); Presek P., Reinacher M., Eigenbrodt E., *FEBS Lett.* 242(1):194-98 (1988)), lysine acetylation (Lv L., Li D., Zhao D., et al., *Mol. Cell* 42(6):719-30 (2011)), cysteine oxidation (Anastasiou D., Poulogiannis G., Asara J. M., et al., *Science* 334(6060): 1278-83 (2011)), and prolyl hydroxylation (Chen N., Rinner O., Czernik D., et al., *Cell Res.* 21(6):983-86 (2011)). In each case, decreased PKM2 activity correlates with increased tumorigenicity. It was recently shown that PKM2 mutations that inhibit tetramerization also increase tumorigenicity (Gao X., Wang H., Yang J. J., Liu X., Liu Z. R., *Mol. Cell* 45(5):598-609 (2012)). In light of such evidence, efforts have focused on the discovery and development of small molecule PKM2 activators (Boxer M. B., Jiang J. K., Vander Heiden M. G., et al., *J. Med. Chem.* 53(3):1048-55 (2010); Jiang J. K., Boxer M. B., Vander Heiden M. G., et al., *Bioorg. Med. Chem. Lett.* 20(11):3387-93 (2010); Walsh M. J., Brimacombe K. R., Veith H., et al., *Bioorg. Med. Chem. Lett.* 21(21):6322-27 (2011)) as a potentially useful anticancer therapy for treatment of sarcoma, brain, colorectal, kidney, head and neck, lung, ovarian, pancreatic and prostate cancers. PKM2 activators can also be used in combination of chemotherapeutic agent(s) to treat the above conditions.

While progress has been made in this field, there remains a need in the art for improved PKM2 modulators (e.g., activators), which are useful for treatment of any number of cancers. The present invention fulfills this need and provides further related advantages.

BRIEF SUMMARY OF THE INVENTION

In brief, the present invention is directed to compounds having activity as PKM2 modulators, including stereoisomers, tautomers pharmaceutically acceptable salts and prodrugs thereof, and the use of such compounds for treatment of various cancers. In certain embodiments, the compounds are activators of PKM2.

In one embodiment, compounds having the following structure (I) are provided:

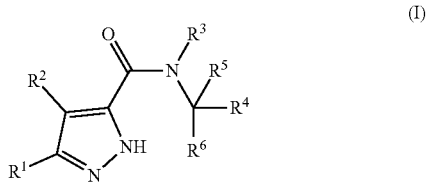

or a stereoisomer, pharmaceutically acceptable salt, tautomer or prodrug thereof, wherein $R^1$, $R^2$, $R^3$, $R^4$, $R^5$ and $R^6$ are as defined herein.

In another embodiment, a pharmaceutical composition is provided comprising a compound having structure (I), or a stereoisomer, pharmaceutically acceptable salt, tautomer or prodrug thereof, and a pharmaceutically acceptable carrier, diluent or excipient.

In another embodiment, a method for modulating PKM2 in a mammal in need thereof is provided, the method comprising administering to the mammal an effective amount of a compound having structure (I), or a stereoisomer, pharmaceutically acceptable salt, tautomer or prodrug thereof. In some embodiments, modulation of PKM2 comprises activating PKM2. In some embodiments the method is for treatment of cancer.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIG. 1A depicts representative compounds.

FIG. 1B is a graph showing PKM2 activity of representative compounds.

FIG. 1C presents normalized PKM2 dose response curves for PEP.

FIG. 1D is a graph of normalized PKM2 dose response curves for ADP.

FIG. 3A provides pyruvate kinase activity in cells treated with a representative compound.

FIG. 3B is a gel showing tetramer formation induced by representative compounds.

FIG. 3C shows pyruvate kinase activity data in cells as a function of time after the representative PKM2 activator has been removed by washing.

FIG. 4A demonstrates viability of lung adenocarcinoma cells treated with representative compounds in the absence of serine.

FIG. 4B is a bar graph depicting rescue of PKM2 activator viability.

FIG. 4C depicts viability of a representative compound against a subset of lung carcinoma cell lines in the absence of serine.

DETAILED DESCRIPTION OF THE INVENTION

Figure 2:
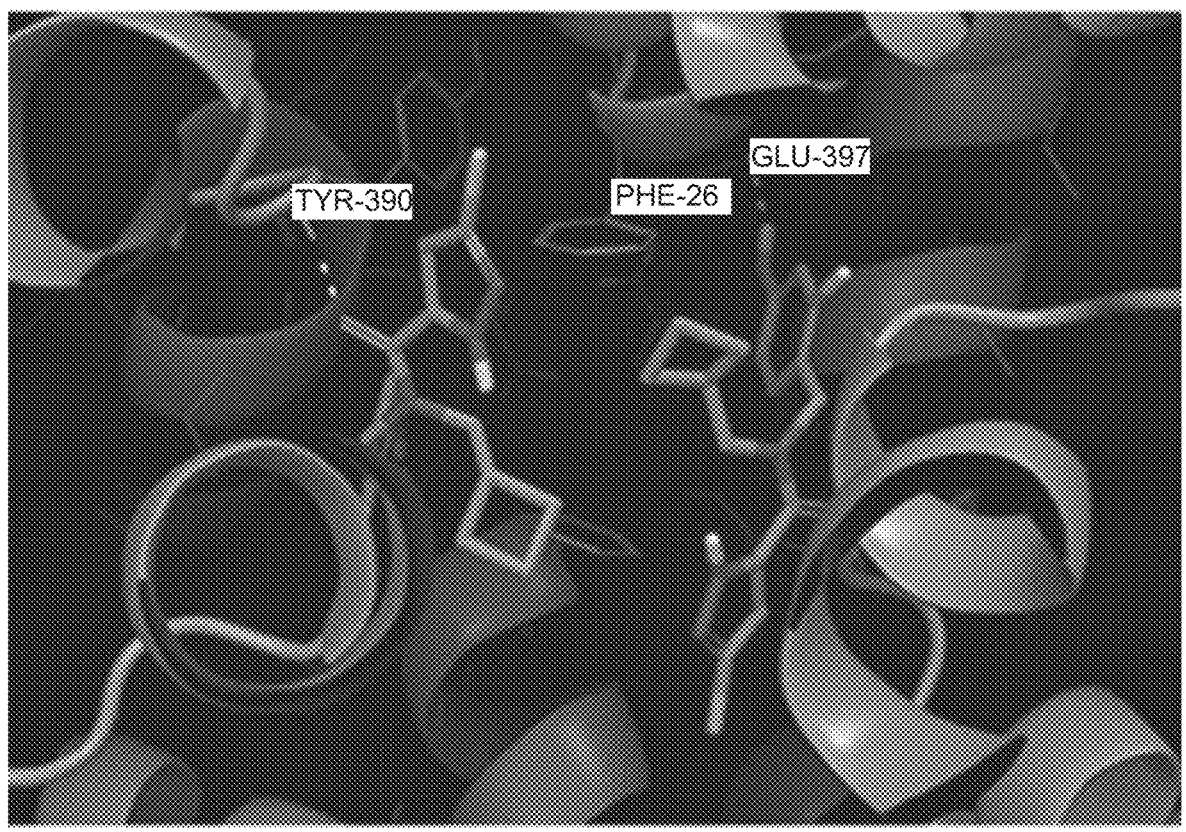
FIG. 2 illustrates a co-crystal structure of PKM2 in complex with a representative compound.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the following terms have the following meanings:

"Amino" refers to the —$NH_2$ radical.

"Cyano" or "nitrile" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkoxyalkyl" refers to a radical of the formula —$R_bOR_a$ where $R_a$ is an alkyl radical as defined above containing one to twelve carbon atoms and $R_b$ is an alkylene radical as defined above. Unless stated otherwise specifically in the specification, an alkoxyalkyl group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Alkylaminoalkyl" refers to a radical of the formula —$R_bNHR_a$ or —$NR_aR_a$ where each $R_a$ is, independently, an alkyl radical as defined above containing one to twelve carbon atoms and $R_b$ is an alkylene radical as defined above. Unless stated otherwise specifically in the specification, an alkylaminoalky group may be optionally substituted.

"Alkylsulfone" refers to a radical of the formula —$S(O)_2R_a$ where $R_a$ is an alkyl radical as defined above containing one to twelve carbon atoms and $R_b$ is an alkylene radical as defined above. Unless stated otherwise specifically in the specification, an alkylsulfone group may be optionally substituted.

"Hydroxylalkyl" refers an alkyl radical as defined above containing one to twelve carbon atoms which has been substituted by one or more hydroxyl groups. Unless stated otherwise specifically in the specification, hydroxylalkyl group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1] heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkoxyalkyl" refers to a radical of the formula —$R_bOR_a$ where $R_a$ is a cycloalkyl radical as defined above and $R_b$ is an alkyl radical as defined above containing one to twelve carbon atoms. Unless stated otherwise specifically in the specification, an alkoxyalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group may be optionally substituted.

"Amino acid ester" refers to an amino acid having an ester group in place of the acid group. Unless stated otherwise specifically in the specification, an amino acid ester group may be optionally substituted.

The term "substituted" used herein means any of the above groups (i.e., alkyl, alkylene, alkoxy, alkoxyalkyl, alkylamino, alkylaminoalkyl, alkylsulfone, hydroxyalkyl, thioalkyl, aryl, aralkyl, cycloalkyl, cycloalkylalkyl, cycloalkoxyalkyl, haloalkyl, heterocyclyl, N-heterocyclyl, heterocyclylalkyl, heteroaryl, N-heteroaryl, heteroarylalkyl and/or amino acid ester) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_g R_h$, —$NR_g C(=O)R_h$, —$NR_g C(=O)NR_g R_h$, —$NR_g C(=O)OR_h$, —$NR_g SO_2 R_h$, —$OC(=O)NR_g R_h$, —$OR_g$, —$SR_g$, —$SOR_g$, —$SO_2 R_g$, —$OSO_2 R_g$, —$SO_2 OR_g$, =$NSO_2 R_g$, and —$SO_2 NR_g R_h$. "Substituted also means any of the above groups in which one or more hydrogen atoms are replaced with —$C(=O)R_g$, —$C(=O)OR_g$, —$C(=O)NR_g R_h$, —$CH_2 SO_2 R_g$, —$CH_2 SO_2 NR_g R_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, alkylamino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of cancer in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts or tautomers may contain one or more asymmetric centers and may thus give rise to enantiomers, diastereomers, and other stereoisomeric forms that may be defined, in terms of absolute stereochemistry, as (R)- or (S)- or, as (D)- or (L) for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule, for example, the conversion of a ketone to an enol via a proton shift. The present invention includes tautomers of any said compounds.

A "chemotherapeutic agent" is a chemical which eradicates, stops or slows the growth of cancer cells.

I. Compounds

As noted above, in one embodiment of the present invention, compounds having activity as PKM2 modulators (e.g., activators) are provided, the compounds having the following structure (I):

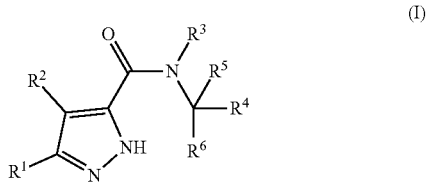

or a stereoisomer, pharmaceutically acceptable salt, tautomer or prodrug thereof, wherein:

$R^1$ is cycloalkyl, haloalkyl, halo, nitrile or amino;

$R^2$ is H or halo;

$R^3$ is alkyl, alkoxyalkyl, cycloalkoxyalkyl, cycloalkyl, cycloalkylalkyl, heterocyclyl, heterocyclylalkyl, heteroaryl, heteroarylalkyl or aralkyl $R^4$ is aryl or heteroaryl $R^5$ and $R^6$ are each independently H or alkyl.

In some embodiments, $R^4$ is aryl. In other embodiments, $R^4$ is heteroaryl.

In some more specific embodiments, $R^4$ has one of the following structures (A), (B) or (C):

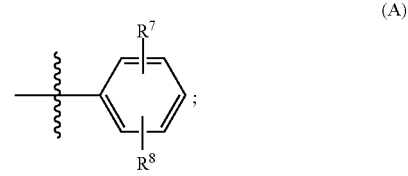

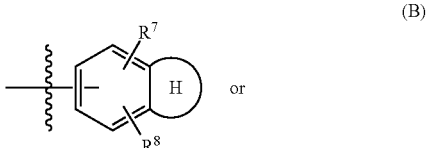

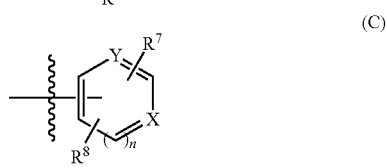

wherein:
H represents a 5 or 6-membered heterocyclic ring;
X is O, N, N$^+$—O$^-$ or S;
Y is CH or N;
$R^7$ and $R^8$ are each independently H, alkyl, alkoxy, halo, hydroxyl, hydroxylalkyl, amino, aminoalkyl, alkylaminoalkyl, nitrile, nitro, —O(CH$_2$)$_m$P(=O)(OH)$_2$, amino acid ester; and
m and n are each independently 0 or 1,
wherein all valences are satisfied.

In some embodiments of the foregoing, $R^4$ has structure (A). For example, in some embodiments, $R^7$ and $R^8$ are each independently H, halo or amino.

In other embodiments, $R^4$ has the following structure:

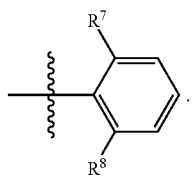

For example, in some embodiments $R^7$ is H or amino, and in other embodiments $R^8$ is chloro or fluoro.

In some other more specific embodiments, $R^4$ has one of the following structures:

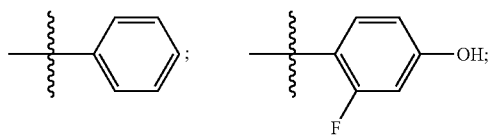

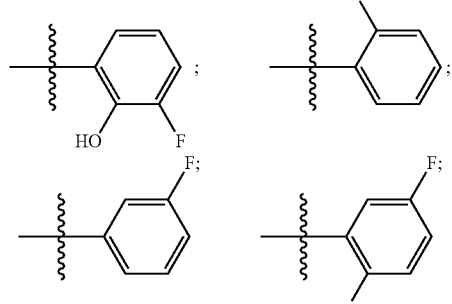

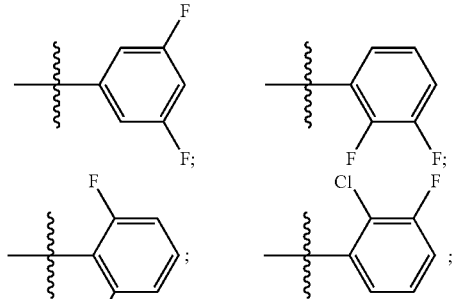

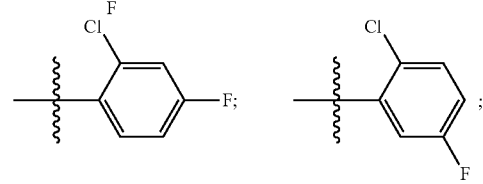

-continued

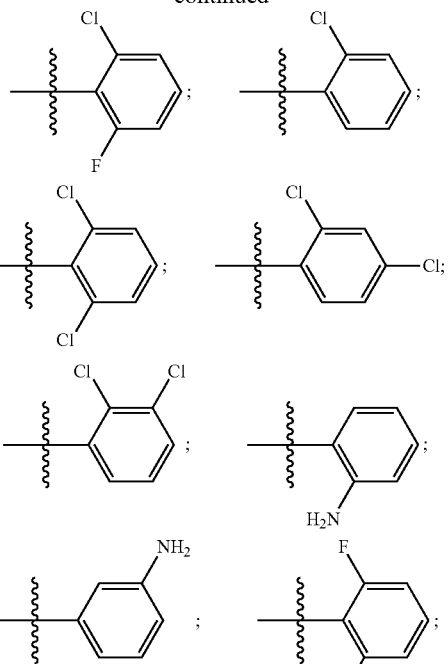

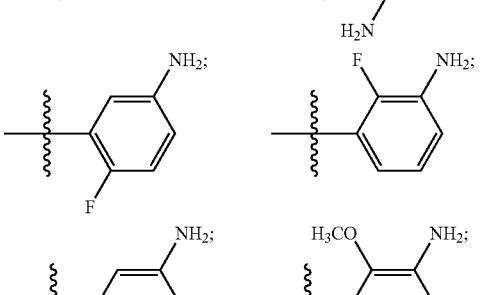

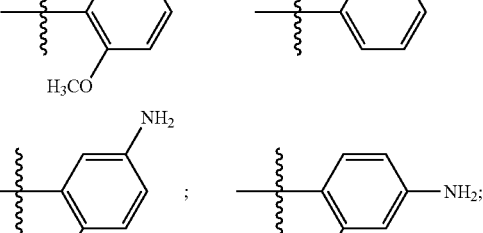

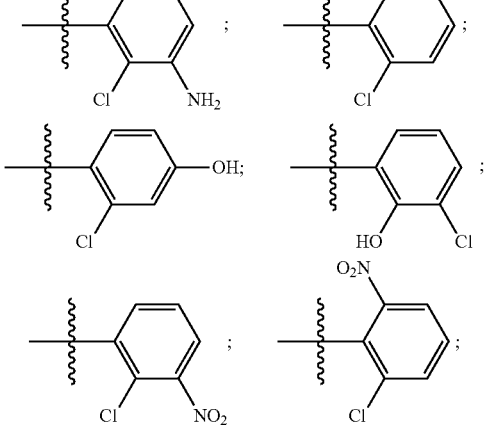

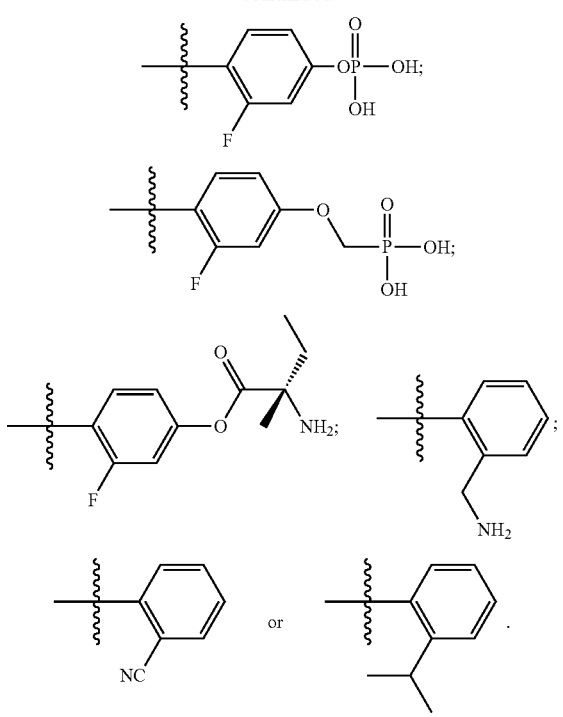

In other embodiments, R⁴ has structure (B). For example, R⁴ has one of the following structures in certain embodiments:

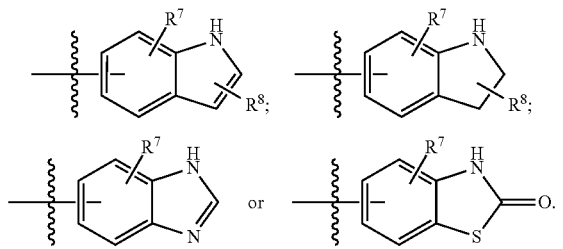

In some of the above embodiments, $R^7$ and $R^8$ are each H, and in other embodiments $R^7$ or $R^8$ is halo or alkylaminoalkyl.

In still other embodiments, R⁴ has one of the following structures:

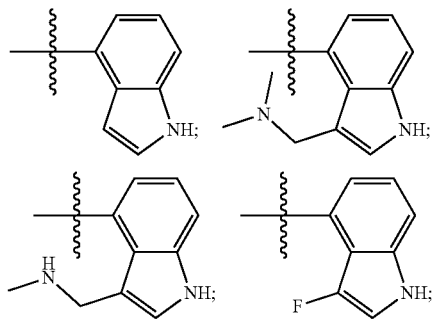

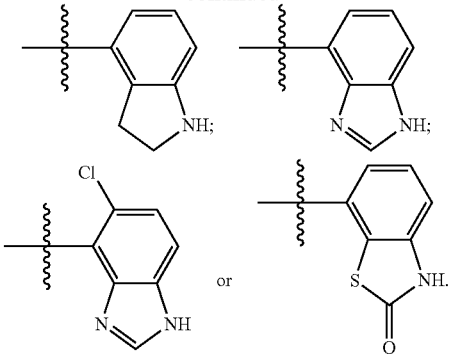

In yet other exemplary embodiments, R⁴ has structure (C). For example, in some embodiments R⁴ has one of the following structures:

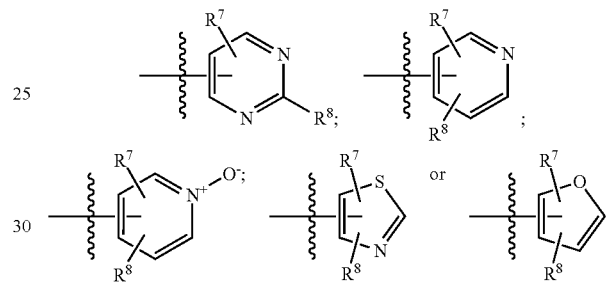

In some embodiments of the foregoing, $R^7$ and $R^8$ are each H. In other embodiments, $R^7$ or $R^8$ is halo, amino or hydroxylalkyl.

In some other specific examples, R⁴ has one of the following structures:

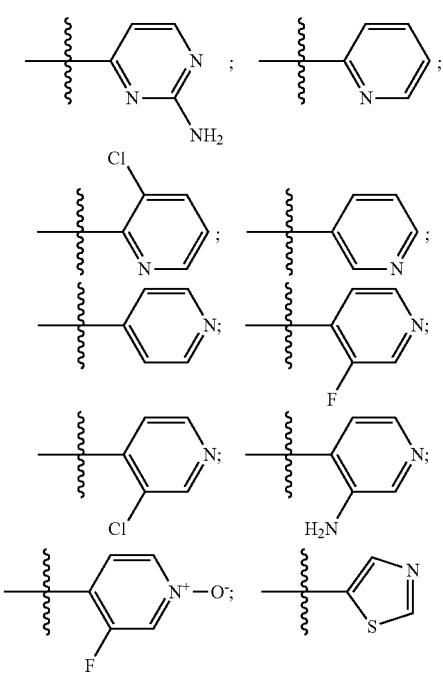

-continued

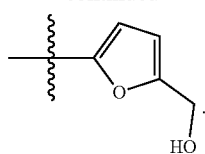

In still other embodiments, R³ has one of the following structures (D), (E) or (F):

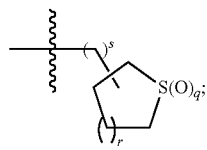
(D)

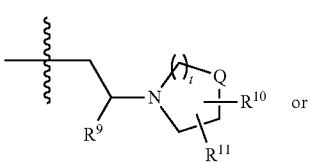
(E)

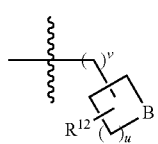
(F)

wherein:

Q is CH₂, O, NR¹³, CF₂, or S(O)$_w$;

B is CH₂, O, NR¹⁴, C(=O) or

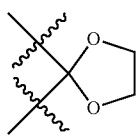 [SMILES: *C1(*)OCCO1]

R⁹, R¹¹ and R¹³ are each independently H or alkyl;

R¹⁰ is H, hydroxyl, halo, alkoxy or alkyl;

R¹² is H, amino or alkoxy;

R¹⁴ is H, alkyl or alkyl sulfone;

q, v and w are each independently 0, 1 or 2;

r and s are each independently 1 or 2;

t is 1, 2 or 3; and u is 0, 1, 2 or 3.

In certain embodiments, R³ has structure (D).

In some embodiments, s is 1. In other embodiments, s is 2. In still other embodiments, r is 1. In more other embodiments, r is 2. In some more embodiments, q is 0. In yet other embodiments, q is 1. In other embodiments, q is 2.

In some more specific examples, R³ has one of the following structures:

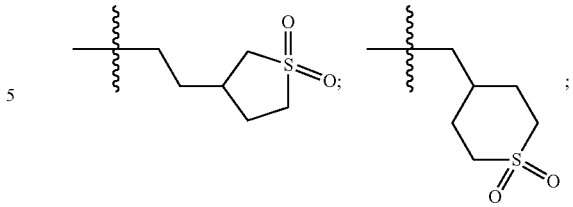

In some other embodiments, R³ has structure (E).

In some embodiments, Q is CH₂. In other embodiments, Q is SO₂. In more embodiments, Q is O. In yet other embodiments, Q is CHF₂. In still other embodiments, Q is NR¹³.

In some of the foregoing embodiments, R¹³ is methyl or ethyl.

In other of the foregoing embodiments, R¹⁰ and R¹¹ are each H. In yet other embodiments, R¹⁰ is methyl, fluoro, hydroxyl or methoxy.

In still other specific embodiments, R³ has one of the following structures:

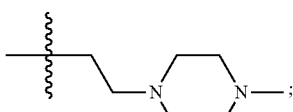

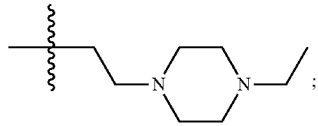

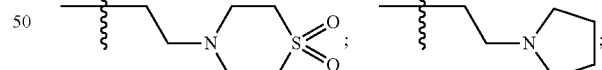

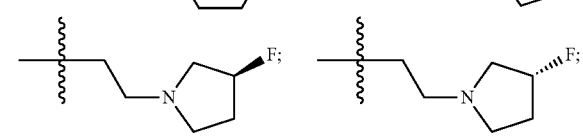

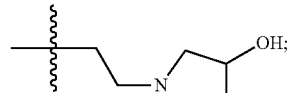

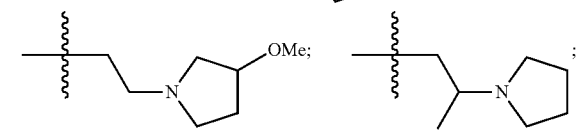

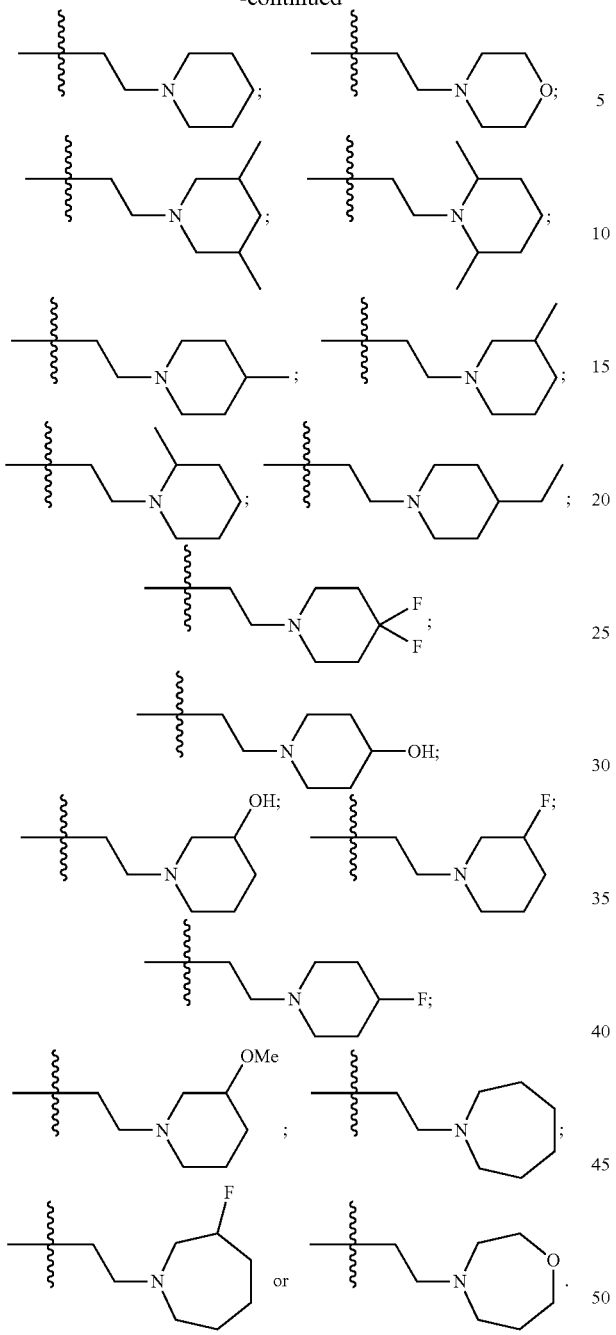
In still other specific embodiments, R³ has structure (F). In some of these embodiments, B is CH₂. In other embodiments, R¹² is H. In some embodiments, R¹² is alkoxy. In still other embodiments, R¹² is methoxy, ethoxy or isopropoxy.
In some other exemplary embodiments, R³ has one of the following structures:
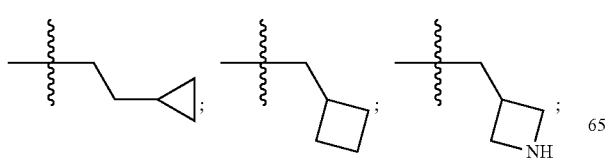
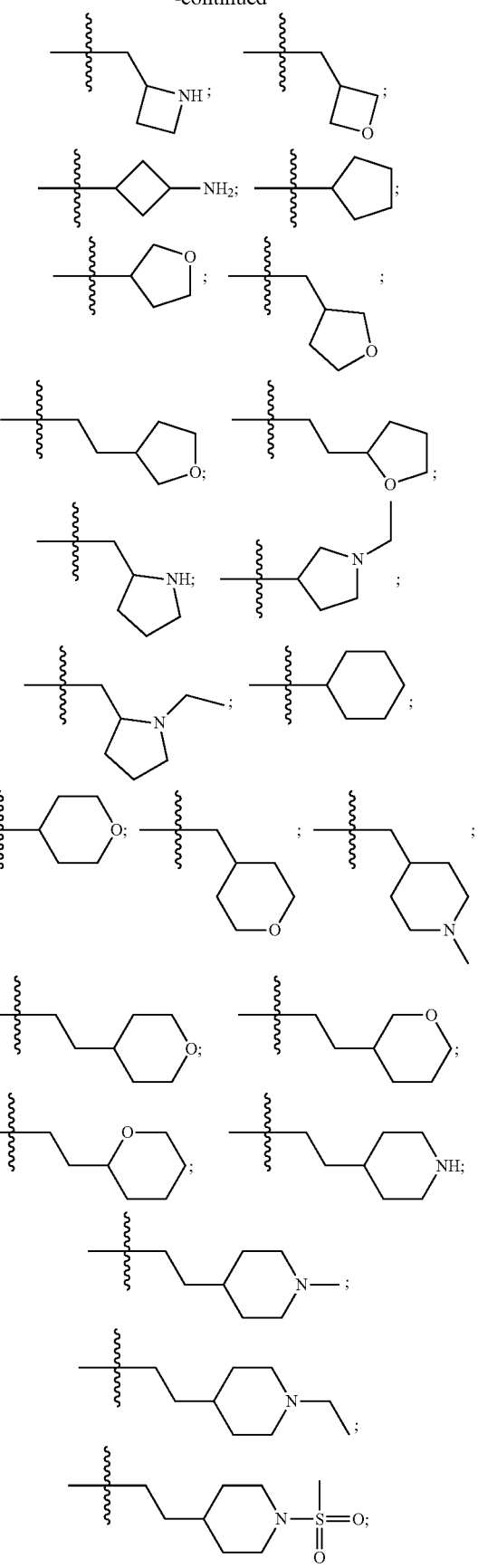

-continued

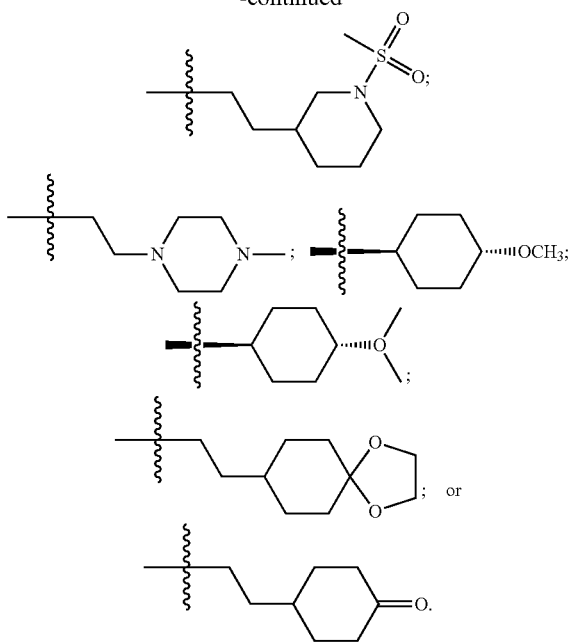

In still other embodiments, R³ is alkoxyalkyl, and in other embodiments R³ is alkyl, for example, in some embodiments the alkyl is substituted with one or more substituents selected from hydroxyl, halo, amino, alkylamino, alkoxy and alkylsulfone. In other embodiments, R³ is heteroaryl. In yet other embodiments, R³ is cycloalkoxyalkyl. In more embodiments, R³ is aralkyl.

In other embodiments, R⁵ and R⁶ are each H.

In some of any of the preceding embodiments, R² is H, and in other embodiments R² is F.

In other embodiments of any of the foregoing embodiments, R¹ is CF₃. In other embodiments, R¹ is Cl. In still other examples, R¹ is Br. In some embodiments, R¹ is cyclopropyl. In other embodiments, R¹ is nitrile. In yet other embodiments, R¹ is amino.

In some embodiments of the compound of structure (I) the compound has the following structure (Ia'):

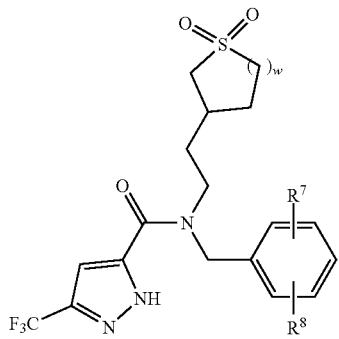

(Ia')

or a stereoisomer, pharmaceutically acceptable salt, tautomer or prodrug thereof,
wherein:
R⁷ and R⁸ are each independently H, alkyl, alkoxy, halo, hydroxyl, hydroxylalkyl, amino, aminoalkyl, alkylaminoalkyl, nitrile, nitro, —O(CH₂)ₘP(=O)(OH)₂, amino acid ester; and
w is 1 or 2.

For example, in some embodiments of the compound of structure (I) the compound has the following structure (Ia):

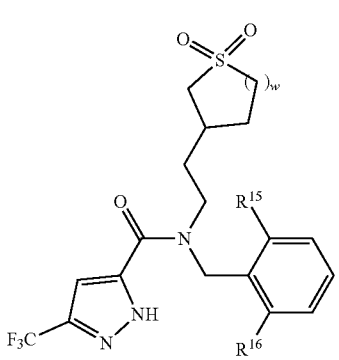

(Ia)

or a stereoisomer, pharmaceutically acceptable salt, tautomer or prodrug thereof,
wherein:
R¹⁵ is halo;
R¹⁶ is H or NH₂; and
w is 1 or 2.

In some embodiments of structure (Ia), R¹⁵ is chloro. In other embodiments, R¹⁵ is fluoro.

In some other embodiments of structure (Ia), R¹⁶ is H. In other embodiments, R¹⁶ is NH₂.

In still other embodiments of structure (Ia), w is 1. In other embodiments, w is 2.

In other specific embodiments of structure (I), the compound has the following structure (Ib'):

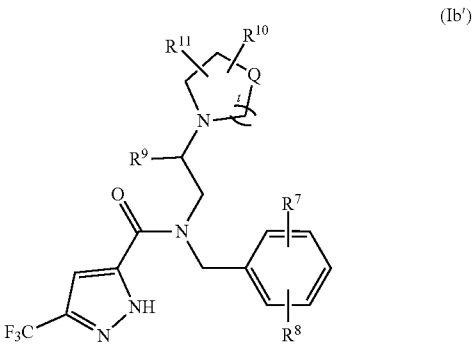

(Ib')

or a stereoisomer, pharmaceutically acceptable salt, tautomer or prodrug thereof,
wherein:
Q is CH₂, O, NR¹³, CF₂, or S(O)ᵥᵥ;
R⁷ and R⁸ are each independently H, alkyl, alkoxy, halo, hydroxyl, hydroxylalkyl, amino, aminoalkyl, alkylaminoalkyl, nitrile, nitro, —O(CH₂)ₘP(=O)(OH)₂, amino acid ester;
R⁹, R¹¹ and R¹³ are each independently H or alkyl;
R¹⁰ is H, hydroxyl, halo, alkoxy or alkyl;
w is 0, 1 or 2; and
t is 1, 2 or 3.

For example, in other specific embodiments of structure (I), the compound has the following structure (Ib):

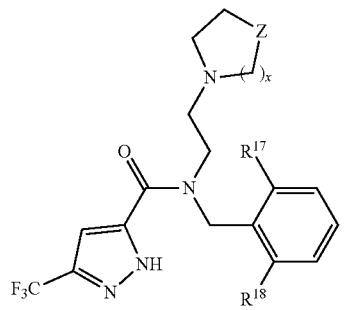

(Ib)

or a stereoisomer, pharmaceutically acceptable salt, tautomer or prodrug thereof, wherein:

$R^{17}$ is halo;

$R^{18}$ is H or $NH_2$;

Z is $CH_2$, O, NH, $NR^{19}$, $CHR^{20}$ or $CF_2$;

$R^{19}$ is alkyl;

$R^{20}$ is alkoxy, hydroxyl or halo; and x is 0, 1, 2 or 3.

For example, in some embodiments, $R^{17}$ is chloro. In other embodiments, $R^{18}$ is $NH_2$.

In still other embodiments of structure (Ib), Z is CHOH. In other embodiments, Z is $CHOCH_3$. In more embodiments, Z is CHF, and in other embodiments Z is O.

In more embodiments, x is 1, and in other embodiments x is 2.

In other exemplary embodiments of the compound of structure (I), the compound has the following structure (Ic'):

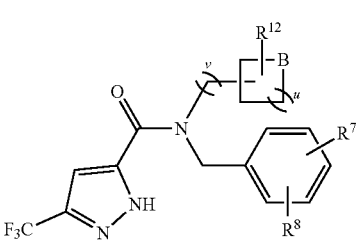

(Ic')

or a stereoisomer, pharmaceutically acceptable salt, tautomer or prodrug thereof, wherein:

B is $CH_2$, O, $NR^{14}$, C(=O) or

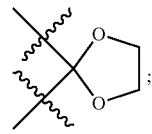

;

$R^7$ and $R^8$ are each independently H, alkyl, alkoxy, halo, hydroxyl, hydroxylalkyl, amino, aminoalkyl, alkylaminoalkyl, nitrile, nitro, —$O(CH_2)_mP(=O)(OH)_2$, amino acid ester;

$R^{12}$ is H, amino or alkoxy;

v is 0, 1 or 2; and u is 0, 1, 2 or 3.

For example, in other exemplary embodiments of the compound of structure (I), the compound has the following structure (Ic):

(Ic)

or a stereoisomer, pharmaceutically acceptable salt, tautomer or prodrug thereof, wherein:

$R^{21}$ and $R^{22}$ are each independently H or halo;

$R^{23}$ is H or alkyl; and y is 1 or 2.

In some embodiments, $R^{21}$ is chloro. In other embodiments, $R^{21}$ is F.

In still other embodiments, $R^{22}$ is H. In other embodiments, $R^{23}$ is methyl, ethyl or isopropyl.

In certain exemplary embodiments, y is 1. In other embodiments, y is 2.

In other certain embodiments, the compound is selected from a compound in Table 1.

TABLE 1

Exemplary Compounds

| EX | Structure | NMR | ES-MS (M⁺ + 1) | PKM₂ AC₅₀ (nM)/ Max. Resp.* (%) | Note† |
|----|-----------|-----|----------------|----------------------------------|-------|
| 1 | 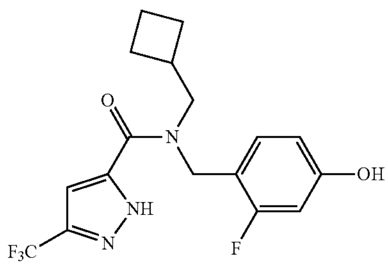 | ¹H-NMR (CDCl₃/400 MHz): 7.10 (m, 1H), 6.80 (m, 1H), 6.59 (d, J = 8.4 Hz, 1H), 6.52 (d, J = 12.0 Hz, 1H), 4.69 (s, 2H), 3.50 (s, 2H), 2.65 (m, 1H), 2.00-1.58 (m, 6H). | 372.1 | 11/100 | — |
| 2 | 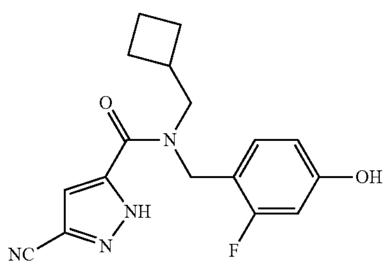 [SMILES: N#Cc1cc(C(=O)N(Cc2ccc(O)cc2F)CC2CCC2)[nH]n1] | ¹H-NMR (CD₃OD/ 400 MHz): 7.31 (m, 1H), 7.00 (m, 3H), 4.80 (m, 2H), 3.56 (m, 2H), 2.66 (m, 1H), 2.00-1.59 (m, 6H). | 410.9 | 3788/ 39 | — |
| 3 | 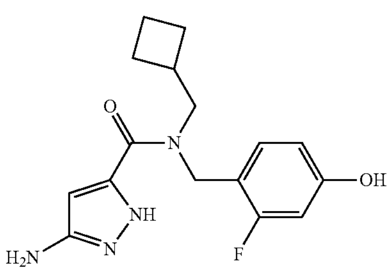 [SMILES: Nc1cc(C(=O)N(Cc2ccc(O)cc2F)CC2CCC2)[nH]n1] | ¹H-NMR (CD₃OD/ 400 MHz): 7.08 (m, 1H), 6.54 (m, 2H), 5.70 (m, 1H), 4.63 (m, 2H), 3.64 (m, 1H), 3.56 (m, 1H), 2.64 (m, 1H), 2.01-1.58 (m, 6H). | 319.0 | 43850/ 45 | — |
| 4 | 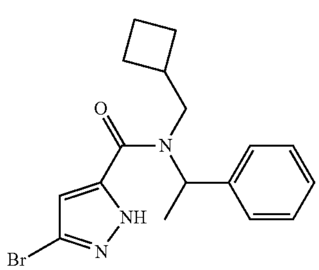 [SMILES: CC(c1ccccc1)N(CC1CCC1)C(=O)c1cc(Br)n[nH]1] | ¹H-NMR (CD₃OD/ 400 MHz): 7.34 (m, 5H), 6.60 (s, 1H), 5.60 (m, 1H), 4.80 (m, 1H), 3.40 (m, 2H), 2.40 (m, 1H), 2.01-1.58 (m, 6H). | 361.9 | 1481/ 52 | — |
| 5 | 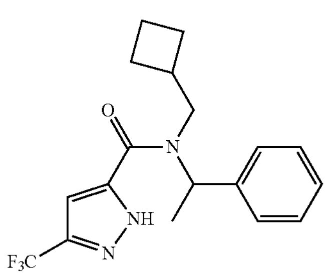 [SMILES: CC(c1ccccc1)N(CC1CCC1)C(=O)c1cc(C(F)(F)F)n[nH]1] | ¹H-NMR (CD₃OD/ 400 MHz): 7.40 (m, 5H), 6.80 (s, 1H), 5.48 (m, 2H), 3.50 (m, 2H), 2.34 (m, 1H), 2.01-1.58 (m, 6H). | 352.0 | 4651/ 106 | — |

TABLE 1-continued

Exemplary Compounds

| EX | Structure | NMR | ES-MS (M+ + 1) | PKM$_2$ AC$_{50}$ (nM)/ Max. Resp.* (%) | Note† |
|---|---|---|---|---|---|
| 6 | 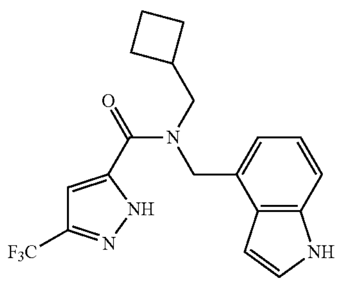 [SMILES: O=C(c1cc(C(F)(F)F)n[nH]1)N(Cc1cccc2[nH]ccc12)CC1CCC1] | $^1$H-NMR (CDCl$_3$/400 MHz; stable amide rotamers were observed by NMR): 7.35 (m, 1H), 7.24 (br, 1H), 7.10 (m, 1H), 6.97 (m, 0.5H), 6.84 (m, 1H), 6.60 (m, 0.5H), 6.50 (m, 0.5H), 6.39 (m, 0.5H), 5.05 (s, 2H), 3.60 (s, 1H), 3.34 (s, 1H), 2.74 (m, 1H), 2.50-1.55 (m, 6H). | 377.0 | 213/ 100 | — |
| 7 | 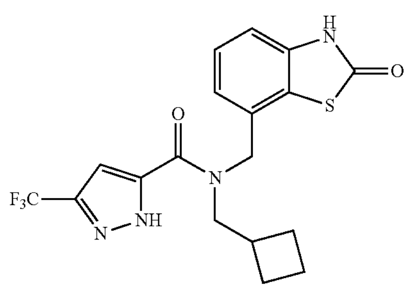 [SMILES: O=C(c1cc(C(F)(F)F)n[nH]1)N(Cc1cccc2[nH]c(=O)sc12)CC1CCC1] | $^1$H-NMR (CD$_3$OD/ 400 MHz): 7.31 (m, 1H), 7.04 (m, 3H), 5.04 (m, 1H), 5.04 (m, 1H), 3.70 (m, 1H), 3.50 (m, 1H), 2.56 (m, 1H), 2.00-1.56 (m, 6H). | 368.0 | 3446/ 87 | — |
| 8 | 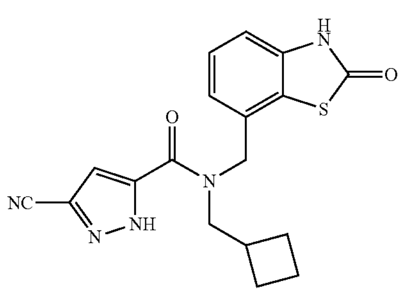 [SMILES: N#Cc1cc(C(=O)N(Cc2cccc3[nH]c(=O)sc23)CC2CCC2)[nH]n1] | $^1$H-NMR (CD$_3$OD/ 400 MHz): 7.05 (m, 2H), 6.54 (m, 2H), 4.68 (m, 2H), 3.67 (m, 1H), 3.46 (m, 1H), 2.67 (m, 1H), 2.01-1.62 (m, 6H). | 328.9 | NA | — |
| 9 | 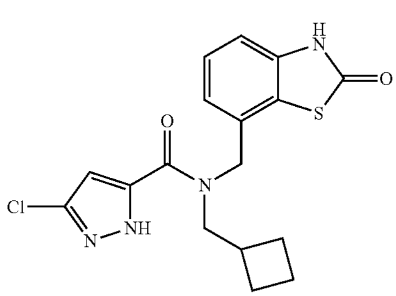 [SMILES: O=C(c1cc(Cl)n[nH]1)N(Cc1cccc2[nH]c(=O)sc12)CC1CCC1] | $^1$H-NMR (CD$_3$OD/400 MHz): 7.30 (m, 1H), 7.10 (m, 2H), 6.50 (m, 1H), 4.77 (m, 2H), 3.53 (m, 2H), 2.66 (m, 1H), 2.00-1.59 (m, 6H). | 377.0 | 15400/ 80 | — |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 10 | 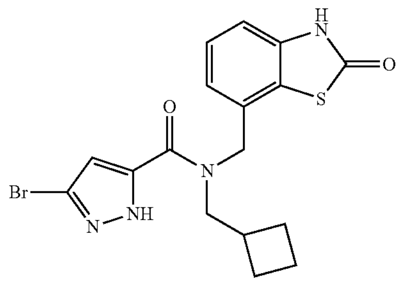 | ¹H-NMR (CD$_3$OD/ 400 MHz): 7.30 (m, 1H), 7.06 (m, 2H), 6.50 (m, 1H), 4.77 (m, 2H), 3.53 (m, 2H), 2.66 (m, 1H), 2.00-1.59 (m, 6H). | 420.9 | 2740/ 127 | — |
| 11 | 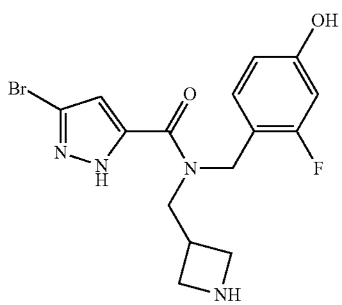 [SMILES: O=C(c1cc(Br)n[nH]1)N(Cc1ccc(O)cc1F)CC1CNC1] | ¹H-NMR (CD$_3$OD/400 MHz): 7.06 (m, 1H), 6.60 (m, 3H), 4.80 (m, 2H), 4.00 (m, 4H), 3.75 (m, 2H), 3.10 (m, 1H). | 382.9 | 10400/ 61 | — |
| 12 | 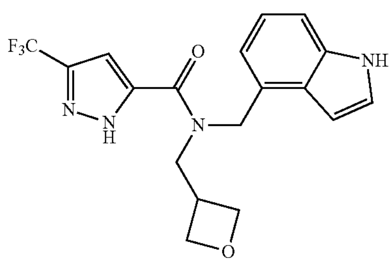 [SMILES: O=C(c1cc(C(F)(F)F)n[nH]1)N(Cc1cccc2[nH]ccc12)CC1COC1] | ¹H-NMR (CD$_3$OD/400 MHz): 7.38 (m, 1H), 7.29 (m, 1H), 7.12 (m, 1H), 6.90 (m, 1H), 6.67 (m, 1H), 6.40 (m, 1H), 5.07 (m, 2H), 4.57 (m, 2H), 4.37 (m, 2H), 4.08 (m, 1H), 3.86 (m, 2H). | 378.9 | 3271/ 101 | — |
| 13 | 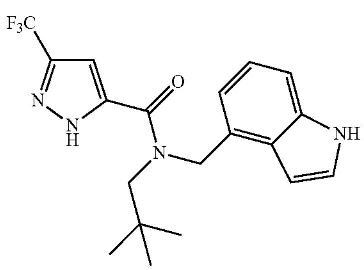 [SMILES: CC(C)(C)CN(Cc1cccc2[nH]ccc12)C(=O)c1cc(C(F)(F)F)n[nH]1] | ¹H-NMR (CD$_3$OD/400 MHz): 7.33 (m, 1H), 7.27 (m, 1H), 7.07 (m, 1H), 6.73 (m, 2H), 6.36 (m, 1H), 6.40 (m, 1H), 5.17 (m, 2H), 3.42 (m, 2H), 1.02 (s, 9H). | 379.0 | 49110/ 33 | — |
| 14 | 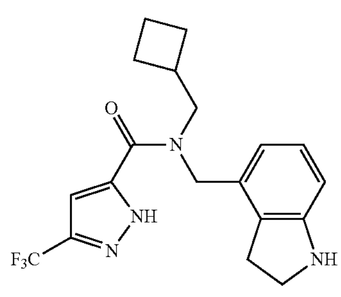 [SMILES: O=C(c1cc(C(F)(F)F)n[nH]1)N(Cc1cccc2c1CCN2)CC1CCC1] | ¹H-NMR (CD$_3$OD/400 MHz): 7.37 (m, 2H), 6.95 (m, 1H), 6.55 (m, 1H), 4.60 (m, 2H), 3.80 (m, 2H), 3.60 (m, 2H), 3.30 (m, 2H), 2.70 (m, 1H), 2.03-1.50 (m, 6H). | 379.0 | 1700/ 81 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 15 | 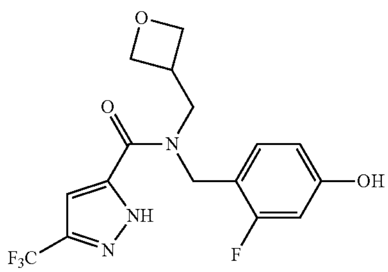 [SMILES: O=C(c1cc(C(F)(F)F)n[nH]1)N(Cc1ccc(O)cc1F)CC1COC1] | ¹H-NMR (CD₃OD/400 MHz): 7.01 (m, 1H), 6.82 (m, 1H), 6.60 (m, 1H), 6.54 (m, 1H), 4.88 (m, 2H), 4.67 (m, 4H), 4.44 (m, 2H), 3.78 (m, 1H). | 373.9 | 150/ 102 | — |
| 16 | 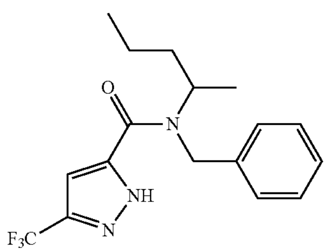 [SMILES: CCCC(C)N(Cc1ccccc1)C(=O)c1cc(C(F)(F)F)n[nH]1] | ¹H-NMR (CD₃OD/400 MHz): 7.32 (m, 5H), 6.80 (m, 1H), 4.78 (m, 2H), 3.77 (m, 1H), 1.29 (m, 4H), 1.20 (m, 3H), 0.89 (m, 3H). | 340.0 | 74820/ 22 | — |
| 17 | 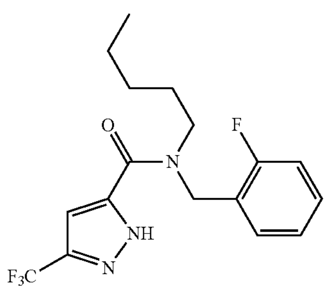 [SMILES: CCCCCN(Cc1ccccc1F)C(=O)c1cc(C(F)(F)F)n[nH]1] | ¹H-NMR (CD₃OD/400 MHz): 7.25 (m, 4H), 6.83 (m, 1H), 4.80 (m, 2H), 3.40 (m, 2H), 1.62 (m, 2H), 1.29 (m, 4H), 0.87 (m, 3H). | 350.7 | 138/83 | — |
| 18 | 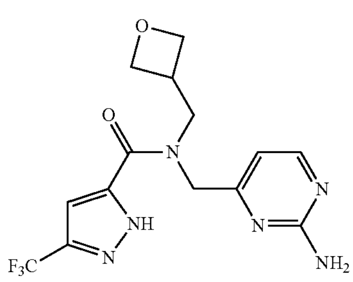 [SMILES: Nc1nccc(CN(CC2COC2)C(=O)c2cc(C(F)(F)F)n[nH]2)n1] | ¹H-NMR (CD₃OD/400 MHz): 8.19 (m, 1H), 6.80 (m, 1H), 6.55 (m, 1H), 4.70 (m, 2H), 4.30 (m, 4H), 3.87 (m, 1H), 3.34 (m, 2H). | 356.9 | NA | — |
| 19 | 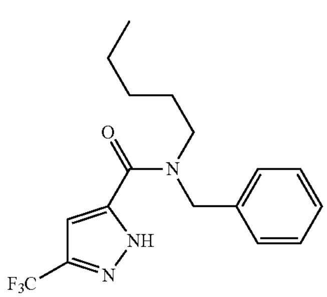 [SMILES: CCCCCN(Cc1ccccc1)C(=O)c1cc(C(F)(F)F)n[nH]1] | ¹H-NMR (CD₃OD/400 MHz): 7.34 (m, 5H), 6.80 (m, 1H), 4.77 (m, 2H), 3.47 (m, 2H), 1.62 (m, 2H), 1.23 (m, 4H), 0.89 (m, 3H). | 340.0 | 920/76 | — |

TABLE 1-continued
Exemplary Compounds
| EX | Structure | NMR | ES-MS (M⁺ + 1) | PKM₂ AC₅₀ (nM)/ Max. Resp.* (%) | Note† |
|---|---|---|---|---|---|
| 20 | 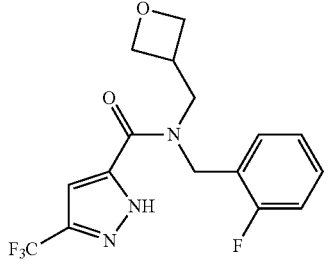 [SMILES: O=C(c1cc(C(F)(F)F)n[nH]1)N(Cc1ccccc1F)CC1COC1] | ¹H-NMR (CD₃OD/400 MHz): 7.31 (m, 1H), 7.12 (m, 4H), 4.88 (m, 2H), 4.67 (m, 4H), 4.40 (m, 2H), 3.83 (m, 1H). | 358.1 | 12000/ 70 | — |
| 21 | 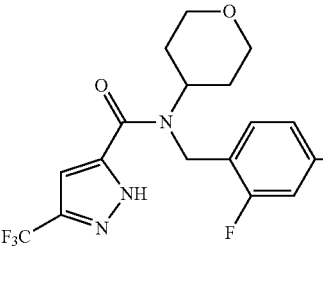 | ¹H-NMR (CD₃OD/400 MHz): 7.28 (m, 1H), 7.14 (m, 2H), 6.56 (m, 1H), 3.93 (m, 3H), 3.80 (m, 2H), 3.40 (m, 2H), 2.77 (m, 1H), 1.89 (m, 2H), 1.44 (m, 2H). | 388.5 | >10000 | — |
| 22 | 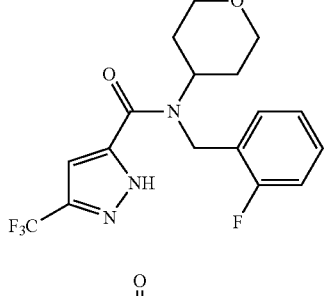 | ¹H-NMR (CD₃OD/400 MHz): 7.38 (m, 2H), 7.14 (m, 3H), 3.95 (m, 2H), 3.40 (m, 2H), 3.40 (m, 3H), 1.95 (m, 2H), 1.86 (m, 2H), 1.10 (m, 2H). | 388.5 | 1516/ 99 | — |
| 23 | 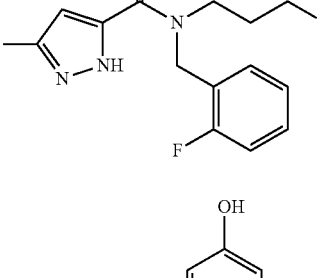 | ¹H-NMR (CD₃OD/400 MHz): 7.35 (m, 2H), 7.15 (m, 2H), 7.15 (m, 2H), 6.86 (m, 1H), 4.89 (s, 2H), 3.65 (m, 2H), 3.36 (m, 2H), 3.26 (m, 2H), 1.89 (m, 3H | 360.4 | 7540/ 75 | — |
| 24 | 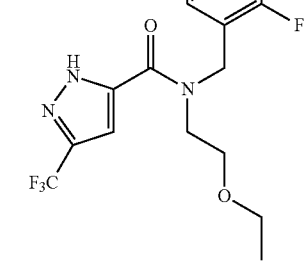 | ¹H-NMR (CD₃OD/400 MHz): 7.11 (m, 2H), 6.55 (m, 2H), 4.76 (m, 2H), 3.67 (m, 4H), 3.31 (m, 2H), 1.16 (m, 3H). | 376.4 | 210/ 100 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 25 | 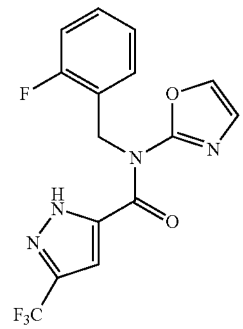 [SMILES: O=C(c1cc(C(F)(F)F)n[nH]1)N(Cc1ccccc1F)c1ncco1] | ¹H-NMR (CD₃OD/400 MHz): 7.84 (m, 1H), 7.47 (m, 1H), 7.34 (m, 1H), 7.21 (m, 1H), 7.13 (m, 2H), 7.02 (m, 2H), 4.78 (m, 2H). | 355.4 | 53000/ 35 | — |
| 26 | 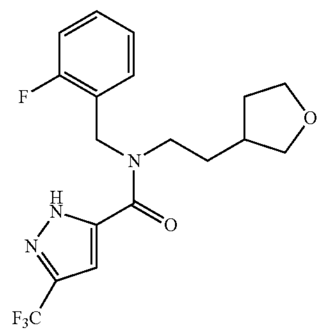 [SMILES: O=C(c1cc(C(F)(F)F)n[nH]1)N(CCC1CCOC1)Cc1ccccc1F] | ¹H-NMR (CD₃OD/400 MHz): 7.40 (m, 2H), 7.15 (m, 2H), 7.84 (m, 1H), 4.90 (m, 2H), 3.78 (m, 4H), 3.32 (m, 2H), 2.07 (m, 2H), 1.69 (m, 2H), 1.50 (m, 1H). | 386.4 | 377/99 | — |
| 27 | 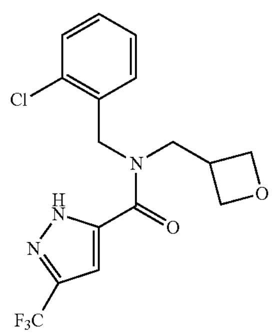 [SMILES: O=C(c1cc(C(F)(F)F)n[nH]1)N(Cc1ccccc1Cl)CC1COC1] | ¹H-NMR (DMSO-d₆/400 MHz): 7.50 (m, 1H), 7.34 (m, 3H), 7.21 (m, 1H), 4.75 (m, 2H), 4.55 (m, 2H), 3.50 (m, 4H), 3.20 (m, 1H). | 374.4 | 33000/ 47 | — |
| 28 | 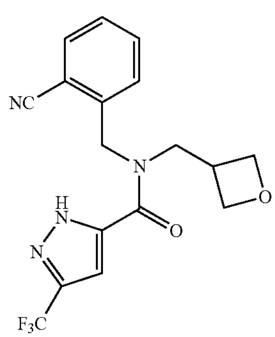 [SMILES: N#Cc1ccccc1CN(CC1COC1)C(=O)c1cc(C(F)(F)F)n[nH]1] | ¹H-NMR (DMSO-d₆/400 MHz): 7.92 (m, 1H), 7.72 (m, 2H), 7.60 (m, 1H), 7.51 (m, 2H), 5.00 (m, 2H), 4.65 (m, 2H), 4.40 (m, 4H), 3.20 (m, 1H). | 365.4 | NA | — |

TABLE 1-continued

Exemplary Compounds

| EX | Structure | NMR | ES-MS (M$^+$ + 1) | PKM$_2$ AC$_{50}$ (nM)/ Max. Resp.* (%) | Note† |
|---|---|---|---|---|---|
| 29 | (structure) | $^1$H-NMR (CD$_3$OD/400 MHz): 7.45 (m, 1H), 7.20 (m, 4H), 5.00 (m, 2H), 3.60 (m, 4H), 3.32 (m, 2H), 1.15 (m, 3H). | 376.4 | 4640/ 87 | — |
| 30 | (structure) | $^1$H-NMR (CD$_3$OD/400 MHz): 7.38 (m, 2H), 7.13 (m, 3H), 4.85 (m, 2H), 3.76 (m, 2H), 3.47 (s, 2H), 3.43 (m, 2H), 1.49 (m, 3H). | 360.4 | 9770/ 72 | — |
| 31 | (structure) | $^1$H-NMR (CD$_3$OD/400 MHz): 7.43 (m, 1H), 7.29 (m, 4H), 4.91 (m, 2H), 3.70 (m, 2H), 3.54 (m, 2H), 3.44 (m, 2H), 3.37 (m, 2H), 3.32 (s, 3H). | 376.4 | 9590/ 82 | — |
| 32 | (structure) | $^1$H-NMR (CD$_3$OD/400 MHz): 7.03 (m, 4H), 6.50 (m, 1H), 4.63 (m, 2H), 3.57 (m, 2H), 3.10 (m, 2H), 3.02 (m, 2H), 1.30 (m, 4H), 1.15 (m, 3H). | 416.4 | 1002/ 107 | — |
| 33 | (structure) | $^1$H-NMR (CD$_3$OD/400 MHz): 7.45 (m, 2H), 7.35 (m, 1H), 6.95 (m, 1H), 5.19 (m, 2H), 3.69 (m, 4H), 3.20 (m, 2H), 1.87 (m, 2H), 1.60 (m, 3H). | 436.4 | 4026/ 81 | — |

TABLE 1-continued

Exemplary Compounds

| EX | Structure | NMR | ES-MS (M+ + 1) | PKM$_2$ AC$_{50}$ (nM)/ Max. Resp.* (%) | Note† |
|---|---|---|---|---|---|
| 34 | (structure with 2-fluoro-4-hydroxybenzyl, tetrahydrofuran-3-yl ethyl, 3-CF$_3$-pyrazole-5-carboxamide) | $^1$H-NMR (CD$_3$OD/400 MHz): 7.15 (m, 1H), 7.02 (m, 1H), 6.58 (m, 1H), 6.52 (m, 1H), 4.74 (m, 2H), 3.77 (m, 4H), 3.44 (m, 2H), 2.14 (m, 2H), 1.64 (m, 3H). | 402.4 | 77/109 | — |
| 35 | (structure with 2-chlorobenzyl, tetrahydropyran-4-yl, 3-CF$_3$-pyrazole-5-carboxamide) | $^1$H-NMR (CD$_3$OD/400 MHz): 7.44 (m, 1H), 7.31 (m, 4H), 4.90 (m, 2H), 3.92 (m, 2H), 3.50 (m, 3H), 1.85 (m, 2H), 1.75 (m, 2H). | 388.4 | 5080/59 | — |
| 36 | (structure with 2-chlorobenzyl, tetrahydropyran-3-yl ethyl, 3-CF$_3$-pyrazole-5-carboxamide) | $^1$H-NMR (CD$_3$OD/400 MHz): 7.44 (m, 1H), 7.32 (m, 3H), 6.80 (m, 1H), 4.91 (m, 2H), 3.68 (m, 2H), 3.47 (m, 2H), 3.11 (m, 2H), 1.45 (m, 7H). | 416.4 | 1218/88 | — |
| 37 | (structure with 2-chlorobenzyl, 2-isopropoxyethyl, 3-CF$_3$-pyrazole-5-carboxamide) | $^1$H-NMR (DMSO-d$_6$/400 MHz): 8.27 (m, 1H), 8.13 (m, 4H), 5.62 (m, 2H), 4.16 (m, 2H), 4.32 (m, 2H), 4.25 (m, 1H), 1.82 (d, 6H). | 390.3 | 42000/37 | — |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 38 | 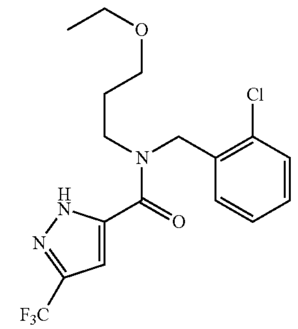 [SMILES: CCOCCCN(Cc1ccccc1Cl)C(=O)c1cc(C(F)(F)F)n[nH]1] | ¹H-NMR (CD₃OD/400 MHz): 7.42 (m, 1H), 7.29 (m, 4H), 4.89 (m, 2H), 3.50 (m, 2H), 3.41 (m, 4H), 1.92 (m, 2H), 1.12 (t, 6H). | 390.3 | 33000/ 47 | — |
| 39 | 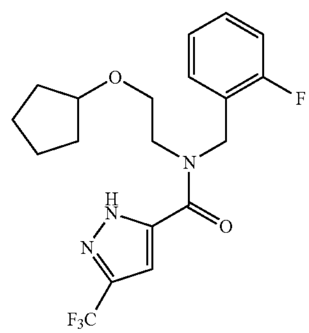 [SMILES: O=C(c1cc(C(F)(F)F)n[nH]1)N(CCOC1CCCC1)Cc1ccccc1F] | ¹H-NMR (CD₃OD/400 MHz): 7.32 (m, 2H), 7.15 (m, 3H), 4.81 (m, 2H), 3.80 (m, 3H), 3.41 (m, 4H), 1.60 (m, 8H). | 400.5 | 47000/ 30 | — |
| 40 | 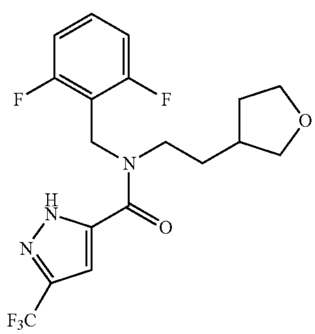 [SMILES: O=C(c1cc(C(F)(F)F)n[nH]1)N(CCC1CCOC1)Cc1c(F)cccc1F] | ¹H-NMR (CD₃OD/400 MHz): 7.41 (m, 1H), 7.00 (m, 3H), 4.88 (m, 2H), 3.70 (m, 4H), 3.40 (m, 2H), 2.05 (m, 2H), 1.62 (m, 2H), 1.40 (m, 1H). | 404.4 | 1171/ 114 | — |
| 41 | 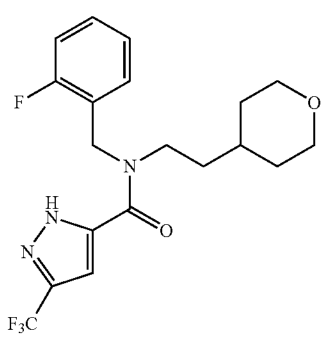 [SMILES: O=C(c1cc(C(F)(F)F)n[nH]1)N(CCC1CCOCC1)Cc1ccccc1F] | ¹H-NMR (CD₃CN/400 MHz): 7.35 (m, 2H), 7.17 (m, 2H), 6.90 (m, 1H), 4.80 (d, 2H), 3.82 (m, 2H), 3.53 (m, 2H), 3.26 (m, 2H), 1.53 (m, 5H), 1.16 (m, 2H). | 400.4 | 1258/ 118 | — |

TABLE 1-continued

Exemplary Compounds

| EX | Structure | NMR | ES-MS ($M^+ + 1$) | PKM$_2$ AC$_{50}$ (nM)/ Max. Resp.* (%) | Note[†] |
|---|---|---|---|---|---|
| 42 | 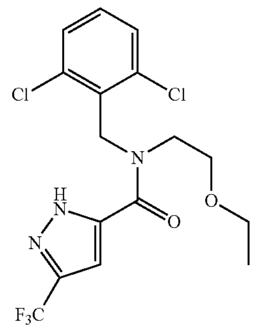 [SMILES: CCOCCN(Cc1c(Cl)cccc1Cl)C(=O)c1cc(C(F)(F)F)n[nH]1] | $^1$H-NMR (CD$_3$OD/400 MHz): 7.44 (d, 2H), 7.34 (t, 1H), 7.01 (m, 1H), 5.16 (m, 2H), 3.60 (m, 2H), 3.40 (m, 4H), 1.10 (m, 3H). | 410.4 | 8780/ 76 | — |
| 43 | 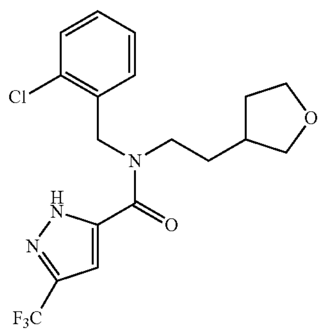 [SMILES: O=C(c1cc(C(F)(F)F)n[nH]1)N(CCC1CCOC1)Cc1ccccc1Cl] | $^1$H-NMR (CD$_3$OD/400 MHz): 7.46 (m, 1H), 7.20 (m, 3H), 6.88 (m, 1H), 4.85 (m, 2H), 3.80 (m, 2H), 3.60 (m, 1H), 3.48 (m, 2H), 3.25 (m, 1H), 2.01 (m, 2H), 1.70 (m, 2H), 1.45 (m, 1H). | 402.4 | 1330/ 110 | — |
| 44 | 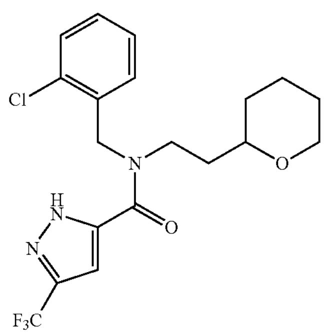 [SMILES: O=C(c1cc(C(F)(F)F)n[nH]1)N(CCC1CCCCO1)Cc1ccccc1Cl] | $^1$H-NMR (CD$_3$OD/400 MHz): 7.45 (m, 1H), 7.29 (m, 4H), 4.83 (m, 2H), 3.80 (m, 2H), 3.36 (m, 3H), 1.80 (m, 4H), 1.47 (m, 4H). | 416.4 | 50000/ 32 | — |
| 45 | 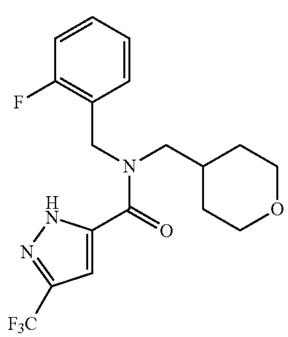 [SMILES: O=C(c1cc(C(F)(F)F)n[nH]1)N(Cc1ccccc1F)CC1CCOCC1] | $^1$H-NMR (Acetone-d$_6$/400 MHz): 7.40 (m, 2H), 7.28 (m, 3H), 4.98 (d, 2H), 3.84 (m, 2H), 3.61 (m, 1H), 3.40 (m, 1H), 3.28 (m, 2H), 2.08 (m, 1H), 1.63 (m, 2H), 1.30 (m, 2H). | 386.4 | 25150/ 52 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 46 | 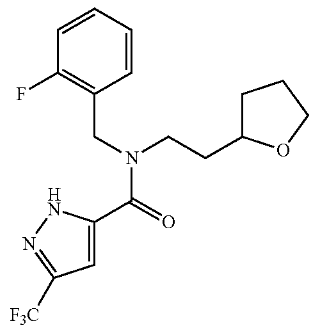 [SMILES: O=C(c1cc(C(F)(F)F)n[nH]1)N(CCC1CCCO1)Cc1ccccc1F] | ¹H-NMR (CD₃CN/400 MHz): 7.28 (m, 2H), 7.16 (m, 3H), 4.80 (d, 2H), 3.80 (m, 2H), 3.60 (m, 3H), 1.95 (m, 1H), 1.80 (m, 4H), 1.41 (m, 1H). | 386.4 | 13410/ 70 | — |
| 47 | 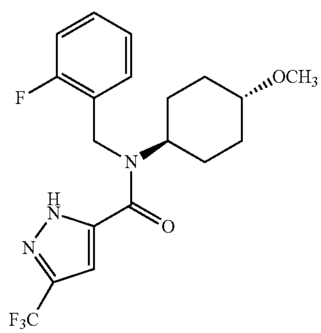 [SMILES: CO[C@H]1CC[C@H](N(Cc2ccccc2F)C(=O)c2cc(C(F)(F)F)n[nH]2)CC1] | ¹H-NMR (CD₃OD/400 MHz): 7.33 (m, 2H), 7.12 (m, 2H), 6.90 (m, 1H), 4.81 (m, 2H), 4.20 (m, 1H), 3.14 (m, 1H), 2.09 (m, 2H), 1.82 (m, 2H), 1.66 (m, 2H), 1.21 (m, 2H). | 400.4 | 435/89 | — |
| 48 | 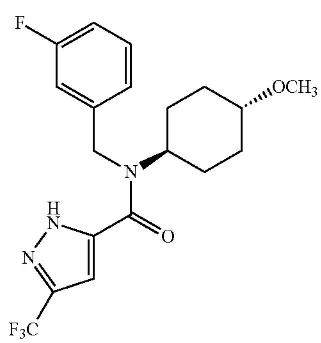 [SMILES: CO[C@H]1CC[C@H](N(Cc2cccc(F)c2)C(=O)c2cc(C(F)(F)F)n[nH]2)CC1] | ¹H-NMR (CD₃OD/400 MHz): 7.33 (m, 1H), 7.00 (m, 4H), 4.80 (m, 2H), 4.20 (m, 1H), 3.28 (s, 3H), 3.12 (m, 1H), 2.07 (m, 2H), 1.80 (m, 2H), 1.70 (m, 2H), 1.23 (m, 2H). | 400.4 | 8580/ 80 | — |
| 49 | 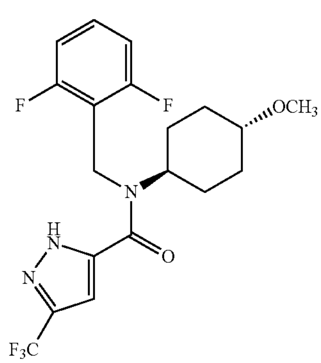 [SMILES: CO[C@H]1CC[C@H](N(Cc2c(F)cccc2F)C(=O)c2cc(C(F)(F)F)n[nH]2)CC1] | ¹H-NMR (Acetone-d₆/400 MHz): 7.40 (m, 1H), 7.00 (m, 3H), 4.92 (m, 2H), 3.24 (s, 3H), 3.00 (m, 2H), 1.76 (m, 4H), 1.15 (m, 4H). | 418.4 | 914/ 122 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 50 | 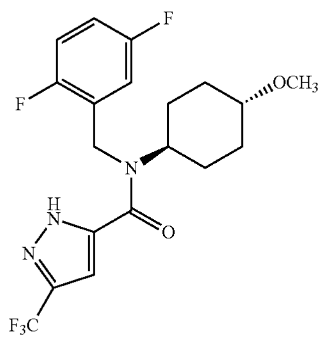 [SMILES: CO[C@H]1CC[C@H](N(Cc2cc(F)ccc2F)C(=O)c2cc(C(F)(F)F)n[nH]2)CC1] | ¹H-NMR (Acetone-d₆/400 MHz): 7.17 (m, 2H), 7.07 (m, 2H), 4.90 (m, 2H), 4.15 (m, 1H), 3.24 (s, 3H), 3.05 (m, 3H), 1.96 (m, 2H), 1.80 (m, 2H), 1.24 (m, 2H). | 418.4 | 1667/ 90 | — |
| 51 | 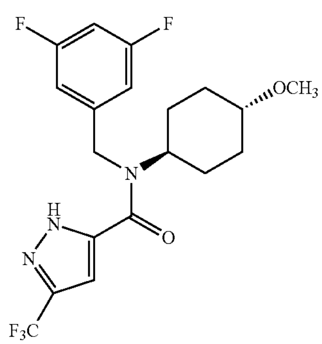 [SMILES: CO[C@H]1CC[C@H](N(Cc2cc(F)cc(F)c2)C(=O)c2cc(C(F)(F)F)n[nH]2)CC1] | ¹H-NMR (Acetone-d₆/400 MHz): 7.03 (m, 3H), 6.89 (m, 1H), 4.80 (m, 2H), 4.32 (m, 1H), 3.25 (s, 3H), 3.05 (m, 3H), 1.96 (m, 2H), 1.80 (m, 2H), 1.20 (m, 2H). | 418.4 | 50380/ 31 | — |
| 52 | 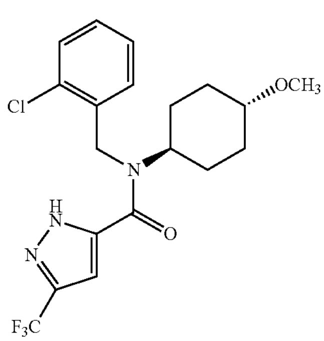 [SMILES: CO[C@H]1CC[C@H](N(Cc2ccccc2Cl)C(=O)c2cc(C(F)(F)F)n[nH]2)CC1] | ¹H-NMR (CD₃OD/400 MHz): 7.40 (m, 1H), 7.30 (m, 4H), 4.81 (m, 2H), 3.29 (s, 3H), 3.13 (m, 2H), 2.10 (m, 2H), 1.85 (m, 2H), 1.62 (m, 2H), 1.23 (m, 2H). | 416.4 | 879/ 100 | — |
| 53 | 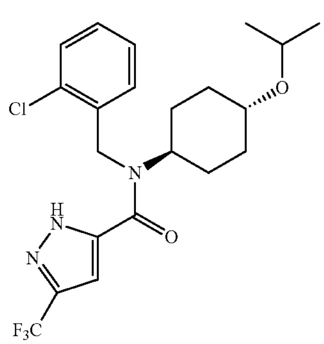 [SMILES: CC(C)O[C@H]1CC[C@H](N(Cc2ccccc2Cl)C(=O)c2cc(C(F)(F)F)n[nH]2)CC1] | ¹H-NMR (CD₃OD/400 MHz): 7.40 (m, 1H), 7.30 (m, 4H), 4.79 (m, 2H), 3.79 (m, 2H), 2.00 (m, 2H), 1.85 (m, 2H), 1.63 (m, 2H), 1.22 (m, 2H), 1.10 (d, 6H). | 444.4 | 2287/ 63 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 54 | 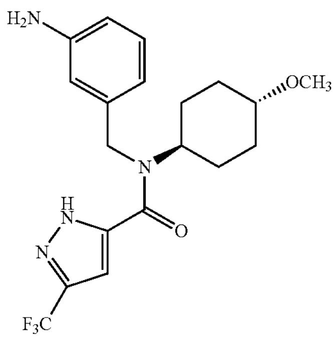 [SMILES: CO[C@H]1CC[C@H](N(Cc2cccc(N)c2)C(=O)c2cc(C(F)(F)F)n[nH]2)CC1] | ¹H-NMR (CD₃OD/400 MHz): 7.45 (m, 1H), 7.27 (m, 3H), 6.80 (m, 1H), 4.80 (m, 2H), 4.22 (m, 1H), 3.25 (s, 3H), 3.05 (m, 1H), 2.05 (m, 2H), 1.84 (m, 2H), 1.66 (m, 2H), 1.20 (m, 2H). | 397.5 | 365/93 | TFA |
| 55 | 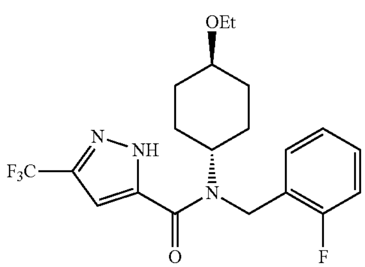 [SMILES: CCO[C@H]1CC[C@H](N(Cc2ccccc2F)C(=O)c2cc(C(F)(F)F)n[nH]2)CC1] | ¹H-NMR (CD₃OD/400 MHz): 7.30 (m, 2H), 7.08 (m, 3H), 4.78 (m, 2H), 4.20 (m, 1H), 3.50 (m, 2H), 3.20 (m, 1H), 2.05 (m, 2H), 1.80 (m, 2H), 1.70 (m, 2H), 1.20 (m, 2H), 1.12 (t, 3H). | 414.4 | 469/101 | — |
| 56 | 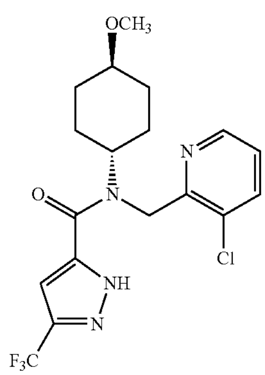 [SMILES: CO[C@H]1CC[C@H](N(Cc2ncccc2Cl)C(=O)c2cc(C(F)(F)F)n[nH]2)CC1] | ¹H-NMR (Acetone-d₆/400 MHz): 8.53 (m, 1H), 7.86 (m, 1H), 7.37 (m, 1H), 6.63 (m, 1H), 5.00 (m, 2H), 4.20 (m, 1H), 3.25 (s, 3H), 3.08 (m, 1H), 1.95 (m, 4H), 1.42 (m, 2H), 1.26 (m, 2H). | 417.4 | 2580/48 | TFA |
| 57 | 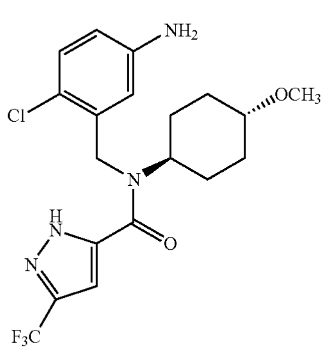 [SMILES: CO[C@H]1CC[C@H](N(Cc2cc(N)ccc2Cl)C(=O)c2cc(C(F)(F)F)n[nH]2)CC1] | ¹H-NMR (dmso-d₆/400 MHz): 7.06 (m, 1H), 6.54 (m, 2H), 6.30 (m, 1H), 4.54 (m, 2H), 4.10 (m, 1H), 3.20 (s, 3H), 3.00 (m, 1H), 1.95 (m, 2H), 1.70 (m, 2H), 1.50 (m, 4H), 1.15 (m, 2H). | 431.4 | TBD | TFA |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 58 | 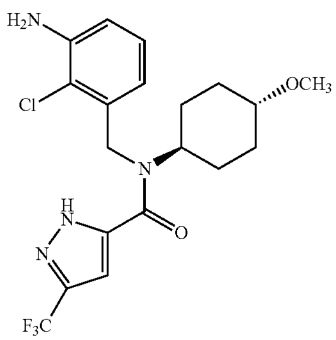 [SMILES: CO[C@H]1CC[C@H](N(Cc2cccc(N)c2Cl)C(=O)c2cc(C(F)(F)F)n[nH]2)CC1] | ¹H-NMR (CD₃OD/400 MHz): 7.10 (m, 1H), 6.89 (m, 1H), 6.71 (m, 1H), 6.38 (m, 1H), 4.75 (m, 2H), 4.31 (m, 1H), 3.20 (s, 3H), 3.10 (m, 1H), 2.10 (m, 2H), 1.90 (m, 2H), 1.65 (m, 2H), 1.28 (m, 2H). | 431.4 | TBD | TFA |
| 59 | 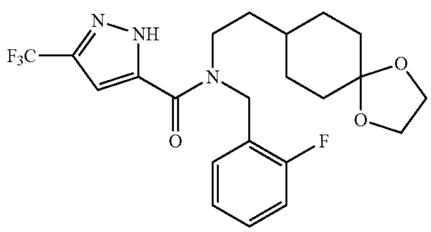 [SMILES: O=C(c1cc(C(F)(F)F)n[nH]1)N(CCC1CCC2(CC1)OCCO2)Cc1ccccc1F] | ¹H-NMR (CD₃CN/400 MHz): 7.35 (m, 2H), 7.16 (m, 2H), 6.80 (m, 1H), 4.77 (m, 2H), 3.85 (m, 4H), 3.52 (m, 2H), 2.30 (m, 2H), 1.62 (m, 5H), 1.17 (m, 4H). | 456.5 | 494/ 100 | — |
| 60 | 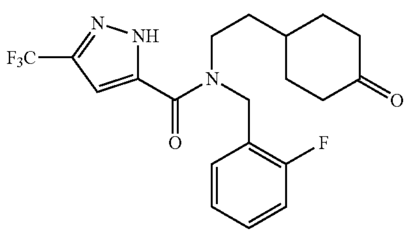 [SMILES: O=C1CCC(CCN(Cc2ccccc2F)C(=O)c2cc(C(F)(F)F)n[nH]2)CC1] | ¹H-NMR (CDCl₃/400 MHz): 7.35 (m, 1H), 7.18 (m, 3H), 6.70 (m, 1H), 4.87 (m, 2H), 3.59 (m, 2H), 2.28 (m, 4H), 2.04 (m, 2H), 1.70 (m, 3H), 1.44 (m, 2H). | 412.5 | 101/ 105 | — |
| 61 | 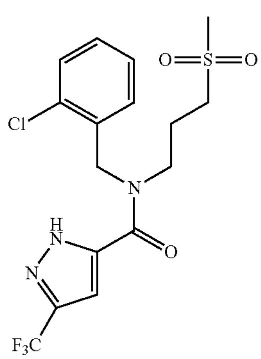 [SMILES: CS(=O)(=O)CCCN(Cc1ccccc1Cl)C(=O)c1cc(C(F)(F)F)n[nH]1] | ¹H-NMR (DMSO-d₆/400 MHz): 7.32 (m, 1H), 7.20 (m, 4H), 4.73 (m, 2H), 3.30 (m, 2H), 3.13 (m, 2H), 2.93 (s, 3H), 1.99 (m, 2H). | 408.4 | NA | — |
| 62 | 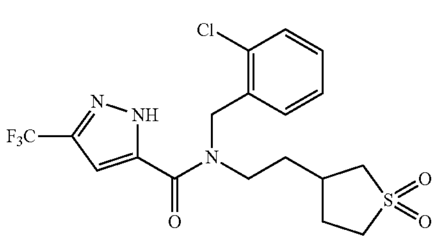 | ¹H-NMR (DMSO-d₆/400 MHz): 7.46 (m, 1H), 7.35 (m, 3H), 6.85 (m, 1H), 4.91 (m, 2H), 3.60 (m, 2H), 3.10 (m, 2H), 2.72 (m, 1H), 2.41 (m, 2H), 1.85 (m, 2H). | 450.4 | 273/ 105 | — |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 63 | 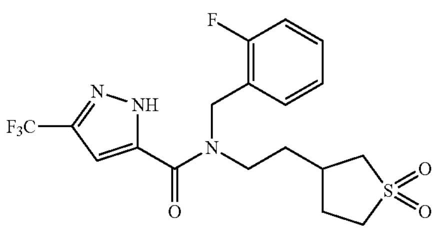 [SMILES: O=C(c1cc(C(F)(F)F)n[nH]1)N(CCC1CCS(=O)(=O)C1)Cc1ccccc1F] | ¹H-NMR (CD₃OD/400 MHz): 7.36 (m, 2H), 7.15 (m, 2H), 6.85 (m, 1H), 4.92 (m, 2H), 3.50 (m, 2H), 3.12 (m, 2H), 3.00 (m, 1H), 2.71 (m, 2H), 2.24 (m, 2H), 1.85 (m, 2H). | 434.4 | 240/87 | — |
| 64 | 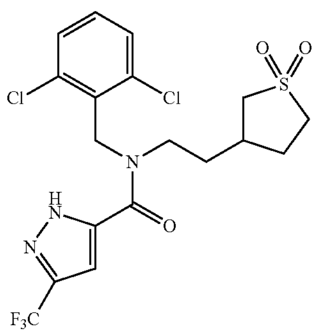 [SMILES: O=C(c1cc(C(F)(F)F)n[nH]1)N(CCC1CCS(=O)(=O)C1)Cc1c(Cl)cccc1Cl] | ¹H-NMR (DMSO-d₆/400 MHz): 7.52 (m, 2H), 7.35 (m, 1H), 7.38 (m, 1H), 5.03 (m, 2H), 3.50 (m, 2H), 3.12 (m, 2H), 2.92 (m, 3H), 2.16 (m, 2H), 1.65 (m, 2H). | 484.3 | 3780/71 | — |
| 65 | 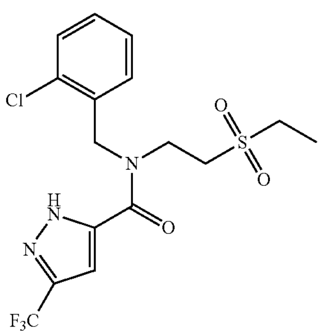 [SMILES: CCS(=O)(=O)CCN(Cc1ccccc1Cl)C(=O)c1cc(C(F)(F)F)n[nH]1] | ¹H-NMR (CD₃OD/400 MHz): 7.47 (m, 1H), 7.37 (m, 3H), 6.80 (m, 1H), 4.97 (m, 2H), 3.90 (m, 2H), 3.42 (m, 2H), 3.12 (m, 2H), 1.33 (m, 3H). | 424.3 | NA | — |
| 66 | 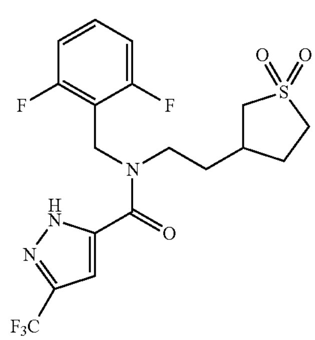 [SMILES: O=C(c1cc(C(F)(F)F)n[nH]1)N(CCC1CCS(=O)(=O)C1)Cc1c(F)cccc1F] | ¹H-NMR (CD₃OD/400 MHz): 7.41 (m, 1H), 7.00 (m, 3H), 5.01 (m, 2H), 3.58 (m, 2H), 3.10 (m, 2H), 2.65 (m, 1H), 2.35 (m, 2H), 1.77 (m, 4H). | 452.4 | 375/102 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 67 | 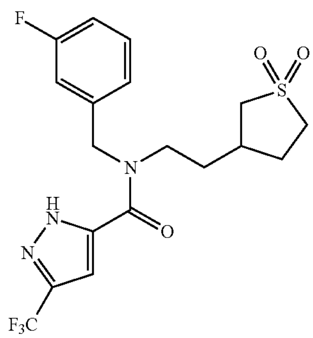 [SMILES: O=C(c1cc(C(F)(F)F)n[nH]1)N(CCC1CCS(=O)(=O)C1)Cc1cccc(F)c1] | ¹H-NMR (CD₃OD/400 MHz): 7.39 (m, 1H), 7.02 (m, 3H), 6.90 (m, 1H), 4.80 (m, 2H), 3.60 (m, 3H), 3.20 (m, 3H), 2.99 (m, 2H), 2.30 (m, 3H). | 434.4 | 1626/95 | — |
| 68 | 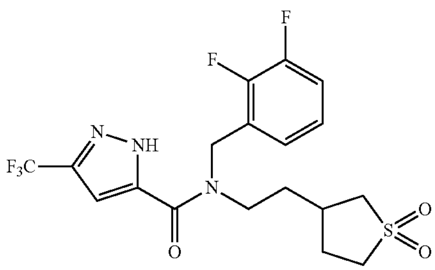 [SMILES: O=C(c1cc(C(F)(F)F)n[nH]1)N(CCC1CCS(=O)(=O)C1)Cc1cccc(F)c1F] | ¹H-NMR (Acetone-d₆/400 MHz): 7.20 (m, 4H), 4.98 (d, 2H), 3.61 (m, 2H), 3.20 (m, 2H), 3.00 (m, 2H), 2.60 (m, 1H), 2.45 (m, 2H), 1.80 (m, 2H). | 452.4 | 766/103 | — |
| 69 | 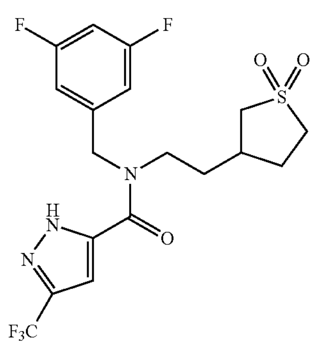 [SMILES: O=C(c1cc(C(F)(F)F)n[nH]1)N(CCC1CCS(=O)(=O)C1)Cc1cc(F)cc(F)c1] | ¹H-NMR (Acetone-d₆/400 MHz): 7.00 (m, 4H), 4.90 (d, 2H), 3.61 (m, 2H), 3.20 (m, 2H), 3.00 (m, 2H), 2.60 (m, 1H), 2.45 (m, 2H), 1.80 (m, 2H). | 452.4 | 1835/74 | — |
| 70 | 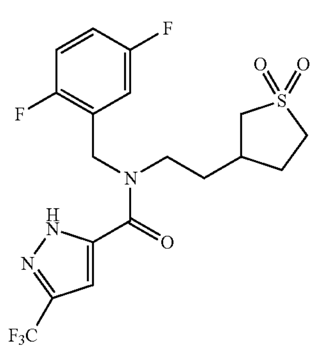 [SMILES: O=C(c1cc(C(F)(F)F)n[nH]1)N(CCC1CCS(=O)(=O)C1)Cc1cc(F)ccc1F] | ¹H-NMR (Acetone-d₆/400 MHz): 7.20 (m, 4H), 4.90 (d, 2H), 3.61 (m, 2H), 3.20 (m, 2H), 3.00 (m, 2H), 2.60 (m, 1H), 2.45 (m, 2H), 1.80 (m, 2H). | 452.4 | 884/91 | — |

TABLE 1-continued

Exemplary Compounds

| EX | Structure | NMR | ES-MS (M$^+$ + 1) | PKM$_2$ AC$_{50}$ (nM)/ Max. Resp.* (%) | Note$^\dagger$ |
|---|---|---|---|---|---|
| 71 | 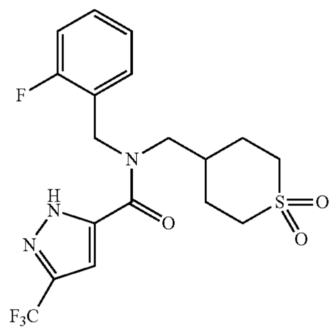 [SMILES: O=C(c1cc(C(F)(F)F)n[nH]1)N(Cc1ccccc1F)CC1CCS(=O)(=O)CC1] | $^1$H-NMR (Acetone-d$_6$/400 MHz): 7.30 (m, 2H), 7.18 (m, 2H), 7.00 (m, 1H), 4.90 (d, 2H), 3.61 (m, 2H), 3.00 (m, 4H), 2.25 (m, 1H), 2.15 (m, 2H), 1.87 (m, 2H). | 434.4 | 10200/ 71 | — |
| 72 | 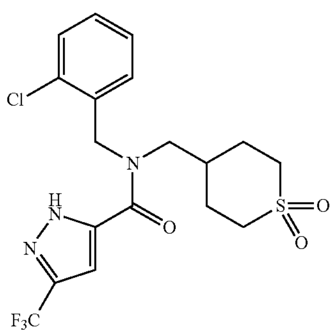 [SMILES: O=C(c1cc(C(F)(F)F)n[nH]1)N(Cc1ccccc1Cl)CC1CCS(=O)(=O)CC1] | $^1$H-NMR (Acetone-d$_6$/400 MHz): 7.36 (m, 4H), 7.00 (m, 1H), 4.95 (d, 2H), 3.61 (m, 2H), 3.00 (m, 4H), 2.25 (m, 1H), 2.15 (m, 2H), 1.87 (m, 2H). | 450.4 | 19660/ 22 | — |
| 73 | 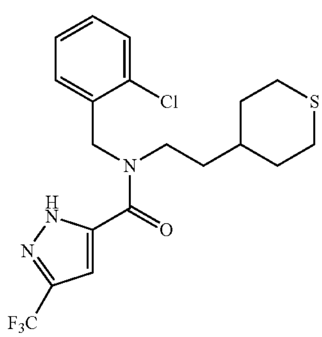 [SMILES: O=C(c1cc(C(F)(F)F)n[nH]1)N(CCC1CCSCC1)Cc1ccccc1Cl] | $^1$H-NMR (Acetone-d$_6$/400 MHz): 7.41 (m, 4H), 6.80 (m, 1H), 4.95 (d, 2H), 3.61 (d, 2H), 2.60 (m, 4H), 1.99 (m, 1H), 1.61 (m, 2H), 1.30 (m, 4H). | 432.4 | 1343/ 79 | — |
| 74 | 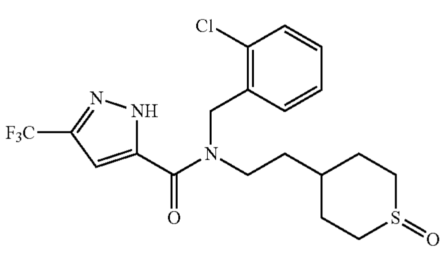 [SMILES: O=C(c1cc(C(F)(F)F)n[nH]1)N(CCC1CCS(=O)CC1)Cc1ccccc1Cl] | $^1$H-NMR (Acetone-d$_6$/400 MHz): 7.41 (m, 4H), 6.90 (m, 1H), 4.95 (d, 2H), 3.61 (d, 2H), 3.16 (m, 2H), 2.81 (m, 1H), 2.53 (m, 2H), 2.08 (m, 2H), 1.73 (m, 4H). | 448.4 | 640/95 | — |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 75 | 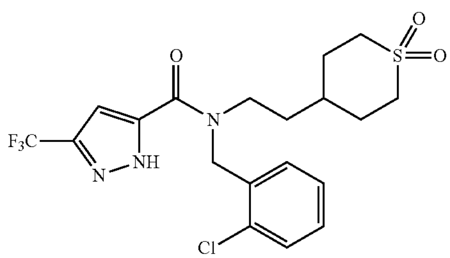 [SMILES: O=C(c1cc(C(F)(F)F)n[nH]1)N(CCC1CCS(=O)(=O)CC1)Cc1ccccc1Cl] | ¹H-NMR (CD$_3$CN/400 MHz): 7.47 (m, 1H), 7.32 (m, 3H), 6.90 (m, 1H), 4.85 (m, 2H), 3.49 (m, 2H), 2.90 (m, 4H), 2.25 (m, 2H), 2.05 (m, 1H), 1.61 (m, 4H). | 464.4 | 188/ 102 | — |
| 76 | 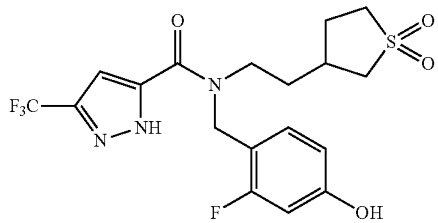 [SMILES: O=C(c1cc(C(F)(F)F)n[nH]1)N(CCC1CCS(=O)(=O)C1)Cc1ccc(O)cc1F] | ¹H-NMR (CD$_3$CN/400 MHz): 7.15 (m, 1H), 6.80 (m, 1H), 6.60 (m, 2H), 4.72 (m, 2H), 3.50 (m, 2H), 3.19 (m, 2H), 2.95 (m, 1H), 2.55 (m, 1H), 2.35 (m, 2H), 1.80 (m, 3H). | 450.4 | 54/93 | — |
| 77 | 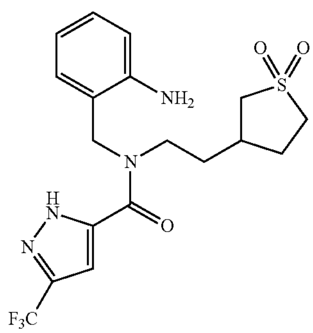 [SMILES: Nc1ccccc1CN(CCC1CCS(=O)(=O)C1)C(=O)c1cc(C(F)(F)F)n[nH]1] | ¹H-NMR (CD$_3$CN/400 MHz): 7.40 (m, 1H), 7.15 (m, 2H), 6.95 (m, 1H), 6.75 (m, 2H), 5.65 (s, 1H), 5.38 (s, 1H), 3.48 (m, 2H), 3.40 (m, 1H), 3.05 (m, 1H), 3.00 (m, 1H), 2.45 (m, 2H), 1.75 (m, 4H). | 431.4 | 34820/ 43 | — |
| 78 | 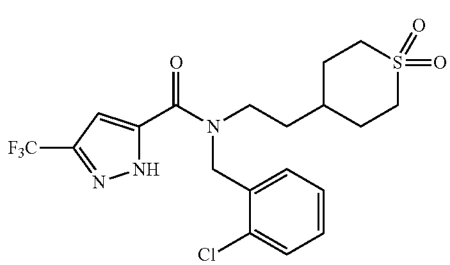 | ¹H-NMR (CD$_3$CN/400 MHz): 7.47 (m, 2H), 7.18 (m, 2H), 6.90 (m, 1H), 4.85 (d, 2H), 3.59 (d, 2H), 2.90 (m, 4H), 2.05 (m, 1H), 2.70 (m, 6H). | 448.4 | 485/ 102 | — |
| 79 | 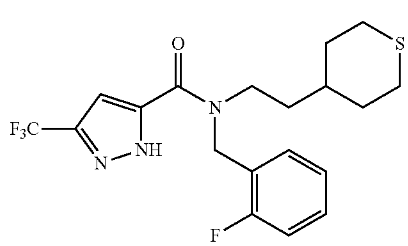 [SMILES: O=C(c1cc(C(F)(F)F)n[nH]1)N(CCC1CCSCC1)Cc1ccccc1F] | ¹H-NMR (Acetone-d$_6$/400 MHz): 7.21 (m, 5H), 4.70 (d, 2H), 3.40 (d, 2H), 2.47 (m, 2H), 1.86 (m, 1H), 1.70 (m, 2H), 1.41 (m, 2H), 1.14 (m, 4H). | 416.4 | 1193/ 95 | — |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 80 | 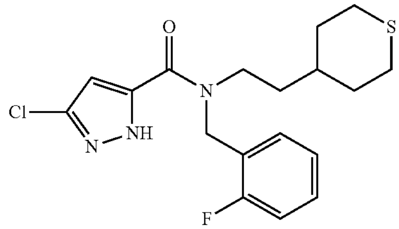 | ¹H-NMR (Acetone-d₆/400 MHz): 7.35 (m, 1H), 7.18 (m, 2H), 4.70 (d, 2H), 3.60 (d, 2H), 2.60 (m, 2H), 2.50 (m, 2H), 2.00 (m, 2H), 1.61 (m, 2H), 1.27 (m, 3H). | 382.4 | 1301/ 46 | — |
| 81 | 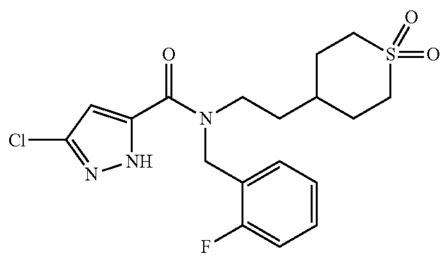 | ¹H-NMR (CD₃CN/400 MHz): 7.36 (m, 2H), 7.17 (m, 2H), 6.60 (m, 1H), 4.90 (d, 2H), 3.63 (d, 2H), 3.01 (m, 4H), 2.18 (m, 3H), 1.70 (m, 4H). | 414.4 | 1366/ 72 | — |
| 82 | 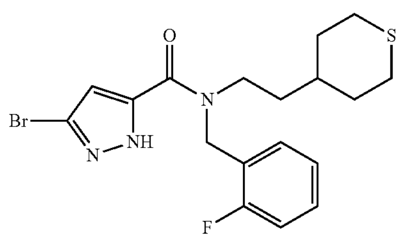 [SMILES: O=C(c1cc(Cl)n[nH]1)N(CCC1CCSCC1)Cc1ccccc1F] | ¹H-NMR (Acetone-d₆/400 MHz): 7.35 (m, 2H), 7.15 (m, 2H), 6.55 (m, 1H), 4.90 (d, 2H), 3.60 (d, 2H), 2.60 (m, 4H), 2.00 (m, 2H), 1.60 (m, 2H), 1.25 (m, 3H). | 426.4 | 1372/ 74 | — |
| 83 | 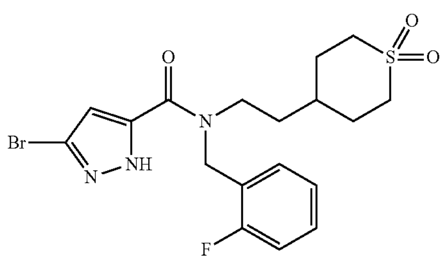 [SMILES: O=C(c1cc(Cl)n[nH]1)N(CCC1CCS(=O)(=O)CC1)Cc1ccccc1F] | ¹H-NMR (CD₃CN/400 MHz): 7.36 (m, 2H), 7.18 (m, 2H), 6.60 (m, 1H), 4.90 (d, 2H), 3.60 (d, 2H), 2.98 (m, 4H), 2.19 (m, 2H), 1.71 (m, 5H). | 458.4 | 1104/ 98 | — |
| 84 | 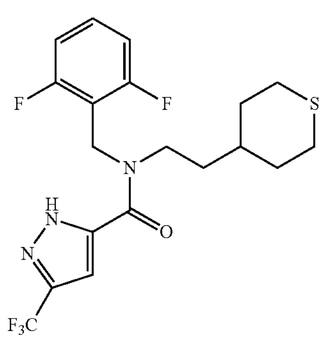 [SMILES: O=C(c1cc(C(F)(F)F)n[nH]1)N(CCC1CCSCC1)Cc1c(F)cccc1F] | ¹H-NMR (ACN-d₆/400 MHz): 7.40 (m, 1H), 7.02 (m, 2H), 6.98 (m, 1H), 4.83 (m, 2H), 3.35 (m, 2H), 2.51 (m, 4H), 2.17 (m, 2H), 1.90 (m, 2H), 1.48 (m, 2H), 1.21 (m, 3H). | 434.4 | 697/73 | — |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 85 | 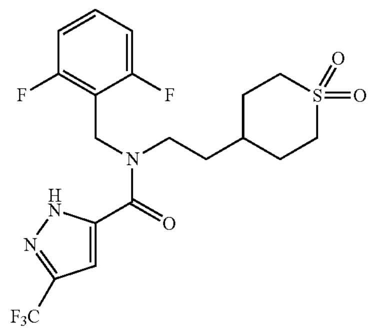 [SMILES: O=C(c1cc(C(F)(F)F)n[nH]1)N(CCC1CCS(=O)(=O)CC1)Cc1c(F)cccc1F] | ¹H-NMR (CD₃CN/400 MHz): 7.36 (m, 2H), 7.05 (m, 3H), 5.00 (m, 2H), 3.60 (m, 2H), 2.99 (m, 4H), 2.90 (m, 2H), 1.68 (m, 5H), 2.98 (m, 4H). | 466.4 | 64/100 | — |
| 86 | 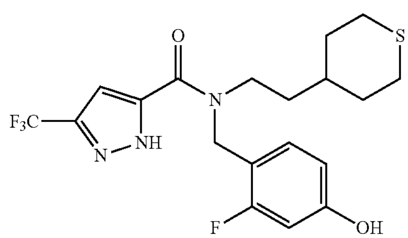 [SMILES: O=C(c1cc(C(F)(F)F)n[nH]1)N(CCC1CCSCC1)Cc1ccc(O)cc1F] | ¹H-NMR (Acetone-d₆/400 MHz): 7.22 (m, 1H), 7.00 (m, 1H), 6.63 (m, 2H), 4.75 (m, 2H), 3.40 (m, 2H), 2.60 (m, 4H), 2.00 (m, 2H), 1.55 (m, 2H), 1.25 (m, 3H). | 432.4 | 93/98 | — |
| 87 | 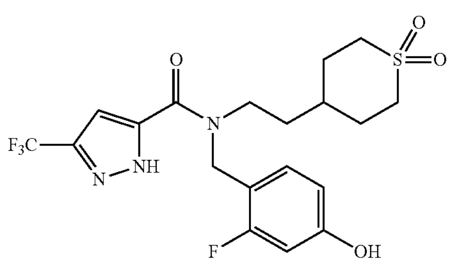 [SMILES: O=C(c1cc(C(F)(F)F)n[nH]1)N(CCC1CCS(=O)(=O)CC1)Cc1ccc(O)cc1F] | ¹H-NMR (CD₃CN/400 MHz): 7.15 (m, 1H), 6.84 (m, 1H), 6.63 (m, 2H), 4.72 (m, 2H), 3.44 (m, 2H), 2.92 (m, 4H), 2.04 (m, 2H), 1.60 (m, 5H). | 464.4 | 64/100 | — |
| 88 | 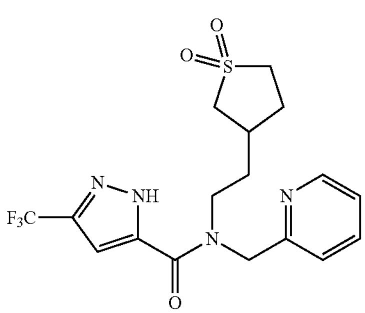 [SMILES: O=C(c1cc(C(F)(F)F)n[nH]1)N(CCC1CCS(=O)(=O)C1)Cc1ccccn1] | ¹H-NMR (CD₃OD/400 MHz): 8.77 (m, 1H), 7.98 (m, 1H), 7.60 (m, 2H), 6.97 (m, 1H), 5.00 (m, 2H), 3.60 (m, 2H), 3.20 (m, 2H), 2.40 (m, 2H), 1.84 (m, 3H). | 417.4 | 3600/ 96 | TFA |

TABLE 1-continued
Exemplary Compounds
| EX | Structure | NMR | ES-MS (M+ + 1) | PKM2 AC50 (nM)/ Max. Resp.* (%) | Note† |
|---|---|---|---|---|---|
| 89 | 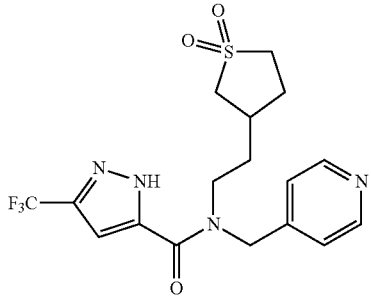 [SMILES: O=C(c1cc(C(F)(F)F)n[nH]1)N(CCC1CCS(=O)(=O)C1)Cc1ccncc1] | 1H-NMR (CD3OD/400 MHz): 8.80 (m, 1H), 7.90 (m, 3H), 6.97 (m, 1H), 5.10 (m, 2H), 3.85 (m, 2H), 3.20 (m, 2H), 2.80 (m, 2H), 2.40 (m, 2H), 1.90 (m, 3H). | 417.4 | 58000/ 35 | TFA |
| 90 | 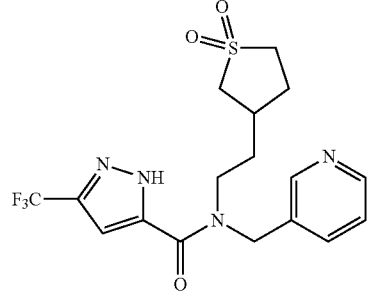 | 1H-NMR (CD3OD/400 MHz): 8.70 (m, 2H), 8.27 (m, 1H), 7.91 (m, 1H), 4.84 (m, 2H), 3.64 (m, 2H), 3.10 (m, 2H), 2.65 (m, 1H), 2.30 (m, 2H), 1.80 (m, 4H). | 417.4 | 52000/ 24 | TFA |
| 91 | 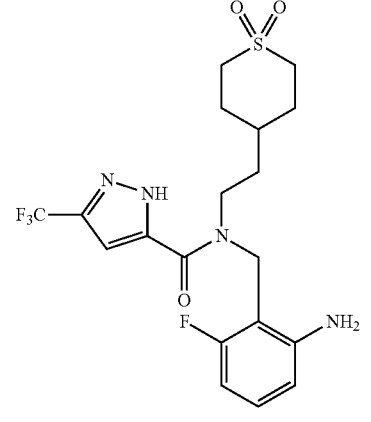 [SMILES: Nc1cccc(F)c1CN(CCC1CCS(=O)(=O)CC1)C(=O)c1cc(C(F)(F)F)n[nH]1] | 1H-NMR (CD3OD/400 MHz): 7.09 (m, 1H), 6.90 (m, 1H), 6.52 (m, 1H), 6.41 (m, 1H), 4.84 (m, 2H), 3.50 (m, 4H), 2.80 (m, 5H), 1.55 (m, 4H). | 463.4 | 58/78 | TFA |
| 92 | 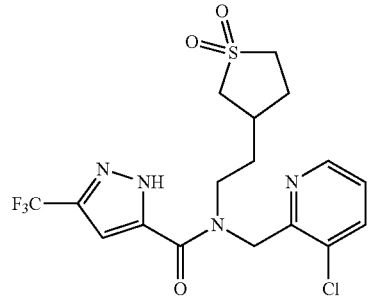 [SMILES: O=C(c1cc(C(F)(F)F)n[nH]1)N(CCC1CCS(=O)(=O)C1)Cc1ncccc1Cl] | 1H-NMR (Acetone-d6/400 MHz): 8.50 (m, 1H), 7.92 (m, 1H), 7.42 (m, 2H), 6.76 (m, 1H), 5.11 (m, 2H), 3.64 (m, 2H), 3.10 (m, 2H), 2.65 (m, 1H), 2.30 (m, 2H), 1.80 (m, 4H). | 451.4 | 1290/ 74 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 93 | 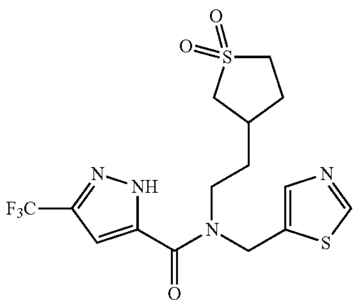 [SMILES: O=C(c1cc(C(F)(F)F)n[nH]1)N(CCC1CCS(=O)(=O)C1)Cc1cncs1] | ¹H-NMR (Acetone-d₆/400 MHz): 8.94 (m, 1H), 7.90 (m, 1H), 7.05 (m, 1H), 5.10 (m, 2H), 3.75 (m, 2H), 3.20 (m, 2H), 2.90 (m, 1H), 2.70 (m, 1H), 2.40 (m, 2H), 1.80 (m, 3H). | 423.6 | 49000/ 26 | — |
| 94 | 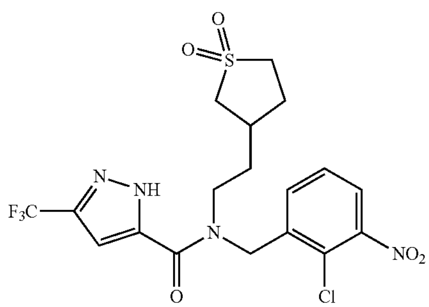 [SMILES: O=C(c1cc(C(F)(F)F)n[nH]1)N(CCC1CCS(=O)(=O)C1)Cc1cccc([N+](=O)[O-])c1Cl] | ¹H-NMR (CDCl₃/400 MHz): 7.83 (m, 1H), 7.46 (m, 2H), 6.50 (m, 1H), 5.10 (m, 2H), 3.60 (m, 2H), 3.20 (m, 2H), 3.00 (m, 1H), 2.90 (m, 1H), 2.70 (m, 1H), 2.40 (m, 2H), 1.88 (m, 3H). | 495.4 | 2380/ 69 | — |
| 95 | 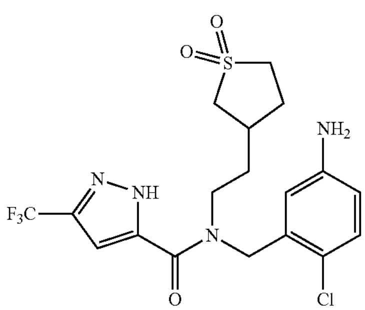 [SMILES: Nc1ccc(Cl)c(CN(CCC2CCS(=O)(=O)C2)C(=O)c2cc(C(F)(F)F)n[nH]2)c1] | ¹H-NMR (CD₃CN/400 MHz): 7.17 (m, 1H), 6.64 (m, 2H), 6.52 (m, 1H), 4.62 (m, 2H), 3.49 (m, 1H), 3.30 (m, 1H), 3.10 (m, 2H), 2.90 (m, 1H), 2.70 (m, 1H), 2.20 (m, 2H), 1.73 (m, 3H). | 465.4 | TBD | TFA |
| 96 | 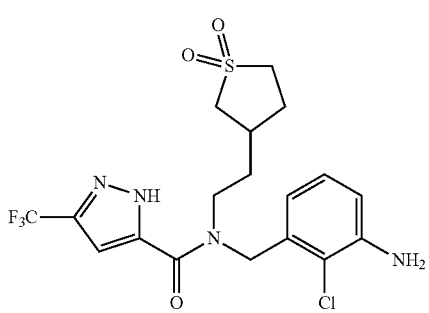 [SMILES: Nc1cccc(CN(CCC2CCS(=O)(=O)C2)C(=O)c2cc(C(F)(F)F)n[nH]2)c1Cl] | ¹H-NMR (CD₃CN/400 MHz): 7.06 (m, 1H), 6.80 (m, 1H), 6.56 (m, 1H), 6.47 (m, 1H), 4.77 (m, 2H), 3.50 (m, 2H), 3.10 (m, 2H), 2.90 (m, 1H), 2.80 (m, 1H), 2.60 (m, 1H), 2.30 (m, 2H), 1.80 (m, 3H). | 465.4 | TBD | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 97 | 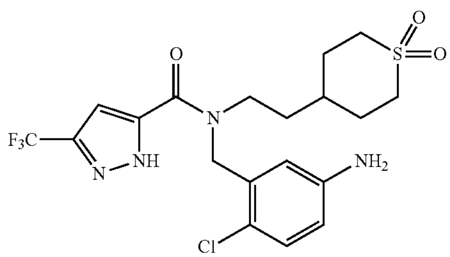 [SMILES: Nc1ccc(Cl)c(CN(CCC2CCS(=O)(=O)CC2)C(=O)c2cc(C(F)(F)F)n[nH]2)c1] | ¹H-NMR (CD₃CN/400 MHz): 7.96 (m, 1H), 7.60 (m, 2H), 7.10 (m, 1H), 5.34 (m, 2H), 4.10 (m, 2H), 3.59 (m, 4H), 2.50 (m, 2H), 2.17 (m, 5H). | 479.4 | TBD | TFA |
| 98 | 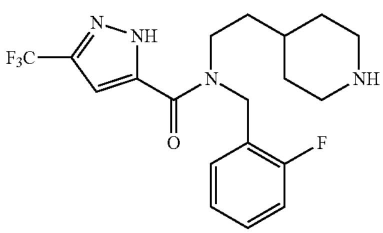 [SMILES: O=C(c1cc(C(F)(F)F)n[nH]1)N(CCC1CCNCC1)Cc1ccccc1F] | ¹H-NMR (Acetone-d₆/400 MHz): 7.37 (m, 2H), 7.13 (m, 2H), 7.00 (m, 1H), 5.00 (m, 2H), 3.62 (m, 4H), 3.00 (m, 2H), 1.55 (m, 7H). | 399.4 | 2050/ 56 | TFA |
| 99 | 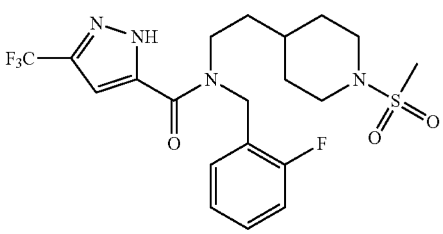 [SMILES: CS(=O)(=O)N1CCC(CCN(Cc2ccccc2F)C(=O)c2cc(C(F)(F)F)n[nH]2)CC1] | H-NMR (CDCl₃/400 MHz): 7.35 (m, 2H), 7.16 (m, 2H), 6.66 (m, 1H), 4.87 (m, 2H), 3.77 (m, 2H), 3.53 (m, 2H), 2.74 (s, 3H), 2.61 (m, 2H), 1.60 (m, 4H), 1.36 (m, 3H). | 477.5 | 110/ 100 | — |
| 100 | 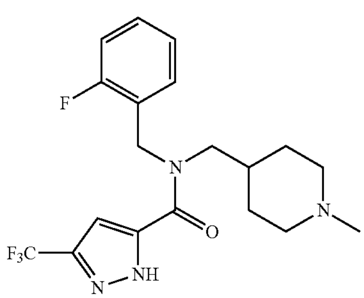 [SMILES: CN1CCC(CN(Cc2ccccc2F)C(=O)c2cc(C(F)(F)F)n[nH]2)CC1] | ¹H-NMR (DMSO-d₆/400 MHz): 9.32 (m, 1H), 7.43 (m, 1H), 7.20 (m, 3H), 6.94 (m, 1H), 4.80 (m, 2H), 3.40 (m, 4H), 2.90 (m, 5H), 1.90 (m, 3H), 1.40 (m, 2H). | 399.5 | 101000/ 29 | TFA |
| 101 | 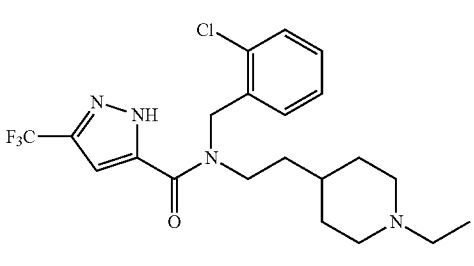 [SMILES: CCN1CCC(CCN(Cc2ccccc2Cl)C(=O)c2cc(C(F)(F)F)n[nH]2)CC1] | ¹H-NMR (DMSO-d₆/400 MHz): 7.92 (m, 1H), 7.72 (m, 2H), 7.60 (m, 1H), 7.51 (m, 2H), 5.00 (m, 2H), 4.65 (m, 2H), 4.40 (m, 4H), 3.20 (m, 1H). | 365.4 | 1856/ 96 | TFA |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 102 | (structure) | ¹H-NMR (CD₃OD/400 MHz): 7.45 (m, 1H), 7.32 (m, 4H), 5.05 (m, 2H), 3.80 (m, 2H), 2.95 (m, 4H), 2.55 (m, 5H), 1.62 (m, 5H). | 441.5 | 767/71 | TFA |
| 103 | (structure) | ¹H-NMR (CD₃OD/400 MHz): 7.34 (m, 2H), 7.14 (m, 2H), 6.80 (m, 1H), 4.94 (m, 2H), 3.74 (m, 2H), 3.31 (m, 4H), 3.12 (m, 4H), 2.85 (m, 5H). | 414.5 | 37000/42 | 2TFA |
| 104 | (structure) | ¹H-NMR (CD₃OD/400 MHz): 7.45 (m, 1H), 7.32 (m, 3H), 6.80 (m, 1H), 5.00 (m, 2H), 3.76 (m, 4H), 3.38 (m, 4H), 2.96 (m, 2H), 2.88 (m, 5H). | 430.3 | 17000/63 | 2TFA |
| 105 | (structure) | ¹H-NMR (CD₃OD/400 MHz): 7.46 (d, 2H), 7.36 (t, 1H), 7.05 (m, 1H), 5.22 (m, 2H), 3.50 (m, 2H), 3.35 (m, 2H), 3.11 (m, 2H), 2.81 (m, 2H), 1.95 (m, 2H), 1.45 (m, 4H), 1.30 (m, 6H). | 477.4 | 3268/71 | TFA |
| 106 | (structure) | ¹H-NMR (Acetone-d₆/400 MHz): 7.37 (m, 2H), 7.16 (m, 3H), 5.00 (m, 2H), 3.90 (m, 2H), 3.60 (m, 6H), 3.25 (m, 6H), 1.34 (m, 3H). | 428.5 | 6300/115 | 2TFA |

TABLE 1-continued

Exemplary Compounds

| EX | Structure | NMR | ES-MS (M+ + 1) | PKM$_2$ AC$_{50}$ (nM)/ Max. Resp.* (%) | Note† |
|---|---|---|---|---|---|
| 107 | 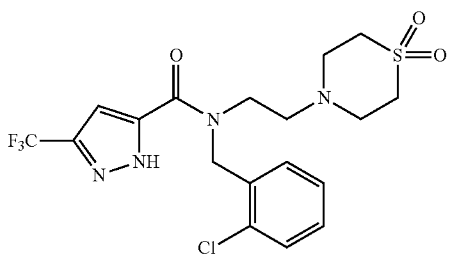 [SMILES: O=C(c1cc(C(F)(F)F)n[nH]1)N(CCN1CCS(=O)(=O)CC1)Cc1ccccc1Cl] | $^1$H-NMR (CD$_3$OD/400 MHz): 7.45 (m, 1H), 7.34 (m, 3H), 6.80 (m, 1H), 5.01 (m, 2H), 3.78 (m, 2H), 3.47 (m, 2H), 3.28 (m, 2H), 3.04 (m, 2H), 2.91 (m, 4H). | 465.4 | 873/85 | TFA |
| 108 | 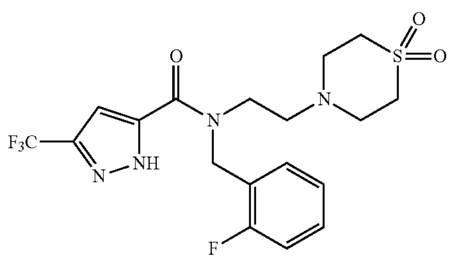 [SMILES: O=C(c1cc(C(F)(F)F)n[nH]1)N(CCN1CCS(=O)(=O)CC1)Cc1ccccc1F] | $^1$H-NMR (CD$_3$OD/400 MHz): 7.40 (m, 2H), 7.20 (m, 3H), 5.00 (m, 2H), 3.65 (m, 2H), 3.50 (m, 2H), 3.40 (m, 2H), 3.25 (m, 2H), 3.00 (m, 4H). | 449.4 | 7800/ 92 | TFA |
| 109 | 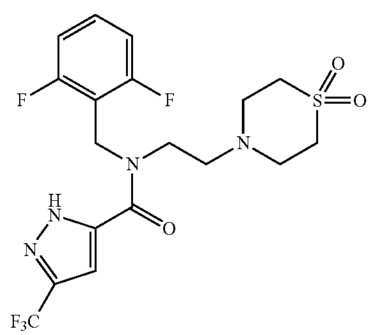 | H-NMR (CD$_3$OD/400 MHz): 7.40 (m, 1H), 7.10 (m, 3H), 5.05 (m, 2H), 3.65 (m, 2H), 3.45 (m, 2H), 3.25 (m, 2H), 3.00 (m, 6H). | 467.4 | 4200/ 94 | TFA |
| 110 | 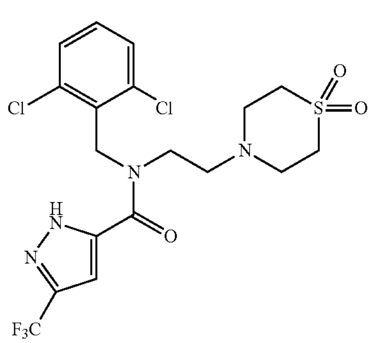 [SMILES: O=C(c1cc(C(F)(F)F)n[nH]1)N(CCN1CCS(=O)(=O)CC1)Cc1c(Cl)cccc1Cl] | $^1$H-NMR (Acetone-d$_6$/400 MHz): 7.52 (m, 2H), 7.43 (m, 1H), 7.20 (m, 1H), 5.20 (m, 2H), 3.60 (m, 2H), 3.00 (m, 10H). | 499.3 | 1644/ 84 | TFA |

TABLE 1-continued
Exemplary Compounds
| EX | Structure | NMR | ES-MS (M⁺ + 1) | PKM₂ AC₅₀ (nM)/ Max. Resp.* (%) | Note† |
|---|---|---|---|---|---|
| 111 | 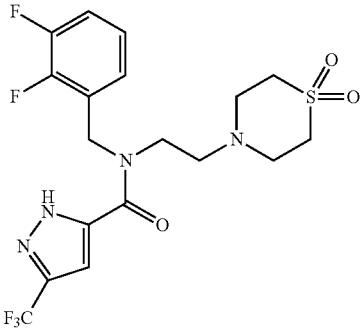 [SMILES: O=C(c1cc(C(F)(F)F)n[nH]1)N(CCN1CCS(=O)(=O)CC1)Cc1cccc(F)c1F] | ¹H-NMR (Acetone-d₆/400 MHz): 7.28 (m, 4H), 5.08 (m, 2H), 3.91 (m, 2H), 3.60 (m, 2H), 3.16 (m, 8H). | 467.4 | 13100/ 64 | TFA |
| 112 | 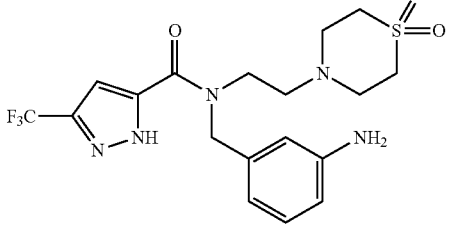 | ¹H-NMR (Acetone-d₆/400 MHz): 7.58 (m, 1H), 7.40 (m, 2H), 6.78 (m, 1H), 5.04 (m, 2H), 3.90 (m, 2H), 3.71 (m, 2H), 3.47 (m, 4H), 3.14 (m, 4H). | 446.4 | 1066/ 91 | 2TFA |
| 113 | 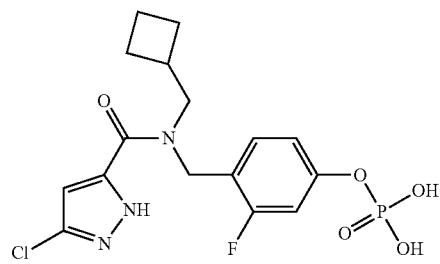 [SMILES: O=C(c1cc(Cl)n[nH]1)N(Cc1ccc(OP(=O)(O)O)cc1F)CC1CCC1] | ¹H-NMR (CD₃OD/400 MHz): δ 7.30 (m, 1H), 7.02 (m, 2H), 6.95 (m, 1H), 4.78 (m, 2H), 3.57 (m, 2H), 2.65 (m, 1H), 2.02 (m, 2H), 1.78 (m, 4H). | 418.0 | 77000/ 21 | — |
| 114 | 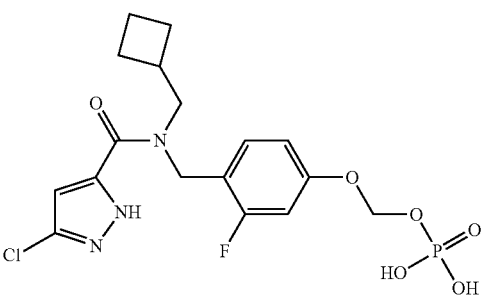 [SMILES: O=C(c1cc(Cl)n[nH]1)N(Cc1ccc(OCOP(=O)(O)O)cc1F)CC1CCC1] | ¹H-NMR (CD₃OD/400 MHz): δ 7.20 (m, 1H), 6.95 (m, 2H), 6.55 (m, 1H), 5.60 (d, 2H), 4.70 (m, 2H), 3.57 (m, 2H), 2.60 (m, 1H), 2.02-1.80 (m, 6H). | 448.0 | TBD | — |
| 115 | 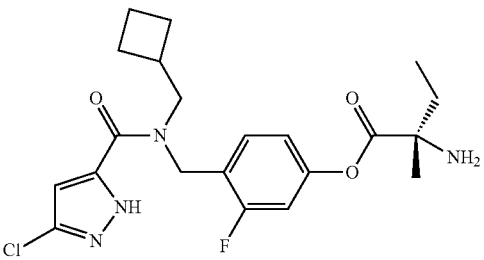 [SMILES: CC[C@@](C)(N)C(=O)Oc1ccc(CN(CC2CCC2)C(=O)c2cc(Cl)n[nH]2)c(F)c1] | H-NMR (CD₃OD/400 MHz): δ 7.34 (m, 1H), 7.05 (m, 2H), 6.55 (m, 1H), 4.95 (d, 2H), 3.60 (m, 2H), 2.80 (m, 1H), 2.05 (m, 1H), 2.00 (m, 5H), 1.80 (m, 5H), 1.00 (t, 3H). | 437.1 | 98/104 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 116 | 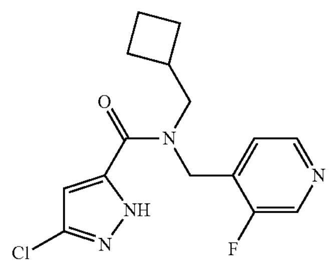 [SMILES: O=C(c1cc(Cl)n[nH]1)N(Cc1ccncc1F)CC1CCC1] | ¹H-NMR (CD₃OD/ 400 MHz): 8.50 (s, 1H), 8.38 (d, 1H), 7.43 (m, 1H), 6.55 (m, 1H), 4.88 (m, 2H), 3.60 (m, 2H), 2.66 (m, 1H), 2.10-1.20 (m, 6H). | 323.4 | 38000/ NA | TFA |
| 117 | 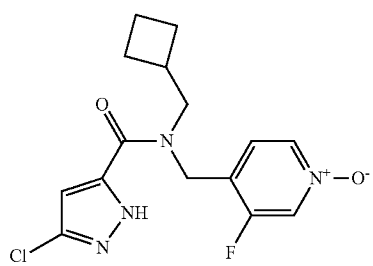 [SMILES: O=C(c1cc(Cl)n[nH]1)N(Cc1cc[n+]([O-])cc1F)CC1CCC1] | ¹H-NMR (CD₃OD/ 400 MHz): 8.44 (d, 1H), 8.15 (d, 1H), 7.43 (m, 1H), 6.60 (m, 1H), 4.74 (m, 2H), 3.70 (m, 2H), 2.66 (m, 1H), 2.10-1.20 (m, 6H). | 339.5 | NA/NA | TFA |
| 118 | 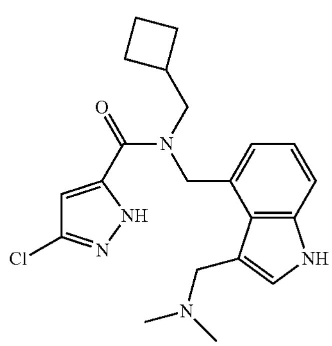 [SMILES: CN(C)Cc1c[nH]c2cccc(CN(CC3CCC3)C(=O)c3cc(Cl)n[nH]3)c12] | ¹H-NMR (CD₃OD/ 400 MHz): 11.4 (s, 1H), 7.57 (s, 1H), 7.43 (d, 1H), 7.21 (t, 1H), 6.60-7.13 (m, 1H), 4.90 (m, 2H), 3.75 (m, 2H), 2.87 (s, 6H), 2.71 (m, 1H), 2.10-1.50 (m, 6H). | 400.4 | 7000/ 100 | TFA |
| 119 | 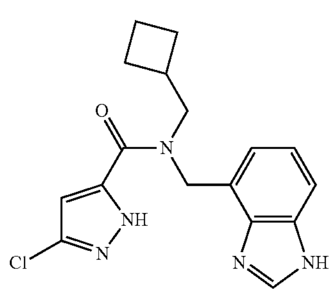 | ¹H-NMR (CD₃OD/ 400 MHz): 8.20 (m, 1H), 7.55 (m, 1H), 7.26 (m, 1H), 7.10 (m, 1H), 6.32-6.58 (m, 1H), 5.00 (s, 2H), 3.52 (m, 2H), 2.60 (m, 1H), 2.00-1.50 (m, 6H). | 344.4 | 2933/ 100 | — |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 120 | 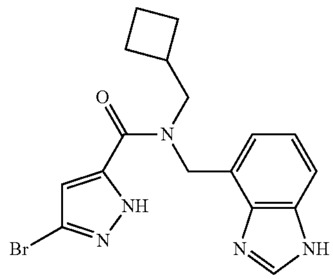 [SMILES: O=C(c1cc(Cl)n[nH]1)N(Cc1cccc2[nH]cnc12)CC1CCC1] | ¹H-NMR (CD$_3$OD/ 400 MHz): 8.20 (m, 1H), 7.56 (m, 1H), 7.28 (m, 1H), 7.11 (m, 1H), 6.43-6.67 (m, 1H), 5.05 (s, 2H), 3.54 (m, 2H), 2.61 (m, 1H), 2.00-1.50 (m, 6H). | 388.4/ 390.4 | 1335/ 100 | — |
| 121 | 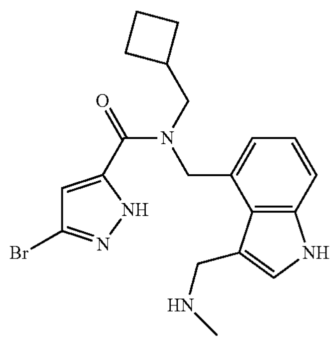 | ¹H-NMR (CD$_3$OD/ 400 MHz): 11.2 (s, 1H), 7.52 (nd, 1H), 7.41 (d, 1H), 7.21 (t, 1H), 6.60-7.13 (m, 1H), 5.03 (bs, 2H), 3.80 (m, 2H), 2.73 (s, 6H), 2.71 (m, 1H), 2.10-1.50 (m, 6H). | | 23,000/ NA | TFA |
| 122 | 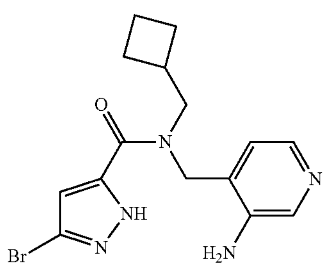 | ¹H-NMR (CD$_3$OD/ 400 MHz): 7.96 (m, 1H), 7.78 (m, 1H), 7.00 (m, 1H), 6.67-6.24 (m, 1H), 4.63 (m, 2H), 3.61 (m, 2H), 2.61 (m, 1H), 2.10-1.50 (m, 6H). | | NA/NA | — |
| 123 | 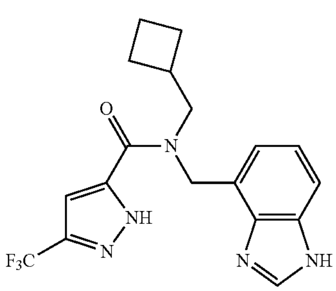 [SMILES: O=C(c1cc(C(F)(F)F)n[nH]1)N(Cc1cccc2[nH]cnc12)CC1CCC1] | ¹H-NMR (CD$_3$OD/ 400 MHz): 8.20 (m, 1H), 7.57 (m, 1H), 7.29 (m, 1H), 7.14 (m, 1H), 6.43-6.67 (m, 1H), 5.03 (s, 2H), 3.54 (m, 2H), 2.61 (m, 1H), 2.00-1.50 (m, 6H). | | 828/100 | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 124 | 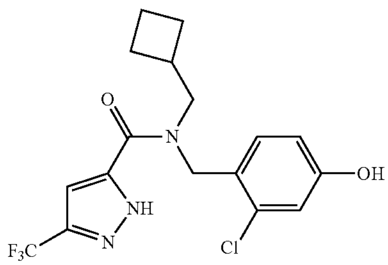 [SMILES: O=C(c1cc(C(F)(F)F)n[nH]1)N(Cc1ccc(O)cc1Cl)CC1CCC1] | ¹H-NMR (CD₃OD/ 400 MHz): 7.08 (m, 1H), 7.00-6.60 (m, 3H), 4.80 (m, 2H), 3.51 (m, 2H), 2.65 (m, 1H), 2.10-1.50 (m, 6H). | | 21/100 | — |
| 125 | 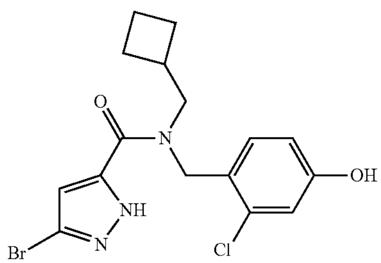 [SMILES: O=C(c1cc(Br)n[nH]1)N(Cc1ccc(O)cc1Cl)CC1CCC1] | ¹H-NMR (CD₃OD/ 400 MHz): 7.08 (m, 1H), 6.83 (m, 1H), 6.71 (m, 1H), 6.63-6.36 (m, 1H), 4.74 (m, 2H), 3.46 (m, 2H), 2.64 (m, 1H), 2.10-1.50 (m, 6H). | | 35/100 | — |
| 126 | 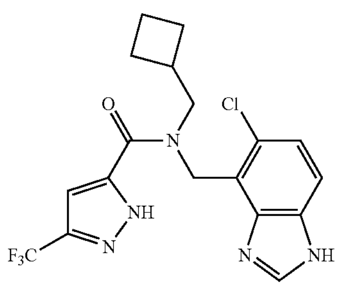 [SMILES: O=C(c1cc(C(F)(F)F)n[nH]1)N(Cc1c(Cl)ccc2[nH]cnc12)CC1CCC1] | ¹H-NMR (CD₃OD/ 400 MHz): 9.00-8.40 (m, 1H), 7.75-7.35 (m, 2H), 6.98 (m, 1H), 5.18 (s, 2H), 3.56 (m, 2H), 2.65 (m, 1H), 2.10-1.50 (m, 6H). | | NA/NA | — |
| 127 | 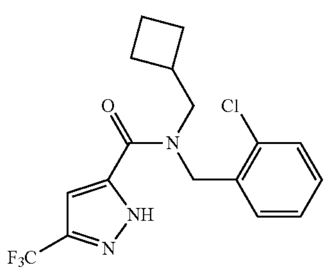 [SMILES: O=C(c1cc(C(F)(F)F)n[nH]1)N(Cc1ccccc1Cl)CC1CCC1] | ¹H-NMR (CD₃OD/ 400 MHz): 7.44 (m, 1H), 7.32 (m, 4H), 4.86 (m, 2H), 3.58 (m, 2H), 2.65 (m, 1H), 2.10-1.50 (m, 6H). | | 258/100 | — |
| 128 | 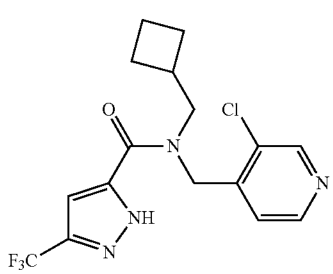 [SMILES: O=C(c1cc(C(F)(F)F)n[nH]1)N(Cc1ccncc1Cl)CC1CCC1] | ¹H-NMR (CD₃OD/ 400 MHz): 8.56 (s, 1H), 8.45 (m, 1H), 7.32 (m, 1H), 7.04 (m, 1H), 4.88 (m, 2H), 3.70 (m, 2H), 2.68 (m, 1H), 2.10-1.50 (m, 6H). | | 9300/75 | — |

TABLE 1-continued

Exemplary Compounds

| EX | Structure | NMR | ES-MS (M$^+$ + 1) | PKM$_2$ AC$_{50}$ (nM)/ Max. Resp.* (%) | Note$^\dagger$ |
|---|---|---|---|---|---|
| 129 | 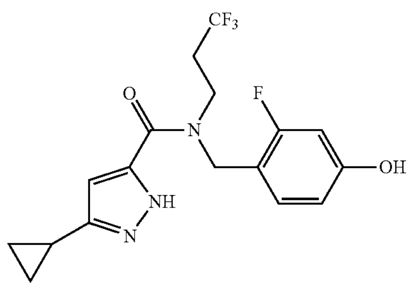 [SMILES: O=C(c1cc(C2CC2)n[nH]1)N(CCC(F)(F)F)Cc1ccc(O)cc1F] | $^1$H-NMR (CD$_3$OD/ 400 MHz): rotomers 7.22 + 7.11 (t, 1H), 6.55 (m, 2H), 6.31 + 6.27 (s, 1H), 4.98 + 4.70 (s, 2H), 3.98 + 3.58 (m, 2H), 2.59 + 2.42 (m, 2H), 1.94 (m, 1H), 0.99 (m, 2H), 0.73 (m, 2H). | | 10500/ NA | — |
| 130 | 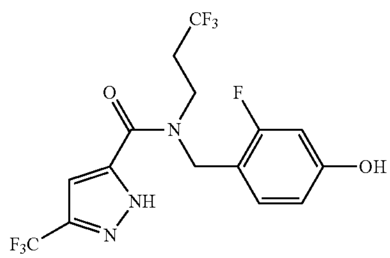 [SMILES: O=C(c1cc(C(F)(F)F)n[nH]1)N(CCC(F)(F)F)Cc1ccc(O)cc1F] | $^1$H-NMR (CD$_3$OD/ 400 MHz): 7.08 (m, 2H), 6.61 (d, 1H), 6.56 (dd, 1H), 4.80 (m, 2H), 3.65 (m, 2H), 2.48 (m, 1H). | | 1000/ 100 | — |
| 131 | 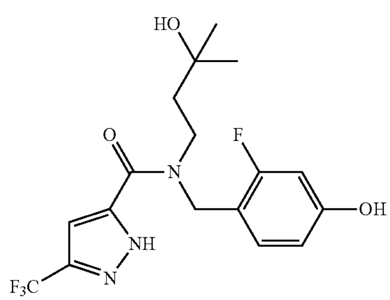 [SMILES: CC(C)(O)CCN(Cc1ccc(O)cc1F)C(=O)c1cc(C(F)(F)F)n[nH]1] | $^1$H-NMR (CD$_3$OD/ 400 MHz): 7.14 (m, 2H), 6.60 (m, 1H), 6.54 (d, 1H), 4.73 (m, 2H), 3.57 (m, 2H), 1.77 (m, 2H), 1.17 (s, 3H), 1.13 (s, 3H). | | 23000/ NA | — |
| 132 | 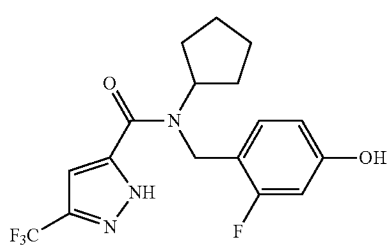 [SMILES: O=C(c1cc(C(F)(F)F)n[nH]1)N(Cc1ccc(O)cc1F)C1CCCC1] | $^1$H-NMR (CD$_3$OD/ 400 MHz): 7.07 (t, 1H), 6.59 (d, 1H), 6.52 (dd, 1H), 4.67 (s, 2H), 4.54 (m, 1H), 2.00-1.50 (m, 8H). | | 213/100 | — |
| 133 | 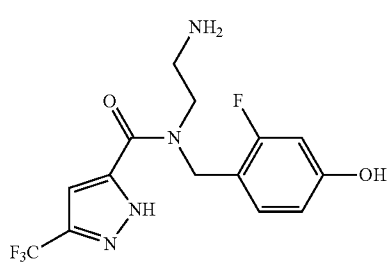 [SMILES: NCCN(Cc1ccc(O)cc1F)C(=O)c1cc(C(F)(F)F)n[nH]1] | $^1$H-NMR (CD$_3$OD/ 400 MHz): 7.08 (m, 1H), 6.84 (m, 1H), 6.63 (d, 1H), 6.58 (dd, 1H), 4.82 (m, 2H), 3.73 (m, 2H), 3.11 (m, 2H). | | 1270/ 100 | TFA |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 134 | 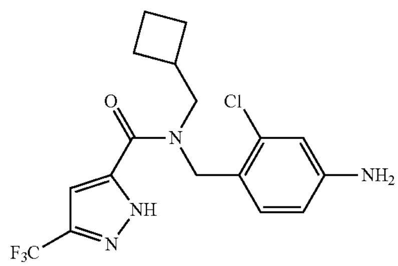 [SMILES: Nc1ccc(CN(CC2CCC2)C(=O)c2cc(C(F)(F)F)n[nH]2)c(Cl)c1] | ¹H-NMR (CD$_3$OD/ 400 MHz): 7.15- 6.55 (m, 4H), 4.73 (m, 2H), 3.51 (m, 2H), 2.65 (m, 1H), 2.10- 1.50 (m, 6H). | | 1075/ 100 | — |
| 135 | 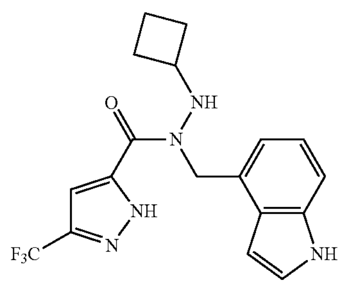 [SMILES: O=C(c1cc(C(F)(F)F)n[nH]1)N(Cc1cccc2[nH]ccc12)NC1CCC1] | ¹H-NMR (d$_6$DMSO/ 400 MHz): 11.2 (s, 1H), 7.33 (m, 3H), 7.06 (t, 1H), 6.88 (d, 1H), 6.52 (m, 1H), 6.42 (s, 1H), 5.05 (s, 1H), 4.84 (d, 1H), 3.54 (m, 1H), 1.94 (m, 2H), 1.68 (m, 2H), 1.53 (m, 2H). | | 68/100 | TFA |
| 136 | 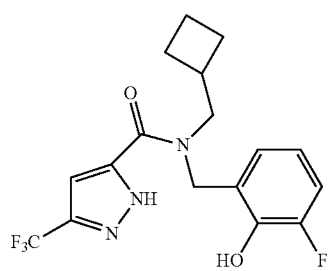 [SMILES: O=C(c1cc(C(F)(F)F)n[nH]1)N(Cc1cccc(F)c1O)CC1CCC1] | ¹H-NMR (CD$_3$OD/ 400 MHz): 7.10- 6.55 (m, 4H), 4.79 (s, 1H), 3.98 (s, 1H), 3.59 (m, 1H), 2.65 (m, 2H), 2.10-1.50 (m, 6H). | | 380/100 | — |
| 137 | 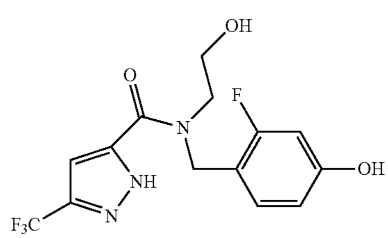 [SMILES: O=C(c1cc(C(F)(F)F)n[nH]1)N(CCO)Cc1ccc(O)cc1F] | ¹H-NMR (CD$_3$OD/ 400 MHz): 7.30- 6.75 (m, 2H), 6.60 (d, 1H), 6.53 (d, 1H), 4.77 (s, 2H), 3.74 (m, 2H), 3.59 (m, 2H). | | 6200/70 | — |
| 138 | 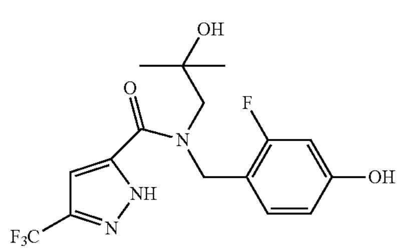 [SMILES: CC(C)(O)CN(Cc1ccc(O)cc1F)C(=O)c1cc(C(F)(F)F)n[nH]1] | ¹H-NMR (CD$_3$OD/ 400 MHz): 7.30- 6.75 (m, 2H), 6.60 (d, 1H), 6.53 (d, 1H), 4.90 (m, 2H), 3.74 (m, 2H), 1.23 (m, 6H). | | NA/NA | — |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 139 | 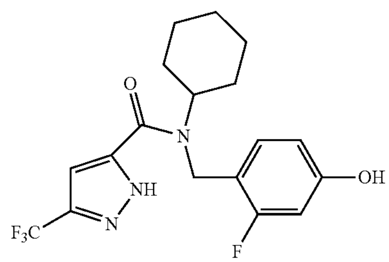 [SMILES: O=C(c1cc(C(F)(F)F)n[nH]1)N(Cc1ccc(O)cc1F)C1CCCCC1] | ¹H-NMR (CD₃OD/ 400 MHz): 7.11 (m, 1H), 6.86 (m, 1H), 6.57 (d, 1H), 6.51 (d, 1H), 4.70 (s, 2H), 4.10 (m, 1H), 1.77 (m, 5H), 1.58 (m, 4H), 1.44-1.04 (m, 4H). | | 152/100 | — |
| 140 | 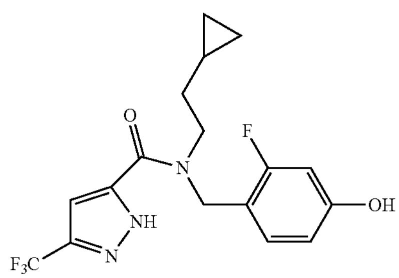 [SMILES: O=C(c1cc(C(F)(F)F)n[nH]1)N(CCC1CC1)Cc1ccc(O)cc1F] | ¹H-NMR (CD₃OD/ 400 MHz): rotomers 7.24 + 7.04 (t, 1H), 6.94 + 6.81 (s, 1H), 6.60 (d, 1H), 6.53 (dd, 1H), 4.76 + 4.72 (s, 2H), 3.59 + 3.50 (m, 2H), 1.48 (q, 2), 0.67 + 0.53 (m, 2H), 0.41 (m, 2H), 0.01 (m, 2H). | | 32/100 | — |
| 141 | 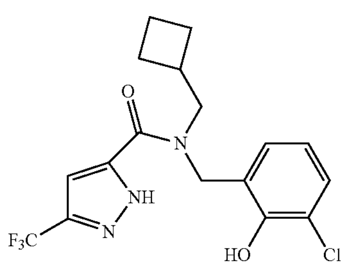 [SMILES: O=C(c1cc(C(F)(F)F)n[nH]1)N(Cc1cccc(Cl)c1O)CC1CCC1] | ¹H-NMR (CD₃OD/ 400 MHz): 8.20- 6.60 (m, 4H), 4.81- 4.45 (m, 2H), 3.61 (m, 1H), 3.22 (m, 1H), 2.65 (m, 1H), 2.10- 1.50 (m, 6H). | | 6500/ 100 | — |
| 142 | 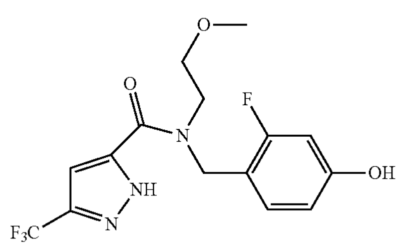 [SMILES: COCCN(Cc1ccc(O)cc1F)C(=O)c1cc(C(F)(F)F)n[nH]1] | ¹H-NMR (CD₃OD/ 400 MHz): 7.30- 6.75 (m, 2H), 6.59 (d, 1H), 6.53 (dd, 1H), 4.76 (s, 2H), 3.63 (m, 4H), 3.31 (s, 3H). | | 1190/ 100 | — |
| 143 | 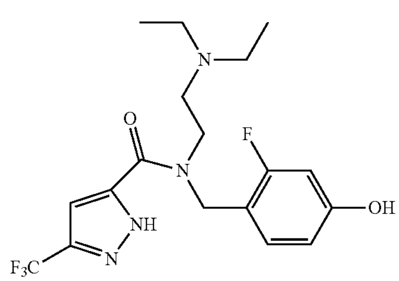 [SMILES: CCN(CC)CCN(Cc1ccc(O)cc1F)C(=O)c1cc(C(F)(F)F)n[nH]1] | ¹H-NMR (CD₃OD/ 400 MHz): 7.15 (nt, 1H), 6.97 (s, 1H), 6.65 (d, 1H), 6.59 (dd, 1H), 4.91 (s, 2H), 3.80 (m, 2H), 3.25 (m, 6H), 1.30 (t, 6H). | | 108/100 | TFA |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 144 | 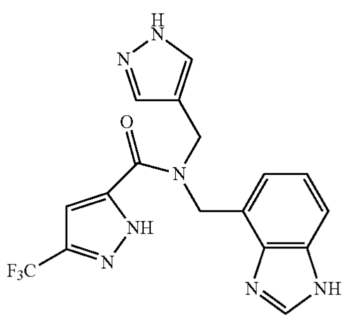 [SMILES: O=C(c1cc(C(F)(F)F)n[nH]1)N(Cc1cn[nH]c1)Cc1cccc2[nH]cnc12] | ¹H-NMR (CD$_3$OD/ 400 MHz): 9.38 (s, 1H), 7.78 (d, 1H), 7.67 (s, 1H), 7.60 (t, 1H), 7.51 (m, 1H), 7.08 (s, 1H), 6.32 (s, 1H), 5.06 (s, 2H). | | 25000/ NA | TFA |
| 145 | 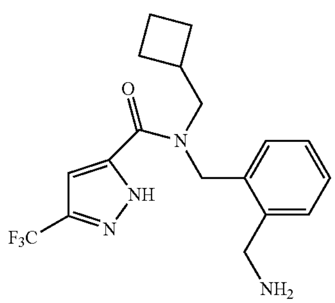 [SMILES: NCc1ccccc1CN(CC1CCC1)C(=O)c1cc(C(F)(F)F)n[nH]1] | ¹H-NMR (CD$_3$OD/ 400 MHz): 7.50- 6.95 (m, 4H), 4.81 (s, 2H), 4.26 (s, 2H), 3.82 (m, 2H), 2.72 (m, 1H), 2.10-1.50 (m, 6H). | | 25500/ NA | TFA |
| 146 | 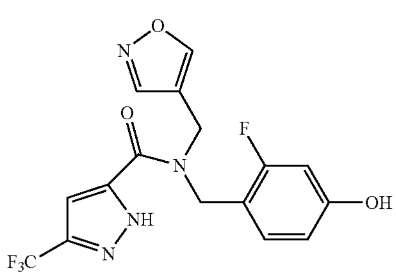 [SMILES: O=C(c1cc(C(F)(F)F)n[nH]1)N(Cc1cnoc1)Cc1ccc(O)cc1F] | ¹H-NMR (CD$_3$OD/ 400 MHz): 9.48 (m, 1H), 7.63 (t, 1H), 7.40-7.00 (m, 3H), 6.62 (m, 1H), 4.49 (m, 2H), 4.26 (m, 2H). | 385.5 | NA/NA | TFA |
| 147 | 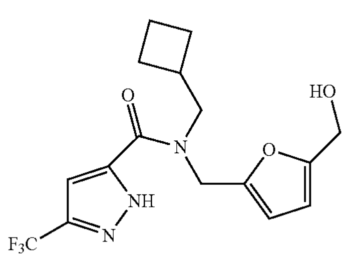 [SMILES: O=C(c1cc(C(F)(F)F)n[nH]1)N(Cc1ccc(CO)o1)CC1CCC1] | ¹H-NMR (CD$_3$OD/ 400 MHz): 7.00 (m, 1H), 6.27 (m, 2H), 4.69 (s, 2H), 4.48 (s, 2H), 3.56 (m, 2H), 2.68 (m, 1H), 2.10- 1.50 (m, 6H). | 358.4 | NA/NA | — |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 148 | 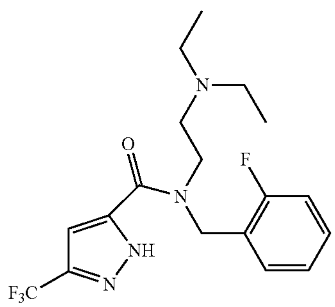 [SMILES: CCN(CC)CCN(Cc1ccccc1F)C(=O)c1cc(C(F)(F)F)n[nH]1] | ¹H-NMR (CD₃OD/ 400 MHz): 7.36 (m, 2H), 7.19 (m, 2H), 6.87 (s, 1H), 4.99 (m, 2H), 3.86 (m, 2H), 3.30 (m, 6H), 1.31 (t, 6H). | 387.5 | 505/100 | TFA |
| 149 | 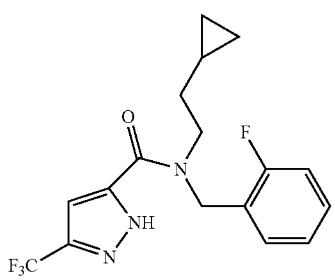 [SMILES: O=C(c1cc(C(F)(F)F)n[nH]1)N(CCC1CC1)Cc1ccccc1F] | ¹H-NMR (CD₃OD/ 400 MHz): 7.46- 7.06 (m, 4H), 7.00- 6.73 (m, 1H), 4.90 (m, 2H), 3.65 (m, 2H), 1.51 (q, 2H), 0.62 (m, 1H), 0.42 (m, 2H), 0.02 (m, 2H). | 356.5 | 1995/ 100 | — |
| 150 | 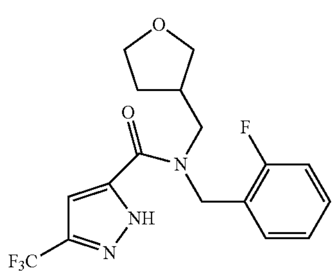 [SMILES: O=C(c1cc(C(F)(F)F)n[nH]1)N(Cc1ccccc1F)CC1CCOC1] | ¹H-NMR (CD₃OD/ 400 MHz): 7.46- 6.70 (m, 5H), 4.92 (m, 2H), 3.96-3.42 (m, 6H), 2.68 (m, 1H), 2.02 (m, 1H), 1.62 (m, 1H). | 372.4 | 16000/ 68 | — |
| 151 | 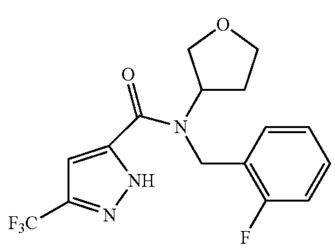 [SMILES: O=C(c1cc(C(F)(F)F)n[nH]1)N(Cc1ccccc1F)C1CCOC1] | ¹H-NMR (CD₃OD/ 400 MHz): 7.39- 7.09 (m, 5H), 4.87 (m, 2H), 4.00 (m, 1H), 3.80 (m, 2H), 3.67 (m, 1H), 3.29 (m, 1H), 2.30 (m, 1H), 2.06 (m, 1H). | 358.4 | NA/NA | — |
| 152 | 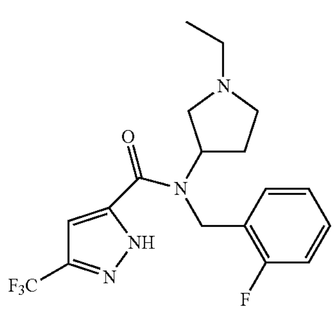 [SMILES: CCN1CCC(N(Cc2ccccc2F)C(=O)c2cc(C(F)(F)F)n[nH]2)C1] | ¹H-NMR (CD₃OD/ 400 MHz): 7.39 (m, 2H), 7.25 (t, 1H), 7.17 (t, 1H), 6.92 (m, 1H), 5.02 (m, 2H), 4.34 (m, 1H), 3.96 (d, 1H), 3.86 (t, 1H), 3.70-3.40 (m, 1H), 3.28 (m, 1H), 2.32 (m, 2H), 1.36 (t, 3H). | 385.5 | 13500/ 68 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 153 | 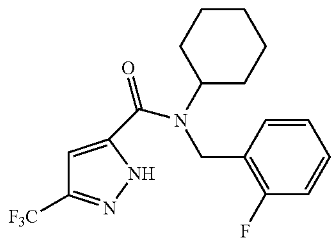 [SMILES: O=C(c1cc(C(F)(F)F)n[nH]1)N(Cc1ccccc1F)C1CCCCC1] | ¹H-NMR (CD₃OD/ 400 MHz): 7.32 (m, 2H), 7.10 (m, 2H), 6.98-6.51 (m, 1H), 4.81 (s, 2H), 4.40-4.00 (m, 1H), 1.79 (m, 4H), 1.70-1.04 (m, 6H). | 370.5 | 19000/ 57 | — |
| 154 | 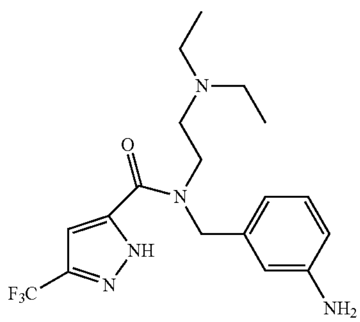 [SMILES: CCN(CC)CCN(Cc1cccc(N)c1)C(=O)c1cc(C(F)(F)F)n[nH]1] | ¹H-NMR (CD₃OD/ 400 MHz): 7.54-6.72 (m, 5H), 5.04 (s, 2H), 3.86 (m, 2H), 3.35 (m, 6H), 1.33 (t, 6H). | 384.5 | 1430/ 100 | TFA |
| 155 | 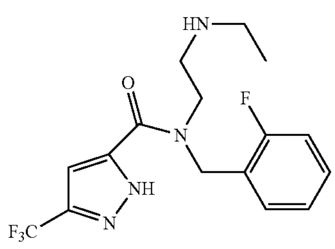 [SMILES: CCNCCN(Cc1ccccc1F)C(=O)c1cc(C(F)(F)F)n[nH]1] | ¹H-NMR (CD₃OD/ 400 MHz): 7.35 (m, 2H), 7.19 (m, 2H), 6.81 (s, 1H), 5.03 (s, 2H), 3.81 (m, 2H), 3.26 (m, 2H), 3.10 (q, 2H), 1.32 (t, 3H). | 359.4 | 2150/ 100 | TFA |
| 156 | 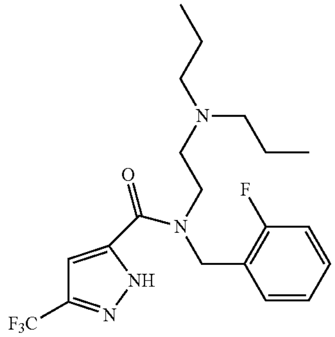 [SMILES: CCCN(CCC)CCN(Cc1ccccc1F)C(=O)c1cc(C(F)(F)F)n[nH]1] | ¹H-NMR (CD₃OD/ 400 MHz): 7.66 (m, 1H), 7.53 (m, 1H), 7.27 (m, 2H), 6.93 (s, 1H), 4.56 (s, 2H), 3.92 (m, 2H), 3.51 (m, 4H), 3.27 (m, 2H), 1.91 (m, 2H), 1.65 (m, 2H), 1.05 (t, 3H), 0.89 (t, 3H). | 415.5 | NA/NA | TFA |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 157 | 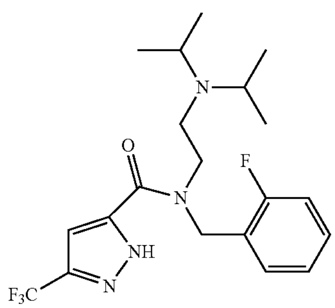 [SMILES: CC(C)N(CCN(Cc1ccccc1F)C(=O)c1cc(C(F)(F)F)n[nH]1)C(C)C] | ¹H-NMR (CD₃OD/ 400 MHz): 7.41 (m, 2H), 7.23 (m, 2H), 6.96 (s, 1H), 5.10 (s, 2H), 3.78 (m, 4H), 3.24 (t, 2H), 1.34 (s, 12H). | 415.5 | NA/NA | TFA |
| 158 | 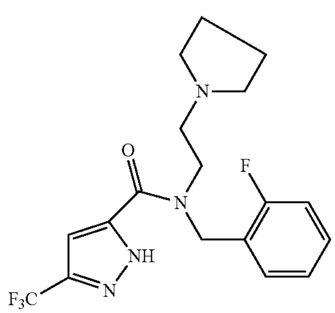 [SMILES: O=C(c1cc(C(F)(F)F)n[nH]1)N(CCN1CCCC1)Cc1ccccc1F] | ¹H-NMR (CD₃OD 400 MHz): 7.34 (m, 2H), 7.19 (m, 2H), 6.81 (s, 1H), 5.03 (s, 2H), 4.20-3.40 (m, 6H), 3.15 (m, 2H), 2.10 (m, 4H). | 385.4 | 265/100 | TFA |
| 159 | 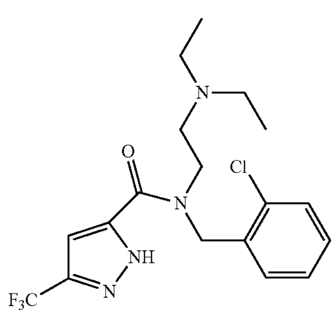 [SMILES: CCN(CC)CCN(Cc1ccccc1Cl)C(=O)c1cc(C(F)(F)F)n[nH]1] | ¹H-NMR (CD₃OD/ 400 MHz): 7.49 (m, 1H), 7.39 (m, 3H), 6.72 (s, 1H), 5.07 (s, 2H), 3.89 (m, 2H), 3.31 (m, 6H), 1.32 (t, 6H). | 403.4 | 73/100 | TFA |
| 160 | 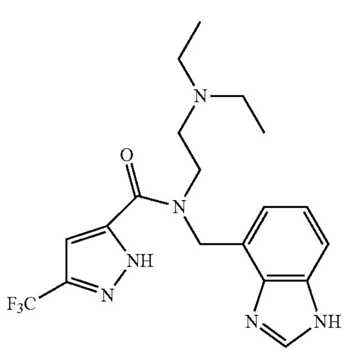 [SMILES: CCN(CC)CCN(Cc1cccc2[nH]cnc12)C(=O)c1cc(C(F)(F)F)n[nH]1] | ¹H-NMR (CD₃OD/ 400 MHz): 9.24 (m, 1H), 7.80 (d, 1H), 7.61 (t, 1H), 7.47 (m, 1H), 7.33-6.72 (m, 1H), 5.39 (m, 2H), 3.94 (m, 2H), 3.41 (m, 6H), 1.33 (t, 6H). | 409.5 | 825/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 161 | 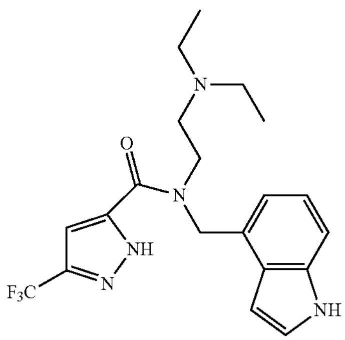 [SMILES: CCN(CC)CCN(Cc1cccc2[nH]ccc12)C(=O)c1cc(C(F)(F)F)n[nH]1] | ¹H-NMR (CD₃OD/ 400 MHz): 7.45 (d, 1H), 7.33 (nd, 1H), 7.17 (t, 1H), 7.00 (d, 1H), 6.94 (s, 1H), 6.37 (m, 1H), 5.24 (m, 2H), 3.88 (m, 2H), 3.20-2.90 (m, 6H), 1.18 (t, 6H). | 408.5 | 76/100 | TFA |
| 162 | 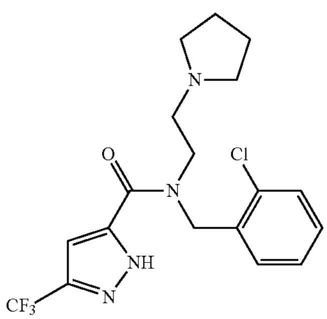 [SMILES: O=C(c1cc(C(F)(F)F)n[nH]1)N(CCN1CCCC1)Cc1ccccc1Cl] | ¹H-NMR (CD₃OD/ 400 MHz): 7.52- 7.22 (m, 5H), 5.03 (s, 2H), 3.85 (m, 4H), 3.45 (m, 2H), 3.13 (m, 2H), 2.10 (m, 4H). | 401.4 | 107/100 | TFA |
| 163 | 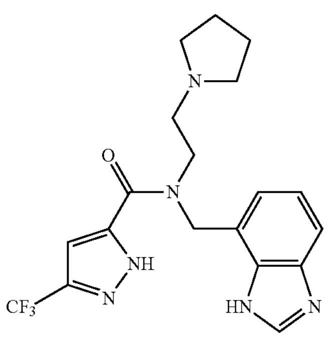 [SMILES: O=C(c1cc(C(F)(F)F)n[nH]1)N(CCN1CCCC1)Cc1cccc2nc[nH]c12] | ¹H-NMR (CD₃OD/ 400 MHz): 9.34 (s, 1H), 7.79 (d, 1H), 7.60 (t, 1H), 7.44 (m, 1H), 7.33-6.72 (m, 1H), 5.38 (m, 2H), 4.30-3.40 (m, 6H), 3.17 (m, 2H), 2.09 (m, 4H). | 407.4 | 1085/100 | TFA |
| 164 | 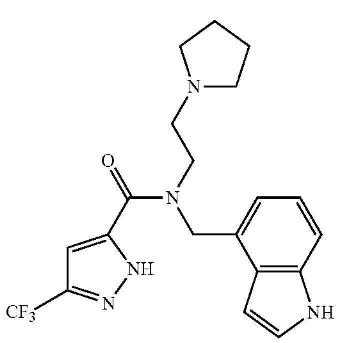 [SMILES: O=C(c1cc(C(F)(F)F)n[nH]1)N(CCN1CCCC1)Cc1cccc2[nH]ccc12] | ¹H-NMR (CD₃OD/ 400 MHz): 7.41 (d, 1H), 7.31 (nd, 1H), 7.14 (t, 1H), 6.92 (d, 1H), 6.78 (s, 1H), 6.39 (m, 1H), 5.20 (s, 2H), 3.86 (m, 2H), 3.70 (m, 2H), 3.29 (m, 2H), 3.01 (m, 2H), 2.02 (m, 4H). | 406.4 | 113/100 | TFA |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 165 | 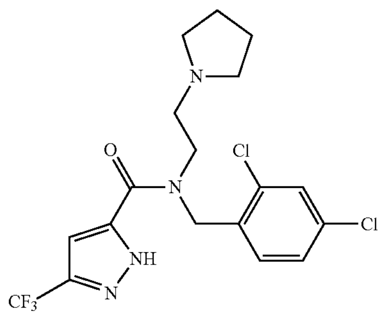 [SMILES: O=C(c1cc(C(F)(F)F)n[nH]1)N(CCN1CCCC1)Cc1ccc(Cl)cc1Cl] | ¹H-NMR (CD$_3$OD/ 400 MHz): 7.55 (m, 1H), 7.37 (m, 1H), 7.29 (d, 1H), 5.02 (s, 2H), 3.83 (m, 4H), 3.46 (m, 2H), 3.15 (m, 2H), 2.10 (m, 4H). | 435.4 + 437.4 | 45000/ 50 | TFA |
| 166 | 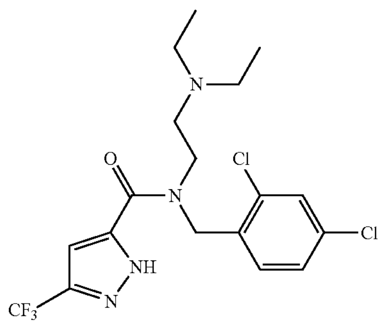 [SMILES: CCN(CC)CCN(Cc1ccc(Cl)cc1Cl)C(=O)c1cc(C(F)(F)F)n[nH]1] | ¹H-NMR (CD$_3$OD/ 400 MHz): 7.56 (s, 1H), 7.36 (m, 2H), 7.29-6.60 (m, 1H), 5.04 (s, 2H), 3.84 (m, 2H), 3.32 (m, 6H), 1.32 (t, 6H). | 437.4 + 439.4 | NA/NA | TFA |
| 167 | 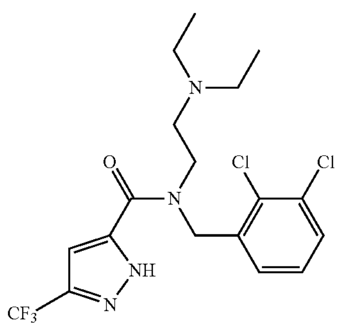 [SMILES: CCN(CC)CCN(Cc1cccc(Cl)c1Cl)C(=O)c1cc(C(F)(F)F)n[nH]1] | ¹H-NMR (CD$_3$OD/ 400 MHz): 7.65- 6.45 (m, 4H), 4.96 (m, 2H), 3.86 (m, 2H), 3.30 (m, 6H), 1.32 (t, 6H). | 437.4 + 439.4 | 186/100 | TFA |
| 168 | 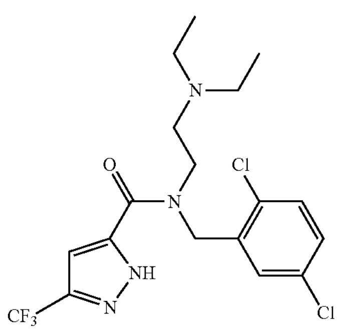 [SMILES: CCN(CC)CCN(Cc1cc(Cl)ccc1Cl)C(=O)c1cc(C(F)(F)F)n[nH]1] | ¹H-NMR (CD$_3$OD/ 400 MHz): 7.55- 6.55 (m, 4H), 4.92 (m, 2H), 3.86 (m, 2H), 3.30 (m, 6H), 1.32 (t, 6H). | 437.4 + 439.4 | 97/100 | TFA |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 169 | 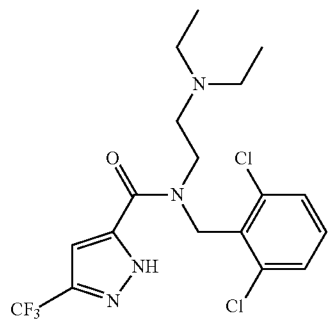 [SMILES: CCN(CC)CCN(Cc1c(Cl)cccc1Cl)C(=O)c1cc(C(F)(F)F)n[nH]1] | ¹H-NMR (CD₃OD/ 400 MHz): 7.51 (m, 2H), 7.41 (m, 1H), 7.20 (s, 1H), 5.32 (s, 2H), 3.67 (m, 2H), 3.21 (m, 4H), 3.04 (m, 2H), 1.24 (t, 6H). | 437.4 + 439.4 | 66/100 | TFA |
| 170 | 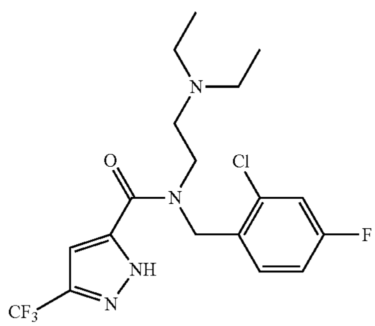 [SMILES: CCN(CC)CCN(Cc1ccc(F)cc1Cl)C(=O)c1cc(C(F)(F)F)n[nH]1] | ¹H-NMR (CD₃OD/ 400 MHz): 7.36 (m, 2H), 7.21-6.68 (m, 2H), 5.03 (s, 2H), 3.84 (m, 2H), 3.32 (m, 6H), 1.32 (t, 6H). | 421.4 | 505/100 | TFA |
| 171 | 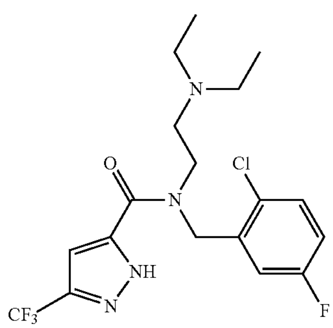 [SMILES: CCN(CC)CCN(Cc1cc(F)ccc1Cl)C(=O)c1cc(C(F)(F)F)n[nH]1] | ¹H-NMR (CD₃OD/ 400 MHz): 7.50 (m, 1H), 7.28-6.50 (m, 3H), 4.95 (m, 2H), 3.87 (m, 2H), 3.30 (m, 6H), 1.33 (t, 6H). | 421.4 | 88/100 | TFA |
| 172 | 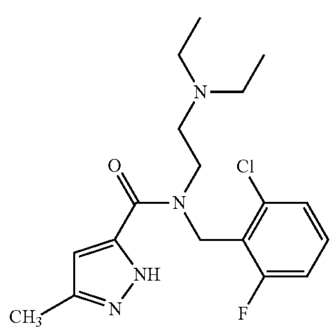 [SMILES: CCN(CC)CCN(Cc1c(F)cccc1Cl)C(=O)c1cc(C)n[nH]1] | ¹H-NMR (CD₃OD/ 400 MHz): 7.43 (m, 1H), 7.35 (d, 1H), 7.20 (t, 1H), 7.16 (s, 1H), 5.15 (s, 2H), 3.71 (m, 2H), 3.22 (m, 4H), 3.12 (m, 2H), 1.26 (t, 6H). | 421.4 | 94/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 173 | 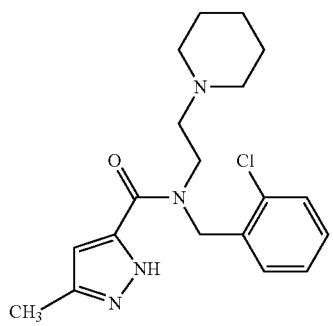 [SMILES: Cc1cc(C(=O)N(CCN2CCCCC2)Cc2ccccc2Cl)[nH]n1] | ¹H-NMR (CD₃OD/ 400 MHz): 7.52-6.42 (m, 5H), 4.97 (s, 2H), 3.88 (m, 2H), 3.68 (m, 2H), 3.32 (m, 2H), 2.97 (m, 2H), 1.96 (m, 2H), 1.78 (m, 3H), 1.54 (m, 1H). | 415.4 | 66/100 | TFA |
| 174 | 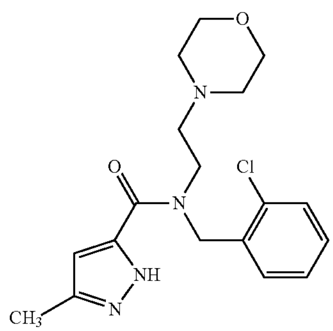 [SMILES: Cc1cc(C(=O)N(CCN2CCOCC2)Cc2ccccc2Cl)[nH]n1] | ¹H-NMR (CD₃OD/ 400 MHz): 7.52-6.42 (m, 5H), 5.03 (s, 2H), 4.20-3.45 (m, 12H). | 417.4 | 1495/100 | TFA |
| 175 | 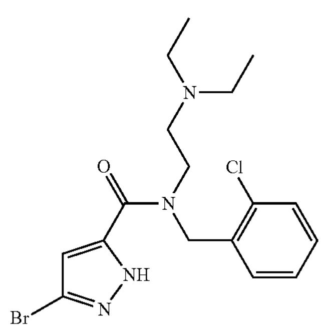 [SMILES: CCN(CC)CCN(Cc1ccccc1Cl)C(=O)c1cc(Br)n[nH]1] | ¹H-NMR (CD₃OD/ 400 MHz): 7.45 (m, 1H), 7.34 (m, 3H), 6.87-6.44 (m, 1H), 5.10 (s, 2H), 3.82 (m, 2H), 3.28 (m, 6H), 1.29 (t, 6H). | 413.4 + 415.4 | 305/100 | TFA |
| 176 | 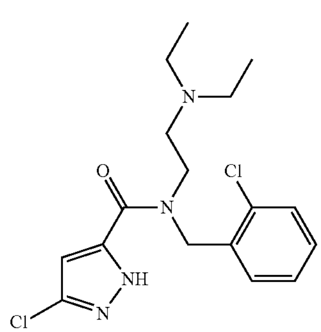 [SMILES: CCN(CC)CCN(Cc1ccccc1Cl)C(=O)c1cc(Cl)n[nH]1] | ¹H-NMR (CD₃OD/ 400 MHz): 7.47 (m, 1H), 7.35 (m, 3H), 6.80-6.32 (m, 1H), 5.06 (s, 2H), 3.83 (m, 2H), 3.29 (m, 6H), 1.30 (t, 6H). | 369.4 | 1150/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 177 | 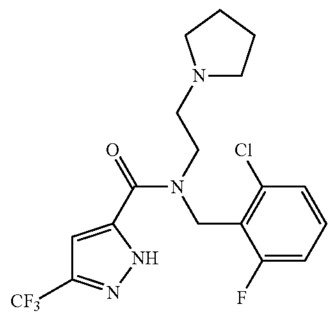 [SMILES: O=C(c1cc(C(F)(F)F)n[nH]1)N(CCN1CCCC1)Cc1c(F)cccc1Cl] | ¹H-NMR (CD₃OD/ 400 MHz): 7.41 (m, 1H), 7.31 (m, 1H), 7.14 (m, 2H), 5.19 (s, 2H), 3.71 (m, 4H), 3.33 (m, 2H), 3.08 (m, 2H), 2.08 (m, 4H). | 419.4 | 180/100 | TFA |
| 178 | 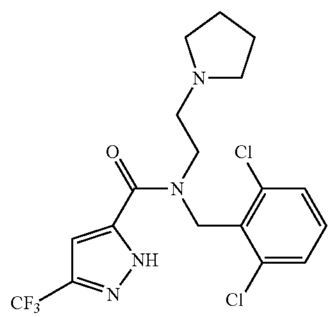 [SMILES: O=C(c1cc(C(F)(F)F)n[nH]1)N(CCN1CCCC1)Cc1c(Cl)cccc1Cl] | ¹H-NMR (CD₃OD/ 400 MHz): 7.48 (m, 2H), 7.38 (m, 1H), 7.18 (s, 1H), 5.31 (s, 2H), 3.64 (m, 4H), 3.26 (m, 2H), 3.25 (m, 2H), 2.02 (m, 4H). | 435.4 | 126/100 | TFA |
| 179 | 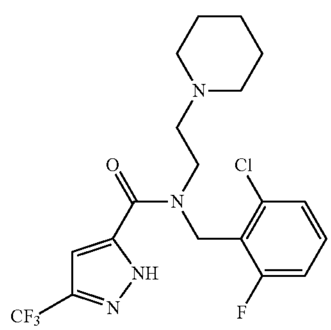 [SMILES: O=C(c1cc(C(F)(F)F)n[nH]1)N(CCN1CCCCC1)Cc1c(F)cccc1Cl] | ¹H-NMR (CD₃OD/ 400 MHz): 7.41 (m, 1H), 7.32 (m, 1H), 7.15 (m, 2H), 5.17 (s, 2H), 3.73 (m, 2H), 3.56 (m, 2H), 3.18 (m, 2H), 2.93 (m, 2H), 1.92 (m, 2H), 1.75 (m, 3H), 1.48 (m, 1H). | 433.5 | 133/100 | TFA |
| 180 | 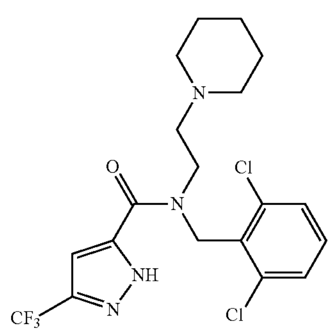 [SMILES: O=C(c1cc(C(F)(F)F)n[nH]1)N(CCN1CCCCC1)Cc1c(Cl)cccc1Cl] | ¹H-NMR (CD₃OD/ 400 MHz): 7.48 (m, 2H), 7.39 (m, 1H), 7.18 (s, 1H), 5.30 (s, 2H), 3.68 (m, 2H), 3.52 (m, 2H), 3.10 (m, 2H), 2.90 (m, 2H), 1.90 (m, 2H), 1.74 (m, 3H), 1.48 (m, 1H). | 449.4 | 154/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 181 | 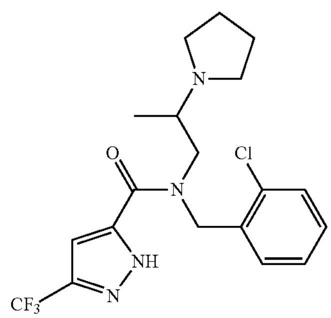 [SMILES: CC(CN(Cc1ccccc1Cl)C(=O)c1cc(C(F)(F)F)n[nH]1)N1CCCC1] | ¹H-NMR (CD₃OD/ 400 MHz): 7.46 (m, 1H), 7.34 (m, 2H), 7.27 (m, 1H), 6.66 (bs, 1H), 5.04 (s, 2H), 4.04 (m, 1H), 3.68 (m, 4H), 3.24 (m, 2H), 2.60 (m, 2H), 1.39 (d, 3H). | 415.5 | 430/100 | TFA |
| 182 | 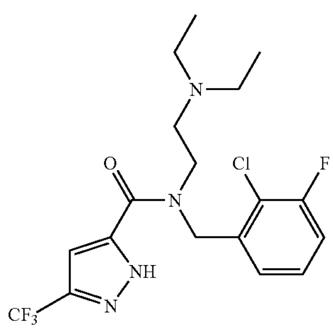 [SMILES: CCN(CC)CCN(Cc1cccc(F)c1Cl)C(=O)c1cc(C(F)(F)F)n[nH]1] | ¹H-NMR (CD₃OD/ 400 MHz): 7.39 (m, 1H), 7.26 (m, 1H), 7.17 (d, 1H), 6.66 (bs, 1H), 5.08 (m, 2H), 3.86 (m, 2H), 3.30 (m, 6H), 1.32 (t, 6H). | 421.5 | 109/100 | TFA |
| 183 | 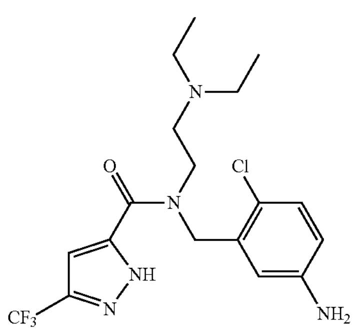 [SMILES: CCN(CC)CCN(Cc1cc(N)ccc1Cl)C(=O)c1cc(C(F)(F)F)n[nH]1] | ¹H-NMR (CD₃OD/ 400 MHz): 7.34-6.66 (m, 4H), 4.96 (s, 2H), 3.85 (m, 2H), 3.29 (m, 6H), 1.31 (t, 6H). | 418.5 | 185/100 | TFA |
| 184 | 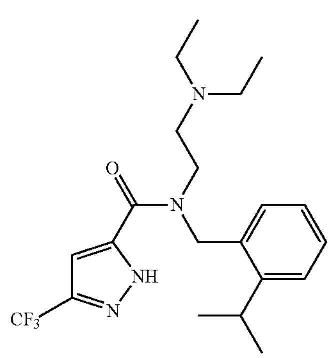 [SMILES: CCN(CC)CCN(Cc1ccccc1C(C)C)C(=O)c1cc(C(F)(F)F)n[nH]1] | ¹H-NMR (CD₃OD/ 400 MHz): 7.41 (m, 1H), 7.37 (m, 1H), 7.24 (m, 1H), 7.16 (m, 1H), 6.54 (bs, 1H), 5.01 (s, 2H), 3.89 (m, 2H), 3.31 (m, 6H), 2.99 (m, 1H), 1.31 (t, 6H), 1.19 (d, 6H). | 411.5 | 1950/85 | TFA |

TABLE 1-continued

Exemplary Compounds

| EX | Structure | NMR | ES-MS (M+ + 1) | PKM$_2$ AC$_{50}$ (nM)/ Max. Resp.* (%) | Note† |
|---|---|---|---|---|---|
| 185 | 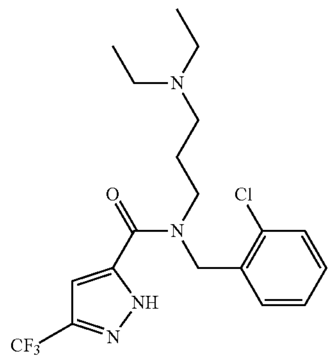 [SMILES: CCN(CC)CCCN(Cc1ccccc1Cl)C(=O)c1cc(C(F)(F)F)n[nH]1] | $^1$H-NMR (CD$_3$OD/ 400 MHz): 7.45 (m, 1H), 7.33 (m, 3H), 7.15-6.59 (m, 1H), 4.99 (s, 2H), 3.59 (m, 2H), 3.18 (m, 6H), 2.01 (m, 2H), 1.29 (t, 6H). | 417.4 | 1750/53 | TFA |
| 186 | 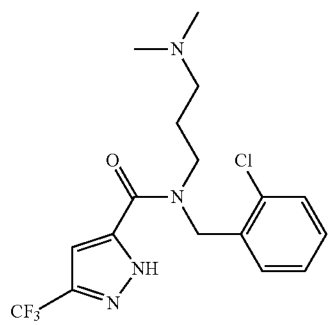 [SMILES: CN(C)CCCN(Cc1ccccc1Cl)C(=O)c1cc(C(F)(F)F)n[nH]1] | $^1$H-NMR (CD$_3$OD/ 400 MHz): 7.45 (m, 1H), 7.33 (m, 3H), 7.15-6.59 (m, 1H), 4.97 (s, 2H), 3.61 (m, 2H), 3.16 (m, 6H), 2.88 (s, 6H), 2.00 (m, 2H). | 389.4 | 375/100 | TFA |
| 187 | 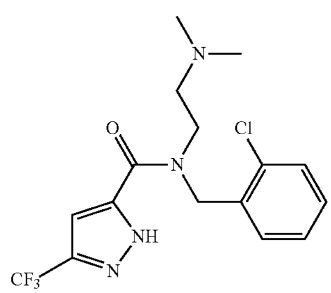 [SMILES: CN(C)CCN(Cc1ccccc1Cl)C(=O)c1cc(C(F)(F)F)n[nH]1] | $^1$H-NMR (CD$_3$OD/ 400 MHz) 7.47 (m, 1H), 7.33 (m, 3H), 6.61 (bs, 1H), 5.04 (bs, 2H), 3.87 (t, 2H), 3.38 (t, 6H), 2.97 (s, 6H). | 375.4 | 295/100 | TFA |
| 188 | 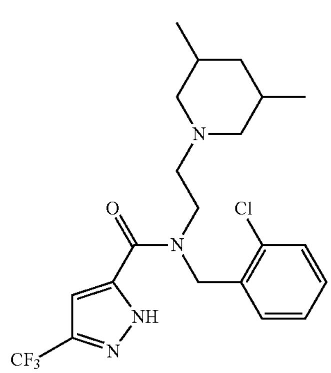 [SMILES: CC1CC(C)CN(CCN(Cc2ccccc2Cl)C(=O)c2cc(C(F)(F)F)n[nH]2)C1] | $^1$H-NMR (CD$_3$OD/ 400 MHz): 7.48 (m, 1H), 7.33 (m, 3H), 6.53 (bs, 1H), 4.99 (bs, 2H), 3.90 (m, 2H), 3.59 (m, 2H), 3.35 (m, 2H), 2.52 (t, 2H), 1.88 (m, 3H), 0.98 (m, 7H). | 443.5 | 46/60 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 189 | 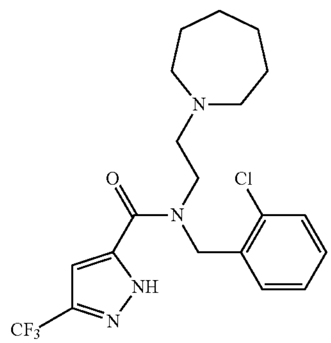 [SMILES: O=C(c1cc(C(F)(F)F)n[nH]1)N(CCN1CCCCCC1)Cc1ccccc1Cl] | ¹H-NMR (CD₃OD/ 400 MHz): 7.47 (m, 1H), 7.34 (m, 3H), 6.62 (bs, 1H), 5.03 (bs, 2H), 3.88 (m, 2H), 3.56 (m, 2H), 3.37 (m, 2H), 3.25 (m, 2H), 1.93 (m, 4H), 1.73 (m, 4H). | 429.4 | 24/100 | TFA |
| 190 | 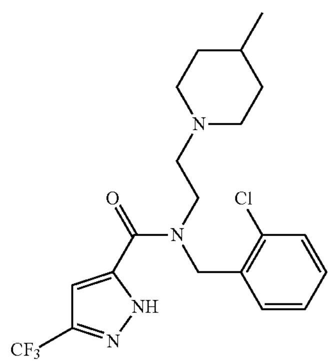 [SMILES: CC1CCN(CCN(Cc2ccccc2Cl)C(=O)c2cc(C(F)(F)F)n[nH]2)CC1] | ¹H-NMR (CD₃OD/ 400 MHz): 7.48 (m, 1H), 7.33 (m, 3H), 6.52 (bs, 1H), 4.98 (bs, 2H), 3.88 (m, 2H), 3.71 (m, 2H), 3.33 (m, 2H), 2.97 (m, 2H), 1.93 (m, 2H), 1.70 (m, 1H), 1.44 (m, 2H), 1.00 (d, 3H). | 429.4 | 42/100 | TFA |
| 191 | 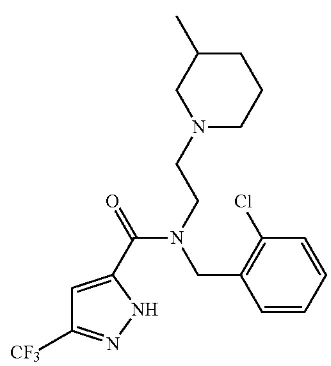 | ¹H-NMR (CD₃OD/ 400 MHz): 7.48 (m, 1H), 7.33 (m, 3H), 6.50 (bs, 1H), 4.97 (bs, 2H), 3.90 (m, 2H), 3.63 (m, 2H), 3.33 (m, 2H), 2.86 (t, 2H), 2.59 (t, 2H), 1.86 (m, 4H), 1.18 (m, 1H), 1.00 (d, 3H). | 429.4 | 29/100 | TFA |
| 192 | 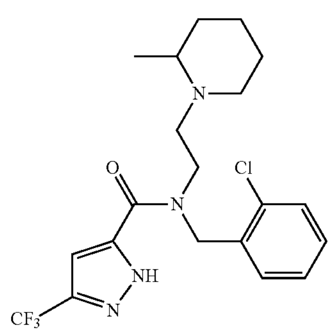 [SMILES: CC1CCCCN1CCN(Cc1ccccc1Cl)C(=O)c1cc(C(F)(F)F)n[nH]1] | ¹H-NMR (CD₃OD/ 400 MHz): 7.48 (m, 1H), 7.33 (m, 3H), 6.50 (bs, 1H), 4.99 (bs, 2H), 3.90 (m, 2H), 3.62 (m, 2H), 3.33 (m, 2H), 2.05-1.20 (m, 10H). | 429.4 | 104/100 | TFA |

TABLE 1-continued

Exemplary Compounds

| EX | Structure | NMR | ES-MS (M+ + 1) | PKM$_2$ AC$_{50}$ (nM)/ Max. Resp.* (%) | Note† |
|---|---|---|---|---|---|
| 193 | 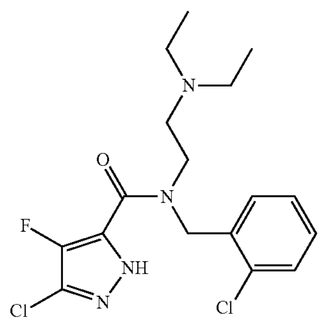 [SMILES: CCN(CC)CCN(Cc1ccccc1Cl)C(=O)c1[nH]nc(Cl)c1F] | $^1$H-NMR (CD$_3$OD/ 400 MHz): 7.40 (m, 4H), 4.94 (s, 2H), 3.76 (m, 2H), 3.22 (m, 6H), 1.26 (t, 6H). | 387.4 | 14000/ 58 | TFA |
| 194 | 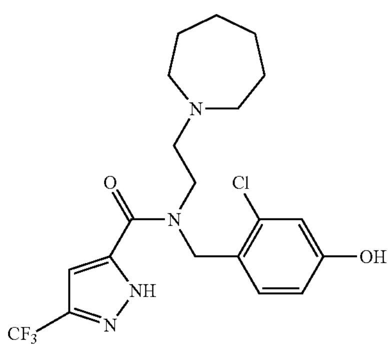 [SMILES: O=C(c1cc(C(F)(F)F)n[nH]1)N(CCN1CCCCCC1)Cc1ccc(O)cc1Cl] | $^1$H-NMR (CD$_3$OD/ 400 MHz): 7.18 (m, 1H), 6.92-6.66 (m, 3H), 4.87 (bs, 2H), 3.81 (m, 2H), 3.50 (m, 2H), 3.28 (m, 4H), 1.93 (m, 4H), 1.73 (s, 4H). | 445.4 | 43/100 | TFA |
| 195 | 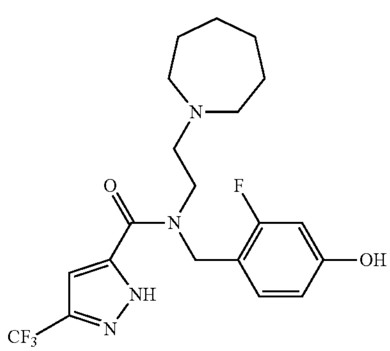 [SMILES: O=C(c1cc(C(F)(F)F)n[nH]1)N(CCN1CCCCCC1)Cc1ccc(O)cc1F] | $^1$H-NMR (CD$_3$OD/ 400 MHz): 7.10 (m, 1H), 6.91 (bs, 1H), 6.62 (d, 1H), 6.57 (d, 1H), 4.88 (bs, 2H), 3.80 (m, 2H), 3.51 (m, 2H), 3.26 (m, 4H), 1.91 (m, 4H), 1.72 (s, 4H). | 429.5 | 95/100 | TFA |
| 196 | 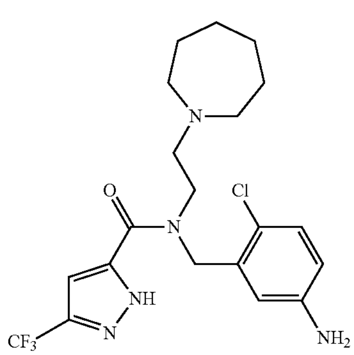 | $^1$H-NMR (CD$_3$OD/ 400 MHz): 7.10 (m, 1H), 6.73 (m, 3H), 4.88 (bs, 2H), 3.86 (m, 2H), 3.54 (m, 2H), 3.28 (m, 4H), 1.92 (m, 4H), 1.74 (s, 4H). | 444.4 | 99/100 | TFA |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 197 | 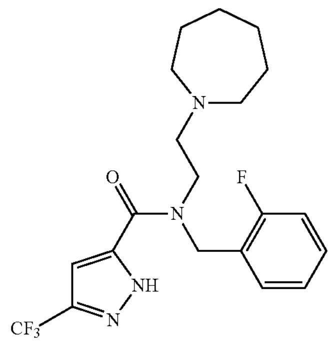 [SMILES: O=C(c1cc(C(F)(F)F)n[nH]1)N(CCN1CCCCCC1)Cc1ccccc1F] | ¹H-NMR (CD₃OD/ 400 MHz): 7.33 (m, 2H), 7.18 (m, 2H), 6.78 (bs, 1H), 5.00 (bs, 2H), 3.85 (m, 2H), 3.55 (m, 2H), 3.37 (m, 2H), 3.25 (m, 2H), 1.91 (m, 4H), 1.72 (s, 4H). | 413.4 | 63/100 | TFA |
| 198 | 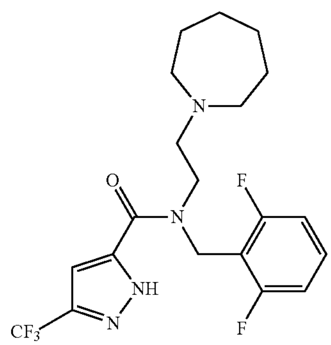 [SMILES: O=C(c1cc(C(F)(F)F)n[nH]1)N(CCN1CCCCCC1)Cc1c(F)cccc1F] | ¹H-NMR (CD₃OD/ 400 MHz): 7.42 (m, 1H), 7.10- 6.95 (m, 32H), 5.09 (bs, 2H), 3.79 (m, 2H), 3.51 (m, 2H), 3.31 (m, 2H), 3.21 (m, 2H), 1.90 (m, 4H), 1.72 (s, 4H). | 431.5 | 130/100 | TFA |
| 199 | 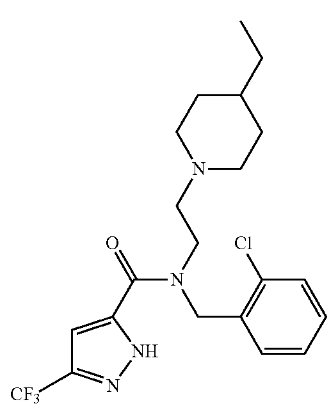 [SMILES: CCC1CCN(CCN(Cc2ccccc2Cl)C(=O)c2cc(C(F)(F)F)n[nH]2)CC1] | ¹H-NMR (CD₃OD/ 400 MHz): 7.49 (m, 1H), 7.33 (m, 3H), 6.50 (bs, 1H), 4.97 (bs, 2H), 3.88 (m, 2H), 3.70 (m, 2H), 3.33 (m, 2H), 2.97 (m, 2H), 2.00 (m, 2H), 1.83 (m, 5H), 0.94 (t, 3H). | 443.5 | 100/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 200 | 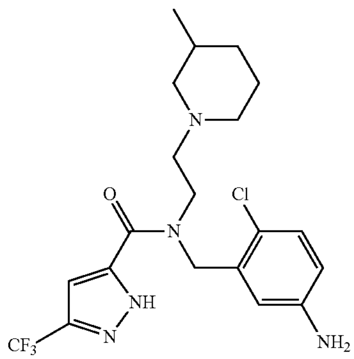 [SMILES: CC1CCCN(CCN(Cc2cc(N)ccc2Cl)C(=O)c2cc(C(F)(F)F)n[nH]2)C1] | ¹H-NMR (CD₃OD/ 400 MHz): 7.22 (m, 1H), 6.74 (m, 3H), 4.90 (bs, 2H), 3.88 (m, 2H), 3.63 (m, 2H), 3.31 (m, 2H), 2.87 (t, 1H), 2.59 (t, 1H), 1.86 (m, 4H), 1.18 (m, 1H), 1.00 (d, 3H). | 444.5 | 130/100 | TFA |
| 201 | 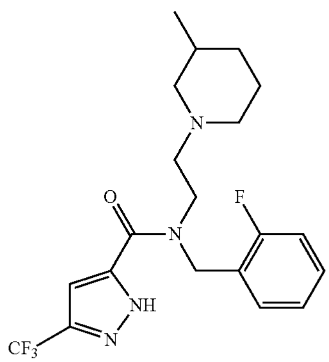 [SMILES: CC1CCCN(CCN(Cc2ccccc2F)C(=O)c2cc(C(F)(F)F)n[nH]2)C1] | ¹H-NMR (CD₃OD/ 400 MHz): 7.34 (m, 2H), 7.18 (m, 2H), 6.81 (bs, 1H), 5.02 (bs, 2H), 3.86 (m, 2H), 3.63 (m, 2H), 3.31 (m, 2H), 2.85 (t, 1H), 2.58 (t, 1H), 1.85 (m, 4H), 1.16 (m, 1H), 0.98 (d, 3H). | 413.5 | 215/100 | TFA |
| 202 | 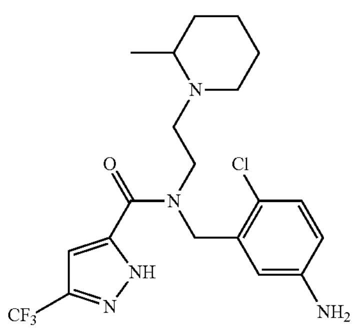 [SMILES: CC1CCCCN1CCN(Cc1cc(N)ccc1Cl)C(=O)c1cc(C(F)(F)F)n[nH]1] | ¹H-NMR (CD₃OD/ 400 MHz): 7.23 (m, 1H), 6.77 (m, 3H), 4.94 (bs, 2H), 3.86 (m, 2H), 3.76 (m, 1H), 3.59 (m, 1H), 3.39 (m, 1H), 3.25 (m, 2H), 3.05 (t, 1H), 2.06-1.68 (m, 5H), 1.57 (m, 2H), 1.38 (m, 3H). | 444.4 | 395/100 | TFA |
| 203 | 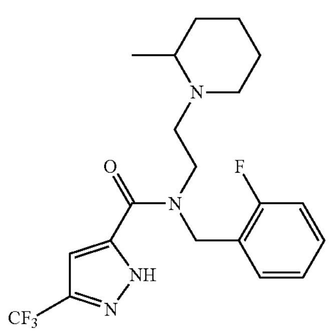 [SMILES: CC1CCCCN1CCN(Cc1ccccc1F)C(=O)c1cc(C(F)(F)F)n[nH]1] | ¹H-NMR (CD₃OD/ 400 MHz): 7.36 (m, 2H), 7.18 (m, 2H), 6.85 (bs, 1H), 5.02 (bs, 2H), 3.86 (m, 2H), 3.77 (m, 1H), 3.59 (m, 1H), 3.40 (m, 1H), 3.26 (m, 2H), 2.85 (t, 1H), 2.58 (t, 1H), 2.22-1.68 (m, 5H), 1.58 (m, 2H), 1.36 (m, 3H). | 413.5 | 550/100 | TFA |

TABLE 1-continued

Exemplary Compounds

| EX | Structure | NMR | ES-MS (M$^+$ + 1) | PKM$_2$ AC$_{50}$ (nM)/ Max. Resp.* (%) | Note† |
|---|---|---|---|---|---|
| 204 | 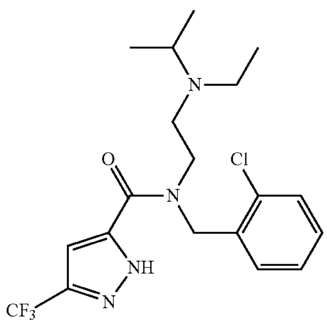 [SMILES: CCN(CCN(Cc1ccccc1Cl)C(=O)c1cc(C(F)(F)F)n[nH]1)C(C)C] | $^1$H-NMR (CD$_3$OD/ 400 MHz): 7.48 (m, 1H), 7.39 (m, 3H), 6.74 (bs, 1H), 5.07 (m, 2H), 3.86 (m, 2H), 3.75 (m, 1H), 3.25 (m, 4H), 1.31 (m, 9H). | 417.4 | 880/53 | TFA |
| 205 | 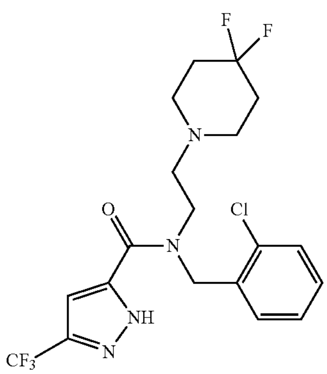 [SMILES: O=C(c1cc(C(F)(F)F)n[nH]1)N(CCN1CCC(F)(F)CC1)Cc1ccccc1Cl] | $^1$H-NMR (CD$_3$OD/ 400 MHz): 7.48 (m, 1H), 7.32 (m, 3H), 6.60 (bs, 1H), 5.04 (s, 2H), 3.92 (m, 2H), 3.80-3.38 (m, 6H), 2.38 (m, 4H). | 451.4 | 2050/100 | TFA |
| 206 | 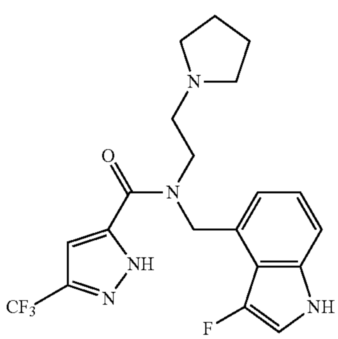 [SMILES: O=C(c1cc(C(F)(F)F)n[nH]1)N(CCN1CCCC1)Cc1cccc2[nH]cc(F)c12] | $^1$H-NMR (CD$_3$OD/ 400 MHz): 7.32 (m, 1H), 7.15 (m, 2H), 6.92 (m, 1H), 6.75 (bs, 1H), 5.27 (m, 2H), 3.88 (t, 2H), 3.73 (m, 2H), 3.33 (t, 2H), 3.04 (m, 2H), 2.02 (m, 4H). | 424.4 | 136/100 | TFA |
| 207 | 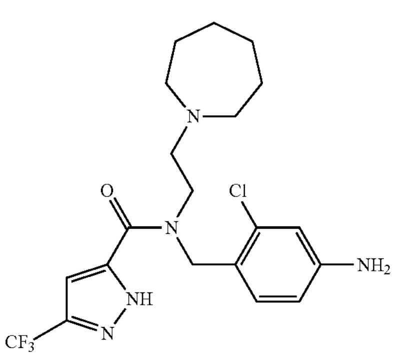 [SMILES: Nc1ccc(CN(CCN2CCCCCC2)C(=O)c2cc(C(F)(F)F)n[nH]2)c(Cl)c1] | $^1$H-NMR (CD$_3$OD/ 400 MHz): 7.10 (d, 1H), 6.84 (m, 2H), 6.71 (d, 1H), 4.89 (s, 2H), 3.80 (m, 2H), 3.49 (m, 2H), 3.22 (m, 4H), 1.90 (m, 4H), 1.72 (s, 4H). | 444.4 | 170/75 | TFA |

TABLE 1-continued

Exemplary Compounds

| EX | Structure | NMR | ES-MS (M+ + 1) | PKM2 AC50 (nM)/ Max. Resp.* (%) | Note† |
|---|---|---|---|---|---|
| 208 | 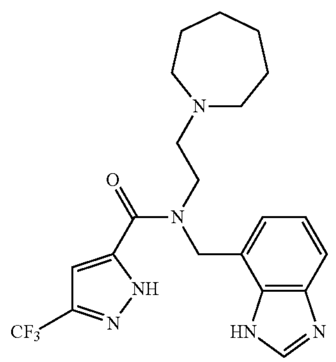 [SMILES: O=C(c1cc(C(F)(F)F)n[nH]1)N(CCN1CCCCCC1)Cc1cccc2nc[nH]c12] | ¹H-NMR (CD3OD/ 400 MHz): 9.26 (m, 1H), 7.77 (m, 1H), 7.58 (m, 1H), 7.44 (bs, 1H), 7.32-6.78, (m, 1H), 5.45-5.07 (m, 2H), 4.35-3.82 (m, 2H), 3.78-3.20 (m, 6H), 1.92 (s, 4H), 1.73 (s, 4H). | 435.5 | 125/100 | TFA |
| 209 | 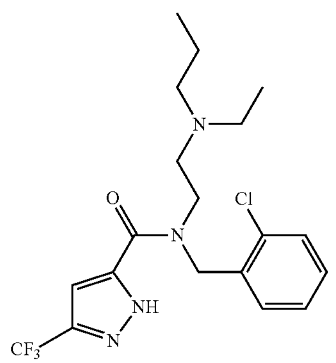 [SMILES: CCCN(CC)CCN(Cc1ccccc1Cl)C(=O)c1cc(C(F)(F)F)n[nH]1] | ¹H-NMR (CD3OD/ 400 MHz): 7.47 (m, 1H), 7.37 (m, 3H), 6.71 (s, 1H), 5.05 (s, 2H), 3.86 (m, 2H), 3.50-3.20 (m, 4H), 3.13 (m, 2H), 1.71 (m, 2H), 1.30 (t, 3H), 0.99 (t, 3H). | 417.5 | 52/100 | TFA |
| 210 | 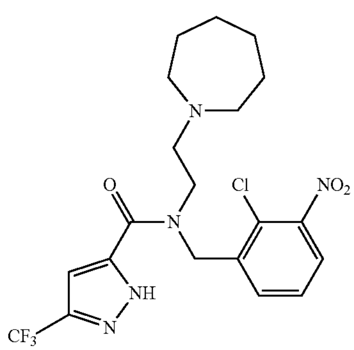 [SMILES: O=C(c1cc(C(F)(F)F)n[nH]1)N(CCN1CCCCCC1)Cc1cccc([N+](=O)[O-])c1Cl] | ¹H-NMR (CD3OD/ 400 MHz): 7.83 (m, 1H), 7.57 (m, 3H), 7.28-6.40, (m, 1H), 5.45-4.90 (m, 2H), 3.90 (m, 2H), 3.60 (m, 2H), 3.46 (m, 2H), 3.28 (m, 2H), 1.92 (m, 4H), 1.74 (s, 4H). | 474.5 | 133/100 | TFA |
| 211 | 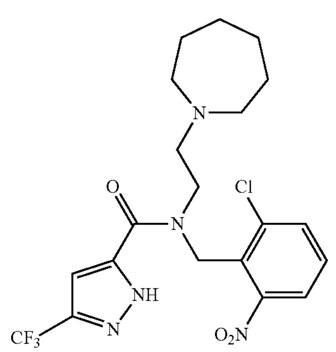 [SMILES: O=C(c1cc(C(F)(F)F)n[nH]1)N(CCN1CCCCCC1)Cc1c(Cl)cccc1[N+](=O)[O-]] | ¹H-NMR (CD3OD/ 400 MHz): 7.89 (m, 1H), 7.83 (m, 1H), 7.63 (m, 1H), 7.15 (s, 1H), 5.24 (bs, 2H), 3.75 (m, 2H), 3.48 (m, 2H), 3.27 (m, 4H), 1.90 (m, 4H), 1.73 (s, 4H). | 474.5 | 123/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 212 | 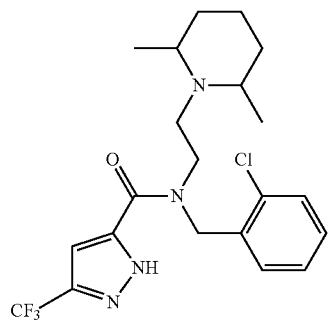 [SMILES: CC1CCCC(C)N1CCN(Cc1ccccc1Cl)C(=O)c1cc(C(F)(F)F)n[nH]1] | ¹H-NMR (CD₃OD/ 400 MHz): 7.49 (m, 1H), 7.39 (m, 3H), 6.76, (bs, 1H), 5.04 (m, 2H), 3.75 (m, 2H), 3.58-3.10 (m, 4H), 2.01-1.25 (m, 12H). | 443.5 | 5812/53 | TFA |
| 213 | 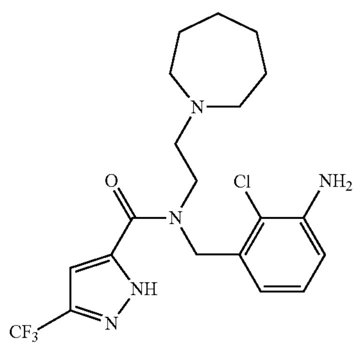 | ¹H-NMR (CD₃OD/ 400 MHz): 7.10 (t, 1H), 6.86 (d, 1H), 6.67 (bs, 1H), 6.60 (d, 1H), 4.95 (s, 2H), 3.86 (t, 2H), 3.54 (m, 2H), 3.31 (t, 2H), 3.22 (m, 2H), 1.92 (m, 4H), 1.73 (m, 4H). | 444.4 | 60/100 | TFA |
| 214 | 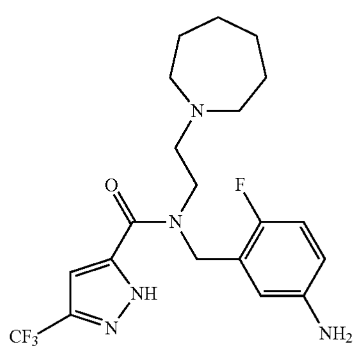 [SMILES: Nc1ccc(F)c(CN(CCN2CCCCCC2)C(=O)c2cc(C(F)(F)F)n[nH]2)c1] | ¹H-NMR (CD₃OD/ 400 MHz): 7.40-6.70 (m, 4H), 5.02 (m, 2H), 3.86 (m, 2H), 3.57 (m, 2H), 3.40 (m, 2H), 3.28 (m, 2H), 1.92 (m, 4H), 1.73 (m, 4H). | 428.5 | 153/100 | TFA |
| 215 | 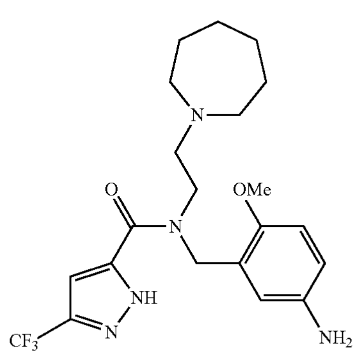 [SMILES: COc1ccc(N)cc1CN(CCN1CCCCCC1)C(=O)c1cc(C(F)(F)F)n[nH]1] | ¹H-NMR (CD₃OD/ 400 MHz): 7.34 (m, 1H), 7.18 (m, 2H), 6.69 (bs, 1H), 4.95 (bs, 2H), 3.86 (m, 5H), 3.56 (m, 2H), 3.38 (m, 2H), 3.28 (m, 2H), 1.92 (m, 4H), 1.73 (bs, 4H). | 440.5 | 1185/ 100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 216 | 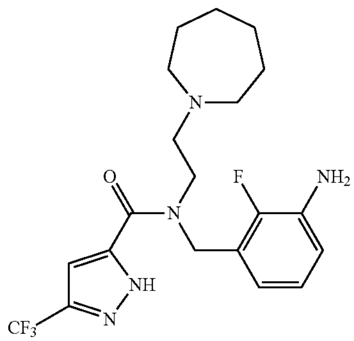 [SMILES: Nc1cccc(CN(CCN2CCCCCC2)C(=O)c2cc(C(F)(F)F)n[nH]2)c1F] | ¹H-NMR (CD₃OD/ 400 MHz): 6.97 (t, 1H), 6.89 (m, 2H), 6.60 (m, 1H), 4.97 (s, 2H), 3.84 (t, 2H), 3.52 (m, 2H), 3.31 (t, 2H), 3.22 (m, 2H), 1.90 (m, 4H), 1.72 (m, 4H). | 428.5 | 117/100 | TFA |
| 217 | 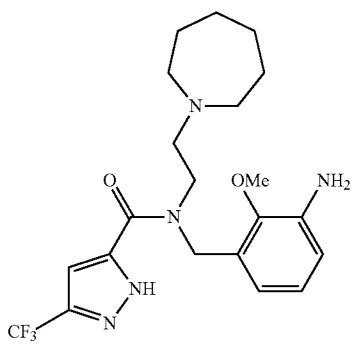 [SMILES: COc1c(N)cccc1CN(CCN1CCCCCC1)C(=O)c1cc(C(F)(F)F)n[nH]1] | ¹H-NMR (CD₃OD/ 400 MHz): 7.04 (t, 1H), 6.97 (d, 1H), 6.88 (bs, 1H), 6.78 (d, 1H), 4.96 (s, 2H), 3.82 (t, 2H), 3.62 (s, 3H), 3.50 (m, 2H), 3.23 (m, 4H), 1.90 (m, 4H), 1.72 (m, 4H). | 440.5 | 230/100 | TFA |
| 218 | 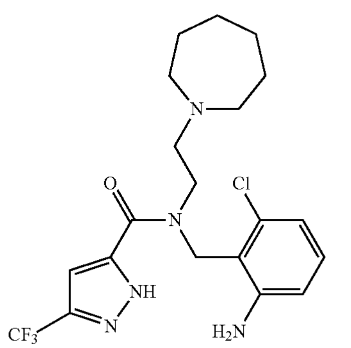 | ¹H-NMR (CD₃OD/ 400 MHz): 7.52 (d, 1H), 7.19 (s, 1H), 7.09 (t, 1H), 6.76 (d, 1H), 5.06 (bs, 2H), 4.41-3.29 (m, 6H), 3.06 (m, 2H), 1.87 (m, 4H), 1.72 (m, 4H). | 444.4 | 41/100 | TFA |
| 219 | 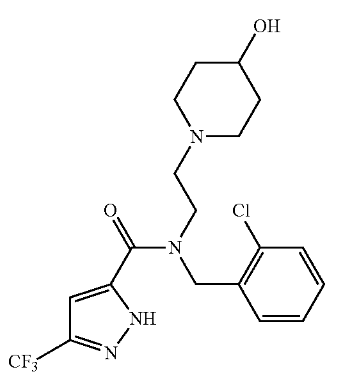 [SMILES: O=C(c1cc(C(F)(F)F)n[nH]1)N(CCN1CCC(O)CC1)Cc1ccccc1Cl] | ¹H-NMR (CD₃OD/ 400 MHz): 7.47 (m, 1H), 7.33 (m, 3H), 6.60 (bs, 1H), 5.03 (bs, 2H), 4.12-3.81 (m, 2H), 3.80-3.48 (m, 2H), 3.36 (m, 2H), 3.06 (m, 1H), 2.13 (m, 1H), 1.94 (m, 2H), 1.71 (m, 1H). | 431.4 | 1300/100 | TFA |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 220 | 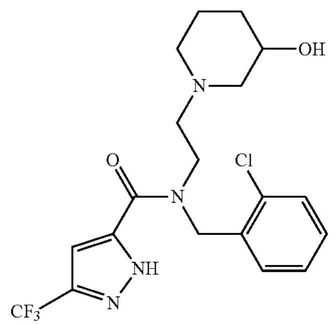 [SMILES: O=C(c1cc(C(F)(F)F)n[nH]1)N(CCN1CCCC(O)C1)Cc1ccccc1Cl] | ¹H-NMR (CD₃OD/ 400 MHz): 7.47 (m, 1H), 7.33 (m, 3H), 6.61 (bs, 1H), 5.02 (bs, 2H), 4.21- 3.25 (m, 7H), 3.19- 2.62 (m, 2H), 2.35- 1.48 (m, 4H). | 431.4 | 465/100 | TFA |
| 221 | 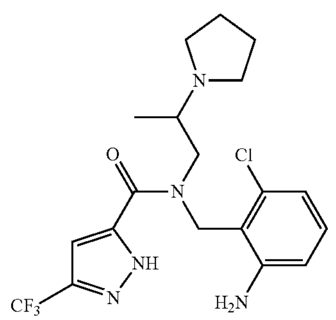 [SMILES: CC(CN(Cc1c(N)cccc1Cl)C(=O)c1cc(C(F)(F)F)n[nH]1)N1CCCC1] | ¹H-NMR (CD₃OD/ 400 MHz): 7.43 (m, 1H), 7.36 (m, 2H), 7.13 (m, 1H), 5.08 (q, 2H), 4.40-4.00 (m, 2H), 3.37 (m, 3H), 2.04 (m, 5H), 1.41 (d, 3H). | 430.4 | 223/60 | TFA |
| 222 | 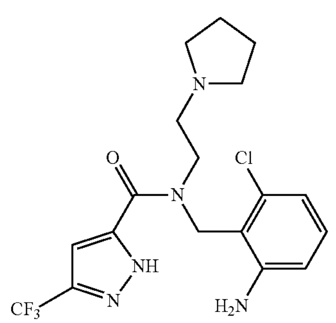 [SMILES: Nc1cccc(Cl)c1CN(CCN1CCCC1)C(=O)c1cc(C(F)(F)F)n[nH]1] | ¹H-NMR (CD₃OD/ 400 MHz): 7.50- 6.68 (m, 4H), 5.12 (s, 2H), 4.20 (t, 2H), 3.81 (t, 2H), 3.43 (m, 4H), 2.10 (m, 4H). | 416.5 | 56/100 | TFA |
| 223 | 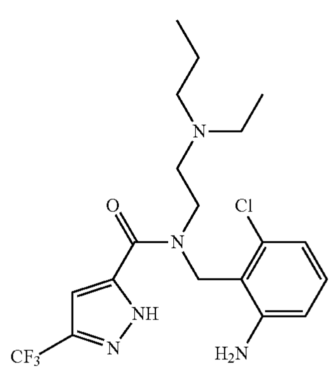 [SMILES: CCCN(CC)CCN(Cc1c(N)cccc1Cl)C(=O)c1cc(C(F)(F)F)n[nH]1] | ¹H-NMR (CD₃OD/ 400 MHz): 7.46- 6.61 (m, 4H), 5.08 (m, 2H), 4.22-3.60 (m, 2H), 3.14 (m, 2H), 2.98 (m, 2H), 1.75 (m, 1H), 1.58 (m, 2H), 1.34 (t, 1H), 1.22 (t, 2H), 0.96 (m, 3H). | 432.5 | 32/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 224 | 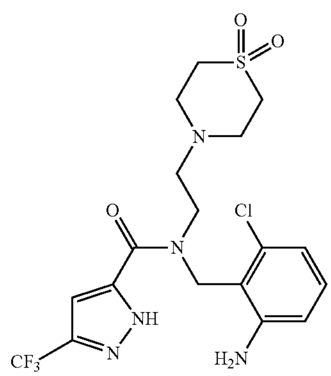 [SMILES: Nc1cccc(Cl)c1CN(CCN1CCS(=O)(=O)CC1)C(=O)c1cc(C(F)(F)F)n[nH]1] | ¹H-NMR (CD₃OD/ 400 MHz): rotomers 7.65-7.10 (m, 4H), 5.16 + 4.41 (s, 2H), 3.92 + 3.31 (t, 2H), 3.16-3.01 (m, 5H), 2.96 (m, 4H), 2.88 (t, 1H). | 480.4 | 410/100 | TFA |
| 225 | 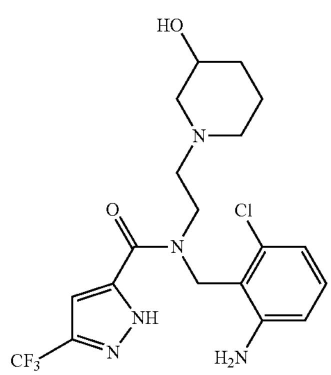 [SMILES: Nc1cccc(Cl)c1CN(CCN1CCCC(O)C1)C(=O)c1cc(C(F)(F)F)n[nH]1] | ¹H-NMR (CD₃OD/ 400 MHz): 7.49 (m, 1H), 7.37 (m, 2H), 7.14 (m, 1H), 5.13 (s, 2H), 4.22 (m, 2H), 4.06 (bs, 1H), 3.74 (t, 2H), 3.25 (m, 7H), 3.28 (m, 4H), 2.14 (m, 1H), 1.77 (m, 3H). | 446.4 | 102/100 | TFA |
| 226 | 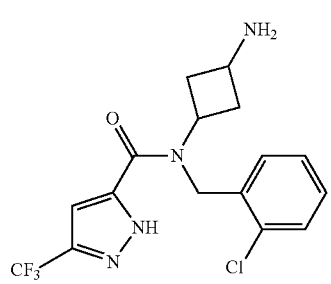 [SMILES: NC1CC(N(Cc2ccccc2Cl)C(=O)c2cc(C(F)(F)F)n[nH]2)C1] | ¹H-NMR (CD₃OD/ 400 MHz): 7.50-7.12 (m, 5H), 4.86 (m, 3H), 3.82 (m, 1H), 2.81 (m, 2H), 2.39 (m, 2H). | 356.3 | 12000/80 | TFA |
| 227 | 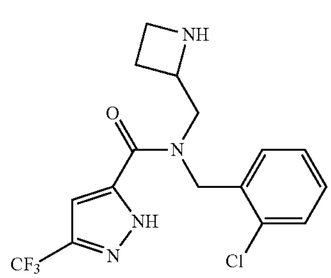 [SMILES: O=C(c1cc(C(F)(F)F)n[nH]1)N(Cc1ccccc1Cl)CC1CCN1] | ¹H-NMR (CD₃OD/ 400 MHz): 7.61-7.22 (m, 4H), 6.54 (bs, 1H), 4.98 (m, 1H), 4.61 (m, 1H), 4.45 (m, 1H), 4.32 (m, 1H), 4.00 (m, 1H), 3.83 (m, 1H), 3.52 (m, 1H), 3.07 (m, 1H), 2.43 (m, 2H), 2.17 (m, 1H). | 373.4 | 215/100 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 228 | 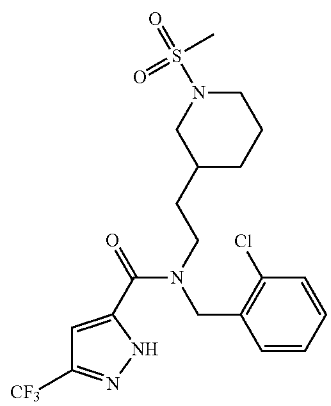 [SMILES: CS(=O)(=O)N1CCCC(CCN(Cc2ccccc2Cl)C(=O)c2cc(C(F)(F)F)n[nH]2)C1] | ¹H-NMR (CD₃OD/ 400 MHz): 7.42 (m, 1H), 7.31 (m, 3H), 7.15 + 6.59 (bs, 1H), 4.89 (m, 2H), 3.52 (m, 5H), 2.74 (m, 4H), 2.48 (m, 1H), 1.60 (m, 6H), 1.07 (m, 1H). | 493.4 | 2000/ 100 | TFA |
| 229 | 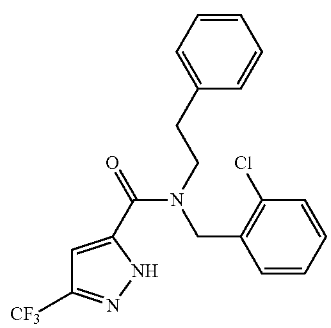 [SMILES: O=C(c1cc(C(F)(F)F)n[nH]1)N(CCc1ccccc1)Cc1ccccc1Cl] | ¹H-NMR (CD₃OD/ 400 MHz): 7.50- 6.90 (m, 9H), 6.72- 6.40 (m, 1H), 4.87 (s, 1H), 4.70 (bs, 1H), 4.00-3.57 (m, 2H), 2.89 (m, 2H). | 408.4 | NA/NA | — |
| 230 | 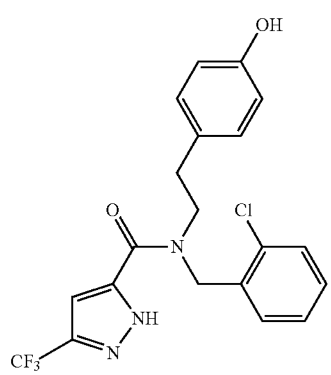 [SMILES: O=C(c1cc(C(F)(F)F)n[nH]1)N(CCc1ccc(O)cc1)Cc1ccccc1Cl] | ¹H-NMR (CD₃OD/ 400 MHz): 7.42 (m, 1H), 7.30 (m, 3H), 6.99 (d, 1H), 6.85 (d, 1H), 6.78-6.42 (m, 3H), 4.86 (s, 1H), 4.74 (bs, 1H), 3.72 (m, 1H), 3.58 (m, 1H), 2.78 (m, 2H). | 424.4 | 12000/ 100 | — |
| 231 | 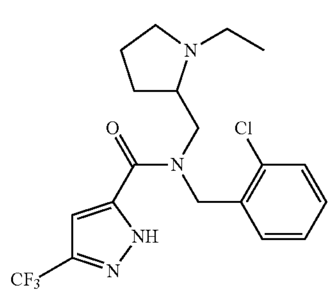 [SMILES: CCN1CCCC1CN(Cc1ccccc1Cl)C(=O)c1cc(C(F)(F)F)n[nH]1] | ¹H-NMR (CD₃OD/ 400 MHz): 7.48 (m, 1H), 7.33 (m, 3H), 6.72 (bs, 1H), 5.09 (m, 2H), 4.01 (m, 1H), 3.71 (m, 3H), 3.47 (m, 1H), 3.22 (m, 1H), 3.10 (m, 1H), 2.24 (m, 1H), 2.07 (m, 2H), 1.88 (m, 1H), 1.36 (t, 1H). | 415.5 | 148/65 | TFA |

TABLE 1-continued

Exemplary Compounds

| EX | Structure | NMR | ES-MS (M⁺ + 1) | PKM₂ AC₅₀ (nM)/ Max. Resp.* (%) | Note† |
|---|---|---|---|---|---|
| 232 | 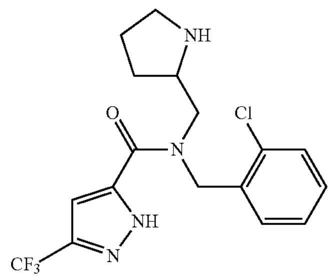 [SMILES: O=C(c1cc(C(F)(F)F)n[nH]1)N(Cc1ccccc1Cl)CC1CCCN1] | ¹H-NMR (CD₃OD/ 400 MHz): 7.56-7.20 (m, 4H),, 6.49 (bs, 1H), 4.99 (bs, 2H), 4.13 (m, 1H), 3.76 (m, 1H), 3.52 (m, 1H), 3.40 (m, 1H), 3.28 (m, 1H), 2.05 (m, 3H), 1.73 (m, 1H). | 387.5 | 320/85 | TFA |
| 233 | 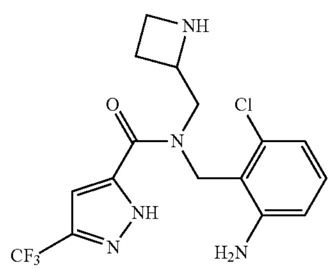 [SMILES: Nc1cccc(Cl)c1CN(CC1CCN1)C(=O)c1cc(C(F)(F)F)n[nH]1] | ¹H-NMR (CD₃OD/ 400 MHz): 7.53 (m, 2H), 7.44 (m, 1H), 7.37 (m, 1H), 4.88 (m, 1H), 4.40 (s, 2H), 4.10 (m, 1H), 3.97 (m, 1H), 3.77 (m, 1H), 3.57 (m, 1H), 2.66 (m, 1H), 2.52 (m, 1H). | 388.4 | 930/75 | TFA |
| 234 | 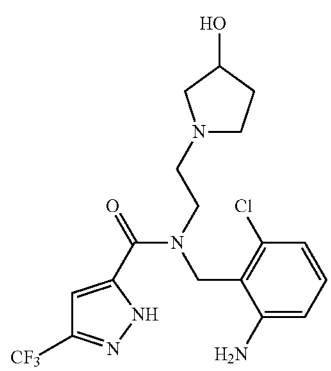 [SMILES: Nc1cccc(Cl)c1CN(CCN1CCC(O)C1)C(=O)c1cc(C(F)(F)F)n[nH]1] | ¹H-NMR (CD₃OD/ 400 MHz): 7.60-7.32 (m, 3H), 7.20-6.66 (m, 1H), 5.13 + 4.39 (s, 2lH), 5.05 + 4.94 (bs, 1H), 4.56 (m, 1H), 4.21 + 3.87 (m, 1H), 3.64 (m, 2H), 3.54 (m, 2H), 3.46 (m, 2H), 2.26 (m, 1H), 2.06 (m, 1H). | 432.5 | 111/100 | TFA |
| 235 | 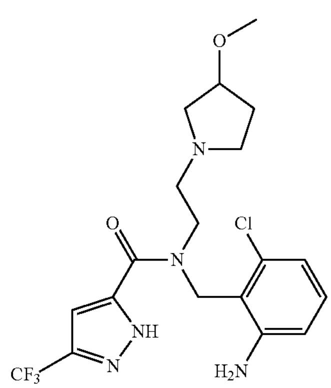 [SMILES: COC1CCN(CCN(Cc2c(N)cccc2Cl)C(=O)c2cc(C(F)(F)F)n[nH]2)C1] | ¹H-NMR (CD₃OD/ 400 MHz): 7.60-7.32 (m, 3H), 7.20-6.66 (m, 1H), 5.12 + 4.37 (s, 2H), 5.05 + 4.10 (bs, 1H), 4.18 (m, 1H), 4.20 + 3.84 (m, 1H), 3.56 (m, 2H), 3.50 (m, 2H), 3.41 (m, 2H), 3.32 (d, 3H), 2.06 (m, 2H). | 446.5 | 133/100 | TFA |

TABLE 1-continued

Exemplary Compounds

| EX | Structure | NMR | ES-MS (M$^+$ + 1) | PKM$_2$ AC$_{50}$ (nM)/ Max. Resp.* (%) | Note† |
|---|---|---|---|---|---|
| 236 | 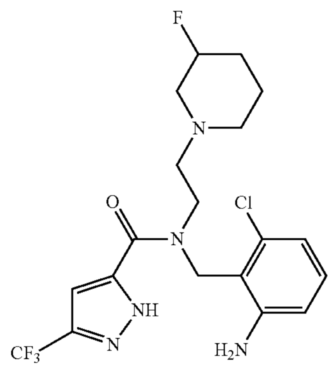 [SMILES: Nc1cccc(Cl)c1CN(CCN1CCCC(F)C1)C(=O)c1cc(C(F)(F)F)n[nH]1] | $^1$H-NMR (CD$_3$OD/ 400 MHz): 7.60-6.66 (m, 4H), 5.20-4.45 (m, 3H), 5.05 + 4.10 (bs, 1H), 4.00-4.12 (m, 1H), 3.80 + 3.52 (m, 2H), 3.41 (m, 2H), 3.23-2.78 (m, 3H), 2.06 (m, 2H), 1.82 (m, 2H). | 448.4 | 160/73 | TFA |
| 237 | 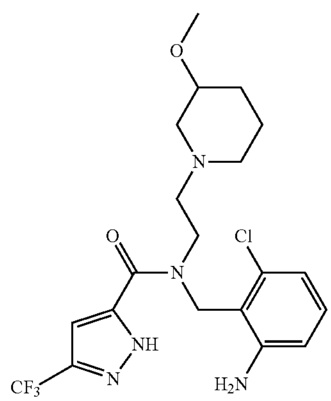 [SMILES: COC1CCCN(CCN(Cc2c(N)cccc2Cl)C(=O)c2cc(C(F)(F)F)n[nH]2)C1] | $^1$H-NMR (CD$_3$OD/ 400 MHz): 7.60-6.66 (m, 4H), 5.12 + 4.38 (s, 2H), 5.00 (m, 1H), 4.22 (m, 1H), 3.80-2.80 (m, 10H), 2.16-1.62 (m, 4H). | 460.5 | 183/100 | TFA |
| 238 | 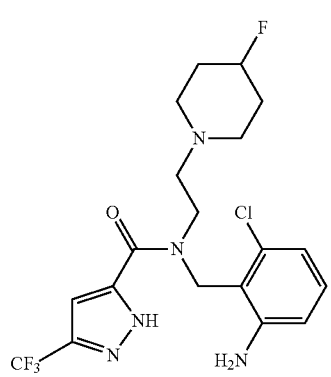 [SMILES: Nc1cccc(Cl)c1CN(CCN1CCC(F)CC1)C(=O)c1cc(C(F)(F)F)n[nH]1] | $^1$H-NMR (CD$_3$OD/ 400 MHz): 7.60-6.66 (m, 4H), 5.14 + 4.38 (s, 2H), 5.07 + 3.10 (bs, 1H), 4.24 + 3.92 (m, 1H), 3.82 (m, 4H), 3.51 (m, 3H), 3.41 (m, 1H), 3.36 (m, 1H), 2.15 (m, 2H). | 446.5 | 116/100 | TFA |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 239 | 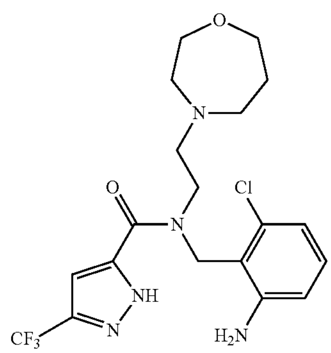 [SMILES: Nc1cccc(Cl)c1CN(CCN1CCCOCC1)C(=O)c1cc(C(F)(F)F)n[nH]1] | ¹H-NMR (CD$_3$OD/ 400 MHz): 7.60-6.66 (m, 4H), 5.13 + 4.39 (s, 2H), 4.99 (m, 1H), 4.25 (m, 1H), 3.76 (m, 1H), 3.56 (m, 1H), 3.50-3.00 (m, 6H), 2.14 (m, 4H). | 448.4 | 115/100 | TFA |
| 240 | 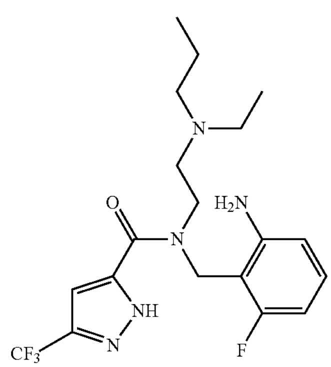 [SMILES: CCCN(CC)CCN(Cc1c(N)cccc1F)C(=O)c1cc(C(F)(F)F)n[nH]1] | ¹H-NMR (CD$_3$OD/ 400 MHz): 7.58-6.35 (m, 4H), 5.08 (m, 2H), 4.22-3.60 (m, 2H), 3.58-2.95 (m, 6H), 1.69 (m, 2H), 1.28 (m, 3H), 0.97 (m, 3H). | 416.5 | 68/100 | TFA |
| 241 | 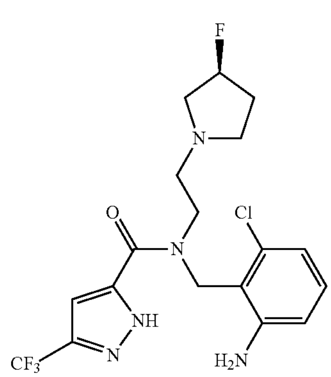 [SMILES: Nc1cccc(Cl)c1CN(CCN1CC[C@H](F)C1)C(=O)c1cc(C(F)(F)F)n[nH]1] | ¹H-NMR (CD$_3$OD/ 400 MHz): 7.60-6.62 (m, 4H), 5.55-4.97 (m, 2H), 4.34 (s, 1H), 4.19 + 3.80 (m, 1H), 3.76-3.05 (m, 7H), 2.30 (m, 2H). | 434.4 | 125/100 | TFA |

TABLE 1-continued

Exemplary Compounds

| EX | Structure | NMR | ES-MS (M⁺ + 1) | PKM$_2$ AC$_{50}$ (nM)/ Max. Resp.* (%) | Note† |
|---|---|---|---|---|---|
| 242 | 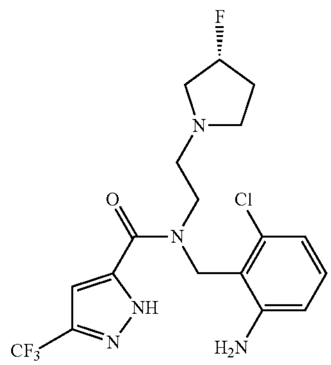 [SMILES: Nc1cccc(Cl)c1CN(CCN1CC[C@@H](F)C1)C(=O)c1cc(C(F)(F)F)n[nH]1] | ¹H-NMR (CD$_3$OD/ 400 MHz): 7.60-6.62 (m, 4H), 5.55-4.97 (m, 2H), 4.34 (s, 1H), 4.19 + 3.80 (m, 1H), 3.76-3.05 (m, 7H), 2.30 (m, 2H). | 434.4 | 465/100 | TFA |
| 243 | 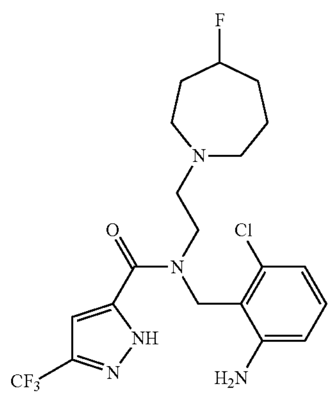 [SMILES: Nc1cccc(Cl)c1CN(CCN1CCCC(F)CC1)C(=O)c1cc(C(F)(F)F)n[nH]1] | ¹H-NMR (CD$_3$OD/ 400 MHz): 7.60-6.60 (m, 4H), 5.16 + 4.24 (s, 2H), 4.95 (m, 1H), 4.19 + 3.85 (m, 1H), 3.76-2.70 (m, 7H), 2.08 (m, 6H). | 462.4 | 106/100 | TFA |
| 244 | 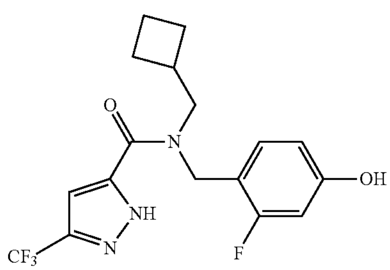 [SMILES: O=C(c1cc(C(F)(F)F)n[nH]1)N(Cc1ccc(O)cc1F)CC1CCC1] | ¹H-NMR (CD$_3$OD/400 MHz): 7.05 (m, 1H), 6.51 (m, 3H), 4.70 (m, 2H), 3.47 (m, 2H), 2.64 (s, 1H), 2.00 (s, 2H), 1.80 (m, 4H). | 337.9 | 62/107 | — |
| 245 | 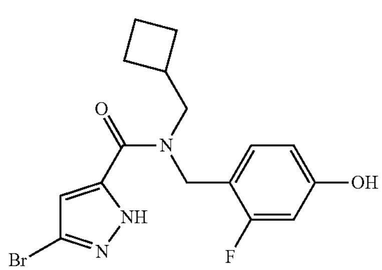 [SMILES: O=C(c1cc(Br)n[nH]1)N(Cc1ccc(O)cc1F)CC1CCC1] | ¹H-NMR (DMSO-d6/ 400 MHz): 13.84 (s, 1H), 9.87 (s, 1H), 7.05 (m, 1H), 6.58 (m, 3H), 4.56 (m, 2H), 3.46 (m, 2H), 2.55 (m, 1H), 1.90-1.54 (m, 6H) | 382.1 | 35/100 | — |

TABLE 1-continued

Exemplary Compounds

| EX | Structure | NMR | ES-MS (M+ + 1) | PKM₂ AC₅₀ (nM)/ Max. Resp.* (%) | Note† |
|---|---|---|---|---|---|
| 246 | 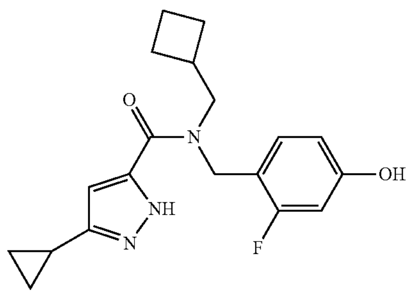 [SMILES: O=C(c1cc(C2CC2)n[nH]1)N(Cc1ccc(O)cc1F)CC1CCC1] | ¹H-NMR (CDCl₃/400 MHz): 8.00 (s, 1H), 7.20 (m, 1H), 6.51 (m, 2H), 6.20 (m, 1H), 4.70 (m, 2H), 3.50 (m, 2H), 2.64 (m, 1H), 1.99 (m, 2H), 1.85-1.79 (m, 5H), 0.93 (m, 2H), 0.70 (m, 2H) | 344.2 | 92/85 | — |

*Max. Resp. (%) represents the % maximum response in a biochemical assay as compared with Fructose 1,6-bisphosphate.
†Indicates salt form if applicable.
TFA = trifluoroacetic acid It is understood that any embodiment of the compounds of structure (I), including structures (Ia), (Ib) and (Ic), as set forth above, and any of the specific substituents set forth herein (e.g., R¹-R²³) in the compounds of structures (I), (Ia), (Ib) and (Ic), as set forth above, may be independently combined with other embodiments and/or substituents of compounds of structures (I), (Ia), (Ib) and (Ic) to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention. It is understood that in the present description, combinations of substituents and/or variables of the depicted formulae are permissible only if such contributions result in stable compounds.

The compounds of the present invention can be prepared according to any number of methods known in the art, including those methods specifically described in the Examples below. The following General Reaction Scheme I illustrates a method of making compounds of this invention, i.e., compounds of structure (I), wherein R¹-R⁵ are as defined above.

General Reaction Scheme I

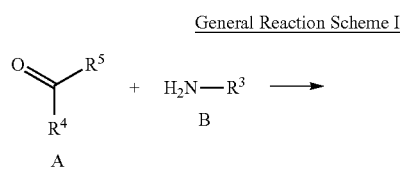

Referring to General Reaction Scheme I, carbonyl compounds (e.g., aldehydes or ketones) of structure A can be reacted under appropriate reductive amination conditions (e.g., MgSO₄/Na₂CO₃ in dichloromethane followed by NaBH₄) with amines (including salts thereof) of structure B to yield amine C. Amine C is then reacted with acid D under appropriate coupling conditions to yield E (a compound of structure (I) wherein R⁶ is H). One of ordinary skill in the art will understand methods for making compounds wherein R⁶ is other than H, for example by reaction of the imine obtained from reaction of A and B.

It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

II. Compositions and Administration

In other embodiments, the present invention is directed to a pharmaceutical composition comprising any of the compounds described herein, or a stereoisomer, pharmaceutically acceptable salt or prodrug thereof, and a pharmaceutically acceptable carrier, diluent or excipient.

For the purposes of administration, the compounds of the present invention may be administered as a raw chemical or may be formulated as pharmaceutical compositions. Pharmaceutical compositions of the present invention comprise a compound of structure (I) (compounds of structure (I) include compounds of structures (Ia), (Ib) and (Ic)) and a pharmaceutically acceptable carrier, diluent or excipient. The compound of structure (I) is present in the composition in an amount which is effective to treat a particular disease or condition of interest—that is, in an amount sufficient to treat various cancers, and preferably with acceptable toxicity to the patient. PKM2 activity of compounds of structure (I) can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

For any compound used in the methods of the invention, the therapeutically effective amount or dose can be estimated initially from cell culture assays. Then, the dosage can be formulated for use in animal models so as to achieve a circulating concentration range that includes the IC50 as determined in cell culture (i.e., the concentration of the test compound which achieves a half-maximal inhibition of the protein kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the IC50 and the LD50 (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, 9th ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m2 to 1500 mg/m2 per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

III. Cancer Treatment Methods

In various other embodiments, the invention is directed to a method for treating cancer by administering any of the above described compounds of structure (I) to a patient (e.g., mammal) in need thereof. In other embodiments, the disclosure provides a method of activating PKM2 in a mammal in need thereof, the method comprising administering to the mammal an effective amount of any of the above described compounds of structure (I) or a pharmaceutical comprising the same. For example, the activating of PKM2 may be for treatment of cancer, such as lung cancer. The invention also provides for treatment of various other cancers as described below.

Representative compounds (Examples 1 and 244) of this invention demonstrate maximal activation levels similar to FBP (FIG. 1B and Table 1, Example 245) and increased the affinity of PKM2 for PEP (FIG. 1C), but not ADP (FIG. 1D). A co-crystal structure of a representative compound (Example 244) bound to tetrameric PKM2 at 2.03 Å resolution was also determined (FIG. 2, for simplicity, only the PKM2 dimer (half of the tetramer) crystal is shown, illustrating a novel 1:1 binding ratio of compound to monomer of PKM2; proposed hydrogen bonds are shown as dashed lines). While not wishing to be bound by theory, the results indicate that this compound did not bind to the FBP site, but instead bound to an allosteric site of unknown physiological significance at the dimer-dimer interface. The compound appears to bind to the allosteric site with occupancy of two molecules per dimer (FIG. 2), whereas other PKM2 activators (Boxer M B, Jiang J K, Vander Heiden M G, Shen M, Skoumbourdis A P, Southall N, et al. *J Med Chem* 2010; 53:1048-55; Jiang J K, Boxer M B, Vander Heiden M G, Shen M, Skoumbourdis A P, Southall N, et al. *Bioorg Med Chem Lett* 2010; 20:3387-93; Walsh M J, Brimacombe K R, Veith H, Bougie J M, Daniel T, Leister W, et al. *Bioorg Med Chem Lett* 2011; 21:6322-7) that bind to the same site did so with occupancy of one molecule per dimer (PDB accession numbers: 3GQY, 3GR4, 3H6O, 3ME3).

Compounds of the invention were also determined to activate pyruvate kinase in cells. NCI-H1299 and A549 lung adenocarcinoma cell lines were selected for this experiments due to previously reported high levels of phospho-PKM2 at Tyr105 (Hitosugi T, Kang S, Vander Heiden M G, Chung T W, Elf S, Lythgoe K, et al. *Sci Signal* 2009; 2:ra73). Phosphorylation of PKM2 at Tyr105 renders the enzyme insensitive to FBP activation. However, certain embodiments of the compounds described herein (e.g., Examples 1 and 244) potently activate pyruvate kinase activity in both cell lines (FIG. 3A and Table 2, Example 245). These results demonstrated that the compounds effectively permeate the cell membrane to activate PKM2. In addition, these results demonstrated that high levels of p-Tyr105 do not block activation by the PKM2 activators of the invention, possibly due to the distinct allosteric binding mechanism discussed previously.

In certain embodiments, the compounds of the invention are also useful to induce tetramer formation in cells. In this regard, FLAG-PKM2 expressing HEK-293 cells were treated with compounds of the invention, and FLAG-PKM2 proteins were immunoprecipitated as previously described (Anastasiou D, Poulogiannis G, Asara J M, Boxer M B, Jiang J K, Shen M, et al. *Science* 2011; 334:1278-83). As shown in FIG. 3B, representative compounds increased the amount of endogenous PKM2 that co-immunoprecipitated with FLAG-PKM2, consistent with an increase of FLAG-tagged and endogenous PKM2 tetramer complexes. Tetramers induced by representative compounds in cells are relatively stable as demonstrated by the slow kinetics of PKM2 inactivation following compound washout (FIG. 3C).

In other embodiments, the compounds of the present invention inhibit cancer cell proliferation. Under normal media conditions, PKM2 activators had no observable growth effect against a broad panel of adherent and suspension cancer cell lines. However, when A549 cells were grown in BME media lacking nonessential amino acids, representative compounds inhibited proliferation with EC50 values of 210 nM and 89 nM respectively (FIG. 4A). The inhibition of cell growth was rescued by adding serine (30 µM) to the media (FIG. 4B), suggesting that serine deprivation sensitizes A459 cells to PKM2 activation.

The effect of a representative compound (Example 1) on 6 different cell lines was also determined (FIG. 4C). These cell lines grew slowly or well in media lacking serine, with moderate or no additional growth benefit when serine was added to the media (data not shown). While not wishing to be bound by theory, it is believed that these cell lines have robust de novo serine biosynthesis. As seen in FIG. 4C, the compound of Example 1 was able to inhibit cell proliferation of certain cell lines at IC50 values as low as 0.1 µM. Cell lines from additional indications other than lung cancer (breast, colon, pancreas, prostate) were also examined and found to have varying sensitivities to both serine deprivation and treatment with a representative compound (data not shown). While not wishing to be bound by theory, it is possible that cell line sensitivity to PKM2 activators in the absence of serine might correlate with PKM2 phosphorylation at Tyr105, either in normal or serine-free media.

Figure 5A:
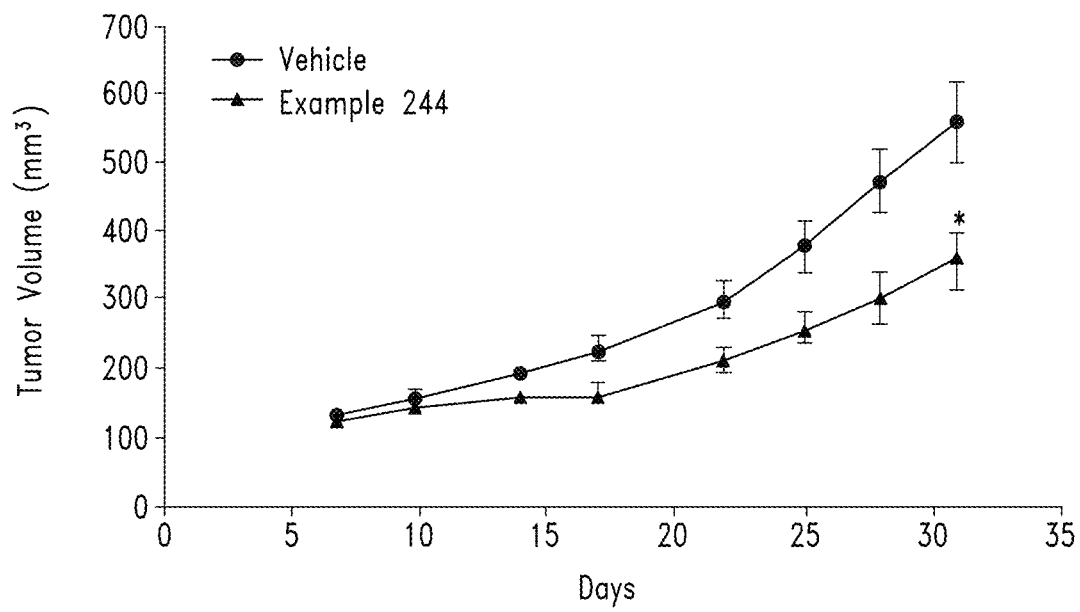
FIGS. 5A and 5B present tumor volume data in mice treated with representative compounds.
Figure 5B:
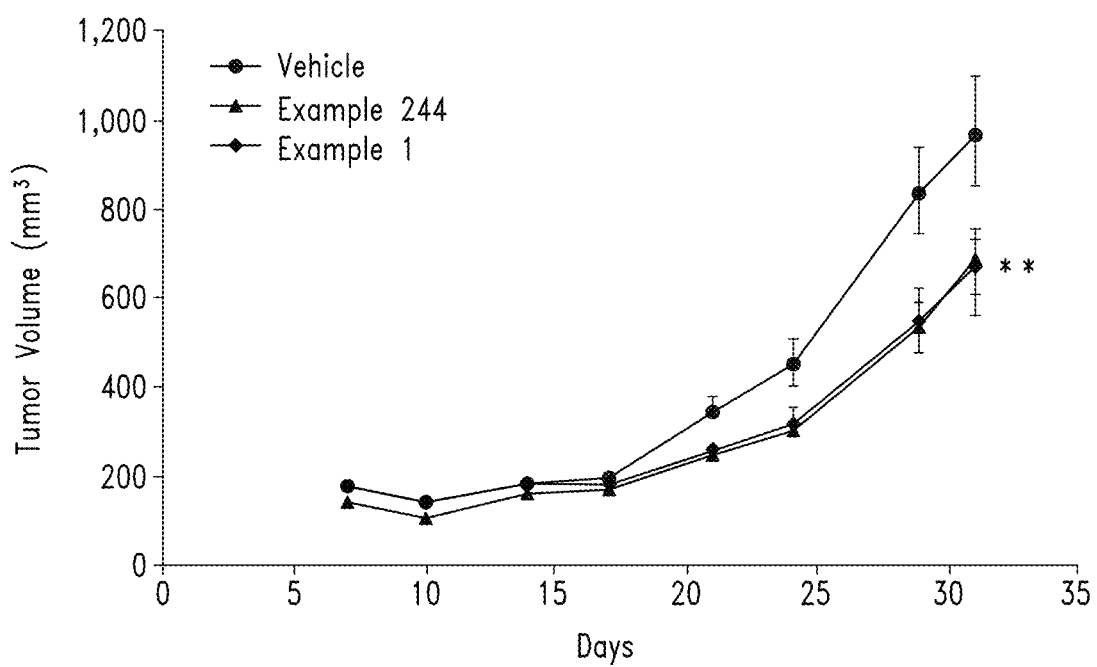

Compounds of the present invention also demonstrate efficacy in a subcutaneous A549 xenograft tumor model. A daily dose of 50 mg/kg of representative compounds administered intraperitoneally significantly slowed tumor growth in two separate xenograft experiments (FIGS. 5A and 5B). The slowed xenograft tumor growth compares with reports in PKM2 genetic models, where PKM2 was replaced with constitutively active PKM1 (Christofk H R, Vander Heiden M G, Harris M H, Ramanathan A, Gerszten R E, Wei R, et al. *Nature* 2008; 452:230-3), or where PKM2 was compared to a mutant resistant to inactivation due to phosphorylation at Tyr105 (Hitosugi T, Kang S, Vander Heiden M G, Chung T W, Elf S, Lythgoe K, et al. *Sci Signal* 2009; 2:ra73). The present inventors believe these experiments are the first documented evidence that pharmacological activation of PKM2 slows tumor growth in vivo. Importantly, no significant body weight loss or other gross toxicity was observed in the cohorts receiving the representative compounds (data not shown), suggesting few on- or off-target toxic effects.

While not wishing to be bound by theory, the above results indicate that certain embodiments of the present compounds are useful for treating cancers where de novo serine biosynthesis is required for tumor growth and regulated by PKM2 inactivation. The serine-rescue experiments with A549 and other lung cancer cell lines suggest that synthesis of serine is necessary for these cells to proliferate, and that pharmacological PKM2 activation leads to increased glycolytic flux that deprives the serine biosynthetic pathway of starting material.

As mentioned above, the compounds and compositions of the invention will find utility in a broad range of diseases and conditions mediated by PKM2. Such diseases may include by way of example and not limitation, cancers such as lung cancer, NSCLC (non-small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, the compounds and compositions of the invention can be used in methods for treating cancers such as hematological malignancies. For example, in some embodiments the compounds and compositions of the invention can be used in methods for treating acute myeloid leukemia (AML). Other methods include treatment of bladder cancer, or treatment of prostate cancer.

The inventive compounds (i.e., compounds of structure (I)) can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the *vinca* alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include Vioxx, CELEBREX (celecoxib), valdecoxib, paracoxib, rofecoxib, and Cox 189.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

An inventive compound can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3 (published Aug. 23, 2001), WO 99/24440 (published May 20, 1999), PCT International Application PCT/IB99/00797 (filed May 3, 1999), WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Pat. No. 6,284,764 (issued Sep. 4, 2001), incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B 1.

The above method can also be carried out in combination with radiation therapy, wherein the amount of an inventive compound in combination with the radiation therapy is effective in treating the above diseases.

Techniques for administering radiation therapy are known in the art, and these techniques can be used in the combination therapy described herein. The administration of the compound of the invention in this combination therapy can be determined as described herein.

The following examples are provided for purposes of illustration, not limitation.

EXAMPLES

Example 1

SYNTHESIS OF N-(CYCLOBUTYLMETHYL)-N-(2-FLUORO-4-HYDROXYBENZYL)-3-(TRIFLUOROMETHYL)-1H-PYRAZOLE-5-CARBOXAMIDE

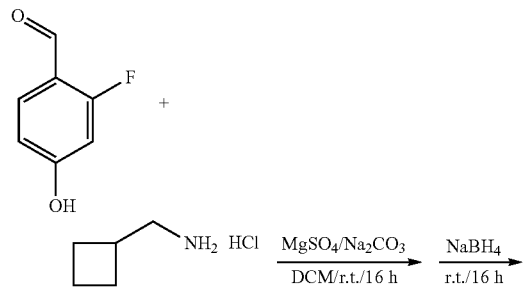

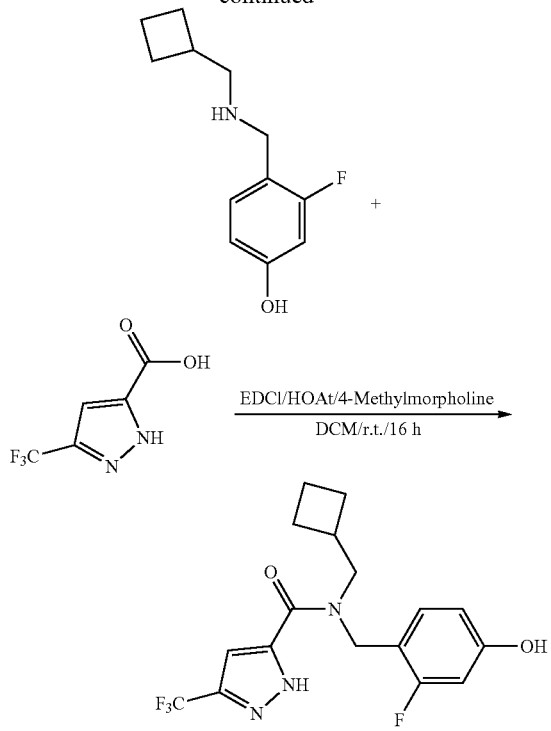

To a solution of 2-fluoro-4-hydroxybenzaldehyde (0.5 g, 3.57 mmol) and cyclobutylmethanamine hydrogen chloride (0.304 g, 3.57 mmol) in methylene chloride (5 mL) was added $MgSO_4$ (1.29 g, 10.71 mmol) and $Na_2CO_3$ (0.78 g, 7.14 mmol). The mixture was stirred at room temperature overnight, and then $NaBH_4$ (0.16 g, 3.57 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with $Na_2SO_4$ and concentrated. The residue was purified by chromatography on silica gel eluting with 0 to 10% methanol in methylene chloride to give (0.7 g, 3.35 mmol, 94% yield) of compound 4-((((cyclobutylmethyl)amino)methyl)-3-fluorophenol.

To a solution of 3-(trifluoromethyl)-1H-pyrazole-5-carboxylic acid (0.1 g, 0.555 mmol) and 4-(((cyclobutylmethyl)amino)methyl)-3-fluorophenol (0.116 g, 0.555 mmol) in DMF (1 mL) was added EDCI (0.160 g, 0.833 mmol), HOAt (0.133 g, 0.833 mmol) and 4-methylmorpholine (0.168 g, 1.666 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with $Na_2SO_4$ and concentrated. The residue was purified by chromatography on silica gel eluting with 0 to 15% methanol in methylene chloride to give (0.050 g, 0.135 mmol, 24% yield) of compound N-(cyclobutylmethyl)-N-(2-fluoro-4-hydroxybenzyl)-3-(trifluoromethyl)-1H-pyrazole-5-carboxamide.

$^1$H-NMR ($CDCl_3$/400 MHz): 7.10 (m, 1H), 6.80 (m, 1H), 6.59 (d, J=8.4 Hz, 1H), 6.52 (d, J=12.0 Hz, 1H), 4.69 (s, 2H), 3.50 (s, 2H), 2.65 (m, 1H), 2.00-1.58 (m, 6H). MS ($ES^+$, m/z): 372.1 ($M^+$+1, 100.0).

Example 2

SYNTHESIS OF 3-CYANO-N-(CYCLOBUTYLMETHYL)-N-(2-FLUORO-4-HYDROXYBENZYL)-1H-PYRAZOLE-5-CARBOXAMIDE

To a solution of 3-cyano-1H-pyrazole-5-carboxylic acid (0.100 g, 0.729 mmol) and 4-(((cyclobutylmethyl)amino)methyl)-3-fluorophenol (0.153 g, 0.729 mmol) in DMF (1 mL) was added EDCI (0.210 g, 1.094 mmol), HOBt (0.148 g, 1.094 mmol) and DIPEA (0.283 g, 2.188 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with $Na_2SO_4$ and concentrated. The residue was purified by chromatography on silica gel eluting with 0 to 15% methanol in methylene chloride to give (0.026 g, 0.079 mmol, 11% yield) of compound 3-cyano-N-(cyclobutylmethyl)-N-(2-fluoro-4-hydroxybenzyl)-1H-pyrazole-5-carboxamide.

$^1$H-NMR ($CD_3OD$/400 MHz): 7.05 (m, 2H), 6.54 (m, 2H), 4.68 (m, 2H), 3.67 (m, 1H), 3.46 (m, 1H), 2.67 (m, 1H), 2.01-1.62 (m, 6H). MS ($ES^+$, m/z): 328.9 ($M^+$+1, 100.0).

Compounds in Examples 2-28, 245 and 246 were prepared using a method analagous to that described in Example 1.

Example 3

SYNTHESIS OF 3-AMINO-N-(CYCLOBUTYLMETHYL)-N-(2-FLUORO-4-HYDROXYBENZYL)-1H-PYRAZOLE-5-CARBOXAMIDE

To a solution of 3-amino-1H-pyrazole-5-carboxylic acid (0.100 g, 0.787 mmol) and 4-(((cyclobutylmethyl)amino)methyl)-3-fluorophenol (0.165 g, 0.787 mmol) in DMF (1 mL) was added EDCI (0.226 g, 1.180 mmol), HOAt (0.159 g, 1.18 mmol) and 4-methylmorpholine (0.040 g, 0.126 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with $Na_2SO_4$ and concentrated. The residue was chromatography eluting with 0 to 15% methanol in methylene chloride to give (0.040 g, 0.126 mmol, 16% yield) of compound 3-amino-N-(cyclobutylmethyl)-N-(2-fluoro-4-hydroxybenzyl)-1H-pyrazole-5-carboxamide.

$^1$H-NMR ($CD_3OD$/400 MHz): 7.08 (m, 1H), 6.54 (m, 2H), 5.70 (m, 1H), 4.63 (m, 2H), 3.64 (m, 1H), 3.56 (m, 1H), 2.64 (m, 1H), 2.01-1.58 (m, 6H). MS ($ES^+$, m/z): 319.0 ($M^+$+1, 100.0).

Example 4

SYNTHESIS OF 3-BROMO-N-(CYCLOBUTYLMETHYL)-N-(1-PHENYLETHYL)-1H-PYRAZOLE-5-CARBOXAMIDE

To a solution of 3-bromo-1H-pyrazole-5-carboxylic acid (0.100 g, 0.524 mmol) and 4-(((cyclobutylmethyl)amino)methyl)-3-fluorophenol (0.099 g, 0.524 mmol) in DMF (1 mL) was added EDCI (0.151 g, 0.785 mmol), HOAt (0.106 g, 0.785 mmol) and 4-methylmorpholine (0.159 g, 1.571 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with $Na_2SO_4$ and concentrated. The residue was purified by chromatography on silica gel eluting with 0 to 15% methanol in methylene chloride to give (0.065 g, 0.179 mmol, 34% yield) of compound 3-bromo-N-(cyclobutylmethyl)-N-(1-phenylethyl)-1H-pyrazole-5-carboxamide.

$^1$H-NMR ($CD_3OD$/400 MHz): 7.34 (m, 5H), 6.60 (s, 1H), 5.60 (m, 1H), 4.80 (m, 1H), 3.40 (m, 2H), 2.40 (m, 1H), 2.01-1.58 (m, 6H). MS ($ES^+$, m/z): 361.9 ($M^+$+1, 100.0).

Example 5

SYNTHESIS OF 3-TRIFLUOROMETHYL-N-(CYCLOBUTYLMETHYL)-N-(1-PHENYLETHYL)-1H-PYRAZOLE-5-CARBOXAMIDE

To a solution of 3-trifluoromethyl-1H-pyrazole-5-carboxylic acid (0.100 g, 0.524 mmol) and 4-(((cyclobutylmethyl)amino)methyl)-3-fluorophenol (0.099 g, 0.524 mmol) in DMF (1 mL) was added EDCI (0.151 g, 0.785 mmol), HOAt (0.106 g, 0.785 mmol) and 4-methylmorpholine (0.159 g, 1.571 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with $Na_2SO_4$ and concentrated. The residue was purified by chromatography on silica gel eluting with 0 to 15% methanol in methylene chloride to give (0.065 g, 0.179 mmol, 34% yield) of compound 3-trifluoromethyl-N-(cyclobutylmethyl)-N-(1-phenylethyl)-1H-pyrazole-5-carboxamide.

$^1$H-NMR ($CD_3OD$/400 MHz): 7.40 (m, 5H), 6.80 (s, 1H), 5.48 (m, 2H), 3.50 (m, 2H), 2.34 (m, 1H), 2.01-1.58 (m, 6H). MS ($ES^+$, m/z): 352.0 ($M^+$+1, 100.0).

Example 6

SYNTHESIS OF N-((1H-INDOL-4-YL)METHYL)-N-(CYCLOBUTYLMETHYL)-3-(TRIFLUOROMETHYL)-1H-PYRAZOLE-5-CARBOXAMIDE

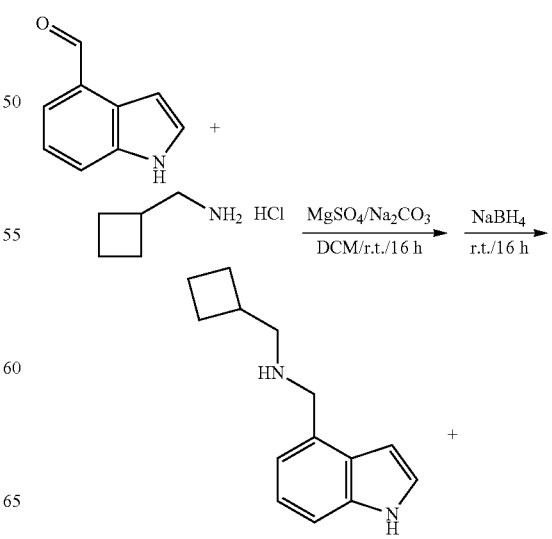

-continued

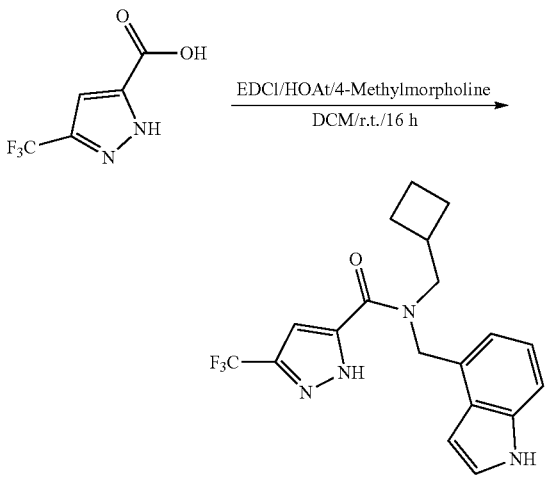

To a solution of 1H-indole-4-carbaldehyde (1.5 g, 10.33 mmol) and cyclobutylmethanamine hydrogen chloride (1.26 g, 10.33 mmol) in methylene chloride (10 mL) was added MgSO$_4$ (3.73 g, 31.0 mmol) and Na$_2$CO$_3$ (2.19 g, 10.33 mmol). The mixture was stirred at room temperature overnight, and then NaBH$_4$ (0.39 g, 10.33 mmol) was added and stirred additional 16 h. It was quenched with methanol and diluted with 30 mL methylene chloride, and washed with water 20 mL. The aqueous layer was extracted with three 20 mL portions of methylene chloride. The combined organic extracts were washed with 20 mL of brine, dried with Na$_2$SO$_4$ and concentrated. The residue was purified by chromatography on silica gel eluting with 0 to 10% methanol in methylene chloride to give (1.8 g, 8.40 mmol, 81% yield) of compound N-((1H-indo-4-yl)methyl)-1-cyclobutylmethanamine.

$^1$H-NMR (CD$_3$OD/400 MHz): 7.30 (d, J=8.0 Hz, 1H), 7.24 (d, J=3.2 Hz, 1H), 7.07 (t, J=8.0 Hz, 1H), 6.96 (d, J=6.8 Hz, 1H), 6.52 (m, 1H), 3.99 (s, 2H), 2.54 (d, J=7.6 Hz, 2H), 2.50 (m, 1H), 2.10 (m, 2H), 1.80 (m, 2H), 1.65 (m, 2H). MS (ES$^+$, m/z): 215.0 (M$^+$+1, 100.0).

To a solution of 3-(trifluoromethyl)-1H-pyrazole-5-carboxylic acid (0.1 g, 0.555 mmol) and N-((1H-indo-4-yl)methyl)-1-cyclobutylmethanamine (0.119 g, 0.555 mmol) in DMF (1 mL) was added EDCI (0.160 g, 0.833 mmol), HOAt (0.133 g, 0.833 mmol) and 4-methylmorpholine (0.168 g, 1.666 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.160 g, 0.425 mmol, 77% yield) of compound N-((1H-indol-4-yl)methyl)-N-(cyclobutylmethyl)-3-(trifluoromethyl)-1H-pyrazole-5-carboxamide.

$^1$H-NMR (CDCl$_3$/400 MHz; stable amide rotamers were observed by NMR): 7.35 (m, 1H), 7.24 (br, 1H), 7.10 (m, 1H), 6.97 (m, 0.5H), 6.84 (m, 1H), 6.60 (m, 0.5H), 6.50 (m, 0.5H), 6.39 (m, 0.5H), 5.05 (s, 2H), 3.60 (s, 1H), 3.34 (s, 1H), 2.74 (m, 1H), 2.50-1.55 (m, 6H). MS (ES$^+$, m/z): 377.0 (M$^+$+1, 100.0).

Example 7

SYNTHESIS OF 3-TRIFLUOROMETHYL-N-(CYCLOBUTYLMETHYL)-N-((2-OXO-2,3-DIHYDROBENZO[D]THIAZOL-7-YL)METHYL)-1H-PYRAZOLE-5-CARBOXAMIDE

To a solution of 3-trifluoromethyl-1H-pyrazole-5-carboxylic acid (0.055 g, 0.403 mmol) and 7-(((cyclobutylmethyl)amino)methyl)benzo[d]thiazol-2(3H)-one (0.10 g, 0.403 mmol) in DMF (1 mL) was added EDCI (0.116 g, 0.604 mmol), HOAt (0.082 g, 0.604 mmol) and 4-methylmorpholine (0.122 g, 1.208 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.060 g, 0.163 mmol, 41% yield) of compound 3-trifluoromethyl-N-(cyclobutylmethyl)-N-((2-oxo-2,3-dihydrobenzo[d]thiazol-7-yl)methyl)-1H-pyrazole-5-carboxamide.

$^1$H-NMR (CD$_3$OD/400 MHz): 7.31 (m, 1H), 7.04 (m, 3H), 5.04 (m, 1H), 5.04 (m, 1H), 3.70 (m, 1H), 3.50 (m, 1H), 2.56 (m, 1H), 2.00-1.56 (m, 6H). MS (ES$^+$, m/z): 368.0 (M$^+$+1, 100.0).

Example 8

SYNTHESIS OF 3-CYANO-N-(CYCLOBUTYLMETHYL)-N-((2-OXO-2,3-DIHYDROBENZO[D]THIAZOL-7-YL)METHYL)-1H-PYRAZOLE-5-CARBOXAMIDE

To a solution of 3-cyano-1H-pyrazole-5-carboxylic acid (0.055 g, 0.403 mmol) and 7-(((cyclobutylmethyl)amino)methyl)benzo[d]thiazol-2(3H)-one (0.10 g, 0.403 mmol) in DMF (1 mL) was added EDCI (0.116 g, 0.604 mmol), HOAt (0.082 g, 0.604 mmol) and 4-methylmorpholine (0.122 g, 1.208 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.060 g, 0.163 mmol, 41% yield) of compound 3-cyano-N-(cyclobutylmethyl)-N-((2-oxo-2,3-dihydrobenzo[d]thiazol-7-yl)methyl)-1H-pyrazole-5-carboxamide.

$^1$H-NMR (CD$_3$OD/400 MHz): 7.31 (m, 1H), 7.04 (m, 3H), 5.04 (m, 1H), 5.04 (m, 1H), 3.70 (m, 1H), 3.50 (m, 1H), 2.56 (m, 1H), 2.00-1.56 (m, 6H). MS (ES$^+$, m/z): 368.0 (M$^+$+1, 100.0).

Example 9

SYNTHESIS OF 3-CHLORO-N-(CYCLOBUTYLMETHYL)-N-((2-OXO-2,3-DIHYDROBENZO[D]THIAZOL-7-YL)METHYL)-1H-PYRAZOLE-5-CARBOXAMIDE

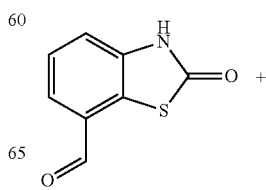

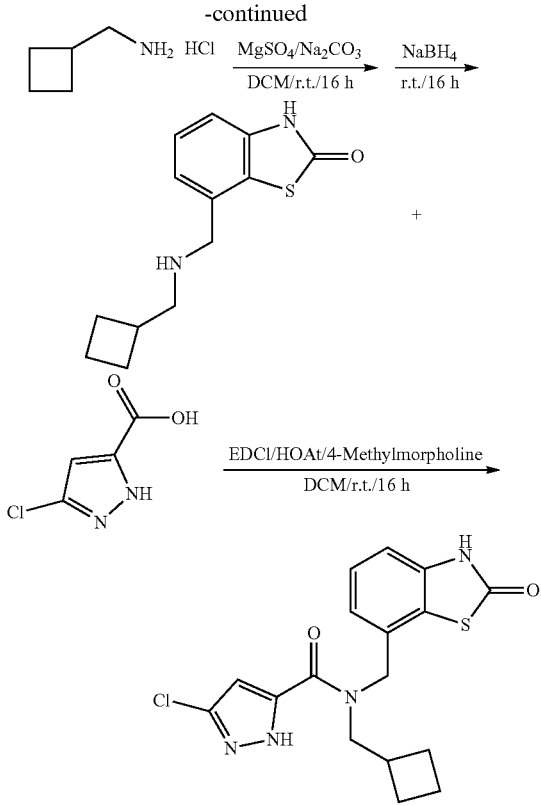

To a solution of 2-oxo-2,3-dihydrobenzo[d]thiazole-7-carbaldehyde (0.4 g, 2.32 mmol) and cyclobutylmethanamine hydrogen chloride (0.190 g, 2.32 mmol) in methylene chloride (5 mL) was added MgSO$_4$ (0.81 g, 6.70 mmol) and Na$_2$CO$_3$ (0.47 g, 4.46 mmol). The mixture was stirred at room temperature overnight, and then NaBH$_4$ (0.084 g, 2.23 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 10% methanol in methylene chloride to give (0.45 g, 1.812 mmol, 81% yield) of compound 7-(((cyclobutylmethyl)amino)methyl)benzo[d]thiazol-2(3H)-one.

To a solution of 3-chloro-1H-pyrazole-5-carboxylic acid (0.1 g, 0.682 mmol) and 7-(((cyclobutylmethyl)amino)methyl)benzo[d]thiazol-2(3H)-one (0.169 g, 0.682 mmol) in DMF (1 mL) was added EDCI (0.196 g, 1.024 mmol), HOAt (0.138 g, 1.024 mmol) and 4-methylmorpholine (0.207 g, 2.047 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.045 g, 0.119 mmol, 16% yield) of compound 3-Chloro-N-(cyclobutylmethyl)-N-((2-oxo-2,3-dihydrobenzo[d]thiazol-7-yl)methyl)-1H-pyrazole-5-carboxamide.

$^1$H-NMR (CD$_3$OD/400 MHz): 7.30 (m, 1H), 7.10 (m, 2H), 6.50 (m, 1H), 4.77 (m, 2H), 3.53 (m, 2H), 2.66 (m, 1H), 2.00-1.59 (m, 6H). MS (ES$^+$, m/z): 377.0 (M$^+$+1, 100.0).

Example 10

Synthesis of 3-Bromo-N-(cyclobutylmethyl)-N-((2-oxo-2,3-dihydrobenzo[d]thiazol-7-yl)methyl)-1H-pyrazole-5-carboxamide To a solution of 3-bromo-1H-pyrazole-5-carboxylic acid (0.077 g, 0.403 mmol) and 7-(((cyclobutylmethyl)amino)methyl)benzo[d]thiazol-2(3H)-one (0.10 g, 0.403 mmol) in DMF (1 mL) was added EDCI (0.116 g, 0.604 mmol), HOAt (0.082 g, 0.604 mmol) and 4-methylmorpholine (0.122 g, 1.208 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.020 g, 0.047 mmol, 12% yield) of compound 3-bromo-N-(cyclobutylmethyl)-N-((2-oxo-2,3-dihydrobenzo[d]thiazol-7-yl)methyl)-1H-pyrazole-5-carboxamide.

$^1$H-NMR (CD$_3$OD/400 MHz): 7.30 (m, 1H), 7.06 (m, 2H), 6.50 (m, 1H), 4.77 (m, 2H), 3.53 (m, 2H), 2.66 (m, 1H), 2.00-1.59 (m, 6H). MS (ES$^+$, m/z): 420.9 (M$^+$+1, 100.0).

Example 11

Synthesis of N-(azetidin-3-ylmethyl)-3-bromo-N-(2-fluoro-4-hydroxybenzyl)-1H-pyrazole-5-carboxamide

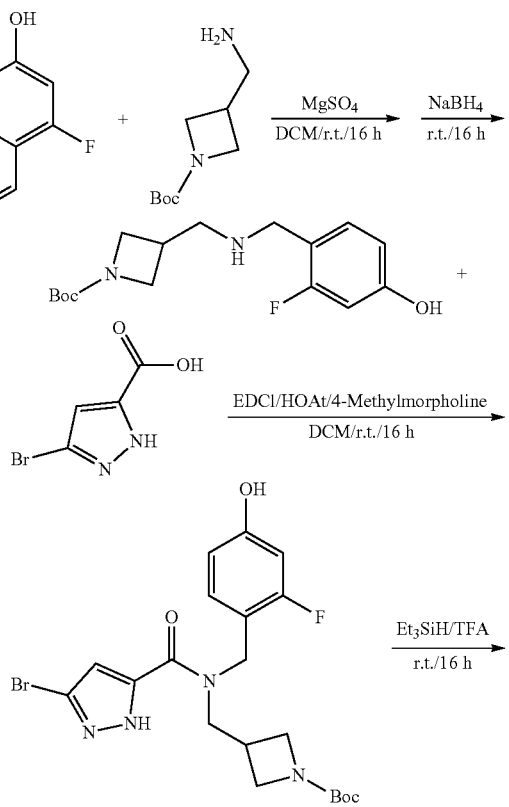

161
-continued

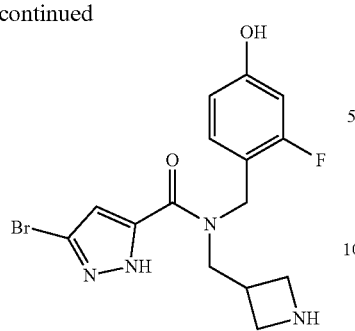

To a solution of 2-fluoro-4-hydroxybenzaldehyde (0.226 g, 1.611 mmol) and tert-butyl 3-(aminomethyl)azetidine-1-carboxylate (0.300 g, 1.611 mmol) in methylene chloride (5 mL) was added MgSO$_4$ (0.582 g, 4.83 mmol). The mixture was stirred at room temperature overnight, and then NaBH$_4$ (0.061 g, 1.611 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 10% methanol in methylene chloride to give (0.399 g, 1.29 mmol, 80% yield) of compound tert-butyl 3-(((2-fluoro-4-hydroxybenzyl)amino)methyl)azetidine-1-carboxylate.

To a solution of 3-bromo-1H-pyrazole-5-carboxylic acid (0.038 g, 0.161 mmol) and tert-butyl 4-(((cyclobutylmethyl)amino)methyl)indoline-1-carboxylate (0.050 g, 0.161 mmol) in DMF (1 mL) was added EDCI (0.037 g, 0.193 mmol), HOAt (0.022 g, 0.161 mmol) and 4-methylmorpholine (0.081 g, 0.81 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was used for the next step directly without further purification.

To a solution of tert-butyl 3-((3-bromo-N-(2-fluoro-4-hydroxybenzyl)-1H-pyrazole-5-carboxamido)methyl)azetidine-1-carboxylate (0.02 g, 0.041 mmol) in DCM (2 mL) was added Et$_3$SiH (0.5 mL), and TFA (0.5 mL). Then the reaction mixture was stirred at r.t. overnight. The resulting reaction mixture was evaporated and the residue was diluted with 30 mL DCM and washed with saturated NaHCO$_3$ 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.010 g, 0.026 mmol, 63% yield) of compound N-(azetidin-3-ylmethyl)-3-bromo-N-(2-fluoro-4-hydroxybenzyl)-1H-pyrazole-5-carboxamide.

$^1$H-NMR (CD$_3$OD/400 MHz): 7.06 (m, 1H), 6.60 (m, 3H), 4.80 (m, 2H), 4.00 (m, 4H), 3.75 (m, 2H), 3.10 (m, 1H). MS (ES$^+$, m/z): 382.9 (M$^+$+1, 100.0).

162

Example 14

SYNTHESIS OF TERT-BUTYL 4-((N-(CYCLOBUTYLMETHYL)-3-(TRIFLUOROMETHYL)-1H-PYRAZOLE-5-CARBOXAMIDO)METHYL)INDOLINE-1-CARBOXYLATE

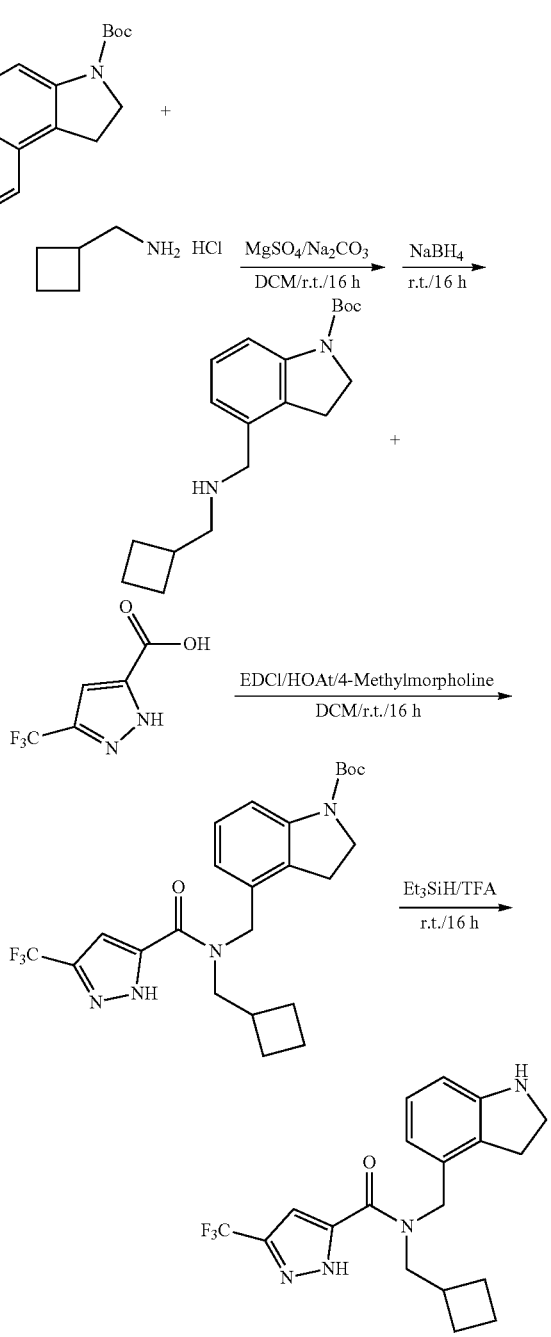

To a solution of tert-butyl 4-formylindoline-1-carboxylate (0.5 g, 2.02 mmol) and cyclobutylmethanamine hydrogen chloride (0.172 g, 2.02 mmol) in methylene chloride (5 mL) was added MgSO$_4$ (0.730 g, 6.07 mmol) and Na$_2$CO$_3$ (0.43 g, 4.04 mmol). The mixture was stirred at room temperature overnight, and then NaBH$_4$ (0.076 g, 2.02 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 10% methanol in methylene chloride to give (0.4 g, 1.26 mmol, 63% yield) of compound tert-butyl 4-(((cyclobutylmethyl)amino) methyl)indoline-1-carboxylate.

$^1$H-NMR (CD$_3$OD/400 MHz): 7.12 (m, 2H), 6.92 (m, 1H), 3.96 (m, 2H), 3.64 (s, 2H), 2.50 (m, 1H), 2.20 (m, 2H), 1.80 (m, 2H), 1.60 (m, 2H), 1.55 (s, 9H). MS (ES$^+$, m/z): 317.0 (M$^+$+1, 100.0).

To a solution of 3-(trifluoromethyl)-1H-pyrazole-5-carboxylic acid (0.06 g, 0.333 mmol) and tert-butyl 4-(((cyclobutylmethyl)amino)methyl)indoline-1-carboxylate (0.105 g, 0.333 mmol) in DMF (1 mL) was added EDCI (0.096 g, 0.500 mmol), HOAt (0.068 g, 0.500 mmol) and 4-methylmorpholine (0.101 g, 1.00 mmol). Then the reaction mixture was stirred at r.t. overnight. The resulting reaction mixture was diluted with 30 mL DCM and washed with water 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.080 g, 0.167 mmol, 50% yield) of compound tert-butyl 4-((N-(cyclobutylmethyl)-3-(trifluoromethyl)-1H-pyrazole-5-carboxamido)methyl)indoline-1-carboxylate.

$^1$H-NMR (CD$_3$OD/400 MHz): 7.22 (m, 1H), 7.15 (m, 1H), 6.75 (m, 1H), 6.67 (m, 0.5H), 6.41 (m, 0.5H), 4.68 (m, 2H), 4.00 (m, 2H), 3.55 (m, 2H), 3.00 (m, 2H), 2.65 (m, 1H), 2.03-1.70 (m, 6H), 1.55 (s, 9H). MS (ES$^+$, m/z): 479.1 (M$^+$+1, 100.0).

To a solution of tert-butyl 4-((N-(cyclobutylmethyl)-3-(trifluoromethyl)-1H-pyrazole-5-carboxamido)methyl)indoline-1-carboxylate (0.1 g, 0.555 mmol) in DCM (2 mL) was added Et$_3$SiH (0.5 mL), and TFA (0.5 mL). Then the reaction mixture was stirred at r.t. overnight. The resulting reaction mixture was evaporated and the residue was diluted with 30 mL DCM and washed with saturated NaHCO$_3$ 20 mL. The aqueous layer was extracted with three 15 mL portions of methylene chloride. The combined organic extracts were washed with 10 mL of brine, dried with Na$_2$SO$_4$ and concentrated. The residue was purified by chromatography on silica gel eluting with 0 to 15% methanol in methylene chloride to give (0.030 g, 0.079 mmol, 95% yield) of compound N-(cyclobutylmethyl)-N-(indolin-4-ylmethyl)-3-(trifluoromethyl)-1H-pyrazole-5-carboxamide.

$^1$H-NMR (CD$_3$OD/400 MHz): 7.37 (m, 2H), 6.95 (m, 1H), 6.55 (m, 1H), 4.60 (m, 2H), 3.80 (m, 2H), 3.60 (m, 2H), 3.30 (m, 2H), 2.70 (m, 1H), 2.03-1.50 (m, 6H). MS (ES$^+$, m/z): 379.0 (M$^+$+1, 100.0).

Example 47

SYNTHESIS OF N-(2-FLUOROBENZYL)-N-(TRANS-4-METHOXYCYCLOHEXYL)-3-(TRIFLUOROMETHYL)-1H-PYRAZOLE-5-CARBOXAMIDE

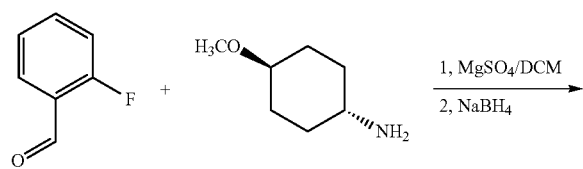

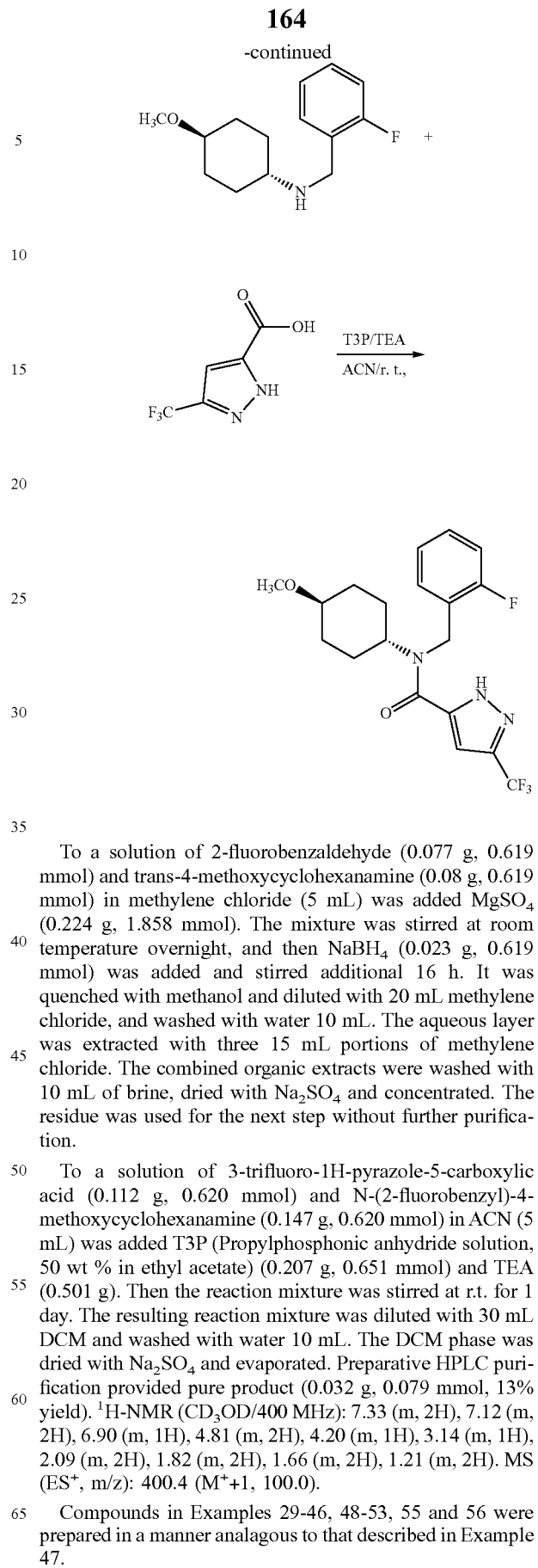

To a solution of 2-fluorobenzaldehyde (0.077 g, 0.619 mmol) and trans-4-methoxycyclohexanamine (0.08 g, 0.619 mmol) in methylene chloride (5 mL) was added MgSO$_4$ (0.224 g, 1.858 mmol). The mixture was stirred at room temperature overnight, and then NaBH$_4$ (0.023 g, 0.619 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was used for the next step without further purification.

To a solution of 3-trifluoro-1H-pyrazole-5-carboxylic acid (0.112 g, 0.620 mmol) and N-(2-fluorobenzyl)-4-methoxycyclohexanamine (0.147 g, 0.620 mmol) in ACN (5 mL) was added T3P (Propylphosphonic anhydride solution, 50 wt % in ethyl acetate) (0.207 g, 0.651 mmol) and TEA (0.501 g). Then the reaction mixture was stirred at r.t. for 1 day. The resulting reaction mixture was diluted with 30 mL DCM and washed with water 10 mL. The DCM phase was dried with Na$_2$SO$_4$ and evaporated. Preparative HPLC purification provided pure product (0.032 g, 0.079 mmol, 13% yield). $^1$H-NMR (CD$_3$OD/400 MHz): 7.33 (m, 2H), 7.12 (m, 2H), 6.90 (m, 1H), 4.81 (m, 2H), 4.20 (m, 1H), 3.14 (m, 1H), 2.09 (m, 2H), 1.82 (m, 2H), 1.66 (m, 2H), 1.21 (m, 2H). MS (ES$^+$, m/z): 400.4 (M$^+$+1, 100.0).

Compounds in Examples 29-46, 48-53, 55 and 56 were prepared in a manner analagous to that described in Example 47.

Example 54

SYNTHESIS OF TERT-BUTYL(3-((N-(TRANS-4-METHOXYCYCLOHEXYL)-3-(TRIFLUOROMETHYL)-1H-PYRAZOLE-5-CARBOXAMIDO)METHYL)PHENYL)CARBAMATE

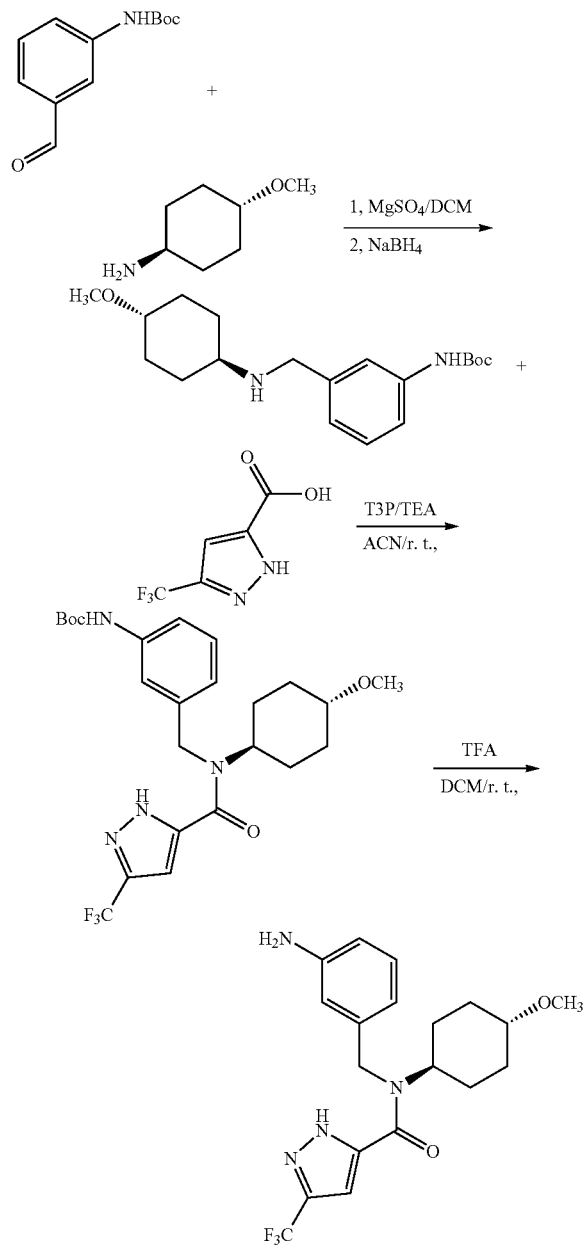

To a solution of tert-butyl (3-formylphenyl)carbamate (0.137 g, 0.619 mmol) and trans-4-methoxycyclohexanamine (0.08 g, 0.619 mmol) in methylene chloride (5 mL) was added MgSO$_4$ (0.224 g, 1.858 mmol). The mixture was stirred at room temperature overnight, and then NaBH$_4$ (0.023 g, 0.619 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was used for the next step without further purification.

To a solution of 3-trifluoro-1H-pyrazole-5-carboxylic acid (0.111 g, 0.619 mmol) and tert-butyl (3-(((trans-4-methoxycyclohexyl)amino)methyl)phenyl)carbamate (0.207 g, 0.619 mmol) in ACN (5 mL) was added T3P (Propylphosphonic anhydride solution, 50 wt % in ethyl acetate) (0.207 g, 0.650 mmol) and TEA (0.500 g). Then the reaction mixture was stirred at r.t. for 1 day. The resulting reaction mixture was diluted with 30 mL DCM and washed with water 10 mL. The DCM phase was dried with Na$_2$SO$_4$ and evaporated. Without purification, the residue was dissolved in DCM (2 mL) and TFA (0.5 mL) was added. Then the reaction mixture was stirred at r.t. overnight. The resulting reaction mixture was evaporated and the residue was diluted with 30 mL DCM and washed with saturated NaHCO$_3$ 20 mL. The aqueous layer was extracted with three 15 mL portions of methylene chloride. The combined organic extracts were washed with 10 mL of brine, dried with Na$_2$SO$_4$ and concentrated. Preparative HPLC purification provided pure product tert-butyl (3-((N-((trans-4-methoxycyclohexyl)-3-(trifluoromethyl)-1H-pyrazole-5-carboxamido)methyl)phenyl)carbamate (0.030 g, 0.076 mmol, 12% yield).

$^1$H-NMR (CD$_3$OD/400 MHz): 7.45 (m, 1H), 7.27 (m, 3H), 6.80 (m, 1H), 4.80 (m, 2H), 4.22 (m, 1H), 3.25 (s, 3H), 3.05 (m, 1H), 2.05 (m, 2H), 1.84 (m, 2H), 1.66 (m, 2H), 1.20 (m, 2H). MS (ES$^+$, m/z): 397.5 (M$^+$+1, 100.0).

Compounds in Examples 57, 77, 95 and 97 were prepared in a manner analagous to that described in Example 54.

Example 59

SYNTHESIS OF N-(2-(1,4-DIOXASPIRO[4.5]DECAN-8-YL)ETHYL)-N-(2-FLUOROBENZYL)-3-(TRIFLUOROMETHYL)-1H-PYRAZOLE-5-CARBOXAMIDE

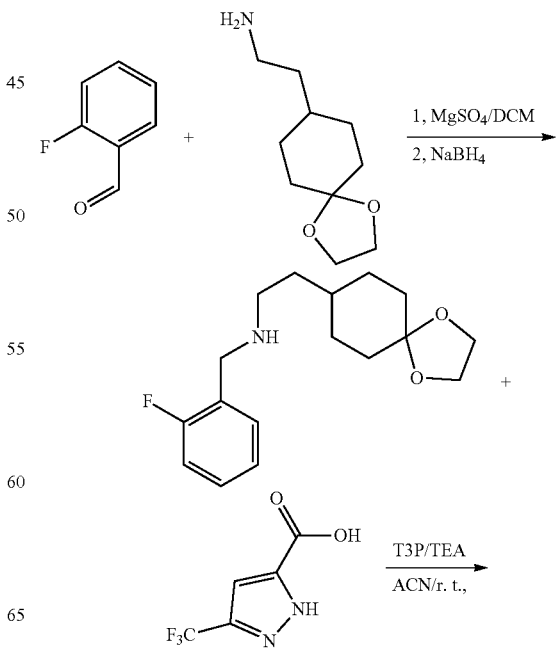

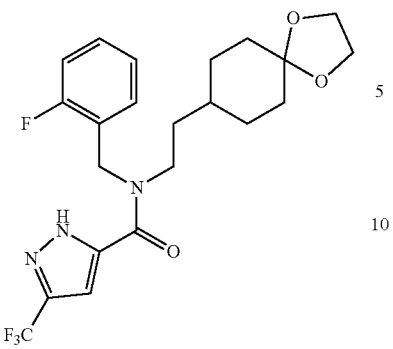

To a solution of 2-fluorobenzaldehyde (0.134 g, 1.080 mmol) and 2-(1,4-dioxaspiro[4.5]decan-8-yl)ethanamine (0.2 g, 1.080 mmol) in methylene chloride (5 mL) was added MgSO₄ (0.390 g, 3.24 mmol). The mixture was stirred at room temperature overnight, and then NaBH₄ (0.041 g, 1.080 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na₂SO₄ and concentrated. The residue was used for the next step without further purification.

To a solution of 3-trifluoro-1H-pyrazole-5-carboxylic acid (0.194 g, 1.080 mmol) and N-(2-fluorobenzyl)-2-(1,4-dioxaspiro[4.5]decan-8-yl)ethanamine (0.317 g, 1.080 mmol) in ACN (5 mL) was added T3P (Propylphosphonic anhydride solution, 50 wt % in ethyl acetate) (0.361 g, 1.134 mmol) and TEA (0.873 g). Then the reaction mixture was stirred at r.t. for 1 day. The resulting reaction mixture was diluted with 30 mL DCM and washed with water 10 mL. The DCM phase was dried with Na₂SO₄ and evaporated. Preparative HPLC purification provided pure product (0.160 g, 0.351 mmol, 33% yield).

¹H-NMR (CD₃CN/400 MHz): 7.35 (m, 2H), 7.16 (m, 2H), 6.80 (m, 1H), 4.77 (m, 2H), 3.85 (m, 4H), 3.52 (m, 2H), 2.30 (m, 2H), 1.62 (m, 5H), 1.17 (m, 4H). MS (ES⁺, m/z): 456.5 (M⁺+1, 100.0).

Example 60

Synthesis of N-(2-(1,4-dioxaspiro[4.5]decan-8-yl)ethyl)-N-(2-fluorobenzyl)-3-(trifluoromethyl)-1H-pyrazole-5-carboxamide

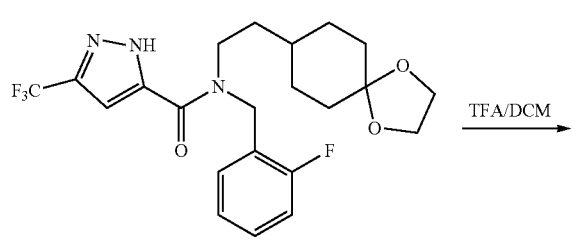

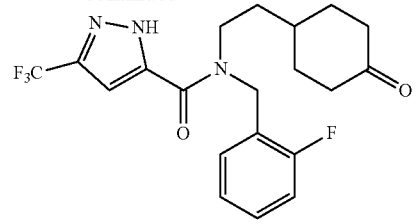

To a solution of N-(2-(1,4-dioxaspiro[4.5]decan-8-yl)ethyl)-N-(2-fluorobenzyl)-3-(trifluoromethyl)-1H-pyrazole-5-carboxamide (0.492 g, 1.080 mmol) in DCM (2 mL) was added TFA (0.5 mL). Then the reaction mixture was stirred at r.t. overnight. The resulting reaction mixture was evaporated and the residu was diluted with 30 mL DCM and washed with saturated NaHCO₃ 20 mL. The aqueous layer was extracted with three 15 mL portions of methylene chloride. The combined organic extracts were washed with 10 mL of brine, dried with Na₂SO₄ and concentrated. The residue was purified by chromatography on silica gel eluting with 0 to 15% methanol in methylene chloride to give (0.200 g, 0.486 mmol, 45% yield) of compound N-(2-fluorobenzyl)-N-(2-(4-oxocyclohexyl)ethyl)-3-(trifluoromethyl)-1H-pyrazole-5-carboxamide.

¹H-NMR (CDCl₃/400 MHz): 7.35 (m, 1H), 7.18 (m, 3H), 6.70 (m, 1H), 4.87 (m, 2H), 3.59 (m, 2H), 2.28 (m, 4H), 2.04 (m, 2H), 1.70 (m, 3H), 1.44 (m, 2H). MS (ES⁺, m/z): 412.5 (M⁺+1, 100.0).

Example 62

Synthesis of N-(2-chlorobenzyl)-N-(2-(1,1-dioxido-tetrahydrothiophen-3-yl)ethyl)-3-(trifluoromethyl)-1H-pyrazole-5-carboxamide

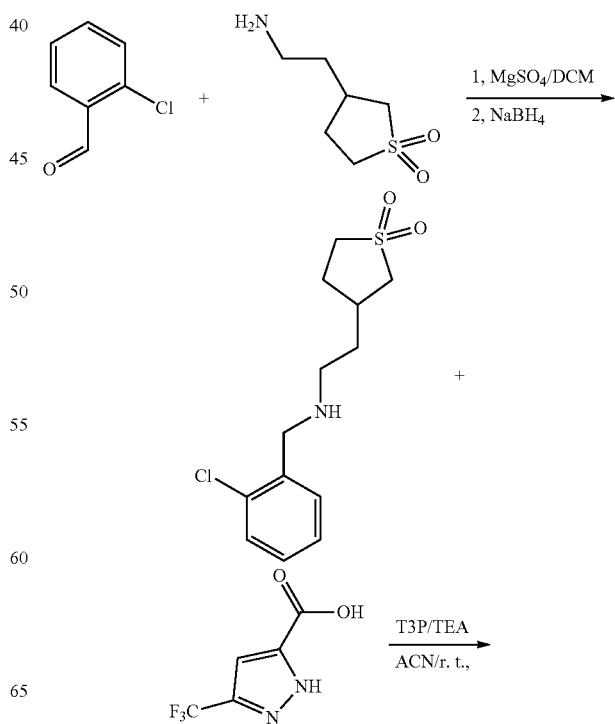

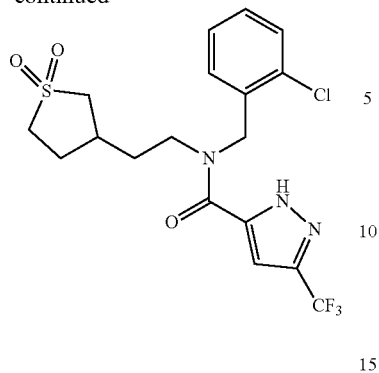

To a solution of 2-chorobenzaldehyde (0.086 g, 0.613 mmol) and 3-(2-aminoethyl)tetrahydrothiophene 1,1-dioxide (0.10 g, 0.613 mmol) in methylene chloride (5 mL) was added MgSO$_4$ (0.221 g, 1.838 mmol). The mixture was stirred at room temperature overnight, and then NaBH$_4$ (0.023 g, 0.613 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was used for the next step without further purification.

To a solution of 3-trifluoro-1H-pyrazole-5-carboxylic acid (0.110 g, 0.613 mmol) and 3-(2-((2-chlorobenzyl)amino)ethyl)tetrahydrothiophene 1,1-dioxide (0.176 g, 0.613 mmol) in ACN (5 mL) was added T3P (Propylphosphonic anhydride solution, 50 wt % in ethyl acetate) (0.205 g, 0.644 mmol) and TEA (0.495 g). Then the reaction mixture was stirred at r.t. for 1 day. The resulting reaction mixture was diluted with 30 mL DCM and washed with water 10 mL. The DCM phase was dried with Na$_2$SO$_4$ and evaporated. Preparative HPLC purification provided pure product N-(2-chlorobenzyl)-N-(2-(1,1-dioxidotetrahydrothiophen-3-yl)ethyl)-3-(trifluoromethyl)-1H-pyrazole-5-carboxamide (0.040 g, 0.087 mmol, 14% yield).

$^1$H-NMR (DMSO-d$_6$/400 MHz): 7.46 (m, 1H), 7.35 (m, 3H), 6.85 (m, 1H), 4.91 (m, 2H), 3.60 (m, 2H), 3.10 (m, 2H), 2.72 (m, 1H), 2.41 (m, 2H), 1.85 (m, 2H). MS (ES$^+$, m/z): 450.4 (M$^+$+1, 100.0).

Compounds in Examples 55, 56, 61, 63-72, 76, 88-90, 92, 93, 100 and 111 were prepared in a manner analagous to that described in Example 62.

Example 73

SYNTHESIS OF N-(2-CHLOROBENZYL)-N-(2-(1,1-DIOXIDO-TETRAHYDROTHIOPHEN-3-YL)ETHYL)-3-(TRIFLUOROMETHYL)-1H-PYRAZOLE-5-CARBOXAMIDE

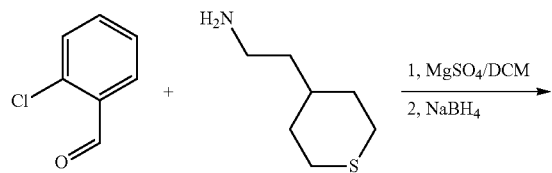

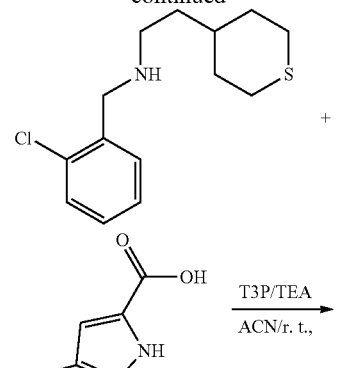

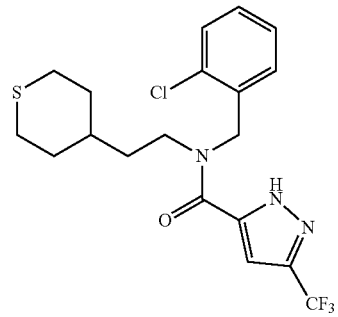

To a solution of 2-chorobenzaldehyde (0.194 g, 1.377 mmol) and 2-(tetrahydro-2H-thiopyran-4-yl)ethanamine (0.20 g, 1.377 mmol) in methylene chloride (5 mL) was added MgSO$_4$ (0.497 g, 4.13 mmol). The mixture was stirred at room temperature overnight, and then NaBH$_4$ (0.052 g, 1.377 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was used for the next step without further purification.

To a solution of 3-trifluoro-1H-pyrazole-5-carboxylic acid (0.248 g, 1.377 mmol) and N-(2-chlorobenzyl)-2-(tetrahydro-2H-thiopyran-4-yl)ethanamine (0.372 g, 1.377 mmol) in ACN (5 mL) was added T3P (Propylphosphonic anhydride solution, 50 wt % in ethyl acetate) (0.460 g, 1.466 mmol) and TEA (0.495 g). Then the reaction mixture was stirred at r.t. for 1 day. The resulting reaction mixture was diluted with 30 mL DCM and washed with water 10 mL. The DCM phase was dried with Na$_2$SO$_4$ and evaporated. Preparative HPLC purification provided pure product N-(2-chlorobenzyl)-N-(2-(tetrahydro-2H-thiopyran-4-yl)ethyl)-3-(trifluoromethyl)-1H-pyrazole-5-carboxamide (0.060 g, 0.139 mmol, 10% yield).

$^1$H-NMR (Acetone-d$_6$/400 MHz): 7.41 (m, 4H), 6.80 (m, 1H), 4.95 (d, 2H), 3.61 (d, 2H), 2.60 (m, 4H), 1.99 (m, 1H), 1.61 (m, 2H), 1.30 (m, 4H). MS (ES$^+$, m/z): 432.4 (M$^+$+1, 100.0).

Compounds in Examples 79, 80, 82, 84, 86 were prepared in a manner analagous to that described in Example 73.

Example 74

Synthesis of N-(2-chlorobenzyl)-N-(2-(1-oxidotetrahydro-2H-thiopyran-4-yl)ethyl)-3-(trifluoromethyl)-1H-pyrazole-5-carboxamide

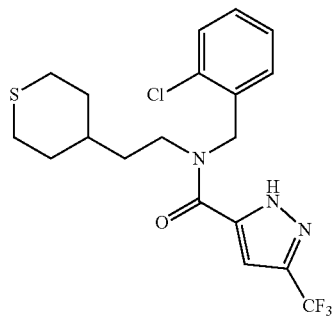

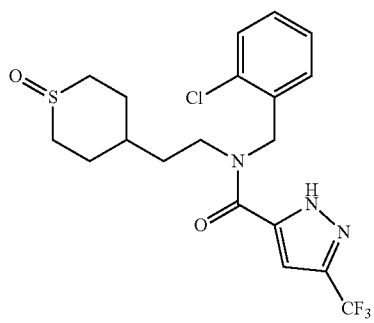

To a solution of N-(2-chlorobenzyl)-N-(2-(tetrahydro-2H-thiopyran-4-yl)ethyl)-3-(trifluoromethyl)-1H-pyrazole-5-carboxamide (0.015 g, 0.035 mmol) in ACN (1 mL) was added t-BuOOH (3.13 mg, 0.035 mmol). Then the reaction mixture was stirred at r.t. for 1 day. The resulting reaction mixture was diluted with 30 mL DCM and washed with saturated Na$_2$S$_2$O$_3$ aqueous solution 10 mL. The DCM phase was dried with Na$_2$SO$_4$ and evaporated. Preparative HPLC purification provided pure product N-(2-chlorobenzyl)-N-(2-(tetrahydro-2H-thiopyran-4-yl)ethyl)-3-(trifluoromethyl)-1H-pyrazole-5-carboxamide (0.010 g, 0.022 mmol, 64% yield).

$^1$H-NMR (Acetone-d$_6$/400 MHz): 7.41 (m, 4H), 6.90 (m, 1H), 4.95 (d, 2H), 3.61 (d, 2H), 3.16 (m, 2H), 2.81 (m, 1H), 2.53 (m, 2H), 2.08 (m, 2H), 1.73 (m, 4H). MS (ES$^+$, m/z): 448.4 (M$^+$+1, 100.0).

Example 75

Synthesis of N-(2-chlorobenzyl)-N-(2-(1,1-dioxidotetrahydro-2H-thiopyran-4-yl)ethyl)-3-(trifluoromethyl)-1H-pyrazole-5-carboxamide

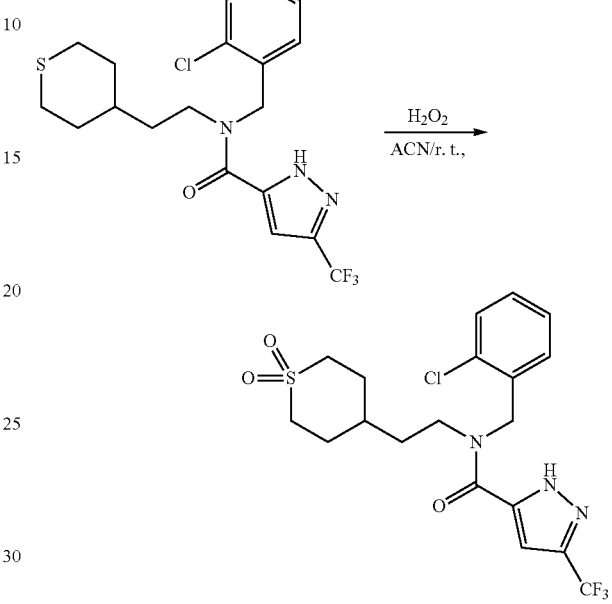

To a solution of N-(2-chlorobenzyl)-N-(2-(tetrahydro-2H-thiopyran-4-yl)ethyl)-3-(trifluoromethyl)-1H-pyrazole-5-carboxamide (0.015 g, 0.035 mmol) in ACN (1 mL) was added H$_2$O$_2$ (1.18 mg, 0.035 mmol) and ammonium molybdate (NH$_4$)$_2$MoO$_4$ (0.1 eq., 1.0 mg). Then the reaction mixture was stirred at r.t. for 1 day. The resulting reaction mixture was diluted with 30 mL DCM and washed with saturated Na$_2$S$_2$O$_3$ aqueous solution 10 mL. The DCM phase was dried with Na$_2$SO$_4$ and evaporated. Preparative HPLC purification provided pure product N-(2-chlorobenzyl)-N-(2-(1,1-dioxidotetrahydro-2H-thiopyran-4-yl)ethyl)-3-(trifluoromethyl)-1H-pyrazole-5-carboxamide (0.012 g, 0.026 mmol, 75% yield).

$^1$H-NMR (CD$_3$CN/400 MHz): 7.47 (m, 1H), 7.32 (m, 3H), 6.90 (m, 1H), 4.85 (m, 2H), 3.49 (m, 2H), 2.90 (m, 4H), 2.25 (m, 2H), 2.05 (m, 1H), 1.61 (m, 4H). MS (ES$^+$, m/z): 464.4 (M$^+$+1, 100.0).

Compounds in Examples 78, 81, 83, 85, 87 were prepared in a manner analagous to that described in Example 75.

Example 91

Synthesis of N-(2-amino-6-fluorobenzyl)-N-(2-(1,1-dioxidotetrahydro-2H-thiopyran-4-yl)ethyl)-3-(trifluoromethyl)-1H-pyrazole-5-carboxamide

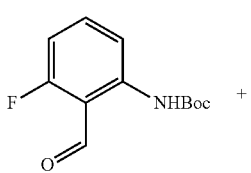 +

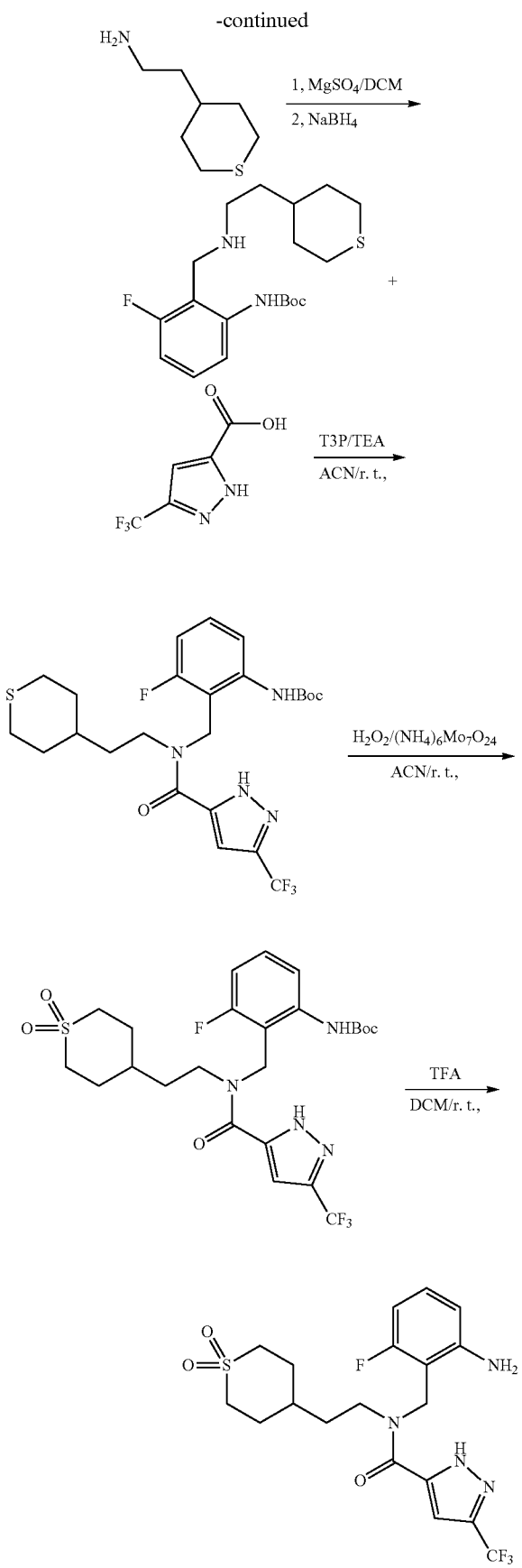

To a solution of tert-butyl (3-fluoro-2-formylphenyl)carbamate (0.132 g, 0.551 mmol) and 2-(tetrahydro-2H-thiopyran-4-yl)ethanamine (0.08 g, 0.551 mmol) in methylene chloride (5 mL) was added MgSO$_4$ (0.199 g, 1.65 mmol). The mixture was stirred at room temperature overnight, and then NaBH$_4$ (0.021 g, 0.551 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was used for the next step without further purification.

To a solution of 3-trifluoro-1H-pyrazole-5-carboxylic acid (0.099 g, 0.551 mmol) and tert-butyl (3-fluoro-2-(((2-(tetrahydro-2H-thiopyran-4-yl)ethyl)amino)methyl)phenyl) carbamate (0.203 g, 0.551 mmol) in ACN (5 mL) was added T3P (Propylphosphonic anhydride solution, 50 wt % in ethyl acetate) (0.184 g, 0.579 mmol) and TEA (0.445 g). Then the reaction mixture was stirred at r.t. for 1 day. The resulting reaction mixture was diluted with 30 mL DCM and washed with water 10 mL. The DCM phase was dried with Na$_2$SO$_4$ and evaporated. Preparative HPLC purification provided pure product tert-butyl (3-fluoro-2-((N-(2-(tetrahydro-2H-thiopyran-4-yl)ethyl)-3-(trifluoromethyl)-1H-pyrazole-5-carboxamido)methyl)phenyl)carbamate (0.080 g, 0.151 mmol, 27% yield).

To a solution of tert-butyl (3-fluoro-2-((N-(2-(tetrahydro-2H-thiopyran-4-yl)ethyl)-3-(trifluoromethyl)-1H-pyrazole-5-carboxamido)methyl)phenyl)carbamate (0.080 g, 0.151 mmol) in ACN (1 mL) was added H$_2$O$_2$ (0.256 g, 7.54 mmol) and ammonium molybdate (NH$_4$)$_2$MoO$_4$ (0.1 eq., 19 mg). Then the reaction mixture was stirred at r.t. for 1 day. The resulting reaction mixture was diluted with 30 mL DCM and washed with saturated Na$_2$S$_2$O$_3$ aqueous solution 10 mL. The DCM phase was dried with Na$_2$SO$_4$ and evaporated. Preparative HPLC purification provided pure product tert-butyl (2-((N-(2-(1,1-dioxidotetrahydro-2H-thiopyran-4-yl)ethyl)-3-(trifluoromethyl)-1H-pyrazole-5-carboxamido)methyl)-3-fluorophenyl)carbamate (0.060 g, 0.107 mmol, 71% yield).

To a solution of tert-butyl (2-((N-(2-(1,1-dioxidotetrahydro-2H-thiopyran-4-yl)ethyl)-3-(trifluoromethyl)-1H-pyrazole-5-carboxamido)methyl)-3-fluorophenyl)carbamate (0.050 g, 0.089 mmol) in DCM (2 mL) was added TFA (0.5 mL). Then the reaction mixture was stirred at r.t. overnight. The resulting reaction mixture was evaporated and the residue was diluted with 30 mL DCM and washed with saturated NaHCO$_3$ 20 mL. The aqueous layer was extracted with three 15 mL portions of methylene chloride. The combined organic extracts were washed with 10 mL of brine, dried with Na$_2$SO$_4$ and concentrated. The residue was purified by preparative HPLC to give (0.035 g, 0.076 mmol, 85% yield) of compound N-(2-amino-6-fluorobenzyl)-N-(2-(1,1-dioxidotetrahydro-2H-thiopyran-4-yl)ethyl)-3-(trifluoromethyl)-1H-pyrazole-5-carboxamide.

$^1$H-NMR (CD$_3$OD/400 MHz): 7.09 (m, 1H), 6.90 (m, 1H), 6.52 (m, 1H), 6.41 (m, 1H), 4.84 (m, 2H), 3.50 (m, 4H), 2.80 (m, 5H), 1.55 (m, 4H). MS (ES$^+$, m/z): 463.4 (M$^+$+1, 100.0).

The compound in Example 97 was prepared in a manner analagous to that described in Example 91.

Example 94

Synthesis of N-(2-chloro-3-nitrobenzyl)-N-(2-(1,1-dioxidotetrahydrothiophen-3-yl)ethyl)-3-(trifluoromethyl)-1H-pyrazole-5-carboxamide

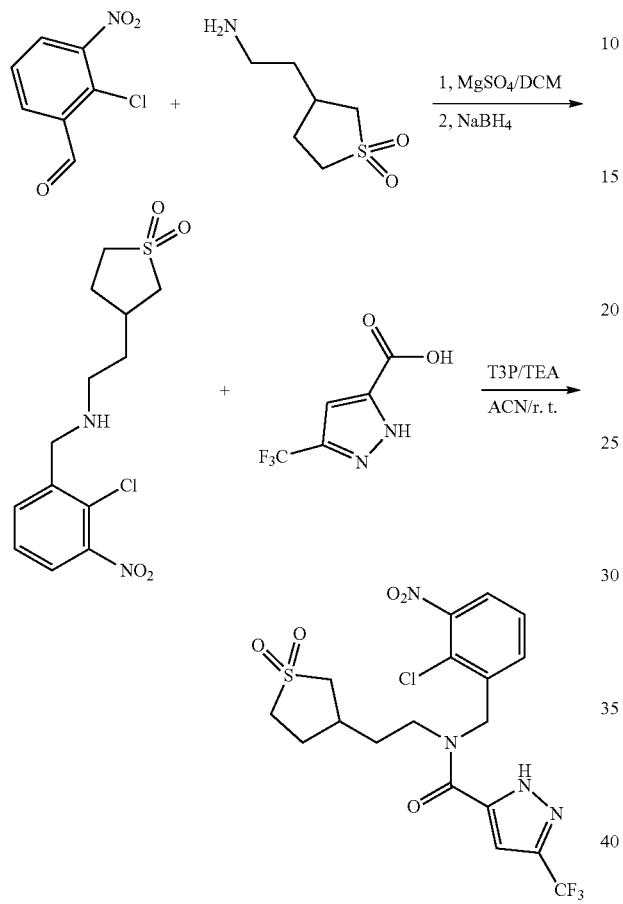

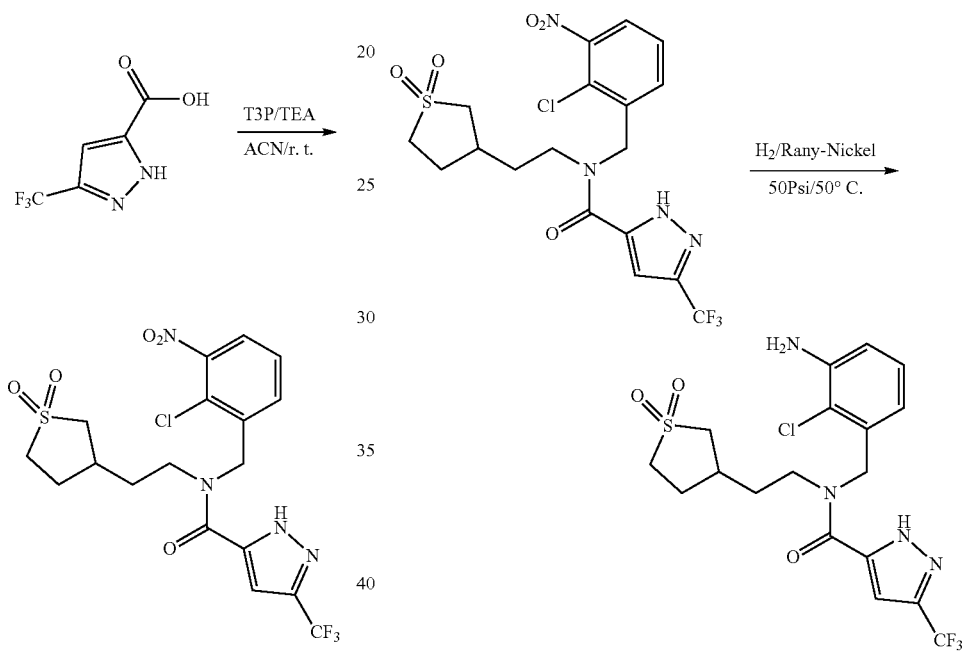

To a solution of 2-chloro-3-nitrobenzaldehyde (0.171 g, 0.919 mmol) and 3-(2-aminoethyl)tetrahydrothiophene 1,1-dioxide (0.150 g, 0.919 mmol) in methylene chloride (5 mL) was added MgSO$_4$ (0.332 g, 2.76 mmol). The mixture was stirred at room temperature overnight, and then NaBH$_4$ (0.035 g, 0.919 mmol) was added and stirred additional 16 h. It was quenched with methanol and diluted with 20 mL methylene chloride, and washed with water 10 mL. The aqueous layer was extracted with three 15 mL portions of methylene chloride. The combined organic extracts were washed with 10 mL of brine, dried with Na$_2$SO$_4$ and concentrated. The residue was used for the next step without further purification.

To a solution of 3-trifluoro-1H-pyrazole-5-carboxylic acid (0.165 g, 0.919 mmol) and 3-(2-((2-chloro-3-nitrobenzyl)amino)ethyl)tetrahydrothiophene 1,1-dioxide (0.306 g, 0.919 mmol) in ACN (5 mL) was added T3P (Propylphosphonic anhydride solution, 50 wt % in ethyl acetate) (0.307 g, 0.965 mmol) and TEA (0.743 g). Then the reaction mixture was stirred at r.t. for 1 day. The resulting reaction mixture was diluted with 30 mL DCM and washed with water 10 mL. The DCM phase was dried with Na$_2$SO$_4$ and evaporated. Preparative HPLC purification provided pure product N-(2-chloro-3-nitrobenzyl)-N-(2-(1,1-dioxidotetrahydrothiophen-3-yl)ethyl)-3-(trifluoromethyl)-1H-pyrazole-5-carboxamide (0.150 g, 0.303 mmol, 33% yield).

$^1$H-NMR (Acetone-d$_6$/400 MHz): 8.94 (m, 1H), 7.90 (m, 1H), 7.05 (m, 1H), 5.10 (m, 2H), 3.75 (m, 2H), 3.20 (m, 2H), 2.90 (m, 1H), 2.70 (m, 1H), 2.40 (m, 2H), 1.80 (m, 3H). MS (ES$^+$, m/z): 423.6 (M$^+$+1, 100.0).

Example 96

Synthesis of N-(3-amino-2-chlorobenzyl)-N-(2-(1,1-dioxidotetrahydrothiophen-3-yl)ethyl)-3-(trifluoromethyl)-1H-pyrazole-5-carboxamide To a solution of N-(2-chloro-3-nitrobenzyl)-N-(2-(1,1-dioxidotetrahydrothiophen-3-yl)ethyl)-3-(trifluoromethyl)-1H-pyrazole-5-carboxamide (0.050 g, 0.101 mmol) in ethanol (50 mL) passed through the H-Cube at a rate of 1.0 mL/min. The catalyst was Rany-Nickle. The hydrogen pressure was 50 Psi and the temperature was 50° C. The combined organic solution was concentrated and purified by preparative HPLC to give (0.038 g, 0.082 mmol, 81% yield) of compound N-(3-amino-2-chlorobenzyl)-N-(2-(1,1-dioxidotetrahydrothiophen-3-yl)ethyl)-3-(trifluoromethyl)-1H-pyrazole-5-carboxamide.

$^1$H-NMR (CD$_3$CN/400 MHz): 7.06 (m, 1H), 6.80 (m, 1H), 6.56 (m, 1H), 6.47 (m, 1H), 4.77 (m, 2H), 3.50 (m, 2H), 3.10 (m, 2H), 2.90 (m, 1H), 2.80 (m, 1H), 2.60 (m, 1H), 2.30 (m, 2H), 1.80 (m, 3H). MS (ES$^+$, m/z): 465.4 (M$^+$+1, 100.0).

The compound in Example 58 was prepared in a manner analagous to that described in Example 96.

Examples 113 to 115 demonstrate exemplary pro-drug approaches utilizing the phenol as the attachment point for water solubilizing groups.

Example 113

Synthesis of 4-((3-chloro-N-(cyclobutylmethyl)-1H-pyrazole-5-carboxamido)methyl)-3-fluorophenyl dihydrogen phosphate

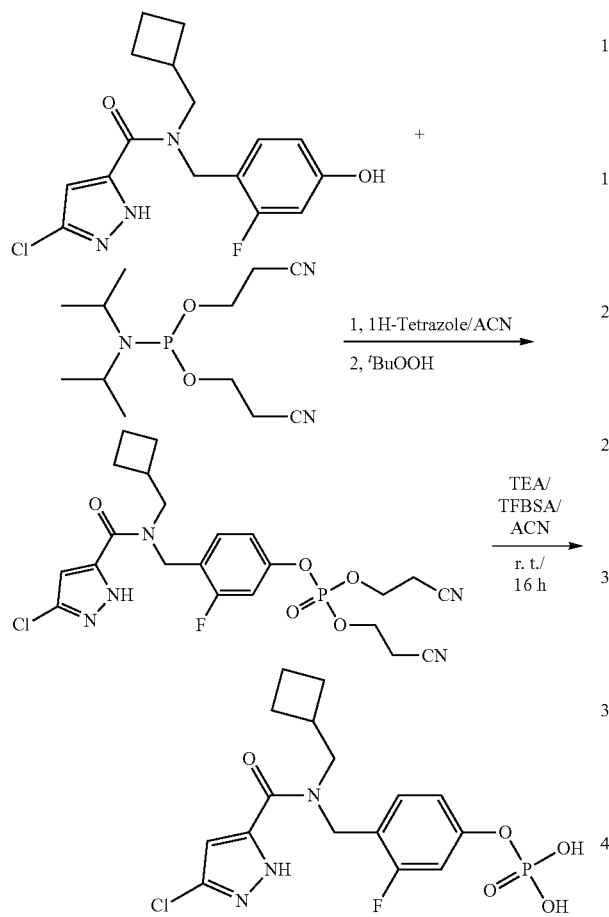

To a solution of 3-chloro-N-(cyclobutylmethyl)-N-(2-fluoro-4-hydroxybenzyl)-1H-pyrazole-5-carboxamide (0.060 g, 0.178 mmol) and diethylcyano diisopropylphosphoramidite (0.048 g, 0.178 mmol, 1.0 equiv) and a solution of 1H-tetrazole in dry acetonitrile (0.037 g, 0.533 mmol, 3 equiv) were added. After 3 h, the solution was cooled to −20° C. and 70% aqueous tert-butyl hydroperoxide (0.016 g, 0.095 mmol, 1 equiv) was added. After 10 min, an aqueous solution of 10% $Na_2S_2O_3$ (2 mL) was added at −20° C. The mixture was subsequently transferred to a separating funnel, extracted with dichloromethane (6 mL×2), and washed again with aqueous 10% $Na_2S_2O_3$ (3 mL×2). The solvent was removed by evaporation under reduced pressure and chromatography purification (ethyl acetate/hexane, 0-15%) provided pure product phosphate (0.050 g, 0.095 mmol, 54% yield).

To a solution of 4-((3-chloro-N-(cyclobutylmethyl)-1H-pyrazole-5-carboxamido)methyl)-3-fluorophenyl bis(2-cyanoethyl) phosphate (0.020 g, 0.038 mmol) in 1 mL ACN was added TEA 0.5 mL and TFBSA 0.5 mL. After 24 h, the reaction mixture was concentrated. The solvent was removed by evaporation under reduced pressure. Preparative HPLC purification (Water/ACN, 10-100%, 15 min; 100%, 5 min.) provide pure product 4-((3-chloro-N-(cyclobutylmethyl)-1H-pyrazole-5-carboxamido)methyl)-3-fluorophenyl dihydrogen (0.010 g, 0.024 mmol).

$^1$H-NMR (CD$_3$OD/400 MHz): δ 7.30 (m, 1H), 7.02 (m, 2H), 6.95 (m, 1H), 4.78 (m, 2H), 3.57 (m, 2H), 2.65 (m, 1H), 2.02 (m, 2H), 1.78 (m, 4H). MS (ES$^+$, m/z): (M+H)$^+$: 418.0.

Example 114

(4-((3-chloro-N-(cyclobutylmethyl)-1H-pyrazole-5-carboxamido)methyl)-3-fluorophenoxy)methyl dihydrogen phosphate

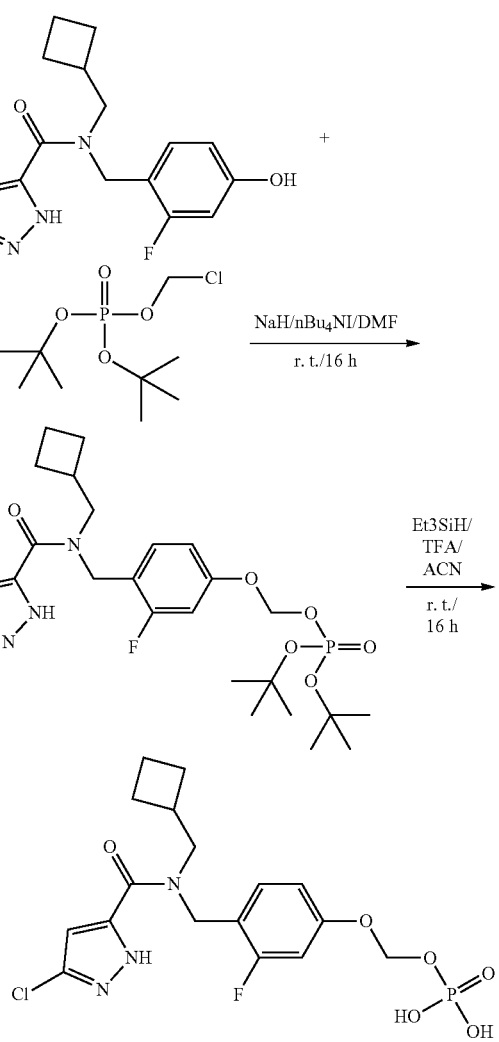

To a mixture of 3-chloro-N-(cyclobutylmethyl)-N-(2-fluoro-4-hydroxybenzyl)-1H-pyrazole-5-carboxamide (0.060 g, 0.178 mmol), sodium hydride (11 mg, 0.444 mmol) and tetra-n-butyl ammonium bromide (0.030 g, 0.037 mmol) in DMF was stirred at rt. for 10 mins. To this mixture was added a solution of di-tert-butyl chloromethyl phosphate (0.054 g, 0.207 mmol) in DMF 1 mL. The resulting mixture was stirred at rt for overnight. The reaction mixture was taken into DCM 50 mL and washed with water, brine, dried over sodium sulfate and concentrated. Product was purified by flash chromatography (0-8% methanol/DCM) on silica gel to provide phosphate (0.040 g, 0.071 mmol, 48% yield) as colorless liquid.

To a solution of di-tert-butyl ((4-((3-chloro-N-(cyclobutylmethyl)-1H-pyrazole-5-carboxamido)methyl)-3-fluorophenoxy)methyl) phosphate (0.030 g, 0.054 mmol) in 1 mL ACN was added TFA 0.5 mL and Et₃SiH 0.5 mL. After 24 h, the reaction mixture was concentrated. The solvent was removed by evaporation under reduced pressure. Preparative HPLC purification (Water/ACN, 10-100%, 15 min; 100%, 5 min.) provide pure product (4-((3-chloro-N-(cyclobutylmethyl)-1H-pyrazole-5-carboxamido)methyl)-3-fluorophenoxy)methyl dihydrogen phosphate (0.010 g, 0.022 mmol, 42% yield).

¹H-NMR (CD₃OD/400 MHz): δ 7.20 (m, 1H), 6.95 (m, 2H), 6.55 (m, 1H), 5.60 (d, 2H), 4.70 (m, 2H), 3.57 (m, 2H), 2.60 (m, 1H), 2.02-1.80 (m, 6H). MS (ES⁺, m/z): (M+H)⁺: 448.0.

Example 115

(S)-4-((3-chloro-N-(cyclobutylmethyl)-1H-pyrazole-5-carboxamido)methyl)-3-fluorophenyl 2-amino-2-methylbutanoate

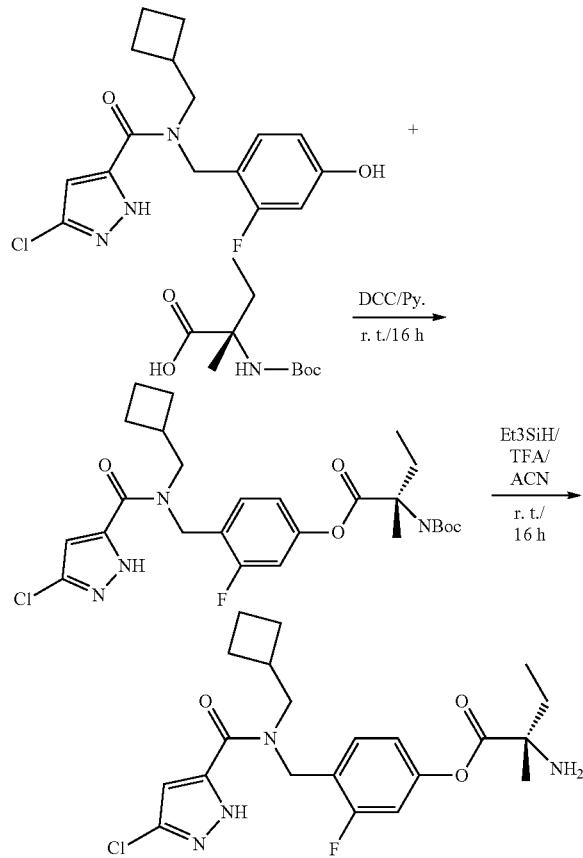

To a solution of 4-chloro-N-(cyclobutylmethyl)-N-(2-fluoro-4-hydroxybenzyl)-1H-pyrrole-2-carboxamide (0.040 g, 0.118 mmol) in 3 mL ethyl acetate was added Boc-iso-Valine (0.026 g, 0.118 mmol), DCC (0.037 g, 0.178 mmol) and pyridine 0.5 mL. The reaction mixture was added at r.t. for overnight. After removal of all the solvent, the residue was purified by chromatography. (0-30% methanol/DCM) (S)-4-((3-chloro-N-(cyclobutylmethyl)-1H-pyrazole-5-carboxamido)methyl)-3-fluorophenyl 2-(Boc-amino)-2-methylbutanoate was obtained (0.030 g, 0.056 mmol, 47% yield).

To a solution of (S)-4-((3-chloro-N-(cyclobutylmethyl)-1H-pyrazole-5-carboxamido)methyl)-3-fluorophenyl 2-(Boc-amino)-2-methylbutanoate (0.020 g, 0.037 mmol) in ACN 2 mL was added 0.5 mL Et₃SiH and 0.5 ml TFA, and then stirred at r.t. for overnight. After removed the solvent, chromatography on silica gel with 0-40% methanol in DCM give the crude product. Then, the crude product was purified one more time by preparative HPLC (Water/ACN, 5-100%, 15 mins, then 100%, 5 mins.) gave pure product (S)-4-((3-chloro-N-(cyclobutylmethyl)-1H-pyrazole-5-carboxamido)methyl)-3-fluorophenyl 2-amino-2-methylbutanoate (0.010 g, 0.023 mmol, 62% yield).

¹H-NMR (CD₃OD/400 MHz): δ 7.34 (m, 1H), 7.05 (m, 2H), 6.55 (m, 1H), 4.95 (d, 2H), 3.60 (m, 2H), 2.80 (m, 1H), 2.05 (m, 1H), 2.00 (m, 5H), 1.80 (m, 5H), 1.00 (t, 3H). MS (ES⁺, m/z): (M+H)⁺: 437.1.

Examples 116-243

The reductive amination and amide formation were carried out using a method analogous to that described in Example 1.

Example 116, 3-chloro-N-(cyclobutylmethyl)-N-((3-fluoropyridin-4-yl)methyl)-1H-pyrazole-5-carboxamide.

Example 119, N-((1H-benzo[d]imidazol-4-yl)methyl)-3-chloro-N-(cyclobutylmethyl)-1H-pyrazole-5-carboxamide.

Example 120, N-((1H-benzo[d]imidazol-4-yl)methyl)-3-bromo-N-(cyclobutylmethyl)-1H-pyrazole-5-carboxamide.

Example 121, 3-bromo-N-(cyclobutylmethyl)-N-((3-((methylamino)methyl)-1H-indol-4-yl)methyl)-1H-pyrazole-5-carboxamide.

Example 123, N-((1H-benzo[d]imidazol-4-yl)methyl)-N-(cyclobutylmethyl)-3-(trifluoromethyl)-1H-pyrazole-5-carboxamide.

Example 124, N-(2-chloro-4-hydroxybenzyl)-N-(cyclobutylmethyl)-3-(trifluoromethyl)-1H-pyrazole-5-carboxamide.

Example 125, N-(2-chloro-4-hydroxybenzyl)-3-bromo-N-(cyclobutylmethyl)-1H-pyrazole-5-carboxamide.

Example 126, N-((5-chloro-1H-benzo[d]imidazol-4-yl)methyl)-N-(cyclobutylmethyl)-3-(trifluoromethyl)-1H-pyrazole-5-carboxamide.

Example 127, N-(2-chlorobenzyl)-N-(cyclobutylmethyl)-3-(trifluoromethyl)-1H-pyrazole-5-carboxamide.

Example 128, N-((3-chloropyridin-4-yl)methyl)-N-(cyclobutylmethyl)-3-(trifluoromethyl)-1H-pyrazole-5-carboxamide.

Example 129, N-(2-fluoro-4-hydroxybenzyl)-3-cyclopropyl-N-(3,3,3-trifluoropropyl)-1H-pyrazole-5-carboxamide.

Example 130, N-(2-fluoro-4-hydroxybenzyl)-3-(trifluoromethyl)-N-(3,3, trifluoropropyl)-1H-pyrazole-5-carboxamide.

Example 131, N-(2-fluoro-4-hydroxybenzyl)-3-(trifluoromethyl)-N-(3-hydroxy-3-methylbutyl)-1H-pyrazole-5-carboxamide.

Example 132, N-(2-fluoro-4-hydroxybenzyl)-N-cyclopentyl-3-(trifluoromethyl)-1H-pyrazole-5-carboxamide.

Example 133, N-(2-fluoro-4-hydroxybenzyl)-N-(2-aminoethyl)-3-(trifluoromethyl)-1H-pyrazole-5-carboxamide.

Example 134, N-(4-amino-2-chlorobenzyl)-N-(cyclobutylmethyl)-3-(trifluoromethyl)-1H-pyrazole-5-carboxamide.

Example 136, N-(3-fluoro-2-hydroxybenzyl)-N-(cyclobutylmethyl)-3-(trifluoromethyl)-1H-pyrazole-5-carboxamide.

Example 137, N-(2-fluoro-4-hydroxybenzyl)-3-(trifluoromethyl)-N-(2-hydroxyethyl)-1H-pyrazole-5-carboxamide.

Example 138, N-(2-fluoro-4-hydroxybenzyl)-3-(trifluoromethyl)-N-(2-hydroxy-2-methylpropyl)-1H-pyrazole-5-carboxamide.

Example 139, N-(2-fluoro-4-hydroxybenzyl)-N-cyclohexyl-3-(trifluoromethyl)-1H-pyrazole-5-carboxamide.

Example 140, N-(2-fluoro-4-hydroxybenzyl)-N-(2-cyclopropylethyl)-3-(trifluoromethyl)-1H-pyrazole-5-carboxamide.

Example 141, N-(3-chloro-2-hydroxybenzyl)-N-(cyclobutylmethyl)-3-(trifluoromethyl)-1H-pyrazole-5-carboxamide.

Example 142, N-(2-fluoro-4-hydroxybenzyl)-3-(trifluoromethyl)-N-(2-methoxyethyl)-1H-pyrazole-5-carboxamide.

Example 143, N-(2-fluoro-4-hydroxybenzyl)-N-(2-(diethylamino)ethyl)-3-(trifluoromethyl)-1H-pyrazole-5-carboxamide.

Example 144, N-((1H-benzo[d]imidazol-4-yl)methyl)-N-((1H-pyrazol-4-yl)methyl)-3-(trifluoromethyl)-1H-pyrazole-5-carboxamide.

Example 145, N-(2-(aminomethyl)benzyl)-N-(cyclobutylmethyl)-3-(trifluoromethyl)-1H-pyrazole-5-carboxamide.

Example 146, N-(2-fluoro-4-hydroxybenzyl)-3-(trifluoromethyl)-N-((isoxazol-4-yl)methyl)-1H-pyrazole-5-carboxamide.

Example 147, N-(cyclobutylmethyl)-3-(trifluoromethyl)-N-((5-(hydroxymethyl)furan-2-yl)methyl)-1H-pyrazole-5-carboxamide.

Example 148, N-(2-fluorobenzyl)-N-(2-(diethylamino)ethyl)-3-(trifluoromethyl)-1H-pyrazole-5-carboxamide.

Example 149, N-(2-fluorobenzyl)-N-(2-cyclopropylethyl)-3-(trifluoromethyl)-1H-pyrazole-5-carboxamide.

Example 150, N-(2-fluorobenzyl)-3-(trifluoromethyl)-N-((tetrahydrofuran-3-yl)methyl)-1H-pyrazole-5-carboxamide.

Example 151, N-(2-fluorobenzyl)-3-(trifluoromethyl)-N-(tetrahydrofuran-3-yl)-1H-pyrazole-5-carboxamide.

Example 152, N-(2-fluorobenzyl)-N-(1-ethylpyrrolidin-3-yl)-3-(trifluoromethyl)-1H-pyrazole-5-carboxamide.

Example 153, N-(2-fluorobenzyl)-N-cyclohexyl-3-(trifluoromethyl)-1H-pyrazole-5-carboxamide.

Example 154, N-(3-aminobenzyl)-N-(2-(diethylamino)ethyl)-3-(trifluoromethyl)-1H-pyrazole-5-carboxamide.

Example 155, N-(2-fluorobenzyl)-N-(2-(ethylamino)ethyl)-3-(trifluoromethyl)-1H-pyrazole-5-carboxamide.

Example 156, N-(2-(dipropylamino)ethyl)-N-(2-fluorobenzyl)-3-(trifluoromethyl)-1H-pyrazole-5-carboxamide.

Example 157, N-(2-(diisopropylamino)ethyl)-N-(2-fluorobenzyl)-3-(trifluoromethyl)-1H-pyrazole-5-carboxamide.

Example 158, N-(2-fluorobenzyl)-3-(trifluoromethyl)-N-(2-(pyrrolidin-1-yl)ethyl)-1H-pyrazole-5-carboxamide.

Example 159, N-(2-chlorobenzyl)-N-(2-(diethylamino)ethyl)-3-(trifluoromethyl)-1H-pyrazole-5-carboxamide.

Example 160, N-((1H-benzo[d]imidazol-4-yl)methyl)-N-(2-(diethylamino)ethyl)-3-(trifluoromethyl)-1H-pyrazole-5-carboxamide.

Example 161, N-((1H-indol-4-yl)methyl)-N-(2-(diethylamino)ethyl)-3-(trifluoromethyl)-1H-pyrazole-5-carboxamide.

Example 162, N-(2-chlorobenzyl)-3-(trifluoromethyl)-N-(2-(pyrrolidin-1-yl)ethyl)-1H-pyrazole-5-carboxamide.

Example 163, N-((1H-benzo[d]imidazol-7-yl)methyl)-3-(trifluoromethyl)-N-(2-(pyrrolidin-1-yl)ethyl)-1H-pyrazole-5-carboxamide.

Example 164, N-((1H-indol-4-yl)methyl)-3-(trifluoromethyl)-N-(2-(pyrrolidin-1-yl)ethyl)-1H-pyrazole-5-carboxamide.

Example 165, N-(2,4-dichlorobenzyl)-3-(trifluoromethyl)-N-(2-(pyrrolidin-1-yl)ethyl)-1H-pyrazole-5-carboxamide.

Example 166, N-(2,4-dichlorobenzyl)-N-(2-(diethylamino)ethyl)-3-(trifluoromethyl)-1H-pyrazole-5-carboxamide.

Example 167, N-(2,3-dichlorobenzyl)-N-(2-(diethylamino)ethyl)-3-(trifluoromethyl)-1H-pyrazole-5-carboxamide.

Example 168, N-(2,5-dichlorobenzyl)-N-(2-(diethylamino)ethyl)-3-(trifluoromethyl)-1H-pyrazole-5-carboxamide.

Example 169, N-(2,6-dichlorobenzyl)-N-(2-(diethylamino)ethyl)-3-(trifluoromethyl)-1H-pyrazole-5-carboxamide.

Example 170, N-(2-chloro-4-fluorobenzyl)-N-(2-(diethylamino)ethyl)-3-(trifluoromethyl)-1H-pyrazole-5-carboxamide Example 171, N-(2-chloro-5-fluorobenzyl)-N-(2-(diethylamino)ethyl)-3-(trifluoromethyl)-1H-pyrazole-5-carboxamide.

Example 172, N-(2-chloro-6-fluorobenzyl)-N-(2-(diethylamino)ethyl)-3-(trifluoromethyl)-1H-pyrazole-5-carboxamide.

Example 173, N-(2-chlorobenzyl)-3-(trifluoromethyl)-N-(2-(piperidin-1-yl)ethyl)-1H-pyrazole-5-carboxamide.

Example 174, N-(2-chlorobenzyl)-3-(trifluoromethyl)-N-(2-morpholinoethyl)-1H-pyrazole-5-carboxamide.

Example 175, N-(2-chlorobenzyl)-3-bromo-N-(2-(diethylamino)ethyl)-1H-pyrazole-5-carboxamide.

Example 176, N-(2-chlorobenzyl)-3-chloro-N-(2-(diethylamino)ethyl)-1H-pyrazole-5-carboxamide.

Example 177, N-(2-chloro-6-fluorobenzyl)-3-(trifluoromethyl)-N-(2-(pyrrolidin-1-yl)ethyl)-1H-pyrazole-5-carboxamide.

Example 178, N-(2,6-dichlorobenzyl)-3-(trifluoromethyl)-N-(2-(pyrrolidin-1-yl)ethyl)-1H-pyrazole-5-carboxamide.

Example 179, N-(2-chloro-6-fluorobenzyl)-3-(trifluoromethyl)-N-(2-(piperidin-1-yl)ethyl)-1H-pyrazole-5-carboxamide.

Example 180, N-(2,6-dichlorobenzyl)-3-(trifluoromethyl)-N-(2-(piperidin-1-yl)ethyl)-1H-pyrazole-5-carboxamide.

Example 181, N-(2-chlorobenzyl)-3-(trifluoromethyl)-N-(2-(pyrrolidin-1-yl)propyl)-1H-pyrazole-5-carboxamide.

Example 182, N-(2-chloro-3-fluorobenzyl)-N-(2-(diethylamino)ethyl)-3-(trifluoromethyl)-1H-pyrazole-5-carboxamide.

Example 183, N-(5-amino-2-chlorobenzyl)-N-(2-(diethylamino)ethyl)-3-(trifluoromethyl)-1H-pyrazole-5-carboxamide.

Example 184, N-(2-isopropylbenzyl)-N-(2-(diethylamino)ethyl)-3-(trifluoromethyl)-1H-pyrazole-5-carboxamide.

Example 185, N-(2-chlorobenzyl)-N-(3-(diethylamino)propyl)-3-(trifluoromethyl)-1H-pyrazole-5-carboxamide.

Example 186, N-(2-chlorobenzyl)-N-(3-(dimethylamino)propyl)-3-(trifluoromethyl)-1H-pyrazole-5-carboxamide.

Example 187, N-(2-chlorobenzyl)-N-(2-(dimethylamino)ethyl)-3-(trifluoromethyl)-1H-pyrazole-5-carboxamide.

Example 188, N-(2-chlorobenzyl)-3-(trifluoromethyl)-N-(2-(3,5-dimethylpiperidin-1-yl)ethyl)-1H-pyrazole-5-carboxamide.

Example 189, N-(2-chlorobenzyl)-N-(2-(azepan-1-yl)ethyl)-3-(trifluoromethyl)-1H-pyrazole-5-carboxamide.

Example 190, N-(2-chlorobenzyl)-3-(trifluoromethyl)-N-(2-(4-methylpiperidin-1-yl)ethyl)-1H-pyrazole-5-carboxamide Example 191, N-(2-chlorobenzyl)-3-(trifluoromethyl)-N-(2-(3-methylpiperidin-1-yl)ethyl)-1H-pyrazole-5-carboxamide.

Example 192, N-(2-chlorobenzyl)-3-(trifluoromethyl)-N-(2-(2-methylpiperidin-1-yl)ethyl)-1H-pyrazole-5-carboxamide.

Example 193, N-(2-chlorobenzyl)-3-chloro-N-(2-(diethylamino)ethyl)-4-fluoro-1H-pyrazole-5-carboxamide.

Example 194, N-(2-chloro-4-hydroxybenzyl)-N-(2-(azepan-1-yl)ethyl)-3-(trifluoromethyl)-1H-pyrazole-5-carboxamide.

Example 195, N-(2-fluoro-4-hydroxybenzyl)-N-(2-(azepan-1-yl)ethyl)-3-(trifluoromethyl)-1H-pyrazole-5-carboxamide.

Example 196, N-(5-amino-2-chlorobenzyl)-N-(2-(azepan-1-yl)ethyl)-3-(trifluoromethyl)-1H-pyrazole-5-carboxamide.

Example 197, N-(2-fluorobenzyl)-N-(2-(azepan-1-yl)ethyl)-3-(trifluoromethyl)-1H-pyrazole-5-carboxamide.

Example 198, N-(2,6-difluorobenzyl)-N-(2-(azepan-1-yl)ethyl)-3-(trifluoromethyl)-1H-pyrazole-5-carboxamide.

Example 199, N-(2-chlorobenzyl)-N-(2-(4-ethylpiperidin-1-yl)ethyl)-3-(trifluoromethyl)-1H-pyrazole-5-carboxamide.

Example 200, N-(5-amino-2-chlorobenzyl)-3-(trifluoromethyl)-N-(2-(3-methylpiperidin-1-yl)ethyl)-1H-pyrazole-5-carboxamide.

Example 201, N-(2-fluorobenzyl)-3-(trifluoromethyl)-N-(2-(3-methylpiperidin-1-yl)ethyl)-1H-pyrazole-5-carboxamide.

Example 202, N-(5-amino-2-chlorobenzyl)-3-(trifluoromethyl)-N-(2-(2-methylpiperidin-1-yl)ethyl)-1H-pyrazole-5-carboxamide.

Example 203, N-(2-fluorobenzyl)-3-(trifluoromethyl)-N-(2-(2-methylpiperidin-1-yl)ethyl)-1H-pyrazole-5-carboxamide.

Example 204, N-(2-chlorobenzyl)-N-(2-(ethyl-isopropylamino)ethyl)-3-(trifluoromethyl)-1H-pyrazole-5-carboxamide.

Example 205, N-(2-chlorobenzyl)-3-(trifluoromethyl)-N-(2-(4,4-difluoropiperidin-1-yl)ethyl)-1H-pyrazole-5-carboxamide.

Example 206, N-((3-fluoro-1H-indol-4-yl)methyl)-3-(trifluoromethyl)-N-(2-(pyrrolidin-1-yl)ethyl)-1H-pyrazole-5-carboxamide.

Example 207, N-(4-amino-2-chlorobenzyl)-N-(2-(azepan-1-yl)ethyl)-3-(trifluoromethyl)-1H-pyrazole-5-carboxamide.

Example 208, N-((1H-benzo[d]imidazol-7-yl)methyl)-N-(2-(azepan-1-yl)ethyl)-3-(trifluoromethyl)-1H-pyrazole-5-carboxamide.

Example 209, N-(2-chlorobenzyl)-N-(2-(ethyl-propylamino)ethyl)-3-(trifluoromethyl)-1H-pyrazole-5-carboxamide.

Example 210, N-(2-chloro-3-nitrobenzyl)-N-(2-(azepan-1-yl)ethyl)-3-(trifluoromethyl)-1H-pyrazole-5-carboxamide.

Example 211, N-(2-chloro-6-nitrobenzyl)-N-(2-(azepan-1-yl)ethyl)-3-(trifluoromethyl)-1H-pyrazole-5-carboxamide.

Example 212, N-(2-chlorobenzyl)-3-(trifluoromethyl)-N-(2-(2,6-dimethylpiperidin-1-yl)ethyl)-1H-pyrazole-5-carboxamide.

Example 213, N-(3-amino-2-chlorobenzyl)-N-(2-(azepan-1-yl)ethyl)-3-(trifluoromethyl)-1H-pyrazole-5-carboxamide.

Example 214, N-(5-amino-2-fluorobenzyl)-N-(2-(azepan-1-yl)ethyl)-3-(trifluoromethyl)-1H-pyrazole-5-carboxamide.

Example 215, N-(5-amino-2-methoxybenzyl)-N-(2-(azepan-1-yl)ethyl)-3-(trifluoromethyl)-1H-pyrazole-5-carboxamide.

Example 216, N-(3-amino-2-fluorobenzyl)-N-(2-(azepan-1-yl)ethyl)-3-(trifluoromethyl)-1H-pyrazole-5-carboxamide.

Example 217, N-(3-amino-2-methoxybenzyl)-N-(2-(azepan-1-yl)ethyl)-3-(trifluoromethyl)-1H-pyrazole-5-carboxamide.

Example 218, N-(2-amino-6-chlorobenzyl)-N-(2-(azepan-1-yl)ethyl)-3-(trifluoromethyl)-1H-pyrazole-5-carboxamide.

Example 219, N-(2-chlorobenzyl)-3-(trifluoromethyl)-N-(2-(4-hydroxypiperidin-1-yl)ethyl)-1H-pyrazole-5-carboxamide.

Example 220, N-(2-chlorobenzyl)-3-(trifluoromethyl)-N-(2-(3-hydroxypiperidin-1-yl)ethyl)-1H-pyrazole-5-carboxamide.

Example 221, N-(2-amino-6-chlorobenzyl)-3-(trifluoromethyl)-N-(2-(pyrrolidin-1-yl)propyl)-1H-pyrazole-5-carboxamide.

Example 222, N-(2-amino-6-chlorobenzyl)-3-(trifluoromethyl)-N-(2-(pyrrolidin-1-yl)ethyl)-1H-pyrazole-5-carboxamide.

Example 223, N-(2-chloro-6-aminobenzyl)-N-(2-(ethylpropylamino)ethyl)-3-(trifluoromethyl)-1H-pyrazole-5-carboxamide.

Example 224, N-(2-amino-6-chlorobenzyl)-N-(2-(4-dioxothiomorpholino)ethyl)-3-(trifluoromethyl)-1H-pyrazole-5-carboxamide.

Example 225, N-(2-amino-6-chlorobenzyl)-3-(trifluoromethyl)-N-(2-(3-hydroxypiperidin-1-yl)ethyl)-1H-pyrazole-5-carboxamide.

Example 226, N-(2-chlorobenzyl)-N-(3-aminocyclobutyl)-3-(trifluoromethyl)-1H-pyrazole-5-carboxamide.

Example 227, N-(2-chlorobenzyl)-N-((azetidin-2-yl)methyl)-3-(trifluoromethyl)-1H-pyrazole-5-carboxamide.

Example 228, N-(2-chlorobenzyl)-N-(2-(1-(methylsulfonyl)piperidin-3-yl)ethyl)-3-(trifluoromethyl)-1H-pyrazole-5-carboxamide.

Example 229, N-(2-chlorobenzyl)-3-(trifluoromethyl)-N-phenethyl-1H-pyrazole-5-carboxamide.

Example 230, N-(2-chlorobenzyl)-N-(4-hydroxyphenethyl)-3-(trifluoromethyl)-1H-pyrazole-5-carboxamide.

Example 231, N-(2-chlorobenzyl)-N-((1-ethylpyrrolidin-2-yl)methyl)-3-(trifluoromethyl)-1H-pyrazole-5-carboxamide.

Example 232, N-(2-chlorobenzyl)-3-(trifluoromethyl)-N-((pyrrolidin-2-yl)methyl)-1H-pyrazole-5-carboxamide.

Example 233, N-(2-amino-6-chlorobenzyl)-N-((azetidin-2-yl)methyl)-3-(trifluoromethyl)-1H-pyrazole-5-carboxamide.

Example 234, N-(2-amino-6-chlorobenzyl)-3-(trifluoromethyl)-N-(2-(3-hydroxypyrrolidin-1-yl)ethyl)-1H-pyrazole-5-carboxamide.

Example 235, N-(2-amino-6-chlorobenzyl)-3-(trifluoromethyl)-N-(2-(3-methoxypyrrolidin-1-yl)ethyl)-1H-pyrazole-5-carboxamide.

Example 236, N-(2-amino-6-chlorobenzyl)-3-(trifluoromethyl)-N-(2-(3-fluoropiperidin-1-yl)ethyl)-1H-pyrazole-5-carboxamide.

Example 237, N-(2-amino-6-chlorobenzyl)-3-(trifluoromethyl)-N-(2-(3-methoxypiperidin-1-yl)ethyl)-1H-pyrazole-5-carboxamide.

Example 238, N-(2-amino-6-chlorobenzyl)-3-(trifluoromethyl)-N-(2-(4-fluoropiperidin-1-yl)ethyl)-1H-pyrazole-5-carboxamide.

Example 239, N-(2-(1,4-oxazepan-4-yl)ethyl)-N-(2-amino-6-chlorobenzyl)-3-(trifluoromethyl)-1H-pyrazole-5-carboxamide'

Example 240, N-(2-fluoro-6-aminobenzyl)-N-(2-(ethyl-propylamino)ethyl)-3-(trifluoromethyl)-1H-pyrazole-5-carboxamide.

Example 241, N-(2-amino-6-chlorobenzyl)-3-(trifluoromethyl)-N-(2-((S)-3-fluoropyrrolidin-1-yl)ethyl)-1H-pyrazole-5-carboxamide.

Example 242, N-(2-amino-6-chlorobenzyl)-3-(trifluoromethyl)-N-(2-((R)-3-fluoropyrrolidin-1-yl)ethyl)-1H-pyrazole-5-carboxamide.

Example 243, N-(2-amino-6-chlorobenzyl)-N-(2-(4-fluoroazepan-1-yl)ethyl)-3-(trifluoromethyl)-1H-pyrazole-5-carboxamide.

Example 244, N-(2-fluoro-4-hydroxybenzyl)-3-chloro-N-(cyclobutylmethyl)-1H-pyrazole-5-carboxamide.

Example 117

3-CHLORO-N-(CYCLOBUTYLMETHYL)-N-((3-FLUOROPYRIDINE-N-OXIDE-4-YL)METHYL)-1H-PYRAZOLE-5-CARBOXAMIDE

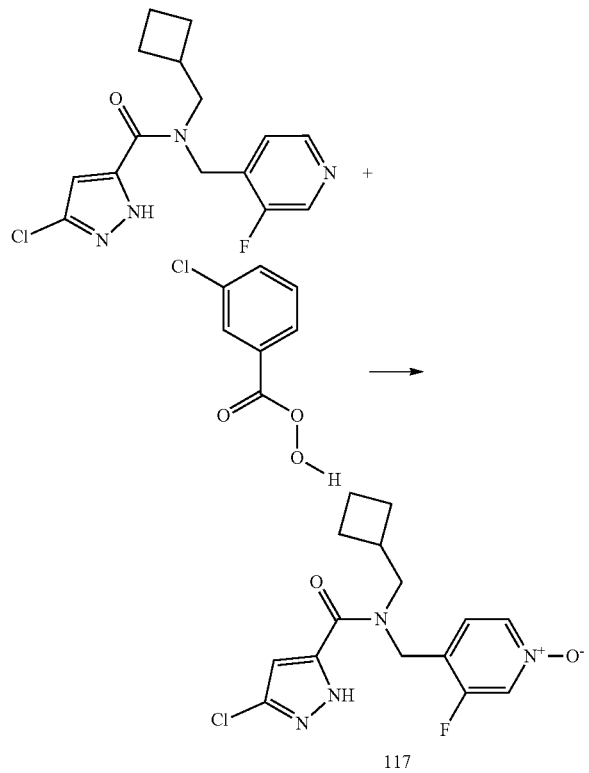

3-Chloro-N-(cyclobutylmethyl)-N-((3-fluoropyridin-4-yl)methyl)-1H-pyrazole-5-carboxamide (46 mg, 0.143 mmol) was dissolved in DCM (1.5 mL) and cooled to 0 C. In a separate vial, MCPBA (30 mg, 0.135 mmol) was dissolved in DCM (1 mL) and cooled to 0 C. The MCPBA solution was added dropwise to the solution containing reactant 1 and the resulting solution was stirred for 1 h. The reaction mixture was then washed with 3 portions of 1 N NaOH (2 mL) and the solvent removed in vacuo. The product was then purified via normal phase chromatography (DCM/MeOH, 0→10%). The purity of the desired product was still too low so the product was re-purified via semi-prep HPLC (ACN/Water+0.05% TFA) to give the product in greater than 99% purity.

Example 118

3-CHLORO-N-(CYCLOBUTYLMETHYL)-N-((3-((DIMETHYLAMINO)METHYL)-1H-INDOL-4-YL)METHYL)-1H-PYRAZOLE-5-CARBOXAMIDE

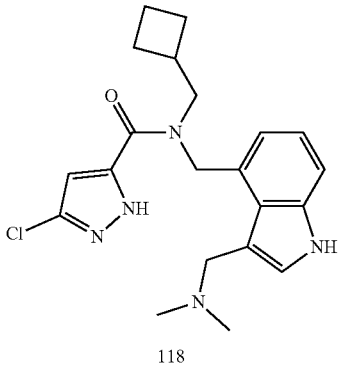

To a solution of dimethyl amine (109 uL of 2 molar, 0.218 mmol) in AcOH (1 mL) was added formaldehyde (7.91 uL of 38% aqueous, 0.109 mmol). After stirring for 15 min a solution of N-((1H-indol-4-yl)methyl)-3-chloro-N-(cyclobutylmethyl)-1H-pyrazole-5-carboxamide (34 mg, 0.099 mmol) in acetic acid (1 mL) was added. The reaction was stirred overnight at 75° C. then cooled to room temperature and diluted with EtOAc (3 mL) and washed with saturated potassium carbonate solution (3 mL) twice and water (2 mL) once. The organic layer was then stripped in vacuo and the product purified by normal phase chromatography (DCM/MeOH, 0→20%). After isolation of the product the purity was not high enough so it was repurified by semi prep HPLC (ACN/Water+0.05% TFA) to give the desired product in 97% purity.

Example 135

N-((1H-INDOL-4-YL)METHYL)-N'-CYCLOBUTYL-3-(TRIFLUOROMETHYL)-1H-PYRAZOLE-5-CARBOHYDRAZIDE

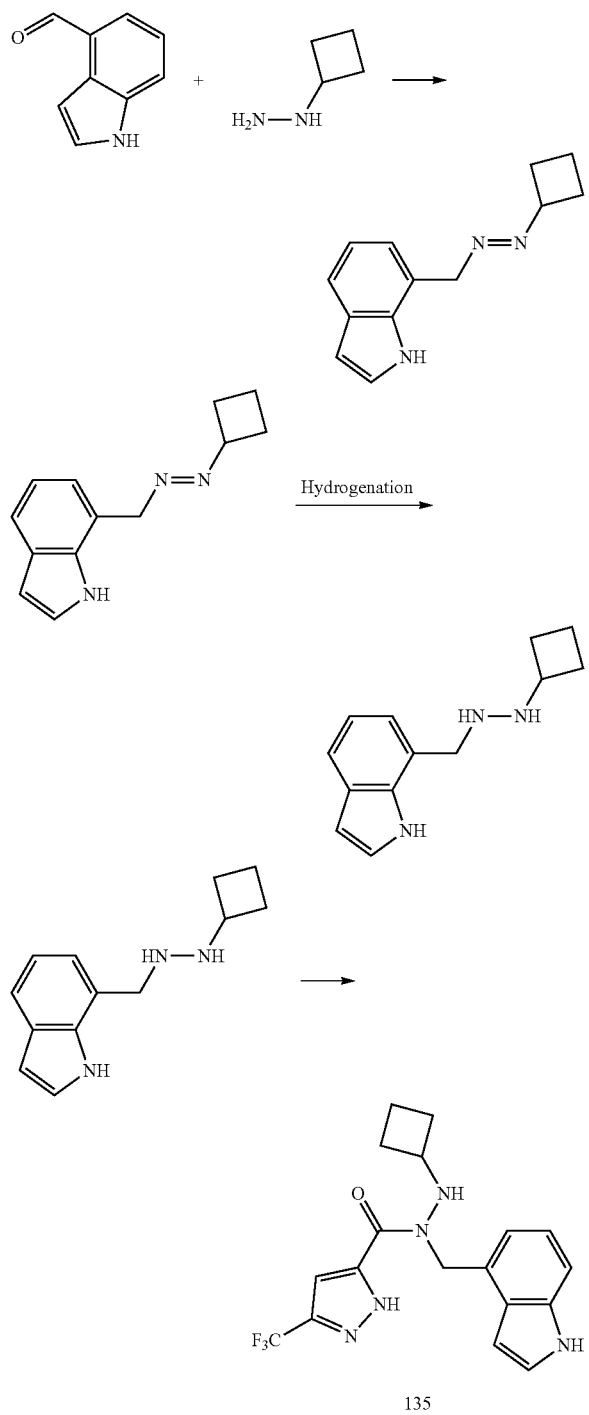

135

A mixture of 1H-indole-4-carbaldehyde (296 mg, 2.039 mmol), cyclobutylhydrazine, HCl (250 mg, 2.039 mmol), sodium carbonate and MgSO$_4$ (491 mg, 4.08 mmol) in methanol was stirred overnight. The solids were then removed by filtrated and the resulting solution diluted with IPA. The resulting hydrazone was then reduced by hydrogenation using an H-Cube continuous flow hydrogenator (75 bar 55 C with Pd/C catalyst cartridge, 0.8 mL/min). After reduction the resulting hydrazine was coupled with the trifluoromethylpyrazole in the standard fashion to give Example 135 as a minor product that was isolated by reverse phase chromatography.

Example 193

N-(2-CHLOROBENZYL)-3-CHLORO-N-(2-(DIETHYLAMINO)ETHYL)-4-FLUORO-1H-PYRAZOLE-5-CARBOXAMIDE

Preparation of 3-chloro-4-fluoro-1H-pyrazole-5-carboxylic acid for the synthesis of Example 193 via amide coupling is shown below.

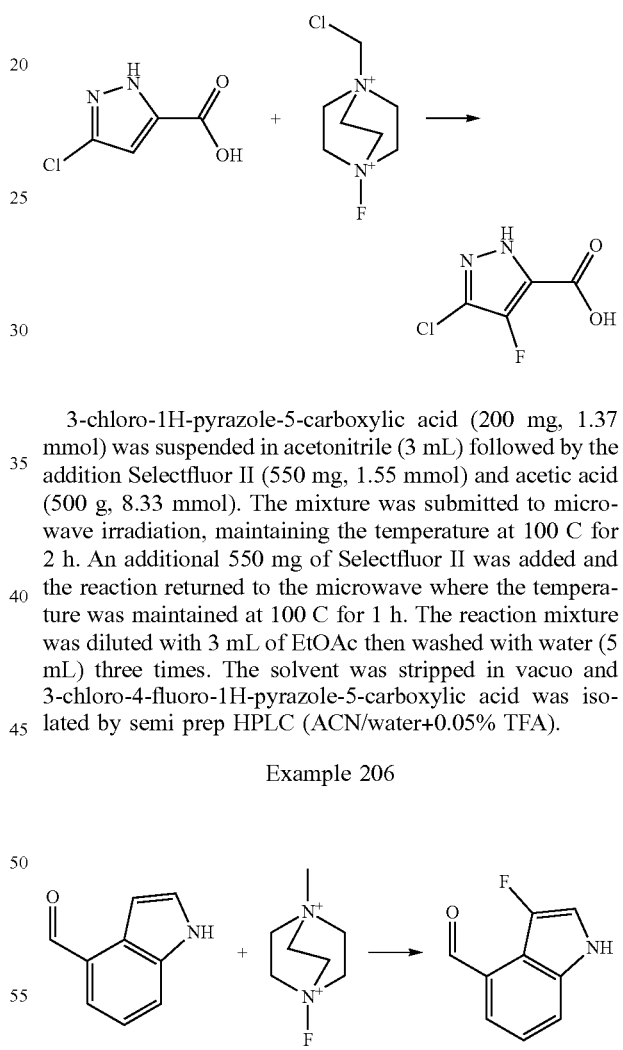

3-chloro-1H-pyrazole-5-carboxylic acid (200 mg, 1.37 mmol) was suspended in acetonitrile (3 mL) followed by the addition Selectfluor II (550 mg, 1.55 mmol) and acetic acid (500 g, 8.33 mmol). The mixture was submitted to microwave irradiation, maintaining the temperature at 100 C for 2 h. An additional 550 mg of Selectfluor II was added and the reaction returned to the microwave where the temperature was maintained at 100 C for 1 h. The reaction mixture was diluted with 3 mL of EtOAc then washed with water (5 mL) three times. The solvent was stripped in vacuo and 3-chloro-4-fluoro-1H-pyrazole-5-carboxylic acid was isolated by semi prep HPLC (ACN/water+0.05% TFA).

Example 206

1H-indole-4-carbaldehyde (2.26 g, 15.5 mmol) was added to Acetonitrile (20 mL) followed by acetic acid (2.25 mL, 39 mmol). The reaction mixture was cooled to 0 C and Selectfluor (2.5 g, 17.1 mmol) was added portion-wise over the course of 15 min. The reaction was aged for 3 hours then diluted with 15 mL of EtOAc and washed with water (25 mL) 3 times. The organics were then stripped in vacuo and the crude product purified via normal phase MPLC (100% DCM).

Example 238

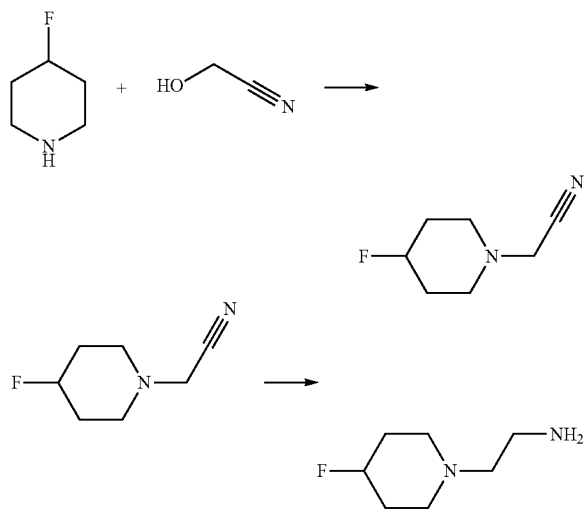

4-Fluoropiperidine HCl (801 mg, 5.74 mmol) was added dropwise to a stirred aqueous solution of glycolonitrile (647 uL of a 52% aqueous solution, 6.31 mmol) at 5° C. Sodium carbonate (912 mg, 8.60 mmol) was added and the solution was stirred at 70° C. for 1.5 h. The solution was cooled, diluted with water (2 mL), washed with Et$_2$O (3×4 ml). The organic fraction was dried and the solvent evaporated to give 2-(4-fluoropiperidin-1-yl)acetonitrile as a colourless oil. The oil was then dissolved in a 7 N solution of ammonia in MeOH (25 mL) and submitted to hydrogenation on the H-Cube using 75 bar of hydrogen pressure at 55 C with a flow rate of 0.8 mL/min and using a Raney nickel catalyst cartridge. After the reaction was complete the solvent was stripped in vacuo to give 2-(4-fluoropiperidin-1-yl)ethanamine as a translucent oil.

Examples 219, 220, 225, 234, 235, 236, 237, 238, 239, 241, 242, 243

The aminoethyl side chain was prepared using a method analogous to the procedure exemplified in example 238. The remaining portions of the compound were prepared using methods analogous to those described above.

Examples 213-218, 221-225, 233-239, 241-243

The nitro group was reduced as demonstrated in example 96

Examples 133, 155, 226, 227, 232

The boc-protected analogue was used in each example. The deprotection was carried out as described in example 11

Examples 183, 196, 200, 202, 240

The Boc-protected analogue was used in each example. The deprotection was carried out as described in example 91

Example 245

Crystallography and Assays

Full length, human PKM2 enzyme was obtained from Promab (Richmond, Calif.). All reagents, unless otherwise noted, were obtained from Sigma (St. Louis, Mo.). Cell lines were obtained from ATCC (Manassas, Va.). Media was obtained from Invitrogen (Grand Island, N.Y.).

PKM2 Biochemical Assay

Compounds were pre-incubated with 2 nM PKM2 in reaction buffer (50 mM Tris-HCl, pH 8.0, 200 mM KCl, 30 mM MgCl$_2$, 2 mM DTT, 5% DMSO) for 30 min at ambient temperature. ADP and PEP were then added to final concentrations of 75 µM and 15 µM, respectively. After 30 min, ATP formation was measured by Kinase Glo (Promega, Madison, Wis.), and AC$_{50}$ values were determined using Prism (GraphPad Software, Inc., La Jolla, Calif.).

FIG. 1B shows representative PKM2 activity dose-response curves for FBP, Example 244 and Example 1. Maximal PKM2 activity for all three compounds was approximately 600% relative to activity in DMSO controls (normalized to 100%±SD).

FIG. 1C depicts normalized PKM2 activity dose-response curves (±SD) for PEP in the presence of 1 mM ADP plus 1 µM FBP, Example 244, Example 1, or DMSO control. EC$_{50}$ values calculated for PEP: FBP (15 µM); Example 244 (15 µM), Example 1 (18 µM); DMSO (87 µM).

FIG. 1D illustrates normalized PKM2 activity dose response curves (+SD) for ADP in the presence 1 mM PEP plus 1 µM FBP, Example 244, Example), or DMSO control. EC$_{50}$ values for PEP: FBP (62 µM); Example 244 (47 µM), Example 1 (45 µM); DMSO (61 µM)

Potency data for representative compounds is shown in Table 2.

TABLE 2

PKM2 biochemical activation profiles for FBP and representative compounds.

|  | FBP | Example 244 | Example 1 |
|---|---|---|---|
| [†]AC$_{50}$ | 23 ± 8 nM (n = 10) | 62 ± 23 nM (n = 6) | 11 ± 4 nM (n = 6) |
| [††]% FBP | 100 ± 0 (n = 10) | 107 ± 10 (n = 6) | 104 ± 11 (n = 6) |
| Molecular Weight | 340 | 338 | 382 |
| clogP | −3.0 | 3.3 | 3.1 |

[†]AC$_{50}$ indicates the concentration of half-maximal PKM2 activation.
[††]% FBP indicates the extent of maximal activation, relative to FBP (normalized to 100%).

X-Ray Crystallography

A publically available human PKM2 (hPKM2) expression construct was obtained from the Structural Genomics Consortium (SGC). His6-hPKM2 was purified using NiNTA affinity capture and Hiload Superdex 16/60 S75 size exclusion chromatography. hPKM2 was crystallized using hanging drop vapor diffusion. Protein solution (20 mg/ml, 25 mM Tris/HCl pH 7.5, 0.1 M KCL, 5 mM MgCl2, 10% (v/v) glycerol) was mixed in a 1:1 ratio with reservoir solution containing 0.1 M KCl, 0.1 M ammonium tartrate, 25% (w/v) PEG3350. Crystals were soaked overnight in a solution containing 2 mM Example 244, cryo-protected and flash frozen in liquid N2. X-ray diffraction data were collected from a single crystal at 100K at Beamline-ID29 at the ESRF. Diffraction data were processed using XDS AutoPROC from Global Phasing and SCALA (CCP4) (32). Molecular replacement was performed using model 3H6O (SGC) in CSEARCH (33) and maximum likelihood refinement carried out using a mixture of automated (34) and manual refinement protocols employing Refmac (CCP4). Ligand fitting was performed using Autosolve (33) and manual rebuilding. Each of the four PKM2 monomers and four activator ligands, comprising the tetramer in the asymmetric unit, were refined as independent entities.

Cell-Based Pyruvate Kinase Activity Assay

Figure 6A:
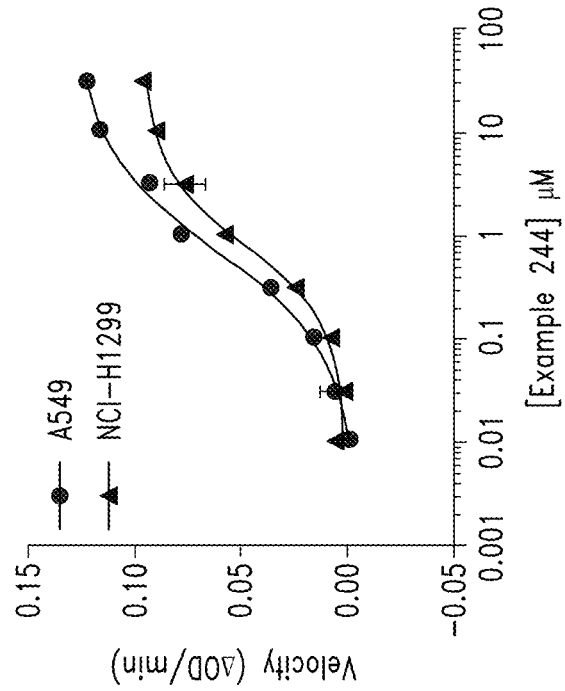
FIGS. 6A and 6B illustrate PKM2 activation profiles for representative compounds in A549 and NCI-H1299 lung cancer cells.
Figure 6B:
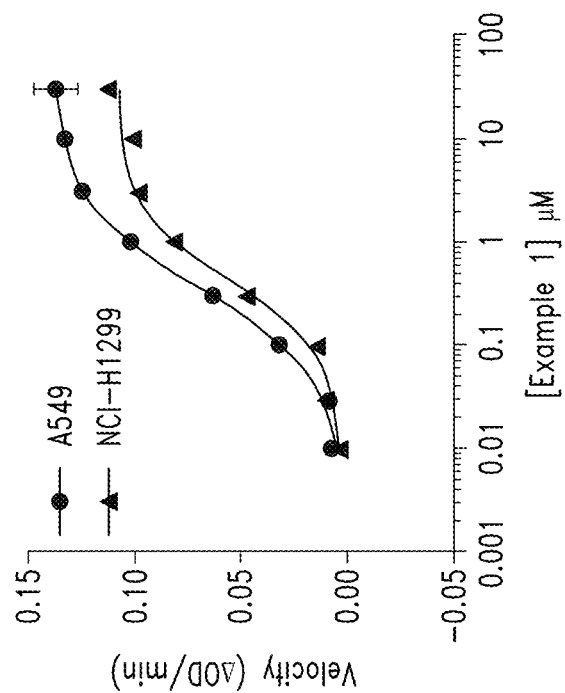

A549 or NCI-H1299 lung cancer cells were plated at 20,000 cells per well (96-well plate) in MEM media plus 10% FBS, with no additional glutamine or pyruvate. Following overnight incubation, cells were washed with PBS followed by 4 hour incubation in MEM media. Compounds were added to the cells in 1% final concentration DMSO. After 30 minutes, cells were lysed, and pyruvate kinase activity in lysates was determined by Pyruvate Kinase Activity Assay (BioVision, Milpitas, Calif.). Maximum velocity values were calculated from the kinetic data, and AC50 values were determined using Prism GraphPad Software (La Jolla, Calif.). Compound washout experiments were as described above, except after a 30 minute incubation with Example 244 (469 nM), the cells were washed with PBS followed by the addition of MEM media for the indicated time period, lysed and pyruvate kinase activity determined. Results are tabulated in Table 3 and presented graphically in FIGS. 6A and 6B.

TABLE 3

Cellular PKM2 activation profiles for Representative Compounds.

| Cell line | Example 244 $EC_{50}$ (nM) | Example 1 $EC_{50}$ (nM) |
|---|---|---|
| A549 | 450 ± 180 (n = 4) | 260 ± 120 (n = 4) |
| NCI-H1299 | 300 ± 70 (n = 4) | 220 ± 50 (n = 4) |

Cell-Based Tetramer Formation Assay

Figure 7:
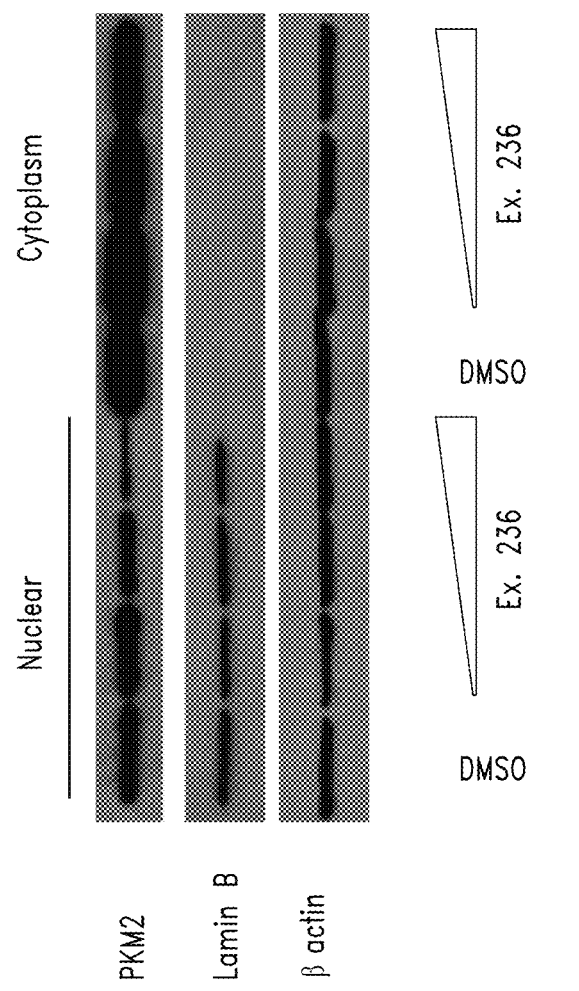
FIG. 7 presents nuclear exclusion assay results for representative compounds.

HEK-293 cells were stably transfected with FLAG-PKM2 (Origene, Rockville, Md.) and grown in RPMI 1640 media. When the cells were 80% confluent in a 6-well plate, the cells were washed with PBS followed by a 3 hour incubation in minimal essential medium (MEM) without pyruvate. Compounds were added in 1% final concentration DMSO. Following 3 hours of incubation with compounds, the cells were washed, lysed in 1% Triton X-100 buffer and immunoprecipitated with FLAG-M2-agarose beads (Sigma, St. Louis, Mo.). Eluted proteins from the immunoprecipitation were separated by SDS gel electrophoresis followed by Western blotting using anti-FLAG M2 antibody (Sigma, St. Louis, Mo.). The increased endogenous PKM2 that co-immunoprecipitated with FLAG-PKM2 indicates tetramer formation. See FIGS. 3B and 7.

Cell Proliferation Assay

Cells were seeded at 5000 cells per well (in 96-well plate) in BME media lacking nonessential amino acids+5% dialyzed serum. After 18 hours, DMSO or compound in 0.1% final concentration DMSO was added. After 72 hours, cell viability was determined by ATPlite assay and EC50 values were determined using Prism GraphPad Software (La Jolla, Calif.) (FIG. 4A).

Serine rescue experiments were performed as above with the exception that 30 μM serine was added simultaneously with compound. Statistical analysis was performed by parametric ANOVA test. *p<0.002 (Example 244 or Example 244+serine vs. DMSO). **p<0.0005 (Example 1 or Example 1+serine vs. DMSO) (FIG. 4B).

Viability effect of Example 1 against a subset of lung carcinoma cell lines was determined as follows. Cells were seeded at 1500 cells per well in 384-well plates in BME media, and compound was added in 0.1% DMSO 18 hours later. Viability was determined by ATPlite assay after 72 hours. (See FIG. 4C).

Example 1 was tested against an expanded panel of cell lines according to the above procedure. Results ($IC_{50}$) are presented in Table 4.

TABLE 4

Cell Line Sensitivity to Example 1

| Indication | Cell line | Sensitivity to Serine | Sensitivity to Example 1 |
|---|---|---|---|
| Bladder | UMUC-3 | Sensitive | >30 μM |
| Brain | A172 | Insensitive | 2.3 μM |
| Breast | MDA-MB453 | Sensitive | >30 μM |
| | MDA-MB468 | Insensitive | >30 μM |
| | MCF7 | Sensitive | >30 μM |
| Colon | HCT15 | Insensitive | >30 μM |
| | HCT116 | Sensitive | 100 nM |
| | HT29 | Sensitive | 100 nM |
| | Ls174T | Insensitive | >30 μM |
| | RKO | Sensitive | >30 μM |
| | SW48 | Sensitive | >30 μM |
| | SW480 | Insensitive | 100 nM |
| | SW620 | Sensitive | 200 nM |
| | SW948 | Insensitive | >30 μM |
| GIST | Gist882 | Insensitive | 800 nM |
| Head/Neck | Detroit562 | Sensitive | 3 μM |
| | FaDu | Sensitive | >30 μM |
| Kidney | 786-O | Sensitive | >30 μM |
| | A498 | Insensitive | >30 μM |
| | Caki-1 | Insensitive | 80 nM |
| | ACHN | Insensitive | 100 nM |
| Liver | HepG2 | Insensitive | >30 μM |
| Lung | A549 | Sensitive | 100 nM |
| | H1299 | Insensitive | 600 nM |
| | NCI-H460 | Sensitive | 5 μM |
| | NCI-H647 | Sensitive | >30 μM |
| | NCI-H23 | Insensitive | N/A |
| | NCI-H522 | Insensitive | >30 μM |
| | NCI-H1975 | Sensitive | 90 nM |
| | NCI-H441 | Sensitive | N/A |
| Melanoma | Malme3M | Insensitive | >30 μM |
| Ovarian | OVCAR-3 | Sensitive | 20 nM |
| | Skov3 | Sensitive | 8 μM |
| Pancreatic | AsPC1 | Sensitive | >30 μM |
| | Capan1 | Insensitive | >30 μM |
| | Capan2 | Sensitive | >30 μM |
| | Panc-1 | Insensitive | 14 nM |
| | Hs766T | Insensitive | 300 nM |
| | PSN-1 | Sensitive | >30 μM |
| | MiaPaCa2 | Sensitive | 200 nM |
| | PL45 | Sensitive | >30 μM |
| Prostate | 22RV1 | Insensitive | >30 μM |
| | Du145 | Insensitive | >30 μM |
| | LNCaP | Sensitive | >30 μM |
| | PC3 | Sensitive | 100 nM |
| Sarcoma | HT1080 | Sensitive | 50 nM |

Figure 8:
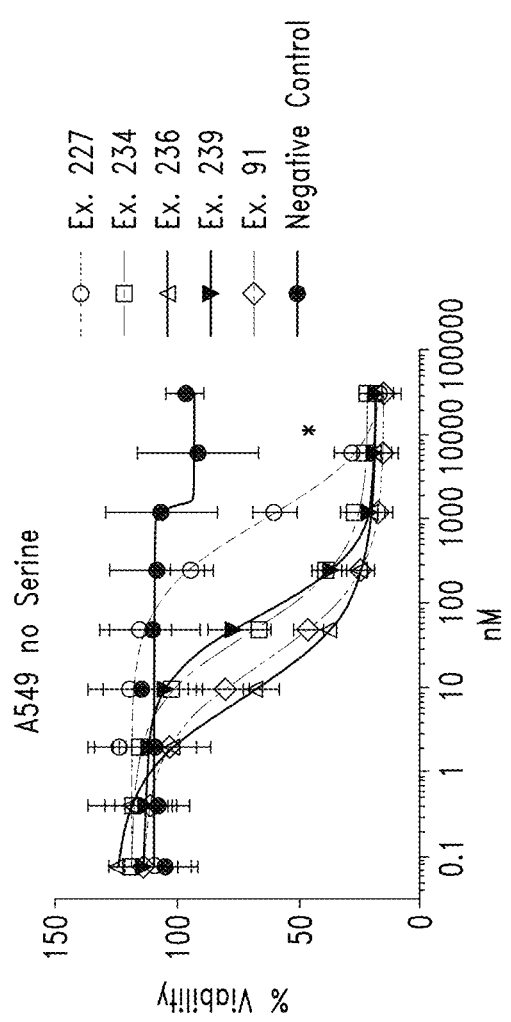
FIG. 8 is a graph showing percent viability of A549 cells in the absence of serine and in the presence of exemplary compounds.

Percent viability ($EC_{50}$) of A549 and PC3 cells was tested against certain exemplary compounds according to the above general procedures. Results are presented in Table 5 and FIG. 8.

TABLE 5

Viability of A549 and PC3 Cells in the Presence of Exemplary Compounds

| | A549 | | PC3 | |
|---|---|---|---|---|
| | Average (nM) | STD | Average (nM) | STD |
| Ex. 236 | 8.1 | 0.7 | 33.0 | 4.7 |
| Ex. 91 | 20.3 | 0.7 | 47.3 | 22.0 |

TABLE 5-continued

Viability of A549 and PC3 Cells in the Presence of Exemplary Compounds

|  | A549 | | PC3 | |
| --- | --- | --- | --- | --- |
|  | Average (nM) | STD | Average (nM) | STD |
| Ex. 223 | 33.5 | 4.4 | 54.0 | 1.0 |
| Ex. 234 | 45.8 | 17.3 | 92.4 | 26.8 |
| Ex. 1 | 70.0 | 2.6 | 155.5 | 17.5 |
| Ex. 239 | 73.1 | 4.3 | 128.7 | 6.4 |
| Ex. 54 | 101.7 | 34.3 | 192.7 | 44.1 |
| Ex. 62 | 107.6 | 15.3 | 166.1 | 24.5 |
| Ex. 75 | 147.9 | 7.8 | 222.9 | 23.2 |
| Ex. 47 | 188.4 | 56.1 | 383.0 | 130.4 |
| Ex. 227 | 928.5 | 353.1 | 1311.5 | 74.2 |

Xenograft Experiments

Figure 9:
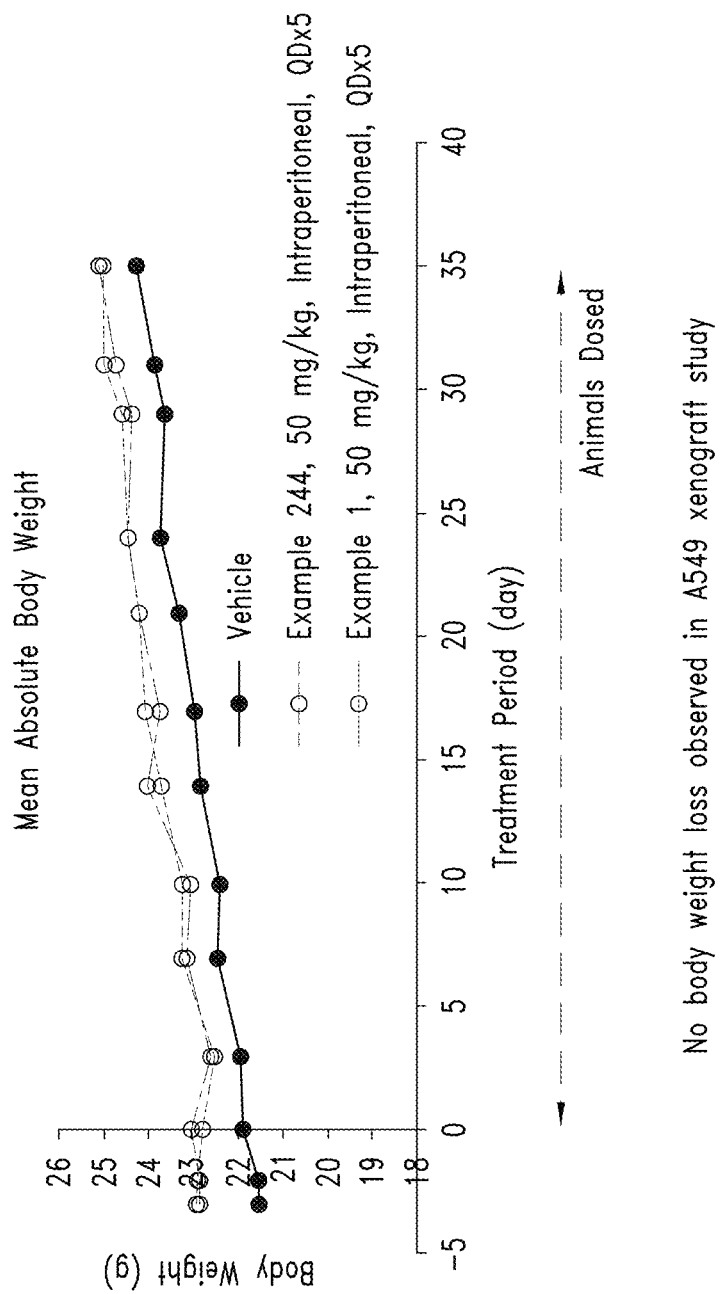
FIG. 9 shows body weight data for mice treated with exemplary compounds.

Female athymic Nu/Nu mice were implanted with $10^7$ A549-luc-C8 cells in 1:1 volume with Matrigel into the right hind flank on day 1, followed by bioluminescent measurement and randomization for each group (n=15 for xenograft study in FIG. 5A; n=18 for xenograft study in FIG. 5B). Mice were dosed intraperitoneally starting on day 1 with either vehicle (5% Ethanol/7.5% DMSO/25% PEG400/12.5% Cremophor EL/50% D5 water) or vehicle plus compound at a dose of 50 mg/kg, once daily, 5 days on, 2 days off, for 5 weeks. Tumor volumes were determined by caliper measurement starting on day 7 after implantation. Statistical significance at day 31 was determined by Student's t-test. Body weight data for the above experiment is presented in FIG. 9.

All of the U.S. patents, U.S. patent application publications, U.S. patent applications, foreign patents, foreign patent applications and non-patent publications referred to in this specification are incorporated herein by reference in their entirety including U.S. Provisional Application No. 61/714,659 filed Oct. 16, 2012 and U.S. Provisional Patent Application No. 61/875,844 filed Sep. 10, 2013, to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for increasing PKM2 activity in the provision of decreased tumorigenicity in a subject in need thereof, the method comprising:

administering an effective amount of a PKM2 activating compound in the form of a free-base or a pharmaceutically acceptable salt, or tautomer or prodrug thereof, to the subject, wherein said compound is:

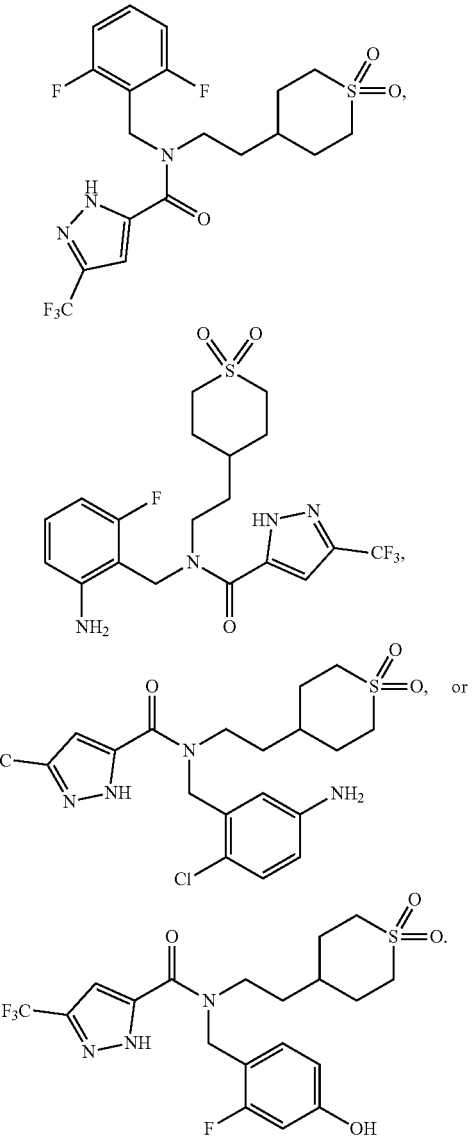

2. The method of claim 1, wherein the tumorigenicity is due to lung cancer, pancreatic cancer, skin cancer, colon cancer, breast cancer, kidney cancer, ovarian cancer, or a hematological malignancy.

3. The method of claim 1, wherein the compound is:

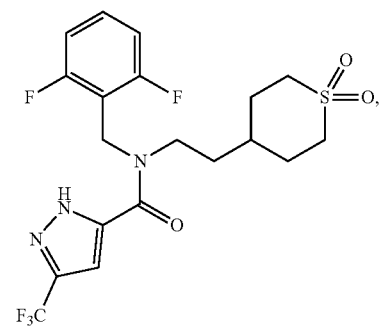 [SMILES: O=C(c1cc(C(F)(F)F)n[nH]1)N(CCC1CCS(=O)(=O)CC1)Cc1c(F)cccc1F]

or a pharmaceutically acceptable salt, tautomer, or prodrug thereof.

4. The method of claim 3, wherein the tumorigenicity is due to lung cancer, pancreatic cancer, skin cancer, colon cancer, breast cancer, kidney cancer, ovarian cancer, or a hematological malignancy.

5. The method of claim 1, wherein the compound is:

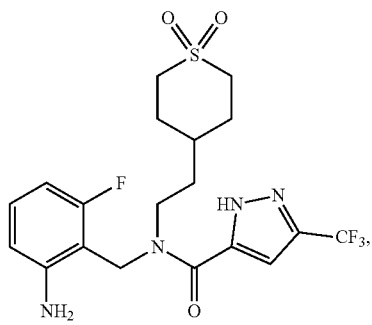 [SMILES: Nc1cccc(F)c1CN(CCC1CCS(=O)(=O)CC1)C(=O)c1cc(C(F)(F)F)n[nH]1]

or a pharmaceutically acceptable salt, tautomer, or prodrug thereof.

6. The method of claim 5, wherein the tumorigenicity is due to lung cancer, pancreatic cancer, skin cancer, colon cancer, breast cancer, kidney cancer, ovarian cancer, or a hematological malignancy.

7. The method of claim 1, wherein the compound is:

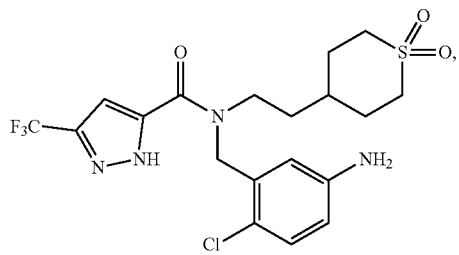 [SMILES: Nc1ccc(Cl)c(CN(CCC2CCS(=O)(=O)CC2)C(=O)c2cc(C(F)(F)F)n[nH]2)c1]

or a pharmaceutically acceptable salt, tautomer, or prodrug thereof.

8. The method of claim 7, wherein the tumorigenicity is due to lung cancer, pancreatic cancer, skin cancer, colon cancer, breast cancer, kidney cancer, ovarian cancer, or a hematological malignancy.

9. The method of claim 1, wherein the compound is:

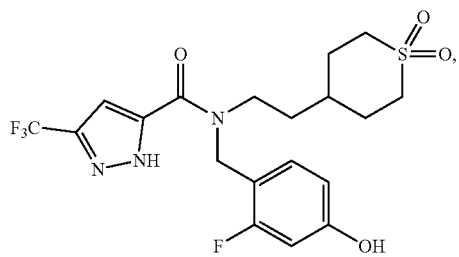 [SMILES: O=C(c1cc(C(F)(F)F)n[nH]1)N(CCC1CCS(=O)(=O)CC1)Cc1ccc(O)cc1F]

or a pharmaceutically acceptable salt, tautomer, or prodrug thereof.

10. The method of claim 9, wherein the tumorigenicity is due to lung cancer, pancreatic cancer, skin cancer, colon cancer, breast cancer, kidney cancer, ovarian cancer, or a hematological malignancy.

11. The method of claim 1, further comprising administering an effective amount of one or more chemotherapeutic agents to the subject.

12. The method of claim 3, further comprising administering an effective amount of one or more chemotherapeutic agents to the subject.

13. The method of claim 5, further comprising administering an effective amount of one or more chemotherapeutic agents to the subject.

14. The method of claim 7, further comprising administering an effective amount of one or more chemotherapeutic agents to the subject.

15. The method of claim 9, further comprising administering an effective amount of one or more chemotherapeutic agents to the subject.

16. The method of claim 1, wherein the compound is:

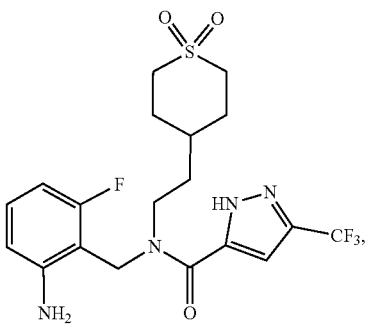 [SMILES: Nc1cccc(F)c1CN(CCC1CCS(=O)(=O)CC1)C(=O)c1cc(C(F)(F)F)n[nH]1]

in the form of a free-base.

17. The method of claim 1, wherein the compound is:

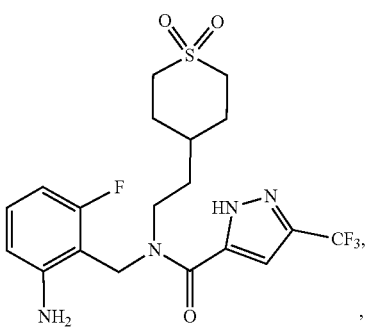 [SMILES: Nc1cccc(F)c1CN(CCC1CCS(=O)(=O)CC1)C(=O)c1cc(C(F)(F)F)n[nH]1]

in the form of a pharmaceutically acceptable salt.

* * * * *